(12) United States Patent
Tang et al.

(10) Patent No.: US 9,073,882 B2
(45) Date of Patent: Jul. 7, 2015

(54) INHIBITORS OF THE RENAL OUTER MEDULLARY POTASSIUM CHANNEL

(75) Inventors: Haifeng Tang, Metuchen, NJ (US);
Alexander Pasternak, Princeton, NJ (US); Lihu Yang, Edison, NJ (US);
Shawn P. Walsh, Bridgewater, NJ (US);
Barbara Pio, West Orange, NJ (US);
Aurash Shahripour, Iselin, NJ (US);
Nardos Teumelsan, Linden, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/881,008

(22) PCT Filed: Oct. 21, 2011

(86) PCT No.: PCT/US2011/057346
§ 371 (c)(1),
(2), (4) Date: Apr. 23, 2013

(87) PCT Pub. No.: WO2012/058116
PCT Pub. Date: May 3, 2012

(65) Prior Publication Data
US 2013/0225561 A1 Aug. 29, 2013

Related U.S. Application Data

(60) Provisional application No. 61/407,181, filed on Oct. 27, 2010, provisional application No. 61/473,861, filed on Apr. 11, 2011.

(51) Int. Cl.
| | |
|---|---|
| *A61K 31/496* | (2006.01) |
| *C07D 295/15* | (2006.01) |
| *C07D 295/135* | (2006.01) |
| *C07D 295/155* | (2006.01) |
| *C07D 213/76* | (2006.01) |
| *C07D 405/14* | (2006.01) |
| *C07D 407/12* | (2006.01) |
| *C07D 213/61* | (2006.01) |
| *C07D 241/04* | (2006.01) |
| *C07D 271/04* | (2006.01) |
| *C07D 295/073* | (2006.01) |
| *C07D 307/88* | (2006.01) |
| *C07D 309/30* | (2006.01) |
| *C07D 405/12* | (2006.01) |
| *C07D 413/12* | (2006.01) |
| *A61K 31/551* | (2006.01) |
| *A61K 31/4745* | (2006.01) |
| *C07D 271/12* | (2006.01) |
| *C07D 471/08* | (2006.01) |
| *C07D 487/08* | (2006.01) |

(52) U.S. Cl.
CPC ......... *C07D 295/135* (2013.01); *C07D 405/14* (2013.01); *C07D 213/61* (2013.01); *C07D 241/04* (2013.01); *C07D 271/04* (2013.01); *C07D 295/073* (2013.01); *C07D 295/155* (2013.01); *C07D 307/88* (2013.01); *C07D 309/30* (2013.01); *C07D 405/12* (2013.01); *C07D 413/12* (2013.01); *C07D 471/08* (2013.01); *C07D 487/08* (2013.01); *C07D 213/76* (2013.01); *C07D 271/12* (2013.01); *C07D 295/15* (2013.01)

(58) Field of Classification Search
None
See application file for complete search history.

(56) References Cited

U.S. PATENT DOCUMENTS

| | | | |
|---|---|---|---|
| 2,988,551 | A | 6/1961 | Morren |
| 3,435,002 | A | 3/1969 | Scotia |
| 3,632,608 | A | 1/1972 | Holub |
| 3,749,722 | A | 7/1973 | Holub |
| 4,579,863 | A | 4/1986 | Horwell et al. |
| 4,806,536 | A | 2/1989 | Cross et al. |
| 4,816,479 | A | 3/1989 | Koga et al. |
| 4,992,547 | A | 2/1991 | Berner et al. |
| 5,112,824 | A * | 5/1992 | Baldwin et al. .......... 514/252.19 |

(Continued)

FOREIGN PATENT DOCUMENTS

| | | |
|---|---|---|
| EP | 0099148 B1 | 2/1988 |
| EP | 0175376 B1 | 4/1991 |

(Continued)

OTHER PUBLICATIONS

ACCF/AHA Practice Guideline, 2009 Focused update incorporated into the ACC/AHA 2005 guidelines . . . , Circulation, 2009, e391-e436, 119.

(Continued)

*Primary Examiner* — Emily Bernhardt
(74) *Attorney, Agent, or Firm* — Nicole M. Beeler; Catherine D. Fitch

(57) ABSTRACT

This invention relates to compounds having structural Formula I:

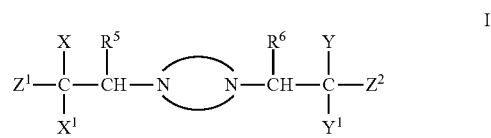

and pharmaceutically acceptable salts thereof which are inhibitors of the Renal Outer Medullary Potassium (ROMK) channel (Kir1.1). The compounds of Formula I are useful as diuretics and natriuretics and therefore are useful for the therapy and prophylaxis of disorders resulting from excessive salt and water retention, including cardiovascular diseases such as hypertension and chronic and acute heart failure.

7 Claims, No Drawings

(56) References Cited

U.S. PATENT DOCUMENTS

| | | |
|---|---|---|
| 5,145,885 A | 9/1992 | Berner et al. |
| 5,215,989 A | 6/1993 | Baldwin et al. |
| 5,614,526 A | 3/1997 | Godel et al. |
| 5,736,546 A | 4/1998 | Kawashima et al. |
| 5,977,116 A | 11/1999 | Castro Pineiro et al. |
| 6,258,813 B1 | 7/2001 | Arlt et al. |
| 6,787,543 B2 | 9/2004 | Take et al. |
| 2004/0204404 A1 | 10/2004 | Zelle et al. |
| 2005/0215526 A1 | 9/2005 | Hulme et al. |
| 2005/0267121 A1 | 12/2005 | Li et al. |
| 2006/0183739 A1 | 8/2006 | Tsaklakidis et al. |
| 2006/0183742 A1 | 8/2006 | Mederski et al. |
| 2006/0211692 A1 | 9/2006 | Mederski et al. |
| 2007/0004750 A1 | 1/2007 | Lorsbach et al. |
| 2007/0093472 A1 | 4/2007 | Mederski et al. |
| 2008/0003214 A1 | 1/2008 | Cezanne et al. |
| 2009/0239843 A1 | 9/2009 | Coleman et al. |
| 2010/0286123 A1 | 11/2010 | Pasternak et al. |

FOREIGN PATENT DOCUMENTS

| | | | |
|---|---|---|---|
| EP | 1094063 A1 | | 4/2001 |
| EP | 1939175 A1 | | 7/2009 |
| FR | 2673182 | | 8/1992 |
| GB | 949088 A | | 2/1964 |
| GB | 1575310 A | | 9/1980 |
| GB | 2116967 | | 7/1986 |
| JP | 10203986 | | 8/1998 |
| WO | 9744329 | | 11/1997 |
| WO | 0051611 A1 | | 9/2000 |
| WO | 0204314 A1 | | 6/2002 |
| WO | 0250061 A1 | | 6/2002 |
| WO | 0232874 | | 11/2003 |
| WO | 2004020422 A1 | | 3/2004 |
| WO | 2004037817 A1 | | 5/2004 |
| WO | 2004046110 | | 6/2004 |
| WO | 2005037843 | | 4/2005 |
| WO | 2005044797 | | 5/2005 |
| WO | 2006034341 A2 | | 3/2006 |
| WO | 2006034769 A1 | | 4/2006 |
| WO | 2006098342 A1 | | 9/2006 |
| WO | 2007009462 A1 | | 1/2007 |
| WO | 2007075629 A2 | | 7/2007 |
| WO | 2008147864 | | 12/2008 |
| WO | 2008147864 A2 | | 12/2008 |
| WO | 2009149508 | | 11/2009 |
| WO | 2010129379 A1 | | 11/2010 |
| WO | 2012058134 A1 | | 5/2012 |
| WO | 2006129199 A1 | | 12/2012 |
| WO | 2013028474 A1 | | 2/2013 |
| WO | 2013039802 A1 | | 3/2013 |
| WO | 2013062892 A1 | | 5/2013 |
| WO | 2013062900 A1 | | 5/2013 |
| WO | 2013066714 A1 | | 5/2013 |
| WO | 2013066717 A1 | | 5/2013 |
| WO | 2013066718 A2 | | 5/2013 |
| WO | 2013090271 A1 | | 6/2013 |
| WO | 2014018764 A1 | | 1/2014 |

OTHER PUBLICATIONS

Baltzly, R., The preparation of N-mono-substituted and unsymmetrically disubstituted piperazines, J. Am. Chemoc., 1944, 263-266, 66.

Bhave, G., Small-molecule modulators of inward rectifier K+ channels: recent advances and future possibilities, Future Med Chem, 2010, 757-774, 2(5).

Bhave, G., Development of a selective small-molecule inhibitor Kir1.1, the renal outer medullary potassium channel, Mol. Pharmacol., 2011, 42-50, 79.

Brater et al., Diuretic Therapy, Drug Therapy, 1998, 387-395, 339.

Brewster et al., Antihypertensive 1,4-bis (2-indol-3-ylethyl)piperazines, Chimie Ther., 1973, 169-172 (English trans.), 2.

Cerkvenik-Flajs V, Determination of residues of azaperone in the kidneys by liquid chromatography with fluorescence, Anal. Chim. Acta., 2007, 374-382, 586.

Chemical Abstracts (2004), Abstract No. 697771-49-6, "1,3-lsobenzofurandione 5-[[4-[(5-chloro-2-methoxyphenyl)sulfonyl]-1-...".

Cheymol et al., Increase in the effects of epinephrine and acetylcholine . . . , Comptes Rendus des seances de la Societe de Biologie, 1951, 496-499 (English trans.), 145.

Fallen, K., The Kir channel immunoglobuling domain is essential for Kir1.1 (ROMK) thermodynamic stability, trafficking and gating, Channels, 2009, 57-66, 3.

Felker et al, Diuretic strategies in patients with acute decompensated heart failure, New Eng. J. Med., 2011, 797-805, 364.

Frank, Managing hypertension using combination therapy, Am. Fam. Physician, 2008, 1279-1286, 77.

International Search Report for PCT/US2011/057346 mailed on Feb. 29, 2012, 5 pages.

Kulkarni, YD, Possible antifertility agents, part III. Synthesis of 4-(substituted aminomethyl)-5,6,7-trimethoxy phthalid . . . (abstract)), Biol. Mem., 1987, 141-144, 13.

Lanyi et al., Piperazine-Derivatives II, Res. Lab. of Chinoin-Fabrik Chemisch-Pharma. Prod., 1968, 1431-1435 (English trans.), 18.

Lewis, L. M., High-throughput screening reveals a small-molecule inhibitor of the Renal Outer Medullary Potassium Channel and Kir7.1, Mol. Pharncol., 2009, 1094-1103, 76.

Lutz, R. E., Antimalarials. Some Piperazine Derivatives, J. Org. Chem., 1947, 771-775, 12, BO.

Miyake et al., Synthesis of 1-substituted isochroman . . . , Takeda Res. Lab., 1982, 24-40 (English trans.), 41.

Sica, D. A., Diuretic use in renal disease, Nature, 2012, 100-109, 8.

Supplementary European Search Report for PCT/US2011/057346, dated Feb. 25, 2014, 4 pages.

Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

RELATED APPLICATIONS

This application is a 35 U.S.C. §371 filing from International Application No. PCT/US2011/057346, filed Oct. 21, 2011, which claims priority to U.S. Provisional Application No. 61/473,861, filed on Apr. 11, 2011, and U.S. Provisional Application No. 61/407,181, filed on Oct. 27, 2010. Each of the aforementioned applications is herein incorporated by reference in its entirety.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are predicted to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first small molecule selective inhibitors of ROMK were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. However, continuing discovery of selective small molecule inhibitors of ROMK is still needed for the development of new treatments for hypertension and related disorders.

SUMMARY OF THE INVENTION

The present invention provides compounds of Formula I

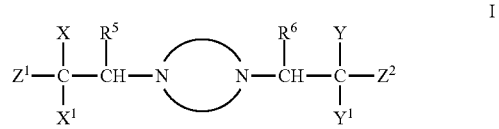

and the pharmaceutically acceptable salts thereof. The compounds of Formula I are inhibitors of the ROMK (Kir1.1) channel and can thus act as diuretics and natriuretics and are valuable pharmaceutically active compounds for the therapy and prophylaxis of diseases, including, but not limited to, cardiovascular diseases such as hypertension and conditions resulting from excessive salt and water retention. Methods of treatment comprising administering a therapeutically or prophylactically effective amount of a compound of Formula I to a patient in need of a diuretic and/or natriuretic agent are also provided. Compounds of Formula I can be used in combination with other therapeutically effective agents, including other drugs useful for the treatment of hypertension and conditions resulting from excessive salt and water retention. The invention furthermore relates to processes for preparing compounds of Formula I, and pharmaceutical compositions which comprise compounds of Formula I. s

DETAILED DESCRIPTION OF THE INVENTION

The present invention is directed to compounds having structural Formula I:

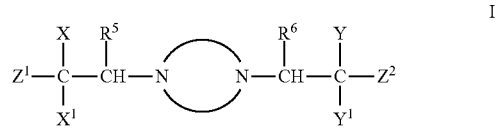

and the pharmaceutically acceptable salts thereof wherein:

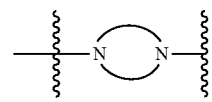

represents a heterocyclic ring selected from the group consisting of:

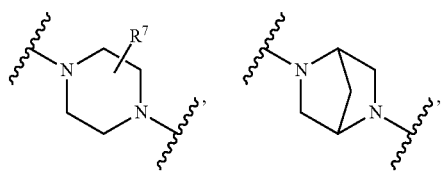

-continued

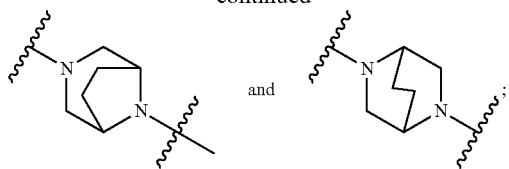

wherein $R^7$ is selected from the group consisting of —H, —F, —CH$_3$, —CF$_3$, —CHF$_2$, —CH$_2$F, —CH$_2$OH, cyclopropyl and —CH$_2$C(=O)O—CH$_3$, or $R^7$ represents di-substitution on a single carbon with two of —F or two of —CH$_3$;

$Z^1$ is selected from the group consisting of:

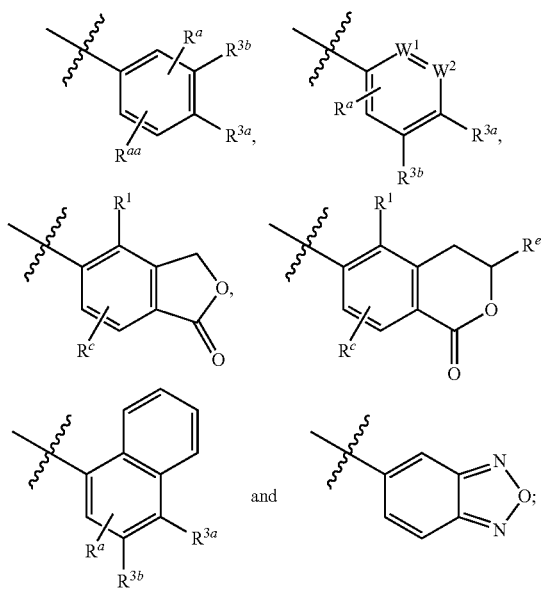

$Z^2$ is selected from the group consisting of:

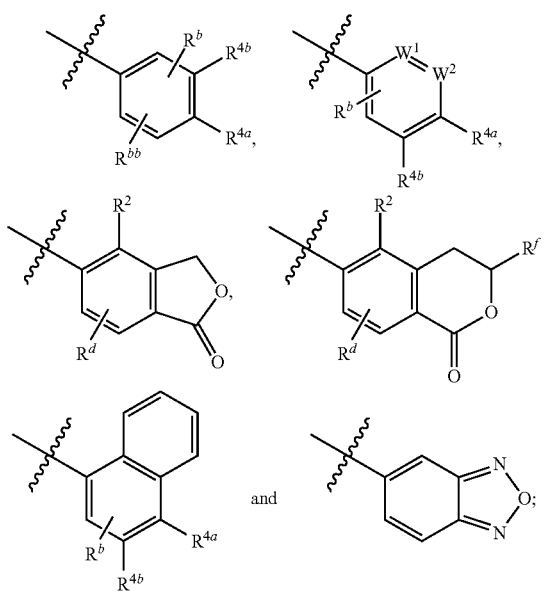

one of $W^1$ and $W^2$ is N and the other is CH;

$R^1$ and $R^2$ are each independently selected from the group consisting of —H, —F, —Cl, —Br, —C$_3$-C$_6$cycloalkyl, —OR$^8$, —SR$^8$, —SOR$^8$, —SO$_2$R$^8$, —(CH$_2$)$_n$OR$^8$ and —C$_{1-6}$ alkyl optionally substituted with 1-3 of —F;

one of $R^{3a}$ and $R^{3b}$ is selected from the group consisting of —CN —NO$_2$ and tetrazoly, and the other is $R^{3c}$ wherein $R^{3c}$ selected from the group consisting of —H, —F, —Cl, —Br, —CH$_3$, —S—CH$_3$, —NH—CH$_3$, —O-cyclopropyl and —OC$_{1-3}$alkyl optionally substituted with 1-3 of —F;

one of $R^{4a}$ and $R^{4b}$ is selected from the group consisting of CN, —NO$_2$ and tetrazolyl, and the other is $R^{4c}$ wherein $R^{4c}$ is selected from the group consisting of —H, —F, —Cl, —Br, —CH$_3$, —S—CH$^3$, —NH—CH$_3$, —O-cyclopropyl and —OC$_{1-3}$alkyl optionally substituted with 1-3 of —F;

$R^a$, $R^{aa}$, $R^b$ and $R^{bb}$ are each independently selected from the group consisting of —H, —F, —Cl, —CH$_3$ optionally substituted with 1 to 3 of —F, and —OCH$_3$ optionally substituted with 1 to 3 of —F;

$R^c$ and $R^d$ are each independently selected from the group consisting of —H, —F, —Cl, —C$_{1-6}$ alkyl optionally substituted with 1 to 3 of —F, —C$_{3-6}$ cycloalkyl and —OC$_{1-6}$ alkyl optionally substituted with 1 to 3 of —F;

$R^e$ and $R^f$ are each independently selected from the group consisting of —H and —CH$_3$;

X and $X^1$ are each independently selected from —H and —C$_{1-6}$alkyl, or $X^1$ is joined together with $Z^1$ and the carbon to which both are attached to form a fused ring system selected from the group consisting of:

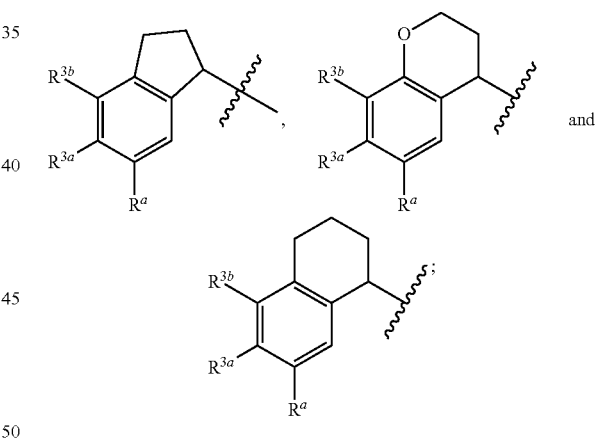

Y and $Y^1$ are each independently selected from —H and —C$_{1-6}$alkyl, or $Y^1$ is joined together with $Z^2$ and the carbon to which both are attached to form a fused ring system selected from the group consisting of:

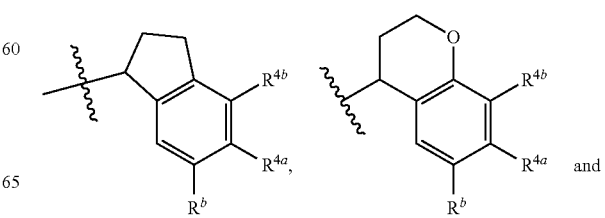

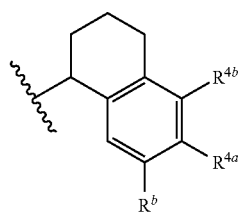

$R^5$ and $R^6$ are each independently selected from —H, —CH₃ and —$C_{1-6}$alkyl and —C(O)O$C_{1-3}$alkyl;

or $R^5$ is joined together with $Z^1$ and the intervening carbons to which each is attached to form a fused ring system selected from:

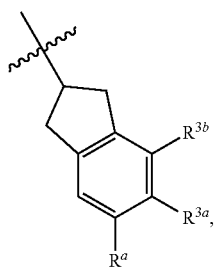 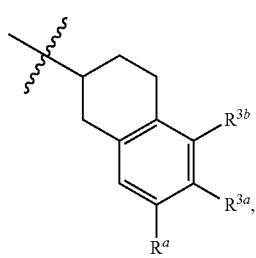

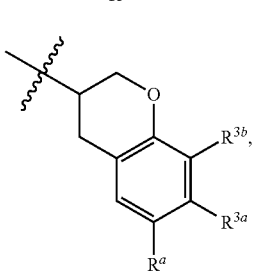 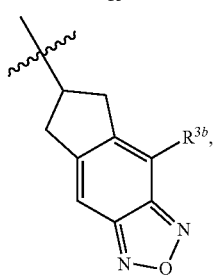

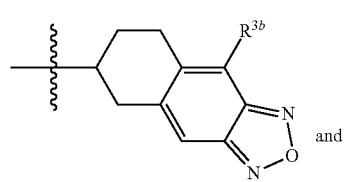 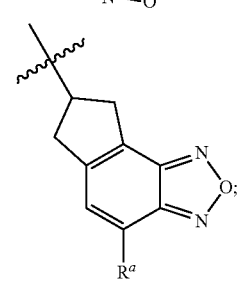

or $R^6$ is joined together with $Z^2$ and the intervening carbons to which each is attached to form a fused ring system selected from:

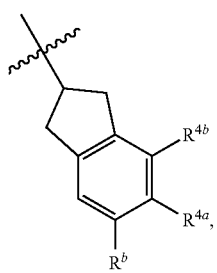 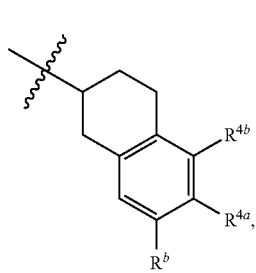

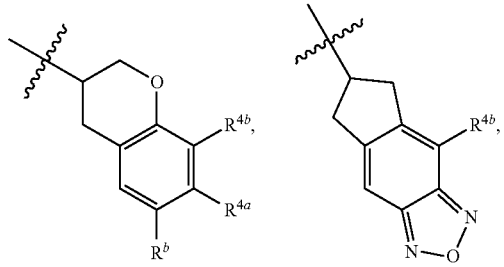

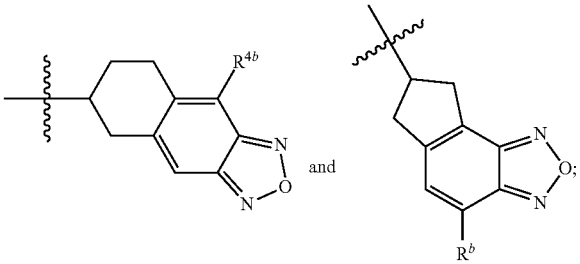

provided that only one of $R^5$ and $Z^1$ or $R^6$ and $Z^2$ is joined to form the fused ring system; and $R^8$ is selected from the group consisting of —$C_{1-6}$alkyl and —$C_{3-6}$cycloalkyl.

In an embodiment of this inventions are compounds of Formula I or Formula II

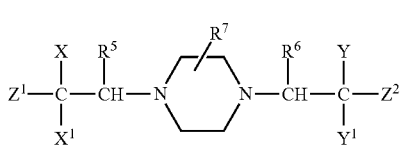

and the pharmaceutically acceptable salts thereof wherein:

$Z^1$ is selected from the group consisting of:

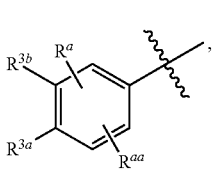 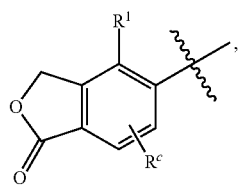

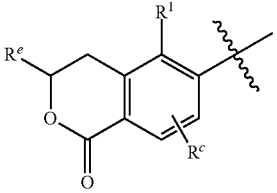 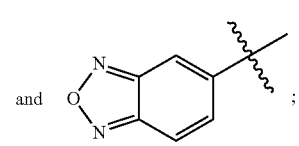

$Z^2$ is selected from the group consisting of:

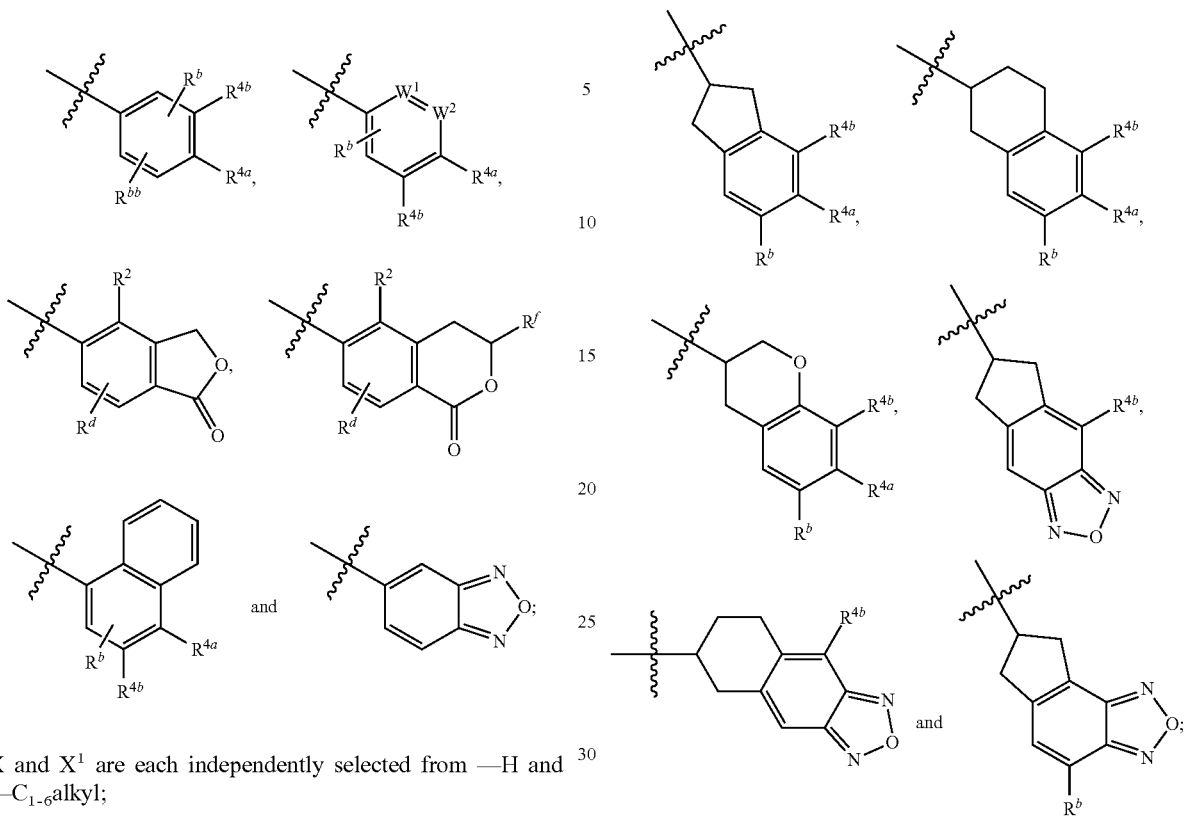

X and $X^1$ are each independently selected from —H and —$C_{1-6}$alkyl;

Y and $Y^1$ are each independently selected from —H and —$C_{1-6}$alkyl, or $Y^1$ is joined together with $Z^2$ and the carbon to which both are attached to form a fused ring system selected from the group consisting of:

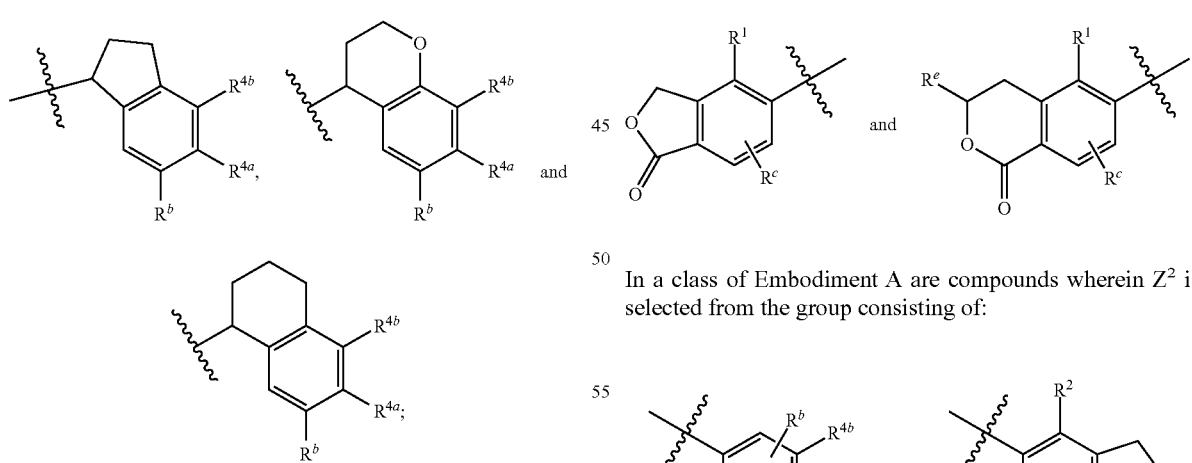

$R^5$ is selected from —H, —$CH_3$, —$C_{1-6}$ alkyl and —C(O)O$C_{1-3}$alkyl; and $R^6$ is selected from —H, —$CH_3$, —$C_{1-6}$ alkyl and —C(O)O$C_{1-3}$alkyl, or $R^6$ is joined together with $Z^2$ and the intervening carbons to which each is attached to form a fused ring system selected from:

and all other variables are as defined in Formula I.

In Embodiment A are compounds of Formula I or II and the pharmaceutically acceptable salts thereof wherein $Z^1$ is selected from:

In a class of Embodiment A are compounds wherein $Z^2$ is selected from the group consisting of:

In a further subclass are compounds wherein $R^2$ is —H or —$CH_3$; and $R^d$ is —H.

In Embodiment B are compounds of Formula I or II and the pharmaceutically acceptable salts thereof wherein $Z^1$ is

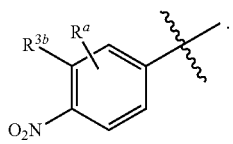

In a class of Embodiment B are compounds selected from those wherein (1) $Z^2$ is selected from the group consisting of:

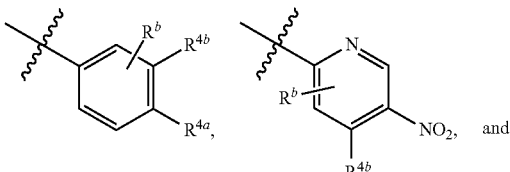

and
(2) compounds wherein $R^6$ is joined with $Z^2$ to form the fused ring system

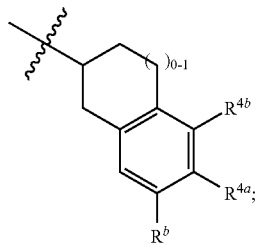

and $R^{4a}$ is —$NO_2$ or —CN. In a further subclass are compounds wherein $Z^2$ is

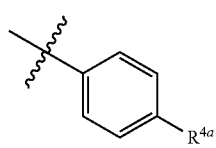

and $R^{4a}$ is —$NO_2$ or —CN.

In Embodiment C are compounds of Formula I or II and the pharmaceutically acceptable salts thereof wherein $Z^1$ is

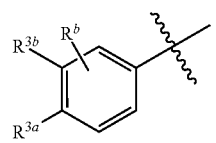

wherein one of $R^{3a}$ and $R^{3b}$ is —CN and the other is selected from —F, —Cl, —$OCH_3$, and —$OCH_2CH_3$.

In Embodiment D are compounds of Formula I or II and the pharmaceutically acceptable salts thereof wherein $Z^1$ is

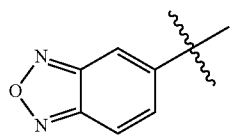

In a class of Embodiment D are compounds wherein (1) $Z^2$ is

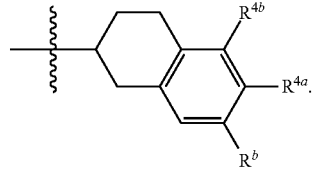

or (2) $R^6$ is joined with $Z^2$ to form the fused ring system

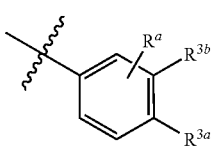

In another embodiment are compounds of Formulas I or II, and Embodiments A, B, C or D and the pharmaceutically acceptable salts thereof wherein $R^7$ is —H.

In another embodiment are compounds of Formulas I or II, and Embodiments A, B, C or D and the pharmaceutically acceptable salts thereof wherein $Z^1$ is selected from the group consisting of:

(1)
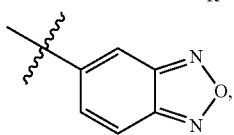

wherein $R^{3a}$ selected from —$NO_2$ and —CN and $R^{3b}$ is $R^{3c}$, or $R^{3b}$ is —CN and $R^{3a}$ is $R^{3c}$, (2)
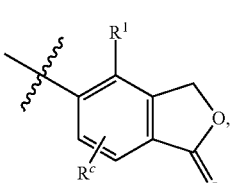

(3)
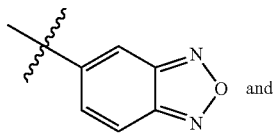 and (4)

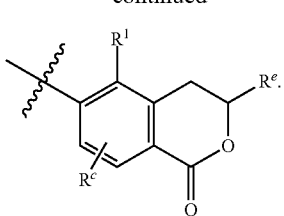

In another embodiment are compounds of Formulas I or II, and Embodiments A, B, C or D and the pharmaceutically acceptable salts thereof wherein $R^1$ and $R^2$ independently selected from —H and —$CH_3$.

In another embodiment are compounds of Formulas I or II, and Embodiments A, B, C or D and the pharmaceutically acceptable salts thereof wherein $R^{3a}$ and $R^{4a}$ are independently selected from the group consisting of —CN and —$NO_2$, and $R^{3b}$ and $R^{4b}$ is are independently selected from the group consisting of —H, —F, —Cl, —Br, —$CH_3$, —S—$CH_3$, —NH—$CH_3$, —O-cyclopropyl and —$OC_{1-3}$alkyl optionally substituted with 1-3 of —F. In a further embodiment, when $R^{3a}$ is —$NO_2$ then $R^{3b}$ and $R^a$ are both —H.

In another embodiment are compounds of Formulas I or II, and Embodiments A, B, C or D and the pharmaceutically acceptable salts thereof wherein when $R^{3a}$ is —CN then $R^{3b}$ is selected from —Cl, —F, —$OCH_3$ and —$OCH_2CH_3$; and when $R^{4a}$ is —CN then $R^{4b}$ is selected from —Cl, —F, —$OCH_3$ and —$OCH_2CH_3$. Preferably, when $R^{3b}$ is —CN then $R^{3a}$ is selected from —F and —$OCH_3$; and when $R^{4b}$ is —CN then $R^{4a}$ is selected from —F and —$OCH_3$.

In another embodiment are compounds of Formulas I or II, and Embodiments A, B, C or D and the pharmaceutically acceptable salts thereof wherein $R^{4a}$ is tetrazolyl.

In another embodiment are compounds of Formulas I or II, and Embodiments A, B, C or D and the pharmaceutically acceptable salts thereof wherein $R^a$ and $R^b$ are each independently selected from the group consisting of —H, —F, —Cl, —$CH_3$ optionally substituted with 1 to 3 of —F, and —$OCH_3$ optionally substituted with 1 to 3 of —F; and more particularly —H, —F, and —$CH_3$.

In another embodiment are compounds of Formulas I or II, and Embodiments A, B, C or D and the pharmaceutically acceptable salts thereof wherein $R^{aa}$ and $R^{bb}$ are each independently —H or —F; and more particularly both are —H.

In another embodiment are compounds of Formulas I or II, and Embodiments A, B, C or D and the pharmaceutically acceptable salts thereof wherein $R^c$ and $R^d$ are each independently selected from the group consisting of —H, —F, —Cl, —$CH_3$ optionally substituted with 1 to 3 of —F, and —$OCH_3$ optionally substituted with 1 to 3 of —F; and more particularly —H, —F, and —$CH_3$.

In another embodiment are compounds of Formulas I or II, and Embodiments A, B, C or D and the pharmaceutically acceptable salts thereof wherein X, $X^1$, Y and $Y^1$ are each —H.

In another embodiment are compounds of Formulas I or II, and Embodiments A, B, C or D and the pharmaceutically acceptable salts thereof wherein $R^5$ and $R^6$ are selected from —H and —$CH_3$.

In another embodiment are compounds of Formula I and the pharmaceutically acceptable salts thereof wherein $X^1$ is joined together with $Z^1$ and the carbon to which both are attached to form a fused ring system.

In another embodiment are compounds of Formula I and the pharmaceutically acceptable salts thereof wherein $R^5$ is joined together with $Z^1$ and the intervening carbons to which each is attached to form a fused ring system.

In another embodiment are compounds of Formulas I or II, and Embodiments A, B, C or D and the pharmaceutically acceptable salts thereof wherein $Y^1$ is joined together with $Z^2$ and the carbon to which both are attached to form a fused ring system. In a class of this embodiment, the fused ring system is:

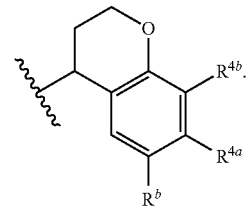

In another embodiment are compounds of Formulas I or II, and Embodiments A, B, C or D and the pharmaceutically acceptable salts thereof wherein $R^6$ is joined together with $Z^2$ and the intervening carbons to which each is attached to form a fused ring system. In a class of this embodiment, the fused ring system is:

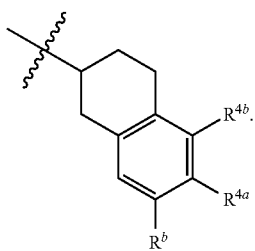

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me).

"Cycloalkyl" is a cyclized alkyl ring having the indicated number of carbon atoms. Examples of cycloalkyl include cyclopropyl, cyclobutyl, cyclopentyl and cyclohexyl. The cycloalkyl ring may be substituted on any available carbon which results in the creation of a stable structure, including the ring carbon which serves as the point of attachment to the rest of the molecule.

In some instances the number of substituents which may be optionally present on a moiety is specified, for example but not limited to, 1 to 3 of —F (fluoro). For example, an alkyl group that can be optionally substituted with 1-3 of —F includes, but is not limited to, —$CH_3$, —$CH_2F$, —$CHF_2$, —$CF_3$, —$CH_2CH_3$, —$CH_2$—$CH_2F$, —$CH_2$—$CHF_2$, —CHF—$CH_2F$, —$CH_2CF_3$, —CHF—$CHF_2$, —$(CH_2)_2CH_3$, —$CH(CF_3)$—$CH_3$, —$(CH_2)_3$—$CF_3$, —$(CH_2)_2CH(CF_3)$ CH$_3$, and —(CH$_2$)$_5$—CF$_3$, as appropriate for the defined number of carbon atoms for the given alkyl group.

Halo or halogen refers to —F (fluoro), —Cl (chloro), —Br (bromo) and —I (iodo). Preferred halogens are —F and —Cl.

Unless expressly depicted or described otherwise, variables depicted in a structural formula with a "floating" bond, such as each of substituents R$^a$, R$^b$, R$^c$, R$^d$, R$^e$ and R$^f$ in structural Formulas I and II, are permitted on any available carbon atom in the ring to which each is attached.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of this invention as those of a specific formula or embodiment, e.g., Formula I and II and embodiments thereof, or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding physiologically or toxicologically acceptable salts, in particular the pharmaceutically utilizable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and are therefore useful as diuretic and/or natriuretic agents. ROMK inhibitors help to increase urination and increase urine volume and also to prevent or reduce reabsorption of sodium in the kidneys leading to increased excretion of sodium and water. Therefore, the compounds are useful for treatment or prophylaxis of disorders that benefit from increased excretion of water and sodium from the body. Accordingly, an object of the instant invention is to provide a method for inhibiting ROMK comprising administering a compound of Formula I in a ROMK-inhibitory effective amount to a patient in need thereof. The inhibition of ROMK by the compounds of Formula I can be examined, for example, in any of the activity assays described below. Another object is to provide a method for causing diuresis, natriuresis or both, comprising administering a compound of Formula I in a therapeutically effective amount to a patient in need thereof.

Due to their activity as diuretics and natriuretic agents, this invention further provides the use of compounds of Formula I in methods for treatment of, prevention of or reduction of risk for developing medical conditions that benefit from increased excretion of water and sodium, such as but not limited to one or more of hypertension, heart failure (both acute and chronic, also known as congestive heart failure) and/or other conditions resulting from excessive salt and water retention. It further includes the use of the compounds of Formula I in methods for treatment of, prevention of or reduction of risk for developing one or more disorders such as pulmonary arterial hypertension (PAH), cardiovascular disease, diabetes, endothelial dysfunction, diastolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, nephrotic syndrome, acute and chronic kidney insufficiency, hypercalcemia, Dent's disease, Meniere's disease, edetamous states, and other conditions for which a diuretic would have therapeutic or prophylactic benefit. The compounds of the invention can be administered to a patient having, or at risk of having, one or more conditions for which a diuretic would have therapeutic or prophylactic benefit such as those described herein.

In general, compounds that are ROMK inhibitors can be identified as those compounds which, when tested, have an $IC_{50}$ of 5 µM or less, preferably 1 µM or less, and more preferably 0.25 µM or less, in at least one of the following assays: 1) the $^{86}Rb^+$ Efflux Assay and 2) the Thallium Flux Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or, in particular when larger amounts are administered, can be divided into several, for example two, three or four individual doses, and may be, for example but not limited to, 0.1 mg, 0.25 mg, 0.5 mg, 0.75 mg, 1 mg, 1.25 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention or reduction of risk of myocardial infarction or prevention and reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of Formula I and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or *acacia*, and lubricating agents, for example, magnesium stearate, stearic acid or talc.

Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from 0.1 to 200 mg, preferably from 0.1 to 50 mg, per dose on a free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

The compounds of Formula I inhibit ROMK. On account of this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. An additional active agent (or agents) is intended to mean a pharmaceutically active agent (or agents) different from the compound of Formula I. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists also known as angiotensis receptor blockers or ARBs (e.g., losartan i.e., COZAAR®, valsartan, candesartan, olmesartan, telmesartan and any of these drugs used in combination with hydrochlorothiazide such as HYZAAR®), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl betaaminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4 (S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators (e.g. nitroprusside), calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., HMG-CoA reductase inhibitors such as simvastatin, lovastatin, pravastatin, atorvastatin, pitavastatin and rosuvastatin, and cholesterol absorption inhibitors such as ezetimibe); niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, e.g., (sitagliptin (JANUVIA®) and saxagliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide.

Several methods for preparing the compounds of this invention are described in the following Schemes and Examples. Starting materials and intermediates are purchased, made from known procedures, or as otherwise illustrated. The Ar group shown in the below schemes can represent any of the substituted aromatic or substituted heterocyclic groups found in $Z^1$ or $Z^2$ as defined previously.

In general, synthesis of the covered compounds starts with alkylation of electrophile 1-1 (such as bromide, iodide, mesylatem or tosylate) with N-Boc protected piperazine (1-2) under basic conditions. The Boc protecting group (Greene, T.; Wuts, P. G. M. *protective Groups in Organic Synthesis*, John Wiley and Sons, Inc., New York, N.Y. 1991) of 1-3 can be removed under acidic conditions, such as with TFA or HCl. The resulting piperazine 1-4 was alkylated for a second time with the corresponding electrophile (E) 1-5 to yield the product 1-6.

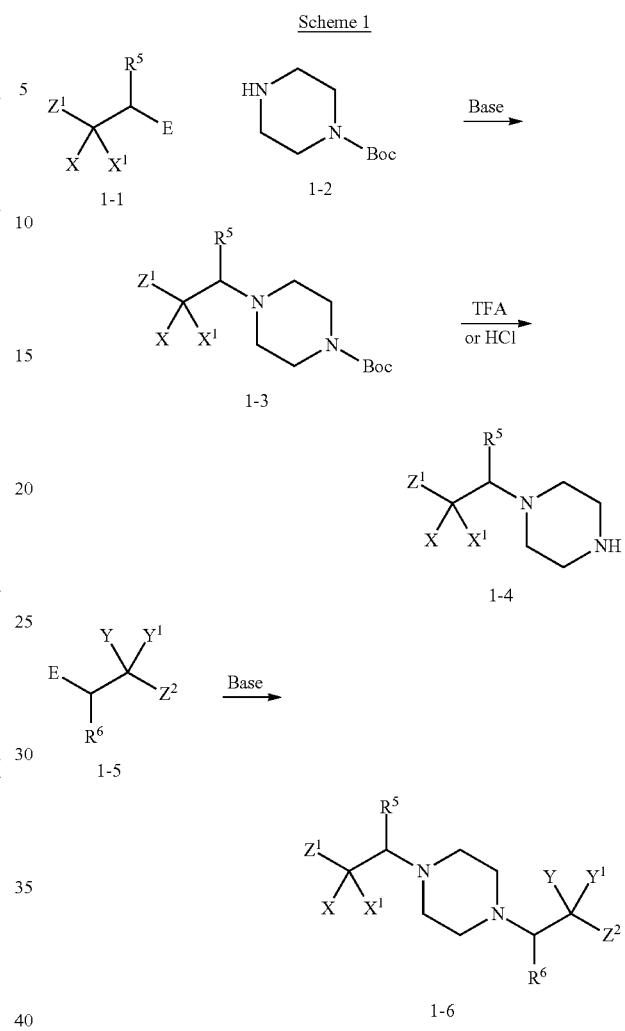

Alternatively, the alkylation can be achieved under reductive amination conditions with the corresponding aldehyde or ketone using $NaCNCH_3$ or $Na(OAc)_3BH$ (Scheme 2). Some compounds were made via a combination of the two alkylation methods, depending on whether the electrophile or aldehyde (ketone) is more easily accessible.

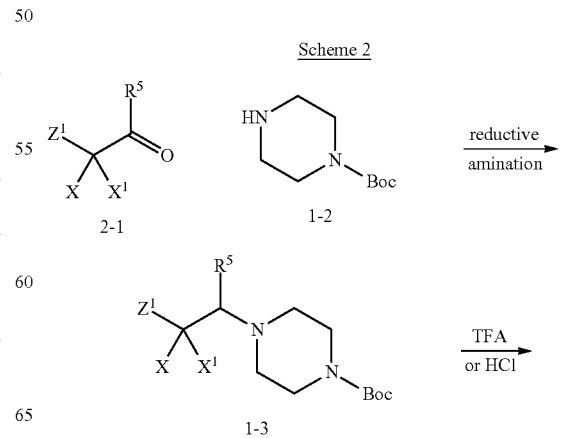

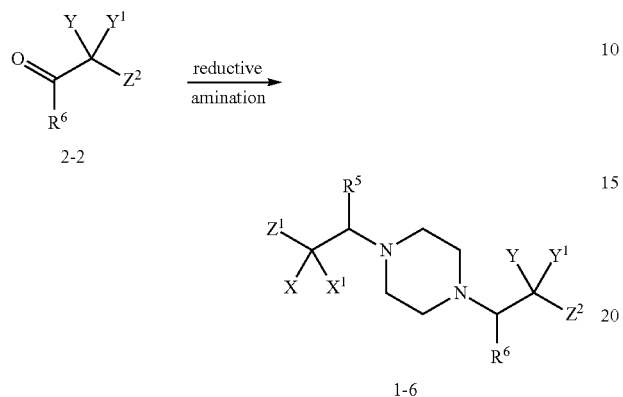

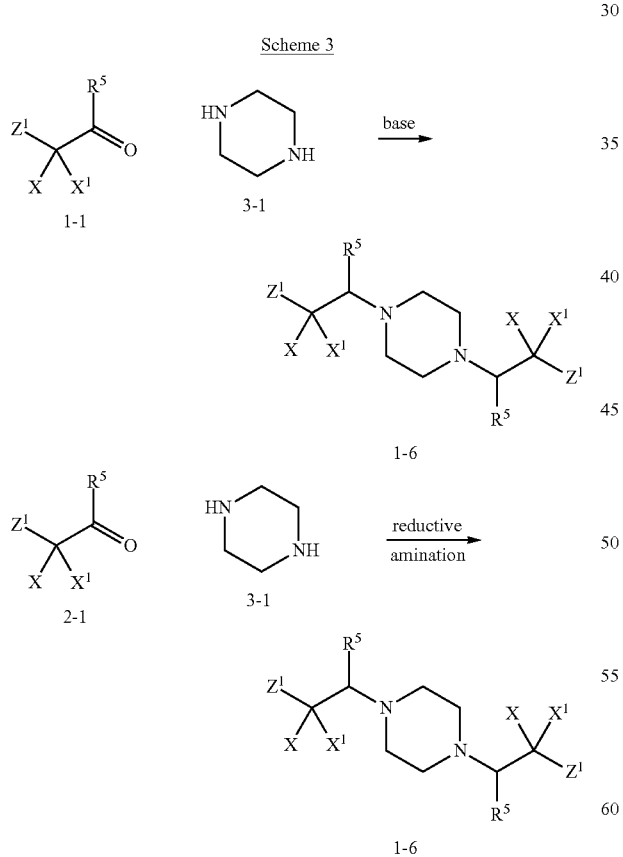

In instances where the compounds are symmetrical, the final product may be prepared in one single step via a double alkylation or reductive amination with piperazine 3-1 (Scheme 3).

Finally, intermediate 1-3 can also be prepared via a one pot ozonolysis—reductive amination method, when amine 4-1 is more easily accessible (Scheme 4). In this operation, tert-butyl diallylcarbamate 4-2 was first treated under ozonolysis conditions, which was followed by addition of amine 4-1, triethylamine, and Na(OAc)₃BH. Further stirring of the reaction gave rise to intermediate 1-3. Removal of the Boc group gave rise to 1-4, which was further alkylated to furnish the final compound.

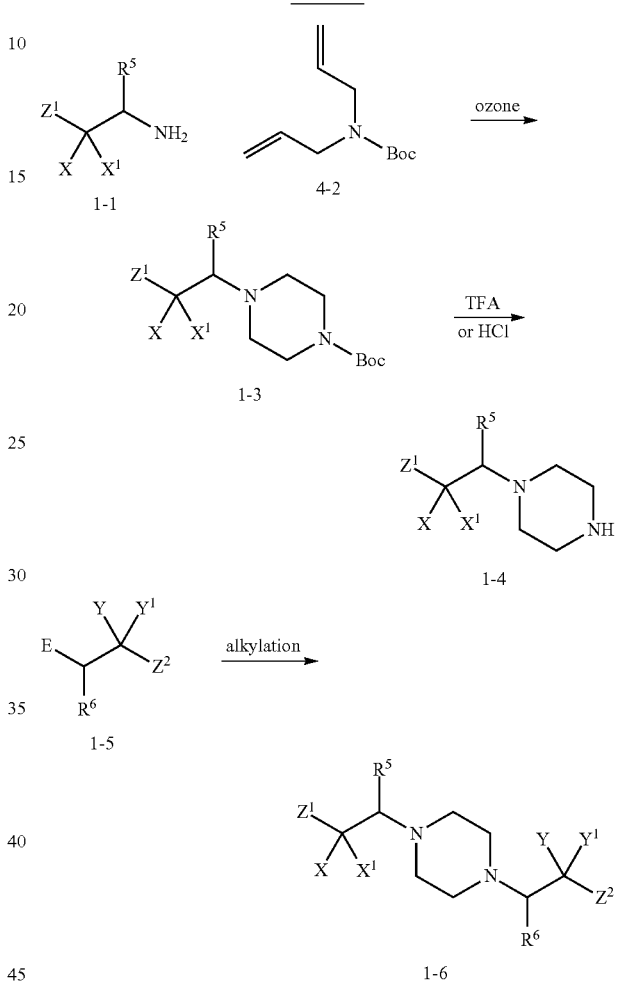

Procedures for making compounds having bridged piperazines are described in the Examples.

General Procedures:

Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60F-254, layer thickness 0.25 mm or liquid chromatography-mass spectrometry (LC-MS). Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detetor, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimiezd for the individual compounds. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions.

Abbreviations used herein include: —C(O)CH$_3$ (Ac); acetic acid (AcOH; HOAc); —OC(O)CH$_3$ (OAc); aqueous (aq); benzyloxycarbonyl (Cbz); (dba) dibenzylideneacetone; tris (dibenzylidineacetone)dipalladium (Pd$_2$(dba)$_3$); N,N-diisopropylethylamine (DIPEA); N;N-dimethylformamide (DMF); dimethylsulfide (DMS); 1,1'-bis(diphenylphosphino)ferrocene (dppf, DPPF); ethyl acetate (EtOAc); diethyl ether (ether or Et$_2$O); petroleum ether (PE); gram(s) (g); hexane (Hex); hour(s) (h or hr); hexamethylphosphoramide (HMPA); high pressure liquid chromatography (HPLC); 2-propanol (IPA); lithium diisopropylamide (LDA); mass spectrum (ms or MS); microliter(s) (µL); milligram(s) (mg); milliliter(s) (mL); millimole (mmol); minute(s) (min); methyl t-butylether (MTBE); medium pressure liquid chromatography (MPLC); N-methylmorpholine-N-oxide (NMO); phenyl (Ph); tetrakis(triphenylphosphine)palladium (Pd(PPh$_3$)$_4$); tris(dibenzylidineacetone)dipalladium (Pd$_2$(dba)$_3$); (benzotriazol-1-yloxy)tripyrrolidino-phosphonium hexafluorophosphate (PyBOP); retention time (R$_t$); room temperature (rt or RT); saturated aq sodium chloride solution (brine); triethylamine (TEA); trifluoroacetic acid (TFA); tetrahydrofuran (THF); flash chromatography (FC); liquid chromatography (LC); liquid chromatography-mass spectrometry (LCMS or LC-MS); supercritical fluid chromatography (SFC); t-butyloxycarbonyl (Boc or BOC); Diethylaminosulfur trifluoride (DAST); dichloromethane (DCM); dimethylacetamide (DMA; DMAC); dimethylsulfoxide (DMSO); 1,3-Bis(diphenylphosphino)propane (DPPP); acetic acid (HOAc); 3-chloroperoxybenzoic acid (m-CPBA); methyl (Me); methanol (MeOH); N-bromosuccinamide (NBS); thin layer chromatography (TLC).

The following are representative procedures for the preparation of the compounds used in the following Examples, or which can be substituted for the compounds used in the following Examples which may not be commercially available.

Intermediate 1

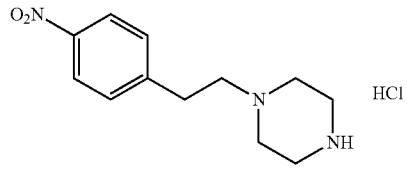 [SMILES: O=[N+]([O-])c1ccc(CCN2CCNCC2)cc1 ; Cl]

1-[2-(4-Nitrophenyl)ethyl]piperazine hydrochloride

To a solution of N-Boc piperazine (2.8 g, 15 mmol) and 1-(2-bromoethyl)-4-nitrobenzene (3.5 g, 15 mmol) in DMF (75 mL) was added TEA (4.7 mL, 34 mmol) at RT. The mixture was heated to 60° C. for 16 hours. The crude mixture was diluted with EtOAc, washed with 0.1 N HCl and brine, dried over sodium sulfate, and concentrated. The product was precipitated by addition of hexane into a EtOAc solution. This solid was used in the bromination step without further purification. LC-MS (IE, m/z): 336 [M+1]$^+$.

The material obtained above was dissolved in dioxane, and treated with 4N HCl. LC showed complete conversion within 2 hours. The solvent was removed under reduced pressure, and the resulting solid was used without further purification. LC-MS (IE, m/z): 236 [M+1]$^+$.

Intermediate 2

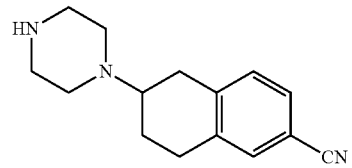 [SMILES: N#Cc1ccc2c(c1)CCC(N1CCNCC1)C2]

6-Piperazin-1-yl-5,6,7,8-tetrahydronaphthalene-2-carbonitrile

Step A:
6-Oxo-5,6,7,8-tetrahydronaphthalene-2-carbonitrile

The 5-bromo-2 tetralone (2.0 g, 8.9 mmol), tetrakis(triphenylphosphine)palladium (0.62 g, 0.53 mmol) and zinc cyanide (0.73 g, 6.2 mmol) were added to 4 ml DMF in a 20 ml microwave tube. The mixture was degassed and microwaved at 80° C. for 30 mins. TLC showed no starting material left and the mixture was diluted with ethyl acetate and washed with ammonium hydroxide (2M, ×4 ml). The organic layer was separated and dried over Na$_2$SO$_4$ then filtered. The solvent was evaporated under reduced pressure. The residue was chromatographed through 40 gm Isco Redi-sep column and eluted with 0-30% ethyl acetate-hexane to yield 6-oxo-5,6,7, 8-tetrahydronaphthalene-2-carbonitrile.

$^1$H-NMR (500 MHz, CDCl$_3$) δ ppm 7.57 (s, 1H), 7.54 (d, J=8.Hz, 1H), 7.26 (d, J=8.Hz, 1H), 3.67 (s, 2H), 3.14 (t, J=6.7.Hz, 2H), 2.63 (t, J=6.7.Hz, 2H).

Step B: tert-Butyl 4-(6-cyano-1,2,3,4-tetrahydronaphthalen-2-yl)piperazine-1-carboxylate Titanium (IV) isopropoxide (0.21 ml, 0.73 mmol), 6-oxo-5,6,7,8-tetrahydronaphthalene-2-carbonitrile (100 mg, 0.58 mmol), and tert-butyl piperazine-1-carboxylate (110 mg, 0.58 mmol) were stirred at room temperature. After 1 hour, ethanol (10 ml) and sodium cyanoborohydride (25.7 mg, 0.409 mmol) were added to the mixture and stirred for 16 hrs. LC-MS showed incomplete formation of product. More sodium cyanoborohydride (77 mg, 1.23 mmol) and 2 drops of HOAc were added and stirred overnight. The reaction was poured into sat'd NaHCO3 and extracted with ethyl acetate. The ethyl acetate layer was washed with brine then dried over MgSO4, filtered and evaporated to dryness. The residue was purified by prep-TLC plate using 50:50 EtOAc:Hexane solvent system. Tert-butyl 4-(6-cyano-1,2,3,4-tetrahydronaphthalen-2-yl) piperazine-1-carboxylate was isolated. LC-MS (IE, m/z): 342 [M+1]$^+$, $^1$H-NMR (500 MHz, DMSO) δ ppm 7.54 (s, 1H), 7.51 (d, J=8.Hz, 1H), 7.21 (d, J=8.Hz, 1H), 3.31-3.28 (m, 4H), 2.67-2.93 (m, 5H), 2.46-2.62 (m, 4H), 1.97 (b, 1H), 1.5-1.60 (m, 1H), 1.38 (s, 9H).

Step C: 6-Piperazin-1-yl-5,6,7,8-tetrahydronaphthalene-2-carbonitrile

Tert-butyl 4-(6-cyano-1,2,3,4-tetrahydronaphthalen-2-yl) piperazine-1-carboxylate (110 mg, 0.32 mmol) was stirred in trifluoroacetic acid (2 ml, 26.0 mmol) at RT overnight. The excess trifluoroacetic acid was then evaporated off under high vacuum. The resulting solid was used without further purification. LC-MS (IE, m/z): 242 [M+1]$^+$.

Intermediate 3

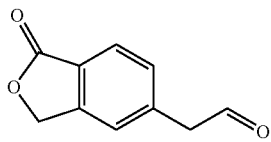 [SMILES: O=CCc1ccc2c(c1)COC2=O]

(1-Oxo-1,3-dihydro-2-benzofuran-5-yl)acetaldehyde

Step A: 5-(1,3-Dioxolan-2-ylmethyl)-2-benzofuran-1(3H)-one

A three-neck 5 L round bottomed flask equipped with a stir bar, firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 470 mmol). DMF (1.88 L) was added to the flask, and the mixture was degassed three times by alternating vacuum and nitrogen purge. Commercially available bromo(1,3-dioxolan-2-ylmethyl)zinc solution (1.03 L, 516 mmol) was added via canula and the mixture was again degassed three times. The mixture was then heated at 85° C. for 5 h. Analysis by HPLC-MS indicated the reaction was not complete. The mixture was stirred at 85° C. for 5 more h. The mixture was then allowed to return to room temperature for overnight. 2-methylTHF (2 L) and brine were added, and the mixture was stirred for 5 min. The layers were separated and the aqueous layer was extracted again with 2-methylTHF. The organic layers were combined, washed three times with brine (4 L each), dried over MgSO$_4$, filtered, and concentrated. The crude product was purified by flash chromatography (1.5 kg silica cartridge), eluting with 0-20% ethyl acetate in dichloromethane to afford 5-(1,3-dioxolan-2-ylmethyl)-2-benzofuran-1(3H)-one. LC-MS (IE, m/z): 221 [M+1]$^+$.

Step B: (1-Oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 h. Then the mixture was stirred overnight at room temperature. The mixture was extracted three times with 2 L of ethyl acetate. The combined organic layers were concentrated to give (1-oxo-1,3-dihydro-2-benzofuran-5-yl)acetaldehyde. LC-MS (IE, m/z): 177 (M+1)$^+$.

Intermediate 4

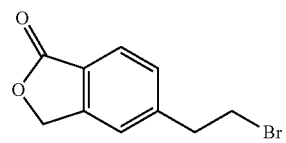 [SMILES: O=C1OCc2cc(CCBr)ccc21]

5-(2-Bromoethyl)-2-benzofuran-1(3H)-one

Step A: 5-Allyl-2-benzofuran-1(3H)-one

A 4-neck, 22-L, round bottom flask equipped with a mechanical stirrer, thermocouple, nitrogen bubbler, and condenser was charged with 5-bromophthalide (650 g, 3.0 mol), allyltri-n-butyltin (1200 g, 3.6 mol), tetrakis(triphenylphosphine)palladium (100 g, 0.089 mol), lithium chloride (250 g, 5.9 mol) and toluene (8.8 L). The mixture was evacuated and flushed with nitrogen 3 times and then was stirred at 100° C. for 4 hours. After slowly cooling to ambient temperature, the mixture was filtered and concentrated. The resulting solid was purified by silica gel column chromatography (heptane: ethyl acetate, 0->40%) to provide 5-allyl-2-benzofuran-1 (3H)-one.

$^1$H NMR (500 MHz, CD$_3$OD) δ 7.83 (d, J=8.0 Hz, 1H), 7.38 (d, J=8.0 Hz, 1H), 7.33 (s, 1H), 5.98 (m, 1H), 5.29 (s, 2H), 5.11-5.18 (m, 2H), 3.52 (d, J=8.2 Hz, 2H).

Step B: 5-(2-Hydroxyethyl)-2-benzofuran-1(3H)-one 5-allyl-2-benzofuran-1(3H)-one (1.53 g, 8.78 mmol) was dissolved in methanol (30 mL). THF was added to solubilize the starting material. The resulting mixture was cooled in a dry ice acetone bath (−78° C.) and ozone was bubbled into the reaction until the color of the mixture changed to orange. Nitrogen was bubbled into the reaction for one minute to remove the excess ozone. Sodium borohydride (0.65 g, 2.9 mmol) was added at −78° C., and the reaction mixture was allowed to warm to ambient temperature. The reaction mixture was concentrated part way and then taken up in ethyl acetate and water. The layers were separated and the organic layer was washed with brine, dried over magnesium sulfate, filtered, and concentrated to provide 5-(2-hydroxyethyl)-2-benzofuran-1(3H)-one. ¹H NMR (500 MHz, CD₃OD) δ 7.77 (m, 1H), 7.37-7.41 (m, 2H), 5.23 (s, 2H), 3.92 (m, 2H), 2.99 (m, 2H).

Step C: 5-(2-Bromoethyl)-2-benzofuran-1(3H)-one

To a solution of 5-(2-hydroxyethyl)-2-benzofuran-1(3H)-one (1.2 g, 6.8 mmol) in DCM at 0° C. was added carbon tetrabromide (2.3 g, 6.8 mmol), triphenylphosphine (1.8 g, 6.8 mmol), and imidazole (0.46 g, 6.8 mmol). The mixture was allowed to stir at 0° C. for 5 minutes, and then allowed to warm to RT and stir for 1.5 hours. The crude was concentrated and purified by silica gel chromatography (43% EtOAc with Hexanes). About 1.3 grams of 5-(2-Bromoethyl)-2-benzofuran-1(3H)-one was collected as a white solid. LC-MS (IE, m/z): 241/243 (M+1)⁺.

Intermediate 5

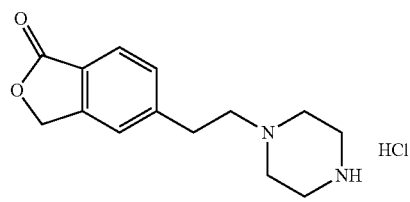 [SMILES: O=C1OCc2cc(CCN3CCNCC3)ccc21 ; Cl]

5-(2-Piperazin-1-ylethyl)-2-benzofuran-1(3H)-one hydrochloride

Step A: 1,1-Dimethylethyl-4-[2-(1-oxo-1,3-dihydro-2-benzofuran-5-yl)ethyl]piperazine-1-carboxylate A three neck 5 L round bottomed flask equipped with a nitrogen bubbler, thermocouple, and stirbar was charged with (1-oxo-1,3-dihydro-2-benzofuran-5-yl)acetaldehyde (46.1 g, 262 mmol) and dichloromethane (1 L). 1-Boc-piperazine (48.7 g, 262 mmol) in 1 L of dichloromethane was added and the mixture was stirred for 5 min. Sodium triacetoxyborohydride (111 g, 523 mmol) was added in portions at room temperature and the resulting mixture was stirred for 1 h. Water (1 L) was added and the mixture was stirred for 10 min. After gas evolution subsided the organic layer was separated and the aqueous layer was extracted with methylene chloride (1 L). The organic layers were combined, washed with brine, and concentrated. The crude product was purified by silica gel MPLC eluting with a 0-100% gradient of 5% methanol/DCM solution (Solvent A) to pure DCM (Solvent B) to afford 1,1-dimethylethyl-4-[2-(1-oxo-1,3-dihydro-2-benzofuran-5-yl)ethyl]piperazine-1-carboxylate.

Step B: 5-(2-Piperazin-1-ylethyl)-2-benzofuran-1(3H)-one hydrochloride

To 1,1-dimethylethyl-4-[2-(1-oxo-1,3-dihydro-2-benzofuran-5-yl)ethyl]piperazine-1-carboxylate (120 g, 347 mmol) in dioxane (800 mL) was added 4 N HCl in dioxane (87.0 mL, 347 mmol) and the resulting mixture was stirred at room temperature over night. The reaction mixture was concentrated and stored under vacuum overnight to afford 5-(2-piperazin-1-ylethyl)-2-benzofuran-1(3H)-one hydrochloride. This can be used as is or converted to the free base by partitioning between an organic solvent and saturated NaHCO₃ solution. LC-MS (IE, m/z): 247 (M+1)⁺.

Intermediate 6

4-Methyl-5-(2-piperazin-1-ylethyl)-2-benzofuran-1(3H)-one hydrochloride

Step A: (3-Bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol.

Step B: 5-Bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a celite pad, washed with EtOAc, adsorbed onto silica and purified by silica gel chromatography to afford 5-bromo-4-methyl-2-benzofuran-1(3H)-one. ¹H-NMR (500 MHz, CDCl₃) δ ppm 7.71 (d, J=8.0 Hz, 1H), 7.58 (d, J=8.0 Hz, 1H), 5.25 (s, 2H), 2.37 (s, 3H).

Step C: 4-Methyl-5-prop-2-en-1-yl-2-benzofuran-1(3H)-one

To a flask charged with 5-bromo-4-methyl-2-benzofuran-1(3H)-one (320 mg, 1.409 mmol) and a stir bar was added allyl tri-n-butyltin (0.655 ml, 2.11 mmol), Pd(PPh₃)₄ (244 mg, 0.211 mmol), lithium chloride (179 mg, 4.23 mmol), and toluene (15 mL). The reaction was purged with nitrogen 2 times then was heated at reflux for 4 hours. The product was separated by silica gel chromatography to give 4-methyl-5-prop-2-en-1-yl-2-benzofuran-1(3H)-one.

Step D: (4-Methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford (4-methyl-1-oxo-1,3-dihydro-2-benzofuran-5-yl)acetaldehyde.

$^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

Step E: 1,1-Dimethylethyl-4-[2-(4-methyl-1-oxo-1,3-dihydro-2-benzofuran-5-yl)ethyl]piperazine-1-carboxylate To a solution of (4-methyl-1-oxo-1,3-dihydro-2-benzofuran-5-yl)acetaldehyde (160 mg, 0.84 mmol) and 1-Boc Piperazine (234 mg, 1.26 mmol) in MeOH (5 mL) was added NaCNBH$_3$ (149 mg, 2.52 mmol) and a few drops of acetic acid. The reaction was allowed to stir at RT for 16 hours. TLC at that point showed good and complete reaction. The reaction was diluted with EtOAc (100 mL), washed with aq. NaHCO$_3$ solution and brine, dried over Na$_2$SO$_4$, adsorbed onto silica gel, and purified by MPLC. 1,1-Dimethylethyl-4-[2-(4-methyl-1-oxo-1,3-dihydro-2-benzofuran-5-yl)ethyl]piperazine-1-carboxylate was collected after removal of solvents.

LC-MS: m/z 361 (M+1)$^+$.

Step F: 4-Methyl-5-(2-piperazin-1-ylethyl)-2-benzofuran-1(3H)-one hydrochloride 1,1-Dimethylethyl-4-[2-(4-methyl-1-oxo-1,3-dihydro-2-benzofuran-5-yl)ethyl]piperazine-1-carboxylate (245 mg) was treated with 4N HCl in dioxane solution and the reaction was monitored until completion. The mixture was concentrated to afford 4-methyl-5-(2-piperazin-1-ylethyl)-2-benzofuran-1(3H)-one hydrochloride. The hydrochloride can be converted to free base as needed by partitioning between organic solvent (EtOAc, DCM, or 30% IPA/CHCl$_3$) and saturated Na$_2$CO$_3$ solution. $^1$H-NMR (500 MHz, DMSO) δ ppm 12.4 (broad, 1H), 9.80 (broad, 2H), 7.71 (d, J=7.5 Hz, 1H), 5.53 (d, J=7.5 Hz, 1H), 5.44 (s, 2H), 3.81 (m, 2H), 3.64-3.27 (m, 10H).

Intermediate 7

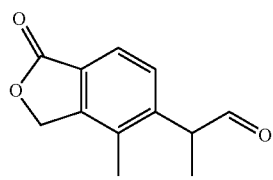

2-(4-Methyl-1-oxo-1,3-dihydro-2-benzofuran-5-yl)propanal

Step A: 4-Methyl-5-prop-2-en-1-yl-2-benzofuran-1(3H)-one

A mixture of 5-bromo-4-methyl-2-benzofuran-1(3H)-one (980 mg, 4.3 mmol), allyl-tributyl-stannane (1.7 g, 5.2 mmol), LiCl (550 mg, 12.9 mmol) and Pd(PPh$_3$)$_4$ (0.1 g) in anhydrous toluene was stirred at reflux under N$_2$ overnight. The solvent was removed under reduced pressure, and the residue was purified with silica gel column chromatography to give the product 4-methyl-5-prop-2-en-1-yl-2-benzofuran-1(3H)-one.

Step B: (4-Methyl-1-oxo-1,3-dihydro-2-benzofuran-5-yl)acetic acid

To a stirred solution of 4-methyl-5-prop-2-en-1-yl-2-benzofuran-1(3H)-one (2.10 g, 11.2 mmol) in CCl$_4$ (50 mL), acetonitrile (50 mL) and water (75 mL) was added sodium periodate (12 g, 55.8 mmol) and ruthenium oxide hydrate (210 mg) and the resulting mixture was stirred at ambient temperature overnight. The mixture was diluted with 100 mL DCM and 100 mL of water. The organic layer was dried over anhydrous sodium sulfate and concentrated. The residue was purified with silica gel column chromatography to afford (4-methyl-1-oxo-1,3-dihydro-2-benzofuran-5-yl)acetic acid.

Step C: 1,1-Dimethylethyl(4-methyl-1-oxo-1,3-dihydro-2-benzofuran-5-yl)acetate

To a solution of (4-methyl-1-oxo-1,3-dihydro-2-benzofuran-5-yl)acetic acid (100 mg, 0.48 mmol) in anhydrous DCM (10 mL) was added 1,1-dimethylethyl-N,N-bis(1-methylethyl)imidocarbamate (485 mg, 2.50 mmol) dropwise at 0° C. under N$_2$. Then the mixture was stirred at r.t. over night. The mixture was filtered and the filtrate was washed with 2N HCl and brine, dried over anhydrous sodium sulfate and concentrated. The residue was purified by preparative TLC to give 1,1-dimethylethyl(4-methyl-1-oxo-1,3-dihydro-2-benzofuran-5-yl)acetate. $^1$H-NMR (400 MHz, CDCl$_3$) δ ppm 7.70 (d, J=7.8 Hz, 1H), 7.38 (d, J=7.0 Hz, 1H), 5.25 (s, 2H), 3.67 (s, 3H), 2.27 (s, 3H), 1.44 (s, 9H).

Step D: 1,1-Dimethylethyl-2-(4-methyl-1-oxo-1,3-dihydro-2-benzofuran-5-yl)propanoate A solution of 1,1-dimethylethyl(4-methyl-1-oxo-1,3-dihydro-2-benzofuran-5-yl)acetate (770 mg, 3.1 mmol) in 30 mL of anhydrous THF was cooled to −78° C. NaHMDS (4.0 mmol) was added to the reaction dropwise at −78° C. After the addition, the mixture was stirred at −78° C. for 1 h and then CH$_3$I (462 mg, 3.20 mmol) was added dropwise at −78° C. The reaction was warmed to room temperature slowly and stirred at ambient temperature over night. The reaction was quenched with NH$_4$Cl solution, and extracted with EtOAc. The organic layer was washed with brine, dried over anhydrous sodium sulfate and concentrated. The residue was purified via preparative TLC to afford 1,1-dimethylethyl-2-(4-methyl-1-oxo-1,3-dihydro-2-benzofuran-5-yl)propanoate. $^1$H-NMR (400 MHz, CDCl$_3$) δ ppm 7.67 (d, J=7.8 Hz, 1H), 7.37 (d, J=7.8 Hz, 1H), 5.19 (s, 2H), 3.80 (dd, J=7.0 Hz, 1H), 2.24 (s, 3H), 1.40 (d, J=7.0 Hz, 1H), 1.32 (s, 9H).

Step E: 2-(4-Methyl-1-oxo-1,3-dihydro-2-benzofuran-5-yl)propanoic acid

To a solution of 1,1-dimethylethyl-2-(4-methyl-1-oxo-1,3-dihydro-2-benzofuran-5-yl)propanoate (400 mg, 1.4 mmol)

in 10 mL of anhydrous DCM was added TFA (2.5 mL) dropwise at r.t. Then the mixture was stirred for 1 hour. The solvent was removed under vacuum to give the crude 2-(4-methyl-1-oxo-1,3-dihydro-2-benzofuran-5-yl)propanoic acid, which was used for next step without purification.

Step F: 5-(2-Hydroxy-1-methylethyl)-4-methyl-2-benzofuran-1(3H)-one

To a solution of 2-(4-methyl-1-oxo-1,3-dihydro-2-benzofuran-5-yl)propanoic acid (300 mg, 1.4 mmol) in 18 mL of anhydrous THF was added $BH_3$.THF (2 mL, 2 mmol) dropwise at 0° C. Then the mixture was warmed to room temperature slowly and then stirred for 3 hours. Then the mixture was quenched with MeOH and the solvent was removed under vacuum. The residue was the purified via prep-TLC to give 5-(2-hydroxy-1-methylethyl)-4-methyl-2-benzofuran-1(3H)-one. $^1$H-NMR (400 MHz, $CDCl_3$) δ ppm 7.73 (d, J=7.8 Hz, 1H), 7.40 (d, J=7.8 Hz, 1H), 5.23 (s, 2H), 3.77 (d, J=7.0 Hz, 2H), 3.36-3.42 (m, 1H), 2.30 (s, 3H), 1.27 (d, J=7.0 Hz, 3H).

Step G: 2-(4-Methyl-1-oxo-1,3-dihydro-2-benzofuran-5-yl)propanal 5-(2-Hydroxy-1-methylethyl)-4-methyl-2-benzofuran-1(3H)-one (161 mg, 0.781 mmol, 1.0 eq) was dissolved in DCM (6 ml). To above solution was added Dess-MartinPeriodinane (397 mg, 0.937 mmol, 1.2 eq). The reaction was stirred at rt for 2 hr. To the reaction was added DCM (10 Ml), $Na_2S_2O_3$ (6 mL) and $H_2O$ (6 mL). The mixture was stirred at r.t. for 30 minutes and formed two layers. The bottom layer was separated and washed with aqueous $NaHCO_3$, brine and water, dried over $Na_2SO_4$, filtered, and concentrated to dryness. The crude product was used to next step without purification. $^1$H NMR (500 MHz, $CDCl_3$, δ in ppm): 9.70 (1H, s, CHO), 7.79 (1H, d, J=7.8 Hz), 7.28 (1H, d, J=7.8 Hz), 5.28 (2H, s), 3.27 (1H, m), 2.32 (3H, s), 1.50 (3H, d, J=7.2 Hz).

Intermediate 8

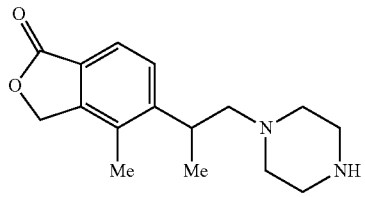 [SMILES: Cc1c(C(C)CN2CCNCC2)ccc2c1COC2=O]

4-Methyl-5-(1-methyl-2-piperazin-1-ylethyl)-2-benzofuran-1(3H)-one

Step A: tert-Butyl-4-[2-(4-methyl-1-oxo-1,3-dihydro-2-benzofuran-5-yl)propyl]piperazine-1-carboxylate In a 100 mL round bottom flask, 2-(4-methyl-1-oxo-1,3-dihydro-2-benzofuran-5-yl)propanal (100 mg, 0.49 mmol, 1.0 eq) and N-Boc Piperazine (91 mg, 0.49 mmol, 1.0 eq) was dissolved in DCM (10 mL). To above solution was added sodium triacetoxyborohydride (208 mg, 0.98 mmol, 2.0 eq). The reaction was stirred at RT for 16 hr. The reaction was then diluted with DCM (10 mL), washed with aqueous bicarbonate, water and brine. The organic phase was dried over $MgSO_4$, filtered and concentrated. The product was obtained after purification by flash column chromatography (5% MeOH/DCM). LC-MS (IE, m/z): 375.4 $[M+1]^+$.

Step B: 4-Methyl-5-(1-methyl-2-piperazin-1-ylethyl)-2-benzofuran-1(3H)-one tert-Butyl-4-[2-(4-methyl-1-oxo-1,3-dihydro-2-benzofuran-5-yl)propyl]piperazine-1-carboxylate (160 mg, 0.43 mmol) was stirred in TFA (3 mL) at r.t for 3 hr. The reaction was concentrated and pump over high vacuum pump overnight to give the desired product, which could be converted to its freebase by partitioning between an organic solvent and saturated $NaHCO_3$ solution. LC-MS (IE, m/z): 275 $[M+1]^+$.

Intermediate 9

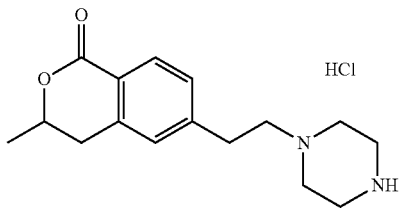 [SMILES: CC1Cc2cc(CCN3CCNCC3)ccc2C(=O)O1 ; Cl]

3-Methyl-6-[2-(piperazin-1-yl)ethyl]-3,4-dihydro-1H-isochromen-1-one hydrochloride Step A: 6-Bromo-3-methyl-3,4-dihydro-1H-isochromen-1-one A solution of diisopropylamine (13 ml, 93 mmol)) in THF (155 ml) at −78° C. was treated with n-BuLi (1.6M in Hexanes; 58 ml, 93 mmol) over a period of 15 minutes using a syringe pump. In a separate flask, a solution of 2-methyl-4-bromo benzoic acid (10 g, 46 mmol) and HMPA (8.3 ml, 46 mmol) in THF (155 ml) was cooled to −78° C. Methyl Lithium (29 ml, 46 mmol) was added slowly via syringe to the cooled solution in order to make the lithio carboxylate. The resulting solution was stirred for 10 minutes and then transferred via cannula to the LDA solution at −78° C. The resulting bright red solution was stirred at −78° C. for an additional 1 hour before being quenched with anhydrous acetaldehyde (7.9 ml, 140 mmol) (color changed from red to orange to clear yellow) and the reaction was then taken out of the dry ice acetone bath and allowed to stir for an additional 1 hour. The flask containing the reaction mixture was then resubmerged in the dry ice acetone bath before it was quenched with 4M HCl in Dioxane (50 mL) followed by 25 mL of MeOH. The reaction was stirred at room temp for an additional 1 hour. The crude reaction was partitioned b/w 200 mL EtOAc and 200 mL water. The organic layer was washed with waster, brine, dried with mag. sulfate, filtered and concentrated. Purification via MPLC (30-70% DCM/Hexanes) afforded 9.4 g (84% yield) of 6-bromo-3-methyl-3,4-dihydro-1H-isochromen-1-one as an off white solid. $^1$H NMR (500 MHz; $CDCl_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H). LC-MS (IE, m/z): 241 $[M+1]^+$.

Step B: 6-(1,3-Dioxolan-2-ylmethyl)-3-methyl-3,4-dihydro-1H-isochromen-1-one

A sealed tube was charged with aryl bromide, palladium (II) acetate (0.028 g, 0.12 mmol) and tri-t-butylphosphine- BF$_4$ complex (0.072 g, 0.249 mmol) and sealed. The tube was evacuated and refilled with nitrogen before DMF (12 ml) and 6-bromo-3-methyl-3,4-dihydro-1H-isochromen-1-one (0.75 g, 3.1 mmol) were added followed by bromo(1,3-dioxolan-2-ylmethyl)zinc (6.2 ml, 3.1 mmol). The tube was heated to 110° C. in the microwave for 75 minutes, after which it was cooled, diluted with EtOAc, filtered, concentrated and purified via MPLC (20-50% EtOAc/Hexanes) to afford 490 mg (64% yield) of 6-(1,3-dioxolan-2-ylmethyl)-3-methyl-3,4-dihydro-1H-isochromen-1-one (Compound 1B) as a clear oil which solidifies on standing. $^1$H NMR (500 MHz; CDCl$_3$): 8.04 (d, J=7.8 Hz, 1H), 7.32 (d, J=8.0 Hz, 1H), 7.17 (s, 1H), 5.11 (t, J=4.7 Hz, 1H), 4.68 (m, 1H), 3.96 (m, 2H), 3.88 (m, 2H), 3.03 (d, J=4.9 Hz, 2H), 2.93 (m, 2H), 1.54 (d, J=6.4 Hz, 3H). LC-MS (IE, m/z): 249 [M+1]$^+$.

Step C: tert-Butyl 4-[2-(3-methyl-1-oxo-3,4-dihydro-1H-isochromen-6-yl)ethyl]piperazine-1-carboxylate A 1:1 solution of dioxane:3N HCl was added to a flask containing of 780 mg (3.2 mmol) of 6-(1,3-dioxolan-2-ylmethyl)-3-methyl-3,4-dihydro-1H-isochromen-1-one. The reaction was then stirred at room temp overnight. The crude reaction mixture was then partitioned between water and DCM. The organic layer was washed with saturated sodium bicarbonate solution, followed by brine. The organic layer was then dried with magnesium sulfate, filtered and concentrated. The crude aldehyde was redissolved in DCM. To the solution was added boc-piperazine (671 mg, 3.6 mmol) followed by sodium triacetoxyborohydride (1.9 g, 9.0 mmol). the reaction mixture was allowed to stir overnight before being quenched with 10 mL of MeOH. The excess solvent was removed and the residue was re-redissolved in DCM; washed with water and brine, dried with magnesium sulfate, filtered, concentrated and purified via MPLC (50-100% EtOAc/Hex) to afford 850 mg of tert-butyl 4-[2-(3-methyl-1-oxo-3,4-dihydro-1H-isochromen-6-yl)ethyl]piperazine-1-carboxylate as a golden oil. $^1$H NMR (500 MHz; CDCl$_3$): 8.02 (d, J=7.8 Hz, 1H), 7.24 (d, J=7.7 Hz, 1H), 7.09 (s, 1H), 4.68 (m, 1H), 3.49 (m, 4H), 2.94 (m, 4H), 2.88 (m, 2H), 2.51 (m, 4H), 1.54 (d, J=6.8 Hz, 3H), 1.48 (s, 9H). LC-MS (IE, m/z): 375 [M+1]$^+$.

Step D: 3-Methyl-6-[2-(piperazin-1-yl)ethyl]-3,4-dihydro-1H-isochromen-1-one hydrochloride A solution of tert-butyl 4-[2-(3-methyl-1-oxo-3,4-dihydro-1H-isochromen-6-yl)ethyl]piperazine-1-carboxylate (850 mg, 2.3 mmol) was stirred in 4N HCl in Dioxane for 4 hours. The excess solvent was then removed to give the free amine as the HCl salt. LC-MS (IE, m/z): 275 [M+1]$^+$.

Intermediate 9A

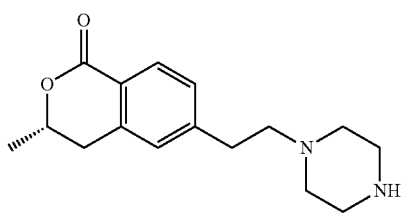 [SMILES: C[C@H]1Cc2cc(CCN3CCNCC3)ccc2C(=O)O1]

tert-butyl 4-{2-[(3S)-3-methyl-1-oxo-3,4-dihydro-1H-isochromen-6-yl]ethyl}piperazine-1-carboxylate Step A: (3S)-6-Bromo-3-methyl-3,4-dihydro-1H-isochromen-1-one Chiral separation of racemic 6-bromo-3-methyl-3,4-dihydro-1H-isochromen-1-one using ChiralPak AS 4.6×250 mm 10 u column, eluting with 60% IPA/Heptane. The faster eluting isomer was identified as the S-isomer. $^1$H NMR (500 MHz, CDCl$_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H). LC-MS (IE, m/z): 241 [M+1]$^+$.

Step B: (3 S)-6-(1,3-Dioxolan-2-ylmethyl)-3-methyl-3,4-dihydro-1H-isochromen-1-one (3S)-6-(1,3-dioxolan-2-ylmethyl)-3-methyl-3,4-dihydro-1H-isochromen-1-one was obtained using the procedure described for the synthesis of 6-(1,3-dioxolan-2-ylmethyl)-3-methyl-3,4-dihydro-1H-isochromen-1-one utilizing the chiral S-enantiomer as the starting material. $^1$H NMR (500 MHz, CDCl$_3$): 8.04 (d, J=7.8 Hz, 1H), 7.32 (d, J=8.0 Hz, 1H), 7.17 (s, 1H), 5.11 (t, J=4.7 Hz, 1H), 4.68 (m, 1H), 3.96 (m, 2H), 3.88 (m, 2H), 3.03 (d, J=4.9 Hz, 2H), 2.93 (m, 2H), 1.54 (d, J=6.4 Hz, 3H). LC-MS (IE, m/z): 249 [M+1]$^+$.

Step C: tert-Butyl 4-{2-[(3S)-3-methyl-1-oxo-3,4-dihydro-1H-isochromen-6-yl]ethyl}piperazine-1-carboxylate tert-Butyl 4-{2-[(3S)-3-methyl-1-oxo-3,4-dihydro-1H-isochromen-6-yl]ethyl}piperazine-1-carboxylate was obtained using the procedure described for the synthesis of tert-butyl 4-{2-[3-methyl-1-oxo-3,4-dihydro-1H-isochromen-6-yl]ethyl}piperazine-1-carboxylate utilizing the chiral S-enantiomer as the starting material in the reaction. $^1$H NMR (500 MHz, CDCl$_3$): 8.02 (d, J=7.8 Hz, 1H), 7.24 (d, J=7.7 Hz, 1H), 7.09 (s, 1H), 4.68 (m, 1H), 3.49 (m, 4H), 2.94 (m, 4H), 2.88 (m, 2H), 2.51 (m, 4H), 1.54 (d, J=6.8 Hz, 3H), 1.48 (s, 9H). LC-MS (IE, m/z): 375 [M+1]$^+$.

Step D: (3S)-3-Methyl-6-[2-(piperazin-1-yl)ethyl]-3,4-dihydro-1H-isochromen-1-one A solution of tert-butyl 4-{2-[(3S)-3-methyl-1-oxo-3,4-dihydro-1H-isochromen-6-yl]ethyl}piperazine-1-carboxylate in 4N HCl indioxane was stirred at room temp for 4 hours and the excess solvent removed. The residue was partitioned between 10% IPA/Chloroform and 1N NaOH. The organic layer was dried over magnesium sulfate, filtered and concentrated. The free amine was used without further purification.

Intermediate 10

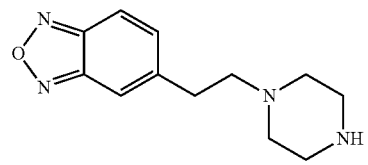 [SMILES: c1cc2nonc2cc1CCN1CCNCC1]

5-(2-Piperazin-1-ylethyl)-2,1,3-benzoxadiazole

Step A: 5-Allyl-2,1,3-benzoxadiazole

5-Bromo-2,1,3-benzoxadiazole (10 g, 50.3 mmol) was dissolved in toluene (300 ml) and added Lithium chloride (6.4 g, 150 mmol), Pd(Ph$_3$P)$_4$ (2.90 g, 2.50 mmol), and allyl tributyltin (19 ml, 60 mmol). The reaction mixture was degassed and refluxed under N$_2$ for 3 hrs. It was cooled and poured into water then extracted with ethyl acetate. The organic layer was washed with brine 1×, dried and evaporated to dryness. The residue was chromatographed through 120 g ISCO Redi-Sep columns and eluted with 0-10% ethyl acetate/hexane to yield 5-allyl-2,1,3-benzoxadiazole.

$^1$H-NMR (500 MHz, DMSO): δ ppm 7.96 (d, J=9.1 Hz, 1H), 7.44 (d, J=9.1 Hz, 2H), 5.95-6.04 (m, 1H), 5.17 (d, J=14.7 Hz, 1H), 5.15 (d, J=8.9 Hz, 1H), 3.50 (d, J=6.7 Hz, 2H)

Step B: 5-(2-Piperazin-1-ylethyl)-2,1,3-benzoxadiazole

To a solution of 5-allyl-2,1,3-benzoxadiazole (480 mg, 3.0 mmol) in DCM was cooled to −78° C. Ozone was bubbled in until a bluish tint then bubbled in nitrogen to get rid of excess ozone. The Boc-piperazine (560 mg, 3.0 mmol) was then added followed by sodium triacetoxyborohydride (2500 mg, 12 mmol). The reaction mixture was warmed up to RT and stirred overnight. Poured the reaction into 1 N NaOH and extracted with ethyl acetate 2×. The ethyl acetate layer was dried over MgSO$_4$, filtered and evaporated to dryness. The residue was purified through a 40 g Redi-sep column to yield tert-butyl 4-[2-(2,1,3-benzoxadiazol-5-yl)ethyl]piperazine-1-carboxylate.

tert-Butyl 4-[2-(2,1,3-benzoxadiazol-5-yl)ethyl]piperazine-1-carboxylate (470 mg, 1.4 mmol) was then dissolved in dioxane (10 mL) and added 7 mL of 4M HCl in dioxane. The reaction was stirred at room temperature overnight. Evaporated off all solvent and the residue was taken up in ethyl acetate basified with 1N NaOH. The ethyl acetate was separated and washed with brine then dried over Na$_2$SO$_4$ and evaporated to dryness. The residue was purified by chromatography using 5% (NH$_4$OH:MeOH 1:10) in 95% DCM to yield 5-(2-piperazin-1-ylethyl)-2,1,3-benzoxadiazole.

$^1$H-NMR (600 MHz, CDCl$_3$): δ 7.72 (d, J=9.2 Hz, 1H), 7.28 (d, J=9.2 Hz, 1H), 2.92 (t, J=4.9 Hz, 2H), 2.88 (t, J=7.6 Hz, 1H), 2.65 (t, J=7.6 Hz, 1H). LC-MS: M+1=233.

Intermediate 11

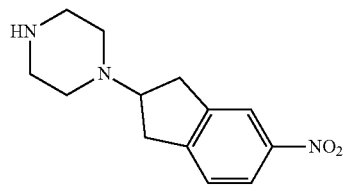 [SMILES: O=[N+]([O-])c1ccc2c(c1)CC(N1CCNCC1)C2]

1-(5-Nitro-2,3-dihydro-1H-inden-2-yl)piperazine

To a solution of 5-nitro-indene-2-one (1.0 g, 5.6 mmol) in methanol (40 mL) containing a stir bar was added sodium cyanoborohydride (1.7 g, 28 mmol) and N-Boc piperazine (1.6 g, 8.5 mmol) followed by addition of few drops of acetic acid; the resulting mixture was stirred for overnight. Analysis of the reaction mixture by LC indicated that reaction had gone to completion. The solution was concentrated in vacuo and the resulting crude was dissolved in EtOAc and washed with saturated sodium bicarbonate solution, and brine, then dried (Na$_2$SO$_4$), filtered and concentrated in vacuo. The crude residue was then subjected for purification by silica gel column chromatography (5% MeOH in DCM) to provide tert-butyl 4-(5-nitro-2,3-dihydro-1H-inden-2-yl) piperazine-1-carboxylate. LC-MS (IE, m/z): 348 [M+1]$^+$. The material was further treated with TFA to remove the Boc group. Removal of volatiles gave rise to 1-(5-nitro-2,3-dihydro-1H-inden-2-yl)piperazine, which was used without further purification.

Intermediate 12

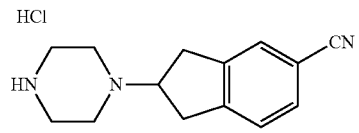 [SMILES: Cl ; N#Cc1ccc2c(c1)CC(N1CCNCC1)C2]

2-Piperazin-1-ylindane-5-carbonitrile hydrochloride

Step A: tert-Butyl 4-(5-bromo-2,3-dihydro-1H-inden-2-yl)piperazine-1-carboxylate In a 100 mL round bottom flask, tert-butyl di(prop-2-en-1-yl)carbamate (0.74 mL, 3.4 mmol) was dissolved in dichloromethane (10 mL). The solution was cooled to −78° C. To above solution was bubbled ozone for 15 min. The solution turned into light blue and the color stayed. To above solution was bubbled nitrogen to remove excess ozone until the solution turned into colorless. To above solution was added (5-bromo-2,3-dihydro-1H-inden-2-amine (1.0 g, 3.4 mmol), triethylamine (0.48 mL, 3.4 mmol) followed by sodium triacetoxyborohydride (4.3 g, 20 mmol). The reaction was allowed to warm up to room temperature and stirred at this temperature overnight. HPLC-MS showed product was formed as major peak. To above solution was added water (5 mL), extracted with dichloromethane (10 mL×3). The organic phase was dried over MgSO$_4$, filtered and concentrated. The product was obtained as white solid after purification by flash column chromatography. LC-MS (IE, m/z): 381.2 [M+1]$^+$. $^1$H NMR (500 MHz, CDCl$_3$, δ in ppm): 7.30 (1H, s), 7.25 (d, J=8.0 Hz, 1H), 7.03 (d, J=8.0 Hz, 1H), 2.0-4.0 (m, 13H), 1.5 (s, 9H).

Step B: tert-Butyl 4-(5-cyano-2,3-dihydro-1H-inden-2-yl)piperazine-1-carboxylate To a 5 mL microwave vial was charged with tert-butyl 4-(5-bromo-2,3-dihydro-1H-inden-2-yl)piperazine-1-carboxylate (370 mg, 0.97 mmol), zinc cyanide (114 mg, 0.97 mmol) and palladium triphenylphosphane (1:4) (56 mg, 0.049 mmol). Above mixture was dissolved in N-methyl-2-pyrrolidinone (1 mL). The reaction vial was degassed, filled with N$_2$ and heated in microwave reactor at 85° C. for 2 hr, then at 100° C. for 20 min. To above reaction was added dichloromethane (5 mL), washed with small amount of water. The organic phase was dried over MgSO$_4$, filtered and concentrated. The product was obtained as white solid after purification by flash column chromatography. LC-MS (IE, m/z):

328.3 [M+1]⁺. ¹H NMR (500 MHz, CDCl₃, δ in ppm): 7.47 (s, 1H), 7.45 (d, J=8.0 Hz, 1H), 7.28 (d, J=8.0 Hz, 1H), 2.4-3.6 (m, 13H), 1.5 (s, 9H).

Step C: 4-(5-Cyano-2,3-dihydro-1H-inden-2-yl)piperazin-1-ium chloride

In a 4 mL reaction vial, was added tert-butyl 4-(5-cyano-2,3-dihydro-1H-inden-2-yl)piperazine-1-carboxylate. To above vial was added 4 N HCl in dioxane (1 mL), let stirred at RT for 2 hr. The reaction mixture was concentrated to give the desired product. LC-MS (IE, m/z): 228.3 [M+1]⁺.

Intermediate 13

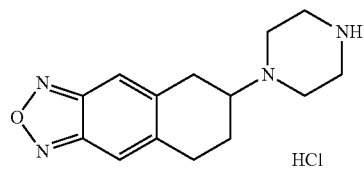 [SMILES: c1c2c(cc3nonc13)CC(N1CCNCC1)CC2 ; Cl]

6-Piperazin-1-yl-5,6,7,8-tetrahydronaphtho[2,3-c][1,2,5]oxadiazole hydrochloride Step A: [3-(1,3-Dioxo-1,3-dihydro-2H-isoindol-2-yl)phenyl]acetic acid A solution of phthalic anhydride (1.2 g, 8.3 mmol) and (3-aminophenyl)acetic acid (1.0 g, 6.9 mmol) in acetic acid (25 mL) was heated to reflux for 16 hours. The reaction was cooled, and diluted with 25 mL of EtOAc. A lot of solids crashed out from the solution. The solids were collected by filtration, and identified as the desired [3-(1,3-dioxo-1,3-dihydro-2H-isoindol-2-yl)phenyl]acetic acid. LC-MS (IE, m/z): 282 [M+1]⁺.

Step B: 2-(7-Oxo-5,6,7,8-tetrahydronaphthalen-2-yl)-1H-isoindole-1,3(2H)-dione

To a solution of [3-(1,3-dioxo-1,3-dihydro-2H-isoindol-2-yl)phenyl]acetic acid (0.75 g, 2.7 mmol) in DCM (25 mL) was added oxalyl chloride (0.28 mL, 3.2 mmol) and a drop of DMF. The mixture was allowed to stir at RT until all solids disappeared. At that point, the solution was cooled to to 0° C. with an ice bath, and aluminum chloride (1.1 g, 8.0 mmol) was added into the reaction slowly. After stirring the mixture for another 10 minutes, ethylene was bubbled through the reaction via a long needle. TLC showed complete reaction within 30 minutes. The reaction was poured into ice water, neutralized with sodium carbonate, extracted with DCM, dried, concentrated, and purified by MPLC (Hexane/EtOAc). LC-MS (IE, m/z): 292 [M+1]⁺.

Step C: tert-Butyl 4-[7-(1,3-dioxo-1,3-dihydro-2H-isoindol-2-yl)-1,2,3,4-tetrahydronaphthalen-2-yl]piperazine-1-carboxylate To a flask charged with 2-(7-oxo-5,6,7,8-tetrahydronaphthalen-2-yl)-1H-isoindole-1,3(2H)-dione (0.25 g, 0.86 mmol), N-Boc piperazine (0.24 g, 1.3 mmol), and a stir bar was added titanium isopropoxide (2.5 mL), ethanol (10 mL), and sodium cyanoborohydride (0.27 g, 4.3 mmol). The mixture was allowed to stir at RT for 2 hours. LC showed formation of the desired product at that point. The reaction was diluted with EtOAc (50 mL), washed with water and brine, dried over sodium sulfate, filtered and concentrated, and purified by MPLC to afford the desired product. LC-MS (IE, m/z): 462 [M+1]⁺.

Step D: 2-{7-[4-(Trifluoroacetyl)piperazin-1-yl]-5,6,7,8-tetrahydronaphthalen-2-yl}-1H-isoindole-1,3(2H)-dione To a flask charged with tert-butyl 4-[7-(1,3-dioxo-1,3-dihydro-2H-isoindol-2-yl)-1,2,3,4-tetrahydronaphthalen-2-yl]piperazine-1-carboxylate (300 mg, 0.65 mmol) and a stir bar was added TFA (2 mL). The mixture was allowed to stir at RT for 1 hour. LC showed complete removal of the Boc group. TFA was removed under reduced pressure, and the residue was dissolved in DCM (5 mL). To the solution was added pyridine and trifluoroacetic anhydride (0.27 mL, 2.0 mmol). LC showed formation of the desired product within 30 minutes. The product was purified by MPLC.

Step E: 2-{3-Nitro-7-[4-(trifluoroacetyl)piperazin-1-yl]-5,6,7,8-tetrahydronaphthalen-2-yl}-1H-isoindole-1,3(2H)-dione To a solution of 2-{7-[4-(Trifluoroacetyl)piperazin-1-yl]-5,6,7,8-tetrahydronaphthalen-2-yl}-1H-isoindole-1,3(2H)-dione (35 mg, 0.77 mmol) in conc. H₂SO₄ (2 mL) was added potassium nitrate (15 mg, 0.15 mmol) at 0° C. LC showed formation of the desired product within 10 minutes. The reaction was poured into ice, and extracted with DCM twice. The product was purified by mass-directed HPLC. LC-MS (IE, m/z): 503 [M+1]⁺.

Step F: tert-Butyl 4-(7-amino-6-nitro-1,2,3,4-tetrahydronaphthalen-2-yl)piperazine-1-carboxylate To a solution of 2-{3-Nitro-7-[4-(trifluoroacetyl)piperazin-1-yl]-5,6,7,8-tetrahydronaphthalen-2-yl}-1H-isoindole-1,3(2H)-dione (150 mg, 0.30 mmol) in Ethanol (5 mL) was added hydrazine (0.094 mL, 3.0 mmol). The solution turned bright yellow right away. LC showed cleavage of the phthalic anhydride as well as the trifluoroacetate group. Boc anhydride (65 mg, 0.30 mmol) and aqueous sodium bicarbonate (5 mL) were added to the reaction. LC showed formation of the product within 15 minutes. The reaction was diluted with water (20 mL), extracted with DCM twice, dried over sodium sulfate, and purified by MPLC (hexane/EtOAc). LC-MS (IE, m/z): 377 [M+1]⁺.

Step G: tert-Butyl 4-(1-oxido-5,6,7,8-tetrahydronaphtho[2,3-c][1,2,5]oxadiazol-6-yl)piperazine-1-carboxylate To a solution of tert-Butyl 4-(7-amino-6-nitro-1,2,3,4-tetrahydronaphthalen-2-yl)piperazine-1-carboxylate (160 mg, 0.42 mmol) in ethanol (3 mL) was added potassium hydroxide (36 mg, 0.64 mmol). The solution was stirred until all solids dissolved. At that point, sodium hypochlorite (1.3 mL, 1.3 mmol) was dropped into the reaction. LC showed quite slow reaction. Another 1.3 mL of sodium hypochlorite was added to complete the reaction. The desired product was separated by reverse phase HPLC (water: Acetonitrile with 0.1% TFA). LC-MS (IE, m/z): 375 [M+1]⁺.

Step H: tert-Butyl 4-(5,6,7,8-tetrahydronaphtho[2,3-c][1,2,5]oxadiazol-6-yl)piperazine-1-carboxylate A solution of tert-Butyl 4-(1-oxido-5,6,7,8-tetrahydronaphtho[2,3-c][1,2,5]oxadiazol-6-yl)piperazine-1-carboxylate (100 mg, 0.27 mmol) and triphenyl phosphine (140 mg, 0.53 mmol) in THF (3 mL) was heated to 140° C. in a microwave reactor for 30 minutes. LC showed formation of the desired product, which was separated by reverse phase HPLC (water: Acetonitrile with 0.1% TFA). LC-MS (IE, m/z): 359 [M+1]+.

Step I: 6-Piperazin-1-yl-5,6,7,8-tetrahydronaphtho[2,3-c][1,2,5]oxadiazole hydrochloride To a flask charged with tert-Butyl-4-(5,6,7,8-tetrahydronaphtho[2,3-c][1,2,5]oxadiazol-6-yl)piperazine-1-carboxylate (50 mg, 0.14 mmol) was added 4N HCl in dioxane (1 mL). The mixture was allowed to stir for 30 minutes at RT. LC showed complete reaction. The solvent was removed under reduced pressure, and the resulting 6-Piperazin-1-yl-5,6,7,8-tetrahydronaphtho[2,3-c][1,2,5]oxadiazole hydrochloride was used without further purification.
LC-MS (IE, m/z): 259 [M+1]+.

Intermediate 14

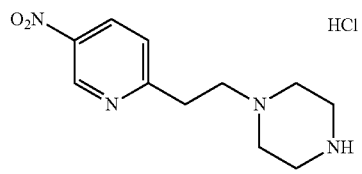 [SMILES: O=[N+]([O-])c1ccc(CCN2CCNCC2)nc1 ; Cl]

1-[2-(6-Nitropyridin-3-yl)ethyl]piperazine hydrochloride

Step A: 5-Nitro-2-vinylpyridine

To a 20 ml, microwave tube was added 2-bromo-5-nitropyridine (0.20 g, 0.98 mmol), potassium vinyltrifluoroborate (145 mg, 1.1 mmol), PdCl$_2$(dppf)-CH$_2$Cl$_2$ complex (40 mg, 0.049 mmol), and a stir bar. The tube was sealed, and ethanol (6 mL) and triethylamine (0.41 mL, 3.0 mmol) was added via syringe. The mixture was purged three times with nitrogen and then heated to 120° C. for 30 minutes. LC at that point showed mostly product. The reaction was diluted with DCM, adsorbed onto silica gel, and purified by silica gel flash chromatography (Hexane:EtOAc). LC-MS (IE, m/z): 151 [M+1]+.

Step B: 1-[2-(6-Nitropyridin-3-yl)ethyl]piperazine hydrochloride

To a flask charged with 5-nitro-2-vinylpyridine (55 mg, 0.37 mmol), N-Boc Piperazine (68 mg, 0.37 mmol), and a stir bar was added dioxane (0.6 mL). The flask was sealed and purged with nitrogen. To the flask was injected a stock solution of 250 mg Ru(COD)(methyallyl)$_2$ and 481 mg 1,3-Bis(diphenylphosphino)propane in 3.2 mL dioxane (0.4 mL) and trifluoromethanesulfonic acid (3.2 uL, 0.037 mmol). The mixture was heated to 100° C. for 16 hours. LC showed formation of the desired product, which was separated by silica gel flash chromatography (Hexane:EtOAc). LC-MS (IE, m/z): 337 [M+1]+. The material was further treated with 4N HCl in dioxane, and the crude 1-[2-(6-nitropyridin-3-yl)ethyl]piperazine hydrochloride was carried on without further purification. LC-MS (IE, m/z): 237 [M+1]+.

Intermediate 15

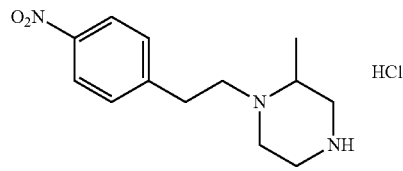 [SMILES: CC1CNCCN1CCc1ccc([N+](=O)[O-])cc1 ; Cl]

2-Methyl-[2-(4-nitrophenyl)ethyl]piperazine hydrochloride

A solution of tert-butyl 3-methylpiperazine-1-carboxylate (100 mg, 0.50 mmol), 1-(2-bromoethyl)-4-nitrobenzene (170 mg, 0.75 mmol), tetrabutylammonium iodide (18 mg, 0.05 mmol), K$_2$CO$_3$ (138 mg, 1.0 mmol), and DMF (2 mL) was heated to 80 degrees for 16 hours. LC showed formation of the desired product. The reaction was diluted with EtOAc (50 mL), washed with aq. LiCl, dried over sodium sulfate, concentrated and purified by MPLC (Hexane: EtOAc). The product was further treated with 4N HCl in dioxane to furnish the piperazine as the HCl salt. LC-MS (IE, m/z): 250 (M+1)+.

Intermediate 16

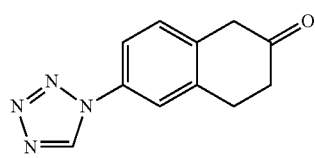 [SMILES: O=C1CCc2cc(-n3cnnn3)ccc2C1]

6-(1H-Tetrazol-1-yl)-3,4-dihydronaphthalen-2(1H)-one

To a solution of [4-(1H-tetrazol-1-yl)phenyl]acetic acid (0.50 g, 2.4 mmol) in DCM (10 mL) was added oxalyl chloride (0.37 g, 2.9 mmol) and a drop of DMF. The mixture was allowed to stir at RT for 2 hours. The solvent was removed under reduced pressure, and the residue was redissolved in DCM. The solution was cooled to 0° C. with an ice bath. To this solution was added aluminum chloride (0.98 g, 7.4 mmol) in small portions. Ethylene was then bubbled into the reaction via a long needle for 2 hours. LC showed formation of the desired product. The reaction was poured into ice and extracted with DCM. The extractions were combined, dried over sodium sulfate, adsorbed onto silica gel, and purified by MPLC (Hexane/EtOAc). The desired 6-(1H-tetrazol-1-yl)-3, 4-dihydronaphthalen-2(1H)-one was collected as a off-white solid. LC-MS (IE, m/z): 215 [M+1]⁺.

Intermediate 17

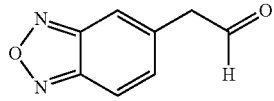 [SMILES: O=CCc1ccc2nonc2c1]

2,1,3-Benzoxadiazol-5-yl acetaldehyde

Step A: 5-Allyl-2,1,3-benzoxadiazole

Lithium chloride (0.64 g, 15.1 mmol) was added to a mixture of 5-bromo-2,1,3-benzoxadiazole (1.0 g, 5.0 mmol), tetrakis(triphenylphosphine)palladium (0.29 g, 0.25 mmol) and allyl tri-n-butyltin (1.87 ml, 6.0 mmol) in 30 ml toluene then refluxed for 3 hours. The reaction was filtered, concentrated, and loaded into an ISCO 120 gm Redi-Sep then eluted with a gradient of 0-50% ethyl acetate/hexane. $^1$H-NMR (500 MHz, CDCl3) δ ppm 7.76 (d, J=9 Hz, 1H), 7.59 (s, 1H), 7.28 (d, J=9 Hz, 1H), 5.95-6.03 (m, 1H), 5.24 (d, J=10 Hz, 1H), 5.20 (d, J=15 Hz, 1H), 3.49 (d, J=6.5 Hz, 2H).

Step B: 2,1,3-Benzoxadiazol-5-ylacetaldehyde

A solution of 5-allyl-2,1,3-benzoxadiazole (500 mg, 3.1 mmol) in DCM (10 ml) was cooled to −78° C. then bubbled in ozone until a faint blue color occurred. The reaction was purged with nitrogen to get rid of excess ozone then added dimethyl sulfide (2.3 ml, 31 mmol) and stirred at room temperature for 2 hours. The reaction was concentrated and used without further purification.

Intermediate 18

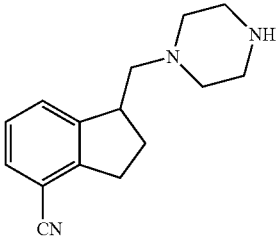 [SMILES: N#Cc1cccc2c1CCC2CN1CCNCC1]

1-(Piperazin-1-ylmethyl)indane-4-carbonitrile

Step A: 1-Oxo-2,3-dihydro-1H-indene-4-carbonitrile

To a solution of 4-bromo-2,3-dihydro-1H-inden-1-one (1.00 g, 4.74 mmol) in 5 mL of DMF was added Zn(CN)₂ (556 mg, 4.74 mmol) and Pd(PPh₃)₄ (77 mg, 0.14 mmol), and the reaction mixture was stirred under microwave irradiation for 1 h at 165° C. The solvent was removed in vacuum to afford the crude compound, which was purified via column chromatography to afford 1-oxo-2,3-dihydro-1H-indene-4-carbonitrile.

Step B: (1E)-1-1[(Methyloxy)methylidene]-2,3-dihydro-1H-indene-4-carbonitrile

Sodium bis(trimethylsilyl)amide (2 mL, 4 mmol, 2M in THF) was added to a stirred suspension of (methoxy methyl)triphenylphosphonium chloride (1.47 g, 4.29 mmol) in dry THF (20 mL) at 0° C. for 35 min and a solution of 1-oxo-2,3-dihydro-1H-indene-4-carbonitrile (450 mg, 2.86 mmol) in THF (10 mL) added over 10 min. The mixture was stirred at 0° C. for 2 h and at room temperature for 1 h. Water was added and the mixture was partitioned between EtOAc and brine. The organic layer was dried and concentrated. The crude product was purified via prep-TLC (PE:EtOAc=10:1) to afford (1E)-1-[(methyloxy)methylidene]-2,3-dihydro-1H-indene-4-carbonitrile. $^1$H-NMR (400 MHz, CDCl₃) δ ppm 8.00 (d, J=8.3 Hz, 0.4H), 7.42 (d, J=8.3 Hz, 0.6H), 7.30-7.40 (m, 1H), 7.18-7.22 (m, 1H), 6.70 (s, 0.6H), 6.22 (s, 0.4H), 3.72 (s, 3H), 3.15 (t, J=5.7 Hz, 2H), 2.70-2.82 (m, 2H).

Step C: 1-Formyl-2,3-dihydro-1H-indene-4-carbonitrile

A solution of (1E)-1-[(methyloxy)methylidene]-2,3-dihydro-1H-indene-4-carbonitrile (250 mg, 1.05 mmol) in DCM (5 mL) was added BBr₃ dropwise at −78° C. under N₂. Then the mixture was stirred at this temperature for 3 h. It was poured into ice-saturated NaHCO₃ solution, and extracted with DCM. The organic layer was washed with brine and dried over Na₂SO₄. The solvent was removed in vacuo to give crude 1-formyl-2,3-dihydro-1H-indene-4-carbonitrile (150 mg, crude), which is used for next step directly. $^1$H-NMR (400 MHz, CDCl₃) δ ppm 9.72 (s, 1H), 7.54 (d, J=7.6 Hz, 2H), 7.34 (t, J=7.6 Hz, 1H), 3.76 (s, 1H), 3.18-3.24 (m, 2H), 2.42-2.58 (m, 2H).

Step D: tert-Butyl 4-[(4-cyano-2,3-dihydro-1H-inden-1-yl)methyl]piperazine-1-carboxylate 1-Formyl-2,3-dihydro-1H-indene-4-carbonitrile (0.22 g, 1.3 mmol) was dissolved in MeOH (8 mL) and treated with tert-butyl piperazine-1-carboxylate (0.35 g, 1.9 mmol) followed by treatment of sodium cyanoborohydride (0.40 g, 6.43 mmol) and few drops of Acetic acid. The resulting mixture was then stirred at room temperature overnight. LC indicated completion of the reaction. The reaction mixture was concentrated in vacuo, treated with EtOAc and washed with saturated NaHCO₃, dried with Na₂SO₄, filtered and loaded into MPLC for separation over silica gel. with 10% MeOH in DCM to afford tert-butyl 4-[(4-cyano-2,3-dihydro-1H-inden-1-yl)methyl]piperazine-1-carboxylate. This material was further treated with TFA to remove the Boc group. Removal of volatiles gave rise to 1-(piperazin-1-ylmethyl)indane-4-carbonitrile, which was used as the crude. LC-MS (IE, m/z): 242 (M+1)⁺.

Intermediate 19

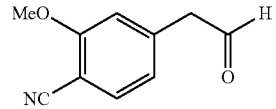

2-(Methyloxy)-4-(2-oxoethyl)benzonitrile

Step A: 2-(Methyloxy)-4-prop-2-en-1-ylbenzonitrile

To a 50 ml, flask containing a stir bar were added 2-methoxy-4-bromobenzonitrile (0.30 g, 1.4 mmol), tetrakis(triphenylphosphine)palladium (82 mg, 0.071 mmol), allyltri-n-butyltin (0.88 mL, 2.8 mmol), and lithium chloride (0.120 g, 2.83 mmol). The resulting mixture was then dissolved in anhydrous toluene (16 mL); the flask was placed in an oil bath and heated at 130° C. LC as well as TLC (hexanes/EtOAc=1/0.3) indicated that reaction had gone to completion. The flask was taken out of the oil bath and cooled to room temperature. To the flask was poured EtOAc (40 mL) and the mixture was transferred into a separatory funnel and washed with aqueous NaCl. The organic phase was dried over $Na_2SO_4$, filtered and concentrated to dryness. It was then dissolved in DCM and absorbed into silica gel. The slica gel was then loaded onto a silica column for separation with the solvent systems of hexanes/EtOAc (1/0.3); this gave 2-(methyloxy)-4-prop-2-en-1-ylbenzonitrile. LC-MS (IE, m/z): 174 $[M+1]^+$.

Step B: 2-(Methyloxy)-4-(2-oxoethyl)benzonitrile

To a 25 ml, flask containing a stir bar was added compound 2-(methyloxy)-4-prop-2-en-1-ylbenzonitrile (0.15 g, 0.87 mmol) and MeOH (8 mL). The flask was placed in a cold bath of −78° C. Ozone was bubbled through the flask for about 10 min. followed by addition of dimethyl sulfide (1.5 mL, 24 mmol). The flask was taken out of the cold bath and stirred at room temperature for 1 h; LC indicated completion of the reaction. The reaction mixture was concentrated to dryness to give 2-(methyloxy)-4-(2-oxoethyl)benzonitrile. LC-MS (IE, m/z): 176 $[M+1]^+$.

Intermediate 20

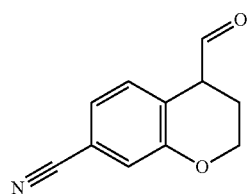 [SMILES: N#Cc1ccc2c(c1)OCCC2C=O]

4-Formyl-3,4-dihydro-2H-chromene-7-carbonitrile

Step A: (4E)-4-(Methoxymethylidene)-3,4-dihydro-2H-chromene-7-carbonitrile

In a 250 mL round bottom flask, (methoxymethyl) (triphenyl)phosphonium chloride (4.0 g, 12 mmol) was dissolved in THF (20 mL). The solution was cooled to −78° C. To above solution was added n-butyl lithium (3.5 mL, 2.50 M in hexane, 8.7 mmol) dropwise. The color of reaction changed to orange. The mixture was cooled to −78° C. and to it was added 4-oxo-3,4-dihydro-2H-chromeme-7-carbonitrile (1 g, 5.8 mmol). The reaction was let warm to RT and stirred for 18 hours. The reaction was then quenched with addition of saturated ammonium chloride (5 mL) and extracted with dichloromethane. The organic phase was washed with brine (5 mL), dried over anhydrous $Na_2SO_4$, filtered, concentrated and purified by flash column chromatography (hexane/EtOAc 0-50%). The desired product was obtained (270 mg, 1.34 mmol, 23%). LC-MS (IE, m/z): 202.3 $[M+1]^+$.

Step B: 4-Formyl-3,4-dihydro-2H-chromene-7-carbonitrile (4E)-4-(methoxymethylidene)-3,4-dihydro-2H-chromene-7-carbonitrile (230 mg, 1.1 mmol) was dissolved in dichloromethane (6 mL). The solution was cooled to −78° C. To above solution was added tribromoborane (1.7 mL, 1 M, 1.7 mmol) dropwise over a course of 5 min and subsequently stirred for 30 min at −78° C. To the reaction mixture was added saturated sodium bicarbonate, extracted with dichloromethane (2×20 mL). The organic phase was washed with brine (5 mL), dried over anhydrous $Na_2SO_4$, filtered, concentrated. The crude product was used without purification. $^1H$ NMR (500 MHz, $CDCl_3$, δ in ppm): 7.0-7.4 (3H, aromatic), 6.58 (1H, s), 4.55 (2H, m), 2.98 (2H, m).

Intermediate 21

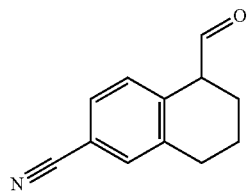 [SMILES: N#Cc1ccc2c(c1)CCCC2C=O]

5-Formyl-5,6,7,8-tetrahydronaphthalene-2-carbonitrile

Step A: (5E)-5-(Methoxymethylidene)-5,6,7-8-tetrahydronaphthalene-2-carbonitrile In a 250 mL round bottom flask, (methoxymethyl) (triphenyl)phosphonium chloride (4.0 g, 12 mmol) was dissolved in THF (20 mL). The solution was cooled to −78° C. To above solution was added n-butyl lithium (3.50 mL, 2.50 M in Hexane, 8.8 mmol) dropwise. Reaction color changed to orange. The mixture was cooled to −78° C. and to it was added 5-oxo-5,6,7,8-tetrahydronaphthalene-2-carbonitrile (1 g, 5.77 mmol). The reaction was let warm to RT and stirred at r.t for 18 hours. The reaction was then quenched with addition of saturated ammonium chloride (5 mL) and extracted with dichloromethane. The organic phase was washed with brine (5 mL), dried over anhydrous $Na_2SO_4$, filtered, concentrated and purified by flash column chromatography (Hexane/EtOAc 0-50%). The desired product was obtained. $^1H$ NMR (500 MHz, $CDCl_3$, δ in ppm): 7.0-7.6 (3H, aromatic), 6.75 (1H, s), 3.88 (3H, s, Me), 3.0 (1H, t), 2.63 (2H, t), 2.23 (1H, t), 2.18 (1H, t), 1.65 (1H, t).

Step B: 5-Formyl-5,6,7,8-tetrahydronaphthalene-2-carbonitrile (5E)-5-(Methoxymethylidene)-5,6,7-8-tetrahydronaphthalene-2-carbonitrile (800 mg, 4.02 mmol) was dissolved in dichloromethane (6 mL). The solution was cooled to −78° C. To above solution was added tribromoborane (6.0 mL, 1 M, 6.0 mmol) dropwise over a course of 5 min and subsequently stirred for 30 min at −78° C. To the reaction mixture was added saturated sodium bicarbonate, extracted with dichloromethane (2×20 mL). The organic phase was washed with brine (5 mL), dried over anhydrous Na$_2$SO$_4$, filtered, concentrated and purified by flash column chromatography. $^1$H NMR (500 MHz, CDCl$_3$, δ in ppm): 9.6 (1H, s), 7.0-7.6 (3H, aromatic), 1.8-3.0 (6H, m).

Intermediate 22

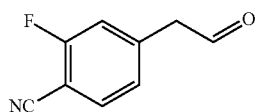 [SMILES: N#Cc1ccc(CC=O)cc1F]

2-Fluoro-4-(2-oxoethyl)benzonitrile

Step A: Methyl(3-fluoro-4-hydroxyphenyl) acetate (3-Fluoro-4-hydroxy-phenyl)-acetic acid (25 g, 150 mmol) was dissolved in methanol (100 mL), and thionyl chloride (5 mL) was added dropwise to the solution. The solution was heated to 85° C. for 16 hours. The reaction mixture was allowed to cool and evaporated to dryness in vacuo. The residue was partitioned between ethyl acetate and saturated NaHCO$_3$. The organic layer was dried over MgSO$_4$, filtered, and the filtrate was evaporated to dryness under reduced pressure to yield the crude title compound as an off white solid (25.3 g). $^1$H NMR (500 MHz, CDCl$_3$): δ 7.07 (d, J=7.07 Hz, 1H), 7.00-6.97 (m, 2H), 3.74 (s, 3H), 3.73 (s, 2H).

Step B: Methyl(3-fluoro-4-{[(trifluoromethyl)sulfonyl]oxy}phenyl)acetate

The crude phenol[methyl(3-fluoro-4-hydroxyphenyl)acetate, 25.3 g] was dissolved in anhydrous dichloromethane (200 mL). 4-Dimethylaminopyridine (1.68 g) was added, followed by triethylamine (23.0 mL, 165 mmol). The solution was then cooled to in a dry ice and acetone bath while under nitrogen. Trifluoromethanesulfonic anhydride (27.9 mL, 165 mmol) was slowly added and the reaction mixture was allowed to warm to ambient temperature. The reaction mixture was then diluted with dichloromethane (200 mL) and washed with water (2×100 mL). The organic layer was dried over magnesium sulfate, filtered, and concentrated to dryness under reduced pressure and a cold water bath to yield the crude triflate. LC-MS (IE, m/z): 316 [M+1]$^+$.

Step C: Methyl(4-cyano-3-fluorophenyl) acetate

The crude triflate (43.4 g) was subsequently dissolved in anhydrous dimethylformamide (100 mL). Zinc cyanide (7.2 g, 78 mmol) was added, and the solution was purged thoroughly with nitrogen. Tetrakis(triphenylphosphine) palladium (12 g, 14 mmol) was then added and the reaction mixture was heated to 80° C. for 4 h. After allowing cooling to ambient temperature and diluting with water (300 mL), ethyl acetate (500 mL) was added. The combined layers were filtered to remove any solids, the filtrate transferred to a reparatory funnel, and the layers separated. The aqueous layer was re-extracted with ethyl acetate (1×100 mL), the organic portions were combined and dried over magnesium sulfate. The dry organics were then filtered and evaporated to dryness under reduced pressure and excess dimethylformamide was removed by evaporation in vacuo at 65° C. for 1.5 h to yield the crude title compound (42 g). The crude product was purified through silica gel chromatography (ethyl acetate:hexanes=2:3) to yield the title nitrile. $^1$H NMR (500 MHz, CDCl$_3$): δ 7.62 (t, J=6.1 Hz, 1H), 7.23-7.21 (m, 2H), 3.76 (s, 3H), 3.73 (s, 2H). LC-MS (IE, m/z): 194 [M+1]$^+$.

Step D: 2-Fluoro-4-(2-hydroxyethyl)benzonitrile

LiBH$_4$ (1.94 mL, 3.88 mmol, 2 M in THF) was added to a stirred solution of methyl(4-cyano-3-fluorophenyl)acetate (0.50 g, 2.59 mmol) in THF (25 ml) at 0° C. The resulting solution was stirred for 12 h. Water (10 ml) was added, and the resulting solution was extracted with dichloromethane (2×50 ml). The combined organic layers were dried over MgSO$_4$, filtered, and evaporated under reduced pressure. The residue was purified by column chromatography eluting with EtOAc-Hexanes (7:3→1:1) to give the product as colorless oil. $^1$H NMR (500 MHz, CDCl$_3$) δ 7.60 (dd, J=7.4, J=7.1 Hz, 1H), 7.30 (s, 1H), 7.18 (dd, J=7.3, J=9.1 Hz, 1H), 3.95 (t, J=6.2 Hz, 2H), 2.93 (t, J=6.3 Hz, 2H).

Step E: 2-Fluoro-4-(2-oxoethyl)benzonitrile

To a stirred solution of 2-fluoro-4-(2-hydroxyethyl)benzonitrile (0.40 g, 2.4 mmol) in dry CH$_2$Cl$_2$ (20 mL) at 0° C. was added Dess-Martin periodinane (1.54 g, 3.6 mmol) in one portion. The mixture was stirred for 12 h at rt and quenched with a 1:1 mixture of saturated Na$_2$S$_2$O$_3$ (10 mL) and saturated NaHCO$_3$ (10 mL). The resulting mixture was diluted with CH$_2$Cl$_2$ (70 mL) and the layers were separated. The aqueous phase was extracted with CH$_2$Cl$_2$ (2×50 mL). The combined organic phases were washed with brine, dried (Na$_2$SO$_4$), and concentrated in vacuo to give crude aldehyde as colorless oil. The residue was used in the next step without further purification. LC-MS (IE, m/z): 164.1 [M+1]$^+$.

Intermediate 23

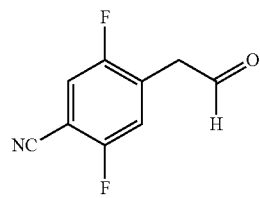 [SMILES: N#Cc1cc(F)c(CC=O)cc1F]

2,5-Difluoro-4-(2-oxoethyl)benzonitrile

Step A: Di-tert-butyl(4-cyano-2,5-difluorophenyl) propanedioate

To a suspension of NaH (2.6 g, 64 mmol, and 60.0% dispersion in oil) in DMF (80 mL) was added a solution of di-tert-butyl malonate (3.57 g, 16.50 mmol) in DMF (20 mL) at 0° C. and this was stirred for 15 min. Subsequently, 2,4,5-trifluorobenzonitrile (3.0 g, 15.0 mmol) was added in one portion and the reaction mixture was stirred for 8 h at 80° C. and three hours at room temperature. Water (50 mL) was added and the aqueous layer was extracted with EtOAc (2×100 mL). The combined organic extracts were washed with water (50 mL) and brine (50 mL), dried over MgSO$_4$ and filtered. After evaporation in vacuo, the residue was purified by flash chromatography (20% EtOAc in hexane) to give 10.0 g of di-tert-butyl(4-cyano-2,5-difluorophenyl)propanedioate as a colorless oil. $^1$H NMR (500 MHz, CDCl$_3$) δ 7.51 (dd, J=5.5, J=5.4 Hz, 1H), 7.37 (dd, J=5, J=6 Hz, 1H), 4.84 (s, 1H), 1.50 (s, 18H). LC-MS (IE, m/z): 298.2 [(M+1)]$^+$-t-Bu].

Step B: (4-Cyano-2,5-difluorophenyl)acetic acid

To the di-tert-butyl(4-cyano-2,5-difluorophenyl)propanedioate (10.0 g, 28.3 mmol) in dichloromethane (30 mL) was added triflouroacetic acid (10 mL) and the mixture stirred for 12 h at room temperature. The solution was concentrated under reduced pressure and chased with toluene (2×) to give the crude product as a yellowish oil (5 g, 90%, 85% purity as indicated by NMR). The residue was used in the next step without further purification. $^1$H NMR (500 MHz, CDCl$_3$) δ 7.31 (dd, J=3, J=2 Hz, 1H), 7.21 (dd, J=5.8, J=5.8 Hz, 1H), 3.67 (s, 2H). LC-MS (IE, m/z): 198 [M+1]$^+$.

Step C: Methyl(4-cyano-2,5-difluorophenyl)acetate (4-Cyano-2,5-difluorophenyl)acetic acid (0.5 g, 2.5 mmol) was dissolved in methanol (20 mL), and thionyl chloride (0.5 mL) was added drop wise to the solution. The reaction was heated to 85° C. for 4 hours. Then it was cooled and evaporated to dryness in vacuo. The residue was partitioned between ethyl acetate and saturated NaHCO$_3$. The organic layer was dried over MgSO$_4$, filtered, and the filtrate was evaporated to dryness under reduced pressure to yield the title compound after purification on silica gel (eluted with 5-20% ethyl acetate-hexanes) as an off white solid. $^1$H NMR (500 MHz, CDCl$_3$): δ 7.31 (dd, J=5.2, J=5.2 Hz, 1H), 7.19 (dd, J=5.7, J=5.8 Hz, 1H), 3.73 (s, 3H), 3.71 (s, 2H). LC-MS (IE, m/z): 212 [M+1]$^+$.

Step D: 2,5-Difluoro-4-(2-hydroxyethyl)benzonitrile

LiBH$_4$ (1.45 mL, 2.9 mmol, 2 M in THF) was added to a stirred solution of methyl(4-cyano-2,5-difluorophenyl)acetate (0.47 g, 2.2 mmol) in THF (25 ml) at 0° C. The resulting solution was stirred for 12 h. Water (15 ml) was added, and the resulting solution was extracted with dichloromethane (2×50 ml). The combined organic layers were dried over MgSO$_4$, filtered, and evaporated under reduced pressure to yield the product after purification on silica gel (eluted with 5-30% ethyl acetate-hexanes) as a clear oil. $^1$H NMR (500 MHz, CDCl$_3$) δ 7.32 (dd, J=5.3, J=5.0 Hz, 1H), 7.23 (dd, J=5.8, J=5.7 Hz, 1H), 3.95 (t, J=6.2, J=6.4 Hz, 2H), 2.98 (t, J=6.4, J=6.2 Hz, 2H). LC-MS (IE, m/z): 184 [M+1]$^+$.

Step E: 2,5-Difluoro-4-(2-oxoethyl)benzonitrile

To a stirred solution of 2,5-difluoro-4-(2-hydroxyethyl) benzonitrile (0.36 g, 2.0 mmol) in dry CH$_2$Cl$_2$ (30 mL) at 0° C. was added Dess-Martin periodinane (0.83 g, 2.0 mmol) in one portion. The mixture was stirred for 12 hours at RT and quenched with a 1:1 mixture of saturated Na$_2$S$_2$O$_3$ (10 mL) and saturated NaHCO$_3$ (10 mL). The resulting mixture was diluted with CH$_2$Cl$_2$ (70 mL) and the layers were separated. The aqueous phase was extracted with CH$_2$Cl$_2$ (2×50 mL). The combined organic phases were washed with brine, dried (Na$_2$SO$_4$), and concentrated in vacuo to give crude aldehyde as light yellow oil. The residue was used in the next step without further purification and analysis.

Intermediate 24

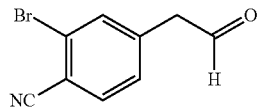

2-Bromo-4-(2-oxoethyl)benzonitrile

Step A:
Di-tert-butyl(3-bromo-4-cyanophenyl)malonate

To a suspension of NaH (0.37 g, 15.4 mmol, 60.0% dispersion in oil) in DMF (40 mL) was added a solution of di-t-butyl malonate (3.6 g, 16 mmol) in DMF (10 mL) at 0° C. and this was stirred for 15 minutes. Subsequently, 2-bromo-4-fluorobenzonitrile (3.0 g, 15.0 mmol) was added in one portion and the reaction mixture was stirred for 8 hours at 80° C. and three hours at room temperature. Water (50 mL) was added and the aqueous layer was extracted with EtOAc (2×100 mL). The combined organic extracts were washed with water (50 mL) and brine (50 mL), dried over MgSO$_4$ and filtered. After evaporation in vacuo, the residue was purified by flash chromatography (20% EtOAc in hexane) to give di-tert-Butyl(3-bromo-4-cyanophenyl)malonate as a light brown solid. $^1$H NMR (500 MHz, DMSO-d$_6$) δ 7.97 (d, J=8 Hz, 1H), 7.88 (s, 1H), 7.60 (d, J=8 Hz, 1H), 4.95 (s, 1H), 1.42 (s, 18H). LC-MS (IE, m/z): 398 [M+1]$^+$.

Step B: (3-Bromo-4-cyanophenyl) acetic acid

To the di-tert-butyl(3-bromo-4-cyanophenyl)malonate (2.2 g, 5.4 mmol) in dichloromethane (30 mL) was added triflouroacetic acid (10 mL) and the reaction mixture stirred for 12 h at room temperature. The solution was concentrated under reduced pressure and chased with toluene (2×) to give the crude product as a yellowish oil (1 g, 77%, and 85% purity as indicated by NMR). The residue was used in the next step without further purification. $^1$H NMR (500 MHz, DMSO-d$_6$) δ 12.80 (br s, 1H), 7.87 (d, J=8 Hz, 1H), 7.80 (s, 1H), 7.48 (d, J=8 Hz, 1H), 3.73 (s, 2H). LC-MS (IE, m/z): 240 [M+1]$^+$.

Step C: Methyl(3-bromo-4-cyanophenyl)acetate (3-Bromo-4-cyanophenyl)acetic acid (1.0 g, 4.2 mmol) was dissolved in methanol (20 mL), and thionyl chloride (0.5 mL) was added drop wise to the solution. The reaction was heated to 85° C. for 4 h. Then it was cooled to room temperature and evaporated to dryness in vacuo. The residue was partitioned between ethyl acetate and sat. NaHCO$_3$. The organic layer was dried over MgSO$_4$, filtered, and the filtrate was evaporated to dryness under reduced pressure to yield the crude title compound as an off white solid. $^1$H NMR (500 MHz, CDCl$_3$): δ 7.07 (d, J=7.07 Hz, 1H), 7.00-6.97 (m, 2H), 3.74 (s, 3H), 3.73 (s, 2H). LC-MS (IE, m/z): 195.2 [(M+1)–CO$_2$CH$_3$]$^+$.

Step D: 2-Bromo-4-(2-hydroxyethyl)benzonitrile

LiBH$_4$ (1.48 mL, 2.95 mmol, 2 M in THF) was added to a stirred solution of methyl(3-bromo-4-cyanophenyl)acetate (0.50 g, 2.0 mmol) in THF (25 ml) at 0° C. The resulting solution was stirred for 12 h. Water (15 ml) was added, and the resulting solution was extracted with dichloromethane (2×50 ml). The combined organic layers were dried over MgSO$_4$, filtered, and evaporated under reduced pressure to yield the crude product as a cloudy oil. $^1$H NMR (500 MHz, CDCl$_3$) δ 7.63 (s, 1H), 7.61 (d, J=5.7, 1H), 7.33 (d, J=7.8 Hz, 1H), 3.93 (t, J=1.6, J=4.8 Hz, 2H), 2.92 (t, J=6.6, J=5.1 Hz, 2H). LC-MS (IE, m/z): 210.1 [(M+1)]$^+$–OH].

Step E: 2-Bromo-4-(2-oxoethyl)benzonitrile

To a stirred solution of 2-bromo-4-(2-hydroxyethyl)benzonitrile (0.51 g, 2.3 mmol) in dry CH$_2$Cl$_2$ (30 mL) at 0° C. was added Dess-Martin periodinane (1.45 g, 3.4 mmol) in one portion. The mixture was stirred for 12 h at RT and quenched with a 1:1 mixture of saturated Na$_2$S$_2$O$_3$ (40 mL) and saturated NaHCO$_3$ (40 mL). The resulting mixture was diluted with CH$_2$Cl$_2$ (70 mL) and the layers were separated. The aqueous phase was extracted with CH$_2$Cl$_2$ (2×50 mL). The combined organic phases were washed with brine, dried (Na$_2$SO$_4$), and concentrated in vacuo to give crude aldehyde as colorless oil. The residue was used in the next step without further purification and analysis.

Intermediate 25

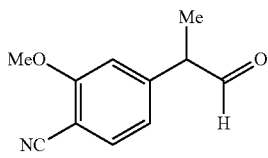

2-Methoxy-4-(1-oxopropan-2-yl)benzonitrile

Step A: Ethyl(3-methoxy-4-{[(trifluoromethyl)sulfonyl]oxy}phenyl)acetate

The crude phenol[ethyl(4-hydroxy-3-methoxyphenyl)acetate, 12.0 g, 57 mmol] was dissolved in anhydrous dichloromethane (200 mL). 4-Dimethylaminopyridine (0.70 g, 0.10 equiv) was added, followed by triethylamine (9.6 mL, 68 mmol). The solution was then cooled to in a dry ice and acetone bath while under nitrogen. Trifluoromethanesulfonic anhydride (9.6 mL, 57 mmol) was slowly added and the reaction mixture was allowed to warm to ambient temperature. The reaction mixture was then diluted with dichloromethane (200 mL) and washed with water (2×100 mL). The organic layer was dried over magnesium sulfate, filtered, and concentrated to dryness under reduced pressure to yield the crude triflate. LC-MS (IE, m/z): 269.0 [(M+1)–CO$_2$Et]$^+$.

Step B: Ethyl(4-cyano-3-methoxyphenyl) acetate

The crude triflate (16.6 g) was subsequently dissolved in anhydrous dimethylformamide (100 mL). Zinc cyanide (3.4 g, 29 mmol) was added, and the solution was purged thoroughly with nitrogen. Tetrakis(triphenylphosphine) palladium (5.6 g, 4.8 mmol) was then added and the reaction mixture was heated to 80° C. for 4 h. After allowing to cool to ambient temperature and diluting with water (200 mL), ethyl acetate (400 mL) was added. The combined layers were filtered to remove any solids, the filtrate transferred to a reparatory funnel, and the layers separated. The aqueous layer was re-extracted with ethyl acetate (2×100 mL), the organic portions were combined and dried over magnesium sulfate. The dry organics were then filtered and evaporated to dryness under reduced pressure and excess dimethylformamide was removed by evaporation in vacuo at 65° C. for 1.5 h to yield the crude title compound (20 g). The crude product was purified through silica gel chromatography (ethyl acetate/hexanes, 2:3) to yield the title nitrile. $^1$H NMR (500 MHz, DMSO-d$_6$), δ 7.67 (d, J=8.0 Hz, 1H), 7.18 (s, 1H), 7.0 (d, J=8.0 Hz, 1H), 4.10 (q, J=7.1 Hz, 2H), 3.89 (s, 3H), 3.78 (s, 2H), 1.19 (t, J=7.1 Hz, 3H); LC-MS (IE, m/z): 220 [M+1]$^+$.

Step C: Ethyl 2-(4-cyano-3-methoxyphenyl)propanoate

To a suspension solution of NaH (0.18 g, 4.6 mmol, 60% dispersion in mineral oil) in THF (50 mL) at ° C. under N$_2$ atm was added a solution of ethyl(4-cyano-3-methoxyphenyl) acetate (1.0 g, 4.6 mmol) in THF (10 mL) dropwise and the mixture was stirred for 30 min at the same temperature. The mixture was then allowed to warm to ambient temperature. The mixture was then allowed to cool back to 0° C. Methyl iodide (0.284 mL, 4.56 mmol) was added and the reaction mixture was stirred for 1 h. The reaction mixture was acidified by 1 M hydrochloric acid and extracted with EtOAc. The organic layer was washed with brine, dried over anhydrous sodium sulfate, and concentrated in vacuo. The residue was purified by silica gel column chromatography (hexane/EtOAc 15/1) to give ethyl 2-(4-cyano-3-methoxyphenyl) propanoate as a colorless oil. $^1$H NMR (500 MHz, CDCl$_3$) δ 7.53 (d, 1H, J=8 Hz), 6.98 (d, 1H, J=8 Hz), 6.95 (s, 1H), 4.17 (q, 2H, J=3.4 Hz), 3.97 (s, 3H), 3.76 (q, 1H, J=9.1 Hz), 1.53 (d, 3H, J=7.1 Hz), 1.25 (t, 3H, J=7.1 Hz); LC-MS (IE, m/z): 234 [M+1]$^+$.

Step D: 4-(1-Hydroxypropan-2-yl)-2-methoxybenzonitrile

LiBH$_4$ (0.55 mL, 1.09 mmol, 2 M in THF) was added to a stirred solution of ethyl 2-(4-cyano-3-methoxyphenyl) propanoate (0.17 g, 0.73 mmol) in THF (25 ml) at 0° C. The resulting solution was stirred for 12 h. Water (15 ml) was added, and the resulting solution was extracted with dichloromethane (2×50 ml). The combined organic layers were dried over MgSO$_4$, filtered, and evaporated under reduced pressure. The residue was purified by column chromatography eluting with EtOAc-Hexanes (7:3→1:1) to give an inseparable mixture of 4-(1-hydroxypropan-2-yl)-2 methoxybenzonitrile as a colorless oil. $^1$H NMR (500 MHz, CDCl$_3$) δ 7.49 (d, 1H, J=7.9 Hz), 6.88 (dd, 1H, J=1.4 Hz), 6.83 (s, 1H), 3.92 (s, 3H), 3.72 (d, 2H, J=6.8 Hz), 2.97 (q, 1H, J=6.8 Hz), 1.28 (d, 3H, J=6.9 Hz); LC-MS (IE, m/z): 192.3 [M+1]$^+$.

Step E: 2-Methoxy-4-(1-oxopropan-2-yl)benzonitrile

To a stirred solution of 4-(1-hydroxypropan-2-yl)-2-methoxybenzonitrile (0.12 g, 0.63 mmol) in dry CH$_2$Cl$_2$ (30 mL) at 0° C. was added Dess-Martin periodinane (0.35 g, 0.82 mmol) in one portion. The mixture was stirred for 12 h at room temperature and quenched with a 1:1 mixture of saturated Na$_2$S$_2$O$_3$ (20 mL) and saturated NaHCO$_3$ (20 mL). The resulting mixture was diluted with CH$_2$Cl$_2$ (50 mL) and the layers were separated. The aqueous phase was extracted with CH$_2$Cl$_2$ (2×50 mL). The combined organic phases were washed with brine, dried (Na$_2$SO$_4$), and concentrated in vacuo to give crude aldehyde as colorless oil. The crude residue was used in the next step without further purification. LC-MS (IE, m/z): 190.3 [M+1]+.

Intermediate 26

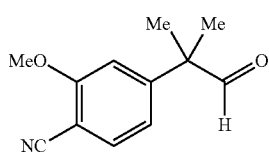 [SMILES: COc1cc(C(C)(C)C=O)ccc1C#N]

2-Methoxy-4-(2-methyl-1-oxopropan-2-yl)benzonitrile

Step A: Ethyl 2-(4-cyano-3-methoxyphenyl)-2-methyl propanoate

To a suspension solution of NaH (0.36 g, 9.1 mmol, 60% dispersion in mineral oil) in THF (50 mL) at ° C. under N₂ was added a solution of ethyl(4-cyano-3-methoxyphenyl) acetate (1.0 g, 4.6 mmol) in THF (10 mL) dropwise and the mixture was stirred for 30 min at the same temperature. The mixture was then allowed to warm to ambient temperature. The mixture was then allowed to cool back to ° C. Methyl iodide (0.57 mL, 9.1 mmol) was added and the reaction mixture was stirred for 1 h. The reaction mixture was acidified by 1 M hydrochloric acid and extracted with EtOAc. The organic layer was washed with brine, dried over anhydrous sodium sulfate, and concentrated in vacuo. The residue was purified by silica gel column chromatography (hexane/EtOAc 15/1) to give ethyl 2-(4-cyano-3-methoxyphenyl)-2-methylpropanoate as a colorless oil. ¹H NMR (500 MHz, CDCl₃) δ 7.54 (d, 1H, J=8.0 Hz), 7.02 (dd, 1H, J=1.6 Hz), 6.95 (d, 1H, J=1.4 Hz), 4.17 (q, 2H, J=7.2 Hz), 3.96 (s, 3H), 1.61 (s, 6H), 1.23 (t, 3H, J=7.1 Hz); LC-MS (IE, m/z): 248.3 [M+1]+.

Step B: 4-(1-Hydroxy-2-methylpropan-2-yl)-2-methoxybenzonitrile

LiBH₄ (0.48 mL, 0.97 mmol, 2 M in THF) was added to a stirred solution of ethyl 2-(4-cyano-3-methoxyphenyl)-2-methylpropanoate (0.16 g, 0.65 mmol) in THF (25 ml) at 0° C. The resulting solution was stirred for 12 h. Water (15 ml) was added, and the resulting solution was extracted with dichloromethane (2×50 ml). The combined organic layers were dried over MgSO₄, filtered, and evaporated under reduced pressure. The residue was purified by column chromatography eluting with EtOAc-Hexanes (7:3→1:1) to give an inseparable mixture of 4-(1-hydroxy-2-methylpropan-2-yl)-2-methoxybenzonitrile as a colorless oil. ¹H NMR (500 MHz, CDCl₃) δ 7.55 (d, 1H, J=8.0 Hz), 6.88 (d, 1H, J=8.0 Hz), 7.02 (s, 1H), 3.98 (s, 3H), 3.69 (s, 2H), 1.38 (s, 6H); LC-MS (IE, m/z): 206.3 [M+1]+.

Step C: 2-Methoxy-4-(2-methyl-1-oxopropan-2-yl)benzonitrile

To a stirred solution of 4-(1-hydroxy-2-methylpropan-2-yl)-2-methoxybenzonitrile (0.12 g, 0.58 mmol) in dry CH₂Cl₂ (30 mL) at 0° C. was added Dess-Martin periodinane (0.32 g, 0.76 mmol) in one portion. The mixture was stirred for 12 h at RT and quenched with a 1:1 mixture of saturated Na₂S₂O₃ (20 mL) and saturated NaHCO₃ (20 mL). The resulting mixture was diluted with CH₂Cl₂ (50 mL) and the layers were separated. The aqueous phase was extracted with CH₂Cl₂ (2×50 mL). The combined organic phases were washed with brine, dried (Na₂SO₄), and concentrated in vacuo to give crude aldehyde as colorless oil. The crude residue was used in the next step without further purification. LC-MS (IE, m/z): 204.4 [M+1]+.

Intermediate 27

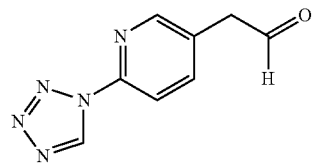 [SMILES: O=CCc1ccc(-n2cnnn2)nc1]

[6-(1H-tetrazol-1-yl)pyridin-3-yl]acetaldehyde

Step A: 2-[6-(1H-tetrazol-1-yl)pyridin-3-yl]ethanol

LiBH₄ (0.48 mL, 0.96 mmol, 2 M in THF) was added to a stirred solution of ethyl[6-(1H-tetrazol-1-yl)pyridin-3-yl]acetate (0.150 g, 0.64 mmol) in THF (20 ml) at 0° C. The resulting solution was stirred for 12 h. Water (5 ml) was added, and the resulting solution was extracted with dichloromethane (2×50 ml). The combined organic layers were dried over MgSO₄, filtered, and evaporated under reduced pressure to yield the product after flash chromatography (eluted with 10-50% ethyl acetate in hexanes) as a colorless oil. ¹H NMR (500 MHz, CDCl₃) δ 9.51 (s, 1H), 8.43 (br s, 1H), 8.01 (dd, J=2.7, J=2.7 Hz, 1H), 7.91 (dd, J=2.1, J=2.0 Hz, 1H), 3.99 (br s, 2H), 3.00 (t, J=6.1, J=6.2 Hz, 2H). LC-MS (IE, m/z): 164.1 [(M+1)+−28].

Step B: [6-(1H-tetrazol-1-yl)pyridin-3-yl]acetaldehyde

To a stirred solution of 2-[6-(1H-tetrazol-1-yl)pyridin-3-yl]ethanol (0.035 g, 0.18 mmol) in dry CH₂Cl₂ (20 mL) at 0° C. was added Dess-Martin periodinane (0.12 g, 0.28 mmol) in one portion. The mixture was stirred for 12 h at rt and quenched with a 1:1 mixture of saturated Na₂S₂O₃ (5 mL) and saturated NaHCO₃ (5 mL). The resulting mixture was diluted with CH₂Cl₂ (50 mL) and the layers were separated. The aqueous phase was extracted with CH₂Cl₂ (2×50 mL). The combined organic phases were washed with brine, dried (Na₂SO₄), and concentrated in vacuo to give crude aldehyde as a light yellow solid. The residue was used in the next step without further purification. LC-MS (IE, m/z): 162.1 [(M+1)+−28].

Intermediate 28

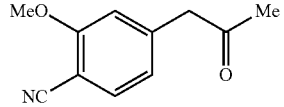 [SMILES: COc1cc(CC(C)=O)ccc1C#N]

2-Methoxy-4-(2-oxopropyl)benzonitrile

Step A: 4-(2-Hydroxypropyl)-2-methoxybenzonitrile

To a stirred solution of 1.48 g (8.47 mmol) of 2-methoxy-4-(2-oxoethyl)benzonitrile in dichloromethane (30 mL) at 0° C. was added 2.82 mL (8.47 mmol) of a 3.0 M solution of methylmagnesium bromide in THF. The reaction mixture was allowed to warm up to RT and stirred for 12 h. The reaction was then quenched by the addition of 10 mL of 1 N hydrochloric acid and extracted with dichloromethane (2×30 mL). The combined organic extracts were dried with magnesium sulfate, filtered, and concentrated in vacuo. The crude residue was purified on silica (30% EtOAc/hexanes as eluent) to afford 4-(2-hydroxypropyl)-2-methoxybenzonitrile as a clear liquid. $^1$H NMR (500 MHz, CDCl$_3$) δ 7.47 (d, 1H, J=7.8 Hz), 6.85 (dd, 1H, J=3.4 Hz), 6.82 (s, 1H), 4.05 (m, 1H), 3.93 (d, 2H), 3.91 (s, 3H), 1.25 (d, 2H, J=6.1 Hz). LC-MS (IE, m/z): 192.3 [M+1]$^+$.

Step B: 2-Methoxy-4-(2-oxopropyl)benzonitrile

To a stirred solution of 4-(2-hydroxypropyl)-2-methoxybenzonitrile (1.45 g, 7.6 mmol) in dry CH$_2$Cl$_2$ (30 mL) at 0° C. was added Dess-Martin periodinane (4.2 g, 9.8 mmol) in one portion. The mixture was stirred for 12 h at RT and quenched with a 1:1 mixture of saturated Na$_2$S$_2$O$_3$ (20 mL) and saturated NaHCO$_3$ (20 mL). The resulting mixture was diluted with CH$_2$Cl$_2$ (50 mL) and the layers were separated. The aqueous phase was extracted with CH$_2$Cl$_2$ (2×50 mL). The combined organic phases were washed with brine, dried (Na$_2$SO$_4$), and concentrated in vacuo to give 2-methoxy-4-(2-oxopropyl)benzonitrile as an oil. The crude residue was used in the next step without further purification. $^1$H NMR (500 MHz, CDCl$_3$) δ 7.55 (dd, 1H, J=1.6 Hz), 6.87 (d, 1H, J=7.8 Hz), 6.83 (s, 1H), 3.96 (s, 3H), 3.79 (s, 2H), 2.25 (s, 3H).

Intermediate 29

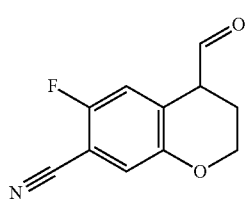 [SMILES: N#Cc1cc2c(cc1F)C(C=O)CCO2]

6-Fluoro-4-formyl-3,4-dihydro-2H-chromene-7-carbonitrile

Step A:
6-Fluoro-7-hydroxy-2,3-dihydro-4H-chromen-4-one

In a 15 mL vial was added 4-fluorobenzene-1,3-diol (500 mg, 3.9 mmol) and 3-chloropropanoic acid (424 mg, 3.9 mmol) and trifluoromethanesulfonic acid (2 mL). The mixture was heated to 80° C. and stirred at that temperature for 4 hour. The reaction was cooled and poured into water (10 mL). The product was extracted with ethyl acetate, dried over anhydrous Na$_2$SO$_4$, filtered, concentrated. To the dark red solid obtained was added sodium hydroxide (2 N, 5 mL) and the solution was let stirred at RT for 18 hours. The mixture was neutralized with 2 N HCl, extracted with EtOAc. The organic phase was dried over anhydrous Na$_2$SO$_4$, filtered, concentrated. The crude was used to next step without purification. $^1$H NMR (500 MHz, CDCl$_3$, δ in ppm): 7.61 (1H, d, J=10.3 Hz), 6.56 (1H, d, J=3.1 Hz), 4.48 (2H, t), 2.78 (2H, t).

Step B:
6-Fluoro-4-oxo-3,4-dihydro-2H-chromen-7-yl trifluoromethanesulfonate

In a 100 ml round bottle flask was added 6-Fluoro-7-hydroxy-2,3-dihydro-4H-chromen-4-one (220 mg, 1.2 mmol) and pyridine (10 mL). The solution was cooled to 0° C. Trifluoromethylsulfonyl anhydride (0.26 mL, 1.6 mmol) was added to above solution dropwise. The reaction was warmed to RT and stirred at that temperature for 2 hours. The mixture was diluted with EtOAc, washed with saturated CuSO$_4$, brine and water. The organic phase was dried over MgSO$_4$, filtered and concentrated. Above crude was purified on flash column chromatography to give the product. LC-MS (IE, m/z): 315.2 [M+1]$^+$.

Step C: 6-Fluoro-4-oxo-3,4-dihydro-2H-chromene-7-carbonitrile

In a 15 mL microwave tube was added 6-Fluoro-4-oxo-3,4-dihydro-2H-chromen-7-yl trifluoromethanesulfonate (370 mg, 1.2 mmol), zinc cyanide (138 mg, 1.2 mmol) and tetrakis (triphenylphosphine)palladium (136 mg, 0.19 mmol, 0.1 eq). The tube was sealed, degased and filled with N$_2$. The mixture was heated to 130° C. in microwave reactor for 30 minutes. The reaction was cooled down, extracted with EtOAc, washed with brine and water. The organic phase was dried over MgSO$_4$, filtered and concentrated. Above crude was purified on flash column chromatography (0-100% EtOAc/Hex) to give the product as white crystal. LC-MS (IE, m/z): 192.3 [M+1]$^+$.

Step D: (4E)-6-fluoro-4-(methyoxymethylidene)-3,4-dihydro-2H-chromene-7-carbonitrile In a 250 ml round bottom flask, (methoxymethyl) (triphenyl)phosphonium chloride (1.3 g, 3.8 mmol) was dissolved in THF (20 mL). The solution was cooled to −78° C. To above solution was added n-butyl lithium (0.49 mL, 2.50 M in Hexane, 1.05 mmol) dropwise. Reaction color changed to orange. The mixture was cooled to −78° C. and to it was added 6-Fluoro-4-oxo-3,4-dihydro-2H-chromene-7-carbonitrile (100 mg, 0.52 mmol). The reaction was let warm to RT and stirred at RT for 18 hours. The reaction was then quenched with addition of saturated ammonium chloride (5 mL) and extracted with dichloromethane. The organic phase was washed with brine (5 mL), dried over anhydrous Na$_2$SO$_4$, filtered, concentrated and purified by flash column chromatography (hexane/EtOAc 0-50%). The desired product was obtained. LC-MS (IE, m/z): 220.3 [M+1]$^+$.

Step E: 6-Fluoro-4-formyl-3,4-dihydro-2H-chromene-7-carbonitrile (4E)-6-fluoro-4-(methyoxymethylidene)-3,4-dihydro-2H-chromene-7-carbonitrile (38 mg, 0.17 mmol) was dissolved in dichloromethane (6 mL). The solution was cooled to −78° C. To above solution was added tribromoborane (260 μL, 1 M, 0.26 mmol) dropwise. The reaction was stirred for 30 min at −78° C. To the reaction mixture was added saturated sodium bicarbonate, extracted with dichloromethane (2×20 mL). The organic phase was washed with brine (5 mL), dried over anhydrous $Na_2SO_4$, filtered, concentrated and used without purification.

Intermediate 30

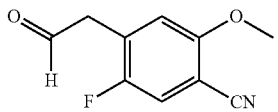

5-Fluoro-2-methoxy-4-(2-oxoethyl)benzonitrile

Step A:
5-fluoro-4-(2-hydroxyethyl)-2-methoxybenzonitrile

To a solution of methyl(4-cyano-2-fluoro-5-methoxyphenyl)acetate (212 mg, 0.95 mmol) in tetrahydrofuran (4 mL) at 0° C. was added lithium borohydride (2.0 M solution in tetrahydrofuran, 0.62 mL). The mixture warmed slowly to room temperature and was quenched with saturated sodium bicarbonate and diluted with ethyl acetate. The layers were separated and the aqueous extracted with ethyl acetate (2×). The combined organics were washed with water and brine, then dried ($Na_2SO_4$), filtered and concentrated. The residue was purified by column chromatography (MPLC, 5-60% Ethyl Acetate:Hexanes) to provide 5-fluoro-4-(2-hydroxyethyl)-2-methoxybenzonitrile. $^1$H-NMR (500 MHz, $CD_3OD$) δ ppm 7.22 (m, 1H), 6.92 (m, 1H), 3.93 (s, 3H), 3.88 (m, 2H), 2.95 (m, 2H), 2.29 (br s, 1H).

Step B:
5-Fluoro-2-methoxy-4-(2-oxoethyl)benzonitrile

To a solution of 5-fluoro-4-(2-hydroxyethyl)-2-methoxybenzonitrile (175 mg, 0.90 mmol) in dichloromethane (4 mL) was added Dess-Martin periodinane (530 mg, 1.3 mmol) at RT. The mixture stirred at room temperature for 2 h, then was diluted with saturated sodium bicarbonate and saturated sodium thiosulfate and stirred 30 min. The mixture was extracted with dichloromethane (3×) and the combined organics dried ($MgSO_4$), filtered and concentrated to provide 5-fluoro-2-methoxy-4-(2-oxoethyl)benzonitrile which was used without further purification. LC-MS (IE, m/z): 194.2 $[M+1]^+$.

Intermediate 31a

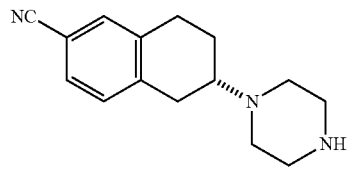 [SMILES: N#Cc1ccc2c(c1)CC[C@H](N1CCNCC1)C2]

(6S)-6-Piperazin-1-yl-5,6,7,8-tetrahydronaphthalene-2-carbonitrile

Step A: tert-butyl[(2S)-6-cyano-1,2,3,4-tetrahydronaphthalen-2-yl]carbamate

A mixture of 6-amino-5,6,7,8-tetrahydronaphthalene-2-carbonitrile (1.0 g, 5.8 mmol, prepared following the procedure published in J. Org. Chem. 1995, 60, 4324-4330) and Boc anhydride in DCM was stirred at RT for 16 hours. The mixture was concentrated and purified by MPLC to furnish 1.14 g of tert-butyl(6-cyano-1,2,3,4-tetrahydronaphthalen-2-yl)carbamate (72% yield). LC-MS (IE, m/z): 273 $[M+1]^+$.

The enantiomers were separated using the AD column with 5% EtOH/heptane. The first peak was assumed as the tert-butyl[(2S)-6-cyano-1,2,3,4-tetrahydronaphthalen-2-yl]carbamate, and the second peak was assumed as the tert-butyl [(2R)-6-cyano-1,2,3,4-tetrahydronaphthalen-2-yl] carbamate.

Step B: (6S)-6-Amino-5,6,7,8-tetrahydronaphthalene-2-carbonitrile

The first peak was treated with TFA for 20 minutes to remove the Boc group. When LC suggested the reaction was done, TFA was removed to afford (6S)-6-amino-5,6,7,8-tetrahydronaphthalene-2-carbonitrile. LC-MS (IE, m/z): 173 $[M+1]^+$.

Step C: (6S)-6-Piperazin-1-yl-5,6,7,8-tetrahydronaphthalene-2-carbonitrile

To a solution of tert-butyl diallylcarbamate (0.63 g, 3.2 mmol) in DCM at −78° C. was bubbled ozone until a blue color persisted. Nitrogen was bubbled through the reaction to remove excess ozone, followed by addition of a DCM solution of (6S)-6-amino-5,6,7,8-tetrahydronaphthalene-2-carbonitrile (0.14 g, 0.80 mmol) and triethylamine (0.22 mL, 1.6 mmol). Then $NaB(OAc)_3H$ (0.85 g, 4.0 mmol) was added to the reaction. The mixture was allowed to warm to RT and stir overnight. LC showed formation of the desired product, which was separated by prep-TLC to furnish 87 mg of tert-butyl 4-[(2S)-6-cyano-1,2,3,4-tetrahydronaphthalen-2-yl] piperazine-1-carboxylate. LC-MS (IE, m/z): 173 $[M+1]^+$. The material was further treated with TFA to afford crude (6S)-6-piperazin-1-yl-5,6,7,8-tetrahydronaphthalene-2-carbonitrile.

Intermediate 31b

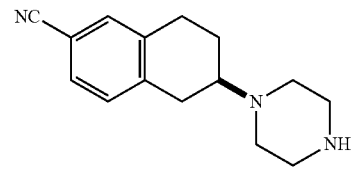 [SMILES: N#Cc1ccc2c(c1)CC[C@@H](N1CCNCC1)C2]

(6R)-6-Piperazin-1-yl-5,6,7,8-tetrahydronaphthalene-2-carbonitrile (6R)-6-piperazin-1-yl-5,6,7,8-tetrahydronaphthalene-2-carbonitrile was prepared following the same procedure as INTERMEDIATE 31a from tert-butyl(6-cyano-1,2,3,4-tetrahydronaphthalen-2-yl)carbamate tert-butyl[(2R)-6-cyano-1,2,3,4-tetrahydronaphthalen-2-yl]carbamate.

Intermediate 32

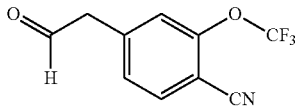 [SMILES: N#Cc1ccc(CC=O)cc1OC(F)(F)F]

4-(2-Oxoethyl)-2-(trifluoromethoxy)benzonitrile

The preparation of the title compound in Step A was based on a literature procedure as found in *Organic Letters*, 2007, 9 (9), 1711-1714.

Step A: Methyl(4-cyano-3-trifluoromethoxyphenyl)acetate

A suspension of methyl(4-chloro-3-trifluoromethoxyphenyl)acetate (4.8 g, 17.8 mmol) in N,N-dimethylacetamide (50 mL) in a 250 mL round bottomed flask was degassed by bubbling nitrogen for 15 minutes. To this suspension was then added zinc dust (0.23 g, 3.55 mmol), DPPF (0.79 g, 1.42 mmol), $Pd_2(dba)_3$ (0.65 g, 0.71 mmol), and $Zn(CN)_2$ (2.50 g, 21.3 mmol) at room temperature. The nitrogen purge was continued for another 15 minutes before the mixture was heated in a 120° C. oil bath for 12 hours. LC-MS indicated that the starting material was consumed to give the product. LC-MS (IE, m/z): 260 [M+1]$^+$. The mixture was partitioned twice between water and ethyl acetate. The organic layers were dried over sodium sulfate, filtered and concentrated in vacuo. The residue was purified on a silica gel column (5-20% ethyl acetate/hexanes) to yield the title product as a yellowish solid. $^1$H-NMR (500 MHz, $CDCl_3$) δ ppm 3.77 (s, 2H), 3.78 (s, 3H), 7.39 (d, J=7.5 Hz, 1H), 7.40 (s, 1H), 7.72 (d, J=7.5 Hz, 1H).

Step B: (4-Cyano-3-trifluoromethoxyphenyl)acetic acid

To a solution of methyl(4-cyano-3-trifluoromethoxyphenyl)acetate (2.15 g, 8.3 mmol) in 1:1 THF:MeOH (10 mL each) was added LiOH—$H_2O$ (0.42 g, 10.0 mmol) in water (30 mL). The reaction mixture was stirred at room temperature for 12 hours at which time the starting ester was consumed by TLC (25% ethyl acetate/hexanes). The mixture was concentrated in vacuo and acidified to pH<3 by dropwise addition of 12N HCl. The acidified solution was then extracted with ethyl acetate, dried over sodium sulfate and concentrated in vacuo to yield the crude title product. LC-MS (IE, m/z): 246 [M+1]$^+$. $^1$H-NMR (500 MHz, $CDCl_3$) δ ppm 3.81 (s, 2H), 7.39 (d, J=7.5 Hz, 1H), 7.40 (s, 1H), 7.75 (d, J=7.5 Hz, 1H).

Step C: 4-(2-Hydroxethyl)-2-(trifluoromethoxy)benzonitrile

A suspension of (4-cyano-3-trifluoromethoxyphenyl)acetic acid (200 mg, 0.82 mmol) in THF (8 mL) was treated with borane dimethyl sulfide complex (2M, 0.41 mL, 0.82 mmol) and the reaction was stirred overnight at room temperature. The reaction was not complete after 20 hours, so an additional aliquot of borane dimethyl sulfide complex (2M, 0.41 mL, 0.82 mmol) was added. After stirring for another 1 hour at room temperature, the reaction was quenched with methanol and the mixture was partitioned with ethyl acetate and 2N HCl/water. The aqueous was extracted again with ethyl acetate and the organic layers were washed with brine, dried over sodium sulfate and evaporated. The residue was purified on a CombiFlash Rf (12 gm, gradient 10-80% ethyl acetate in hexanes) to afford the title alcohol (142 mg) as an oil. $^1$H-NMR (500 MHz, $CDCl_3$) δ ppm 1.62 (s, 1H), 2.971 (t, J=6.4 Hz, 2H), 3.936 (t, J=6.4 Hz, 2H), 7.315 (s, 1H), 7.322 (d, J=8.5 Hz, 1H), 7.660 (d, J=8.5 Hz, 1H).

Step D: 4-(2-Oxoethyl)-2-(trifluoromethoxy)benzonitrile

A solution of 4-(2-hydroxethyl)-2-(trifluoromethoxy)benzonitrile (140 mg, 0.61 mmol) in DCM (3 mL) was treated with Dess-Martin periodinane (360 mg, 0.85 mmol) and was stirred at room temperature for 1.5 hours. MS/LC showed mostly aldehyde product by UV (no M+1 detected in the MS) and a small amount of alcohol. After a total of 2.25 hours the reaction was quenched by partitioning with DCM and water containing sodium bicarbonate and sodium thiosulfate (3×). The organic layer was then washed with brine, dried over sodium sulfate and evaporated to give crude title aldehyde as an oil which was used directly in subsequent reductive amination reactions.

Intermediate 33

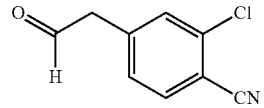 [SMILES: N#Cc1ccc(CC=O)cc1Cl]

2-Chloro-4-(2-oxoethyl)benzonitrile

Step A: 2-Chloro-4-(2-hydroxethyl)benzonitrile

A suspension of (3-chloro-4-cyanophenyl)acetic acid (200 mg, 1.02 mmol) in THF (8 mL) was treated with borane dimethyl sulfide complex (2M, 0.5 mL, 1.0 mmol) and the reaction was stirred overnight at room temperature. The reaction was not complete after 20 hours, so an additional aliquot of borane dimethyl sulfide complex (2M, 0.5 mL, 1.0 mmol) was added. After stirring for another 1 hour at room temperature, the reaction was quenched with methanol and the mixture was partitioned with ethyl acetate and 2N HCl/water. The aqueous layer was extracted again with ethyl acetate and the organic layers were washed with brine, dried over sodium sulfate and evaporated. The residue (199 mg) was purified on a CombiFlash Rf (12 gm, gradient 10-80% ethyl acetate in hexanes) to afford the title alcohol as an oil. $^1$H-NMR (500 MHz, $CDCl_3$) δ ppm 1.62 (s, 1H), 2.925 (t, J=6.4 Hz, 2H), 3.92 (t, J=6.4 Hz, 2H), 7.27 (d, J=7.5 Hz, 1H), 7.44 (s, 1H), 7.62 (d, J=8.1 Hz, 1H).

Step B: 2-Chloro-4-(2-oxoethyl)benzonitrile

A solution of 2-chloro-4-(2-hydroxethyl)benzonitrile (160 mg, 0.88 mmol) in DCM (3 mL) was treated with Dess-Martin periodinane (520 mg, 1.2 mmol) and was stirred at room temperature for 1.5 hours. LC-MS showed an aldehyde peak by UV (no M+1 detected in the MS) and a small amount of alcohol starting material. After a total of 2.25 hours the reaction was quenched by partitioning with DCM and water containing sodium bicarbonate and sodium thiosulfate (3×).

The organic layer was then washed with brine, dried over sodium sulfate and evaporated to give crude title aldehyde as an oil which was used directly in subsequent reductive amination reactions.

Intermediate 34

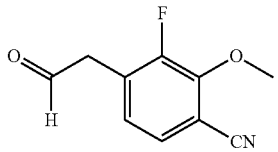

3-Fluoro-2-methoxy-4-(2-oxoethyl)benzonitrile

Step A:
3-Fluoro-2-methoxy-4-(2-hydroxethyl)benzonitrile

A suspension of (4-cyano-2-fluoro-3-methoxyphenyl)acetic acid (200 mg, 0.96 mmol) in THF (8 mL) was treated with borane dimethyl sulfide complex (2M, 0.96 mL, 1.9 mmol) and the reaction was stirred for 3 hours at room temperature. The reaction was quenched with methanol and the mixture was partitioned with ethyl acetate and 2N HCl/water. The aqueous was extracted again with ethyl acetate and the organic layers were washed with brine, dried over sodium sulfate and evaporated. The residue was purified on a CombiFlash Rf (12 gm, gradient 10-80% ethyl acetate in hexanes) to afford the title alcohol as an oil. LC-MS (IE, m/z): 196 [M+1]. $^1$H-NMR (500 MHz, CDCl$_3$) δ ppm 1.60 (br s, 1H), 2.891 (t, J=6.4 Hz, 2H), 3.834 (t, J=6.4 Hz, 2H), 4.055 (s, 3H), 6.952 (t, J=8.1 Hz, 1H), 7.62 (d, J=8.1 Hz, 1H).

Step B:
3-Fluoro-2-methoxy-4-(2-oxoethyl)benzonitrile

A solution of 3-fluoro-2-methoxy-4-(2-hydroxethyl)benzonitrile (60 mg, 0.31 mmol) in DCM (5 mL) was treated with Dess-Martin periodinane (183 mg, 0.43 mmol) and was stirred at room temperature for 2.5 hours. LC-MS showed the aldehyde product peak by UV (no M+1 detected in the MS) and a small amount of starting material alcohol. The reaction was quenched by partitioning with DCM and water containing sodium bicarbonate and sodium thiosulfate (3×). The organic layer was then washed with brine, dried over sodium sulfate and evaporated to give crude title aldehyde as an oil which was used directly in subsequent reductive amination reactions.

Intermediate 35

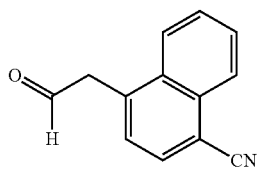 [SMILES: N#Cc1ccc(CC=O)c2ccccc12]

4-(2-Oxoethyl)naphthalene-1-carbonitrile

Step A:
4-(2-hydroxyethyl)naphthalene-1-carbonitrile

A suspension of (4-cyanonaphthalen-1-yl)acetic acid (100 mg, 0.47 mmol) in THF (6 mL) was treated with borane dimethyl sulfide complex (2M, 0.47 mL, 0.94 mmol) and the reaction was stirred for 3 hours at room temperature. The reaction was quenched with methanol and the mixture was partitioned with ethyl acetate and 2N HCl/water. The aqueous was extracted again with ethyl acetate and the organic layers were washed with brine, dried over sodium sulfate and evaporated. The residue was purified on a CombiFlash Rf (12 gm, gradient 10-80% ethyl acetate in hexanes) to afford the title alcohol as an oil. $^1$H-NMR (500 MHz, CDCl$_3$) δ ppm 1.80 (br s, 1H), 3.48 (t, J=6.4 Hz, 2H), 4.10 (t, J=6.4 Hz, 2H), 7.52 (d, J=7.3 Hz, 1H), 7.75 (m, 2H), 7.92 (d, J=7.2 Hz, 1H), 8.22 (d, J=8.2 Hz, 1H). 8.34 (d, J=8.0 Hz, 1H).

Step B: 4-(2-Oxoethyl)naphthalene-1-carbonitrile

A solution of 4-(2-hydroxyethyl)naphthalene-1-carbonitrile (25 mg, 0.13 mmol) in DCM (4 mL) was treated with Dess-Martin periodinane (75 mg, 0.18 mmol) and was stirred at room temperature for 3 hours. The reaction was quenched by partitioning with DCM and water containing sodium bicarbonate and sodium thiosulfate (3×). The organic layer was then washed with brine, dried over sodium sulfate and evaporated to give the title aldehyde as an oil which was used directly in subsequent reductive amination reaction.

Intermediate 36

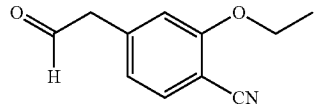

2-Ethoxy-4-(2-oxoethyl)benzonitrile

Step A: 2-(Ethoxy)-4-(2-hydroxethyl)benzonitrile

A suspension of (4-cyano-3-ethoxyphenyl)acetic acid (100 mg, 0.49 mmol) in THF (5 mL) was treated with borane dimethyl sulfide complex (2M, 0.49 mL, 0.98 mmol) and the reaction was stirred 1 hour at room temperature. The reaction was not complete, so an additional aliquot of borane dimethyl sulfide complex (2M, 0.49 mL, 0.98 mmol) was added. After stirring for another 1 hour at room temperature, the reaction was quenched with methanol and the mixture was partitioned with ethyl acetate and 2N HCl/water. The aqueous was extracted again with ethyl acetate and the organic layers were washed with brine, dried over sodium sulfate and evaporated. The residue was purified on a silica gel column (gradient 20-50% ethyl acetate in hexanes) to afford the title alcohol as an oil. $^1$H-NMR (500 MHz, CDCl$_3$) δ ppm 1.451 (t, J=7.0 Hz, 3H), 1.76 (br s, 1H), 2.865 (t, J=6.3 Hz, 2H), 3.863 (t, J=6.3 Hz, 2H), 4.127 (q, J=7.0 Hz, 2H), 6.814 (s, 1H), 6.841 (d, J=7.9 Hz, 1H), 7.449 (d, J=7.7 Hz, 1H).

Step B: 2-(Ethoxy)4-(2-oxoethyl)-benzonitrile

A solution of 2-(ethoxy)-4-(2-hydroxethyl)benzonitrile (56 mg, 0.29 mmol) in DCM (5 mL) was treated with Dess- Martin periodinane (250 mg, 0.59 mmol) and was stirred at room temperature for 2.5 hours. The reaction was quenched by partitioning with DCM and water containing sodium bicarbonate and sodium thiosulfate (3×). The organic layer was then washed with brine, dried over sodium sulfate and evaporated to give the title aldehyde as an oil which was used directly in subsequent reductive amination reactions.

Intermediate 37

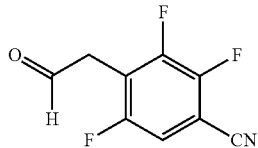 [SMILES: N#Cc1cc(F)c(CC=O)c(F)c1F]

4-(2-Oxo ethyl)-2,3,5-trifluorobenzonitrile

Step A: 4-(2-Hydroxethyl)-2,3,5-trifluorobenzonitrile

A suspension of (4-cyano-2,3,6-trifluorophenyl)acetic acid (140 mg, 0.65 mmol) in THF (8 mL) was treated with borane dimethyl sulfide complex (2M, 0.65 mL, 1.30 mmol) and the reaction was stirred for 3 hours at room temperature. The reaction was quenched with methanol and the mixture was partitioned with ethyl acetate and 2N HCl/water. The aqueous was extracted again with ethyl acetate and the organic layers were washed with brine, dried over sodium sulfate and evaporated. The residue was purified on a silica gel column (gradient 30-50% ethyl acetate in hexanes) to afford the title alcohol as an oil. $^1$H-NMR (500 MHz, CDCl$_3$) δ ppm 1.50 (br s, 1H), 2.959 (t, J=6.5 Hz, 2H), 3.820 (t, J=6.5 Hz, 2H), 7.064 (br t, 1H).

Step B: 4-(2-Oxo ethyl)-2,3,5-trifluorobenzonitrile

A solution of 4-(2-hydroxethyl)-2,3,5-trifluorobenzonitrile (44 mg, 0.22 mmol) in DCM (5 mL) was treated with Dess-Martin periodinane (186 mg, 0.44 mmol) and was stirred at room temperature for 1.5 hours when another aliquot of periodinane (50 mg) was added. After 2.5 hours, the reaction was quenched by partitioning with DCM and water containing sodium bicarbonate and sodium sulfite (3×). The organic layer was then washed with brine, dried over sodium thiosulfate and evaporated to give the title aldehyde as an oil which was used directly in subsequent reductive amination reactions.

Intermediate 38

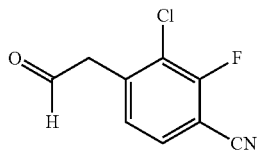 [SMILES: N#Cc1ccc(CC=O)c(Cl)c1F]

3-Chloro-2-fluoro-4-(2-oxoethyl)benzonitrile

Step A: tert-Butyl methyl(2-chloro-4-cyano-3-fluorophenyl)malonate tert-Butyl methyl malonate (7.5 g, 43 mmol) in anhydrous DMF (50 mL) under nitrogen was cooled in an ice bath. Sodium hydride (60% in mineral oil, 1.00 g, 42 mmol) was added portionwise over 5 minutes. The reaction was allowed to warm to room temperature for 30 minutes at which time all was in solution and hydrogen gas had ceased. To the solution was then added 2,4-difluoro-3-chlorobenonitrile (5.0 g, 29 mmol) as a solid in one portion. The reaction was heated in a 90° C. oil bath for 4 hours and then stirred at room temperature for 16 hours. The reaction was quenched by addition of 2N HCl in water. The mixture was partitioned with ether (2×), and the organic layers were washed with brine, dried over sodium sulfate and evaporated in vacuo. TLC (15% ethyl acetate/hexanes) indicated a small amount of di-fluoro starting material, but mostly the desired product and excess malonate. The crude residue was purified by flash chromatography (5-10% % ethyl acetate/hexanes to elute excess malonate and starting material, then 10-20% ethyl acetate/hexanes for products). The first product fractions were a mixture with some of the minor t-butyl methyl(2-chloro-6-cyano-3-fluorophenyl)malonate side product isomer (900 mg, mostly desired title product by NMR), then later fractions were clean desired title isomer. $^1$H-NMR (500 MHz, CDCl$_3$) δ ppm 1.464 (s, 9H), 3.793 (s, 3H), 5.145 (s, 1H), 7.448 (d, J=8.3 Hz, 1H), 7.560 (dd, J=6.2 and 8.3 Hz, 1H).

Step B: Methyl(2-chloro-4-cyano-3-fluorophenyl)acetate

To a solution of t-butyl methyl(2-chloro-4-cyano-3-fluorophenyl)malonate (4.8 g, 15 mmol) in DCM (50 mL) was added TFA (50 mL) at room temperature and the mixture was aged for 20 hours. LC-MS and TLC (20% ethyl acetate/hexanes) indicated lack of starting malonate diester, but still some mono-acid/mono-ester intermediate. The volatiles were removed in vacuo and the residue was taken up in methanol and heated to reflux for 1 hour. The volatiles were again removed in vacuo and the residue was purified on a CombiFlash Rf (40 gm, 10-40% ethyl acetate/hexanes) to give several main fractions of clean title product by NMR. $^1$H-NMR (500 MHz, CDCl$_3$) δ ppm 3.734 (s, 3H), 3.860 (s, 2H), 7.234 (d, J=8.0 Hz, 1H), 7.512 (dd, J=6.1 and 8.0 Hz, 1H).

Step C: (3-Chloro-2-fluoro-4-(2-hydroxyethyl)benzonitrile

A suspension of methyl(2-chloro-4-cyano-3-fluorophenyl)acetate (400 mg, 1.8 mmol) in THF (5 mL) was treated with lithium borohydride solution in THF (2M, 1.1 mL, 2.2 mmol) and the reaction was stirred overnight at room temperature. The reaction was quenched with 2N HCl and the mixture was partitioned with ethyl acetate and water. The aqueous was extracted again with ethyl acetate and the organic layers were washed with brine, dried over sodium sulfate and evaporated. The residue was purified on a CombiFlash Rf (24 gm, gradient 10-40% ethyl acetate in hexanes) to afford the title alcohol. $^1$H-NMR (500 MHz, CDCl$_3$) δ ppm 1.66 (br s, 1H), 3.088 (t, J=6.4 Hz, 2H), 3.922 (t, J=6.4 Hz, 2H), 7.242 (d, J=8.1 Hz, 1H), 7.469 (dd, J=6.5 and 8.1 Hz, 1H).

Step D:
(3-Chloro-2-fluoro-4-(2-oxoethyl)benzonitrile

A solution of 3-chloro-2-fluoro-4-(2-hydroxethyl)benzonitrile (62 mg, 0.31 mmol) in DCM (6 mL) was treated with Dess-Martin periodinane (263 mg, 0.621 mmol) and was stirred at room temperature for 2 hours. The reaction was quenched by stirring with water containing sodium bicarbonate and sodium sulfite for 30 minutes. The mixture was extracted twice with DCM and the organic layers were washed with brine, dried over sodium sulfate and evaporated to give the crude title aldehyde which was used directly in subsequent reductive amination reactions. NMR of the crude mixture indicated a mixture of aldehyde and some periodinane by-product. $^1$H-NMR (500 MHz, CDCl$_3$) δ ppm 4.032 (s, 2H), 7.190 (d, J=8.0 Hz, 1H), 7.571 (d, J=8.1 Hz, 1H), 9.820 (s, 1H).

Intermediate 39

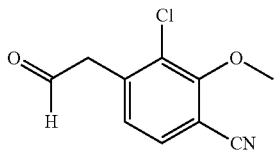

(3-Chloro-2-methoxy-4-(2-oxoethyl)benzonitrile

Step A:
Methyl(2-chloro-4-cyano-3-methoxyphenyl)acetate

A solution of methyl(2-chloro-4-cyano-3-fluorophenyl)acetate (1.40 g, 6.2 mmol) from example XX, Step B, was divided into 2 reactions in 2×20 mL Micro Wave (MW) vials, potassium carbonate (0.85 g, 6.2 mmol each vial) and MeOH (15 mL each vial) were added. Each reaction was heated at 130° C. for 60 minutes. The reactions were combined and concentrated, the residue was diluted with water, acidified with 2M HCl and extracted 2× with ethyl acetate, and the organic layers were washed with brine, dried over sodium sulfate and evaporated in vacuo. The residue was taken up in 1:1 MeOH:DCM (40 mL) and excess 2M trimethylsilyldiazomethane in ether was added until the yellow color persisted, the excess was quenched with acetic acid and the solution was concentrated in vacuo. Flash chromatography (40% DCM/hexanes to 100% DCM) gave the title ester. $^1$H-NMR (500 MHz, CDCl$_3$) δ ppm 3.724 (s, 3H), 3.829 (s, 2H), 4.069 (s, 3H), 7.139 (d, J=8.0 Hz, 1H), 7.465 (d, J=8.0 Hz, 1H).

Step B:
3-Chloro-4-(2-hydroxethyl)-2-methoxybenzonitrile

A suspension of methyl(2-chloro-4-cyano-3-methoxyphenyl)acetate (700 mg, 2.9 mmol) in THF (15 mL) was treated with lithium borohydride solution in THF (2M, 1.46 mL, 2.9 mmol) and the reaction was stirred overnight at room temperature. The reaction was quenched with 2N HCl and the mixture was partitioned with ethyl acetate and water. The aqueous layer was extracted again with ethyl acetate and the organic layers were washed with brine, dried over sodium sulfate and evaporated. The residue was purified on a silica gel column (gradient 10-40% ethyl acetate in hexanes) to afford the title alcohol as a white solid. LC-MS (IE, m/z): 212 [M+1]$^+$. $^1$H-NMR (500 MHz, CDCl$_3$) δ ppm 1.58 (br s, 1H), 3.096 (t, J=6.5 Hz, 2H), 3.943 (t, J=6.4 Hz, 2H), 4.083 (s, 3H), 7.175 (d, J=7.8 Hz, 1H), 7.462 (d, J=8.0 Hz, 1H).

Step C:
3-Chloro-2-methoxy-4-(2-oxoethyl)benzonitrile

A solution of 3-chloro-2-methoxy-4-(2-hydroxethyl)benzonitrile (80 mg, 0.38 mmol) in DCM (6 mL) was treated with Dess-Martin periodinane (320 mg, 0.76 mmol) and was stirred at room temperature for 2.5 hours. LC-MS showed an aldehyde peak by UV (no M+1 detected in the MS) and a small amount of alcohol. The reaction was quenched by partitioning with DCM and water containing sodium bicarbonate and sodium thiosulfate (3×). The organic layer was then washed with brine, dried over sodium sulfate and evaporated to give crude title aldehyde as an oil which was used directly in subsequent reductive amination reactions. NMR of the crude mixture indicated a mixture of aldehyde and periodinane by-product. $^1$H-NMR (500 MHz, CDCl$_3$) δ ppm 3.976 (s, 2H), 4.101 (s, 3H), 7.112 (d, J=8.0 Hz, 1H), 7.513 (d, J=8.0 Hz, 1H), 9.798 (s, 1H).

Intermediate 40

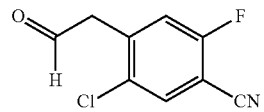 [SMILES: N#Cc1cc(Cl)c(CC=O)cc1F]

5-Chloro-2-fluoro-4-(2-oxoethyl)benzonitrile

Step A:
5-Chloro-2-fluoro-4-(2-hydroxethyl)benzonitrile

A suspension of methyl(2-chloro-4-cyano-5-fluorophenyl)acetate (250 mg, 1.10 mmol) (prepared from 5-chloro-2,4-difluorobenzonitrile as in Intermediate 39) in THF (7 mL) was treated with lithium borohydride solution in THF (2M, 1.1 mL, 2.2 mmol) and the reaction was stirred overnight at room temperature. The reaction was nearly complete after 20 hours by LC-MS from the UV trace. The reaction was quenched 2N HCl and the mixture was partitioned with ethyl acetate and water. The aqueous layer was extracted again with ethyl acetate and the organic layers were washed with brine, dried over sodium sulfate and evaporated. The residue was purified on a CombiFlash Rf (12 gm, gradient 10-20% ethyl acetate in hexanes with 5% DCM for solubility) to afford the title alcohol as an oil. $^1$H-NMR (500 MHz, CDCl$_3$) δ ppm 1.45 (br s, 1H), 3.01 (t, J=6.4 Hz, 2H), 3.92 (t, J=6.4 Hz, 2H), 7.218 (d, J=9.3 Hz, 1H), 7.581 (d, J=5.7 Hz, 1H).

Step B: 5-Chloro-2-fluoro-4-(2-oxoethyl)benzonitrile

A solution of 5-chloro-2-fluoro-4-(2-hydroxethyl)benzonitrile (85 mg, 0.88 mmol) in DCM (5 mL) was treated with Dess-Martin periodinane (360 mg, 0.85 mmol) and was stirred at room temperature for 2.5 hours. The reaction was quenched by partitioning with DCM and water containing sodium bicarbonate and sodium thiosulfate (3×). The organic layer was then washed with brine, dried over sodium sulfate and evaporated to give crude title aldehyde as an oil which was used directly in subsequent reductive amination reactions. NMR of the crude product indicated a mixture of aldehyde and still some periodinane by-product. ¹H-NMR (500 MHz, CDCl₃) δ ppm 3.967 (s, 2H), 7.172 (d, J=8.7 Hz, 1H), 7.693 (d, J=5.7 Hz, 1H), 9.802 (s, 1H).

Intermediate 41

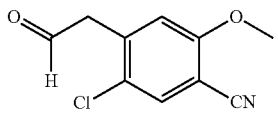

(5-Chloro-2-methoxy-4-(2-oxoethyl)benzonitrile

Step A: (2-Chloro-4-cyano-5-methoxyphenyl)acetic acid

To a solution of methyl(2-chloro-4-cyano-5-fluorophenyl)acetate (0.55 g, 2.4 mmol), which was prepared as in the synthesis of Intermediate 40, in MeOH (15 mL) in a 20 mL MW vial was added potassium carbonate (1.00 g, 7.2 mmol). The reaction was heated at 130° C. for 45 minutes. The reaction was then concentrated, the residue was diluted with water, acidified with 2M HCl and extracted 2× with ethyl acetate, and the organic layers were washed with brine, dried over sodium sulfate and evaporated in vacuo. Flash chromatography (10-50% ethyl acetate/hexanes with 1% HOAc) gave the title acid as a white solid. ¹H-NMR (500 MHz, CDCl₃) δ ppm 3.77 (s, 2H), 3.90 (s, 3H), 6.90 (s, 1H), 7.53 (s, 1H).

Step B: Methyl(2-chloro-4-cyano-5-methoxyphenyl)acetate (2-Chloro-4-cyano-5-methoxyphenyl)acetic acid (545 mg, 2.4 mmol) was taken up in 1:1 MeOH:DCM (50 mL) and excess 2M trimethylsilyldiazomethane in ether was added until the yellow color persisted, the excess was quenched with acetic acid and the solution was concentrated in vacuo. Flash chromatography (10-50% ethyl acetate/hexanes) gave the title ester as a white solid. ¹H-NMR (500 MHz, CDCl₃) δ ppm 3.703 (s, 3H), 3.767 (s, 2H), 3.897 (s, 3H), 6.896 (s, 1H), 7.526 (s, 1H).

Step C: 5-Chloro-4-(2-hydroxyethyl)-2-methoxybenzonitrile

A suspension of methyl(2-chloro-4-cyano-5-methoxyphenyl)acetate (200 mg, 2.9 mmol) in THF (15 mL) was treated with lithium borohydride solution in THF (2M, 1.46 mL, 2.9 mmol) and the reaction was stirred overnight at room temperature. The reaction was quenched with 2N HCl and the mixture was partitioned with ethyl acetate and water. The aqueous layer was extracted again with ethyl acetate and the organic layers were washed with brine, dried over sodium sulfate and evaporated. The residue was purified on a silica gel column (gradient 10-40% ethyl acetate in hexanes) to afford the title alcohol as a white solid. ¹H-NMR (500 MHz, CDCl₃) δ ppm 1.558 (br s, 1H), 3.035 (t, J=6.5 Hz, 2H), 3.927 (t, J=6.4 Hz, 2H), 3.927 (s, 3H), 6.927 (s, 1H), 7.536 (s, 1H).

Step D: 5-Chloro-2-methoxy-4-(2-oxoethyl)benzonitrile

A solution of 5-chloro-2-methoxy-4-(2-hydroxethyl)benzonitrile (60 mg, 0.33 mmol) in DCM (6 mL) was treated with Dess-Martin periodinane (281 mg, 0.66 mmol) and was stirred at room temperature for 2.5 hours. The reaction was quenched by partitioning with DCM and water containing sodium bicarbonate and sodium thiosulfate (3×). The organic layer was then washed with brine, dried over sodium sulfate and evaporated to give crude title aldehyde as an oil which was used directly in subsequent reductive amination reactions. NMR of the crude mixture indicated a mixture of aldehyde and periodinane by-product. ¹H-NMR (500 MHz, CDCl₃) δ ppm 3.951 (s, 2H), 3.958 (s, 3H), 6.880 (s, 1H), 7.625 (s, 1H), 9.810 (s, 1H).

Intermediate 42

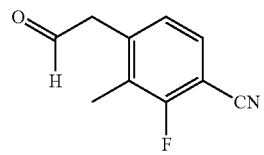

2-Fluoro-3-methyl-4-(2-oxoethyl)benzonitrile

Step A: t-Butyl methyl(4-cyano-3-fluoro-2-methylphenyl)malonate t-Butyl methyl malonate (0.71 g, 4.1 mmol) in anhydrous DMF (20 mL) under nitrogen was cooled in an ice bath. Sodium hydride (60% in mineral oil, 176 mg, 7.4 mmol) was added portionwise over 5 minutes. The reaction was allowed to warm to room temperature for 30 minutes at which time all was in solution and hydrogen gas had ceased. To the solution was then added 2,4-difluoro-3-methylbenonitrile (0.500 g, 3.3 mmol) as a solid in one portion. The reaction was heated in a 95° C. oil bath for 5 hours and then stirred at room temperature for 16 hours. The reaction was quenched by addition of 2N HCl in water. The mixture was portioned with ether (2×), and the organic layers were washed with brine, dried over sodium sulfate and evaporated in vacuo. TLC (10% ethyl acetate/hexanes) indicated a small amount of di-fluoro starting material, major desired product plus some minor isomer (slightly higher Rf) and excess malonate. The crude residue was purified by FC (5-7% to elute excess malonate, starting material and minor isomer, then 10-15% ethyl acetate/hexanes to elute the product) to afford several clean product fractions. ¹H-NMR (500 MHz, CDCl₃) δ ppm 1.371 (s, 9H), 2.200 (s, 3H), 3.692 (s, 3H), 4.725 (s, 1H), 7.237 (d, J=8.2 Hz, 1H), 7.389 (br t, J=7.3 Hz, 1H).

Step B: Methyl(4-cyano-3-fluoro-2-methylphenyl)acetate

To a solution of tert-Butyl methyl(4-cyano-3-fluoro-2-methylphenyl)malonate (0.75 g, 2.4 mmol) in DCM (10 mL) was added TFA (10 mL) at room temperature and the mixture was aged for 3 hours. LC-MS and TLC (15% ethyl acetate/hexanes) indicated the lack of starting diester, but still some mono-acid/mono-ester intermediate. The volatiles were removed in vacuo and the residue was taken up in dioxane with a few drops of acetic acid and heated to reflux for 1 hour. The volatiles were again removed in vacuo and the residue was purified by flash chromatography (5-15% ethyl acetate/hexanes) to give several main fractions of clean title ester product. $^1$H-NMR (500 MHz, CDCl$_3$) δ ppm 2.254 (s, 3H), 3.709 (s, 5H), 7.102 (d, J=8.0 Hz, 1H), 7.414 (br t, J=7.3 Hz, 1H).

Step C:
2-Fluoro-3-methyl-4-(2-hydroxethyl)benzonitrile

A suspension of methyl(4-cyano-3-fluoro-2-methylphenyl)acetate (170 mg, 0.82 mmol) in THF (3 mL) was treated with lithium borohydride solution in THF (2M, 0.82 mL, 1.6 mmol) and the reaction was stirred overnight at room temperature. The reaction was quenched with 2N HCl and the mixture was partitioned with ethyl acetate and water. The aqueous was extracted again with ethyl acetate and the organic layers were washed with brine, dried over sodium sulfate and evaporated. The residue was purified on a silica gel column (gradient 10-40% ethyl acetate in hexanes) to afford the title alcohol as an oil. $^1$H-NMR (500 MHz, CDCl$_3$) δ ppm 1.88 (br s, 1H), 2.303 (s, 3H), 2.971 (t, J=6.6 Hz, 2H), 3.886 (t, J=6.6 Hz, 2H), 7.129 (d, J=8.0 Hz, 1H), 7.403 (br t, J=7.5 Hz, 1H).

Step D:
2-Fluoro-3-methyl-4-(2-oxoethyl)benzonitrile

A solution of 2-fluoro-3-methyl-4-(2-hydroxyethyl)benzonitrile (66 mg, 0.37 mmol) in DCM (5 mL) was treated with Dess-Martin periodinane (312 mg, 0.74 mmol) and was stirred at room temperature for 2.5 hours. The reaction was quenched by partitioning with DCM and water containing sodium bicarbonate and sodium thiosulfate. The organic layer was then washed with brine, dried over sodium sulfate and evaporated to give crude title aldehyde as an oil which was used directly in subsequent reductive amination reactions. NMR of the crude product indicated a mixture of aldehyde and still some periodinane by-product. $^1$H-NMR (500 MHz, CDCl$_3$) δ ppm 2.210 (s, 3H), 3.846 (s, 2H), 7.054 (d, J=8.0 Hz, 1H), 7.449 (br t, J=8.0 Hz, 1H), 9.757 (s, 1H).

Intermediate 43

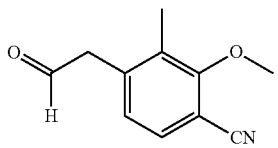

(2-Methoxy-3-methyl-4-(2-oxoethyl)benzonitrile

Step A:
Methyl(4-cyano-3-methoxy-2-methylphenyl)acetate

A solution of methyl(4-cyano-3-fluoro-2-methylphenyl)acetate (0.38 g, 1.8 mmol) from the Example 42, Step B, was taken up in methanol (6 mL), potassium carbonate (0.51 g, 3.7 mmol) was added and the reaction was heated at 135° C. for 2.5 hours (not complete after 1 hour). The reaction was concentrated, the residue was diluted with water and extracted 2× with ethyl acetate, and the organic layers were washed with brine, dried over sodium sulfate and evaporated in vacuo. Flash chromatography (5-10% ethyl acetate/hexanes) still gave a mixture so repeated chromatography (25-100% DCM in hexanes) gave clean title ester (220 mg). $^1$H-NMR (500 MHz, CDCl$_3$) δ ppm 2.22 (s, 3H), 3.68 (s, 2H), 3.70 (s, 3H), 3.97 (s, 3H), 7.04 (d, J=8.0 Hz, 1H), 7.39 (d, J=8.0 Hz, 1H).

Step B:
4-(2-Hydroxethyl)-2-methoxy-3-methylbenzonitrile

A suspension of methyl(4-cyano-3-methoxy-2-methylphenyl)acetate (175 mg, 0.80 mmol) in THF (5 mL) was treated with lithium borohydride solution in THF (2M, 0.79 mL, 1.6 mmol) and the reaction was stirred overnight at room temperature. The reaction was quenched with 2N HCl and the mixture was partitioned with ethyl acetate and water. The aqueous layer was extracted again with ethyl acetate and the organic layers were washed with brine, dried over sodium sulfate and evaporated. The residue was purified on a silica gel column (gradient 10-15% ethyl acetate in hexanes to elute some remaining starting material, then 15-25% to elute the product) to afford the title alcohol. $^1$H-NMR (500 MHz, CDCl$_3$) δ ppm 1.57 (br s, 1H), 2.266 (s, 3H), 2.931 (t, J=6.8 Hz, 2H), 3.860 (t, J=6.8 Hz, 2H), 3.961 (s, 3H), 7.030 (d, J=8.1 Hz, 1H), 7.374 (d, J=8.1 Hz, 1H).

Step C:
2-Methoxy-3-methyl-4-(2-oxoethyl)benzonitrile

A solution of 2-methoxy-3-methyl-4-(2-hydroxyethyl)benzonitrile (60 mg, 0.31 mmol) in DCM (5 mL) was treated with Dess-Martin periodinane (266 mg, 0.63 mmol) and was stirred at room temperature for 2 hours. MS/LC showed an aldehyde peak by UV (no M+1 detected in the MS) and no alcohol. The reaction was quenched by partitioning with DCM and water containing sodium bicarbonate and sodium thiosulfate. The organic layer was then washed with brine, dried over sodium sulfate and evaporated to give crude title aldehyde as an oil which was used directly in subsequent reductive amination reactions. LC-MS of the crude mixture (72 mg) indicated a mixture of aldehyde and a trace of periodinane by-product.

Intermediate 44

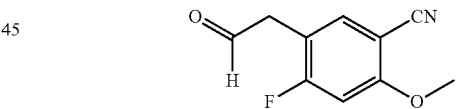

4-Fluoro-2-methoxy-5-(2-oxoethyl)benzonitrile

Step A: 4-Fluoro-5-iodo-2-methoxybenzonitrile

To 4-fluoro-2-methoxybenzonitrile (3.00 g, 20 mmol) and N-iodosuccinimide (NIS) (4.7 g, 21 mmol) under nitrogen was added TFA (35 mL) and the reaction was stirred at room temperature for 20 hours. The volatiles were removed in vacuo and the residue was taken up in 1:1 ethyl acetate:ether and was washed with aqueous sodium bicarbonate and then brine containing enough sodium sulfite to remove the iodine color. The aqueous layers were back extracted with more 1:1 ethyl acetate:ether and the combined organic layers were dried over sodium sulfate and evaporated. The residue was treated with ether/hexanes to afford clean iodo title product as a white solid. $^1$H-NMR (500 MHz, CDCl$_3$) δ ppm 3.930 (s, 3H), 6.730 (d, J=9.4 Hz, 1H), 7.900 (d, J=6.8 Hz, 1H).

Step B: 4-Fluoro-2-methoxy-5-(prop-2-en-1-yl)benzonitrile

To a mixture of 4-fluoro-5-iodo-2-methoxybenzonitrile (2.5 g, 9.0 mmol), Pd(Ph$_3$P)$_4$ (1.0 g, 0.90 mmol) and lithium chloride (0.96 g, 23 mmol) under nitrogen was added anhydrous toluene (50 mL) and the mixture was flushed (3×) with nitrogen. Allyltributyltin (4.15 mL, 14 mmol) was added and the mixture was flushed again with nitrogen. The reaction was heated under nitrogen at 115° C. for 2.5 hours and then let cool to room temperature. TLC (10% ethyl acetate/Hexanes) showed several spots with a strongly charring product spot right above the starting material. The reaction was diluted with hexanes and filtered to remove insoluble material. The mother liquor was concentrated and the residue was purified on a Biotage 65+M column with a gradient elution from 0 to 40% ethyl acetate in hexanes to afford the title product which had some residual tributylstanane by-product contaminant by NMR. $^1$H-NMR (500 MHz, CDCl$_3$) δ ppm 3.327 (d, J=6.5 Hz, 2H), 3.902 (s, 3H), 5.102 (2 d, J=10.0 and 17 Hz, 2H), 5.868 (m, 1H), 6.668 (d, J=11.1 Hz, 1H), 7.390 (d, J=8.0 Hz, 1H).

Step C: 4-Fluoro-5-(2-hydroxyethyl)-2-methoxybenzonitrile

A solution of 4-fluoro-2-methoxy-5-(prop-2-en-1-yl)benzonitrile (1.2 g, 6.0 mmol) in methanol (50 mL) was cooled in a dry ice acetone bath and treated with ozone. Since the starting material was contaminated with some tributylstanane residue from the previous reaction, the reaction turned brown at first. The mixture was flushed with nitrogen and quenched with dimethylsulfide (4 mL). The solution was allow to warm to about 0° C. which resulted in a clear yellow solution and then sodium borohydride (0.27 g, 7.2 mmol) was added under nitrogen and the reaction was stirred for 30 minutes at room temperature. TLC of an aliquot in ether/water (30% ethyl acetate in hexanes) indicated a product band without evidence of starting material. After a total of 1 hour, the reaction was quenched with 18% aqueous citric acid and concentrated in vacuo to remove the methanol. The residue was partitioned between ethyl acetate and 18% citric acid, washed with brine, dried over sodium sulfate and evaporated. Purification of the residue with a Biotage 40+M column (10 to 60% ethyl acetate in hexanes) gave the title alcohol as a white solid. $^1$H-NMR (500 MHz, CDCl$_3$) δ ppm 1.60 (br s, 1H), 2.842 (t, J=6.5 Hz, 2H), 3.853 (t, J=6.5 Hz, 2H), 3.904 (s, 3H), 6.682 (d, J=11.2 Hz, 1H), 7.487 (d, J=8.1 Hz, 1H).

Step D: 4-Fluoro-2-methoxy-5-(2-oxoethyl)benzonitrile

A solution of 4-fluoro-5-(2-hydroxyethyl)-2-methoxybenzonitrile (72 mg, 0.37 mmol) in DCM (5 mL) was treated with Dess-Martin periodinane (313 mg, 0.74 mmol) and was stirred at room temperature for 3 hours. The reaction was quenched by partitioning with DCM and water containing sodium bicarbonate and sodium thiosulfate for 30 minutes. The organic layer was then washed with brine, dried over sodium sulfate and evaporated to give crude title aldehyde as an oil which was used directly in subsequent reductive amination reactions. NMR of the crude mixture indicated an apparent mixture of aldehyde and acid (2:1 ratio) and some periodinane by-product. $^1$H-NMR (500 MHz, CDCl$_3$) δ ppm 3.726 and 3.741 (2 s, 2H, 2:1 ratio), 3.933 (s, 3H), 6.745 (d, J=11.0 Hz, 1H), 7.419 and 7.490 (2 d, J=8.0 Hz, 1H, 2:1 ratio).

Final products in the Examples are named as their free base/free acid forms, although synthesis of some of the compounds may have resulted in a salt form of the final product. IC$_{50}$ results derived from testing each compound in the $^{86}$Rb$^+$ Efflux Assay described below are provided in parentheses at the end of each Example. For example, the compound of Example 1 had an IC$_{50}$ of 0.052 μM in the $^{86}$Rb$^+$ Efflux Assay.

Example 1

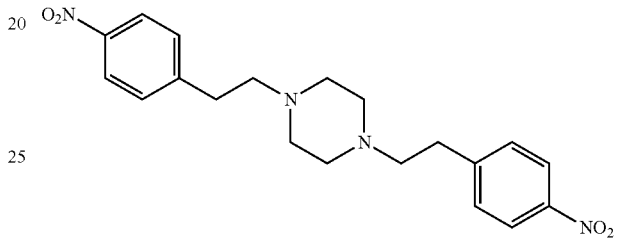

1,4-Bis[2-(4-nitrophenyl)ethyl]piperazine

To a solution of 1-[2-(4-nitrophenyl)ethyl]piperazine hydrochloride (30 mg, 0.11 mmol) in DMF (2 mL) was added 1-(2-bromoethyl)-4-nitrobenzene (31 mg, 1.3 mmol) and TEA (46 uL, 0.33 mmol). The mixture was heated to 80° C. for 16 hours. LC showed some desired product at that point. The desired 1,4-bis[2-(4-nitrophenyl)ethyl]piperazine was purified by mass-directed HPLC. LC-MS (IE, m/z): 385 [M+1]$^+$. (0.052 μM)

Example 2

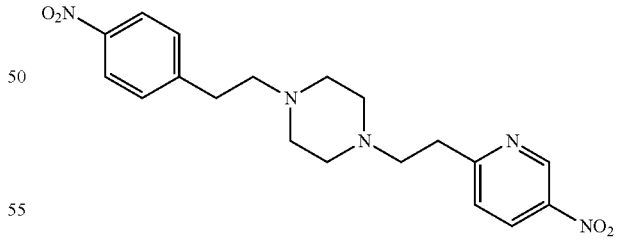

1-[2-(4-Nitrophenyl)ethyl]-4-[2-(5-nitropyridin-2-yl)ethyl]piperazine

To a flask charged with 1-[2-(6-nitropyridin-3-yl)ethyl]piperazine hydrochloride (40 mg, 0.15 mmol) and a stir bar was added 1-(2-bromoethyl)-4-nitrobenzene (40 mg, 0.18 mmol), DMF (2 mL), and triethylamine (0.082 mL, 0.59 mmol). The mixture was heated to 60° C. for 16 hours. LC showed formation of the desired product, which was separated by mass-directed HPLC. LC-MS (IE, m/z): 386 [M+1]+. (0.28 μM)

Example 3

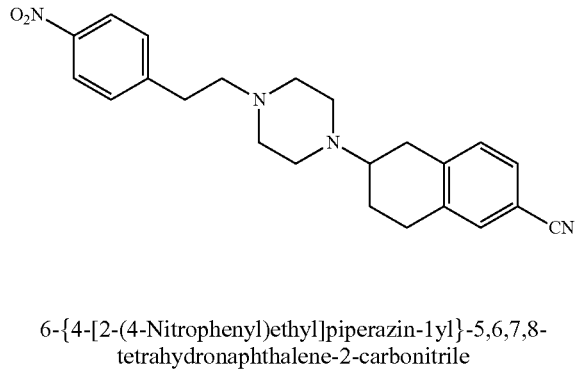

6-{4-[2-(4-Nitrophenyl)ethyl]piperazin-1yl}-5,6,7,8-tetrahydronaphthalene-2-carbonitrile A mixture of 6-piperazin-1-yl-5,6,7,8-tetrahydronaphthalene-2-carbonitrile (generated from treateating tert-Butyl 4-(6-cyano-1,2,3,4-tetrahydronaphthalen-2-yl) piperazine-1-carboxylate (110 mg, 0.32 mmol) with trifluoroacetic acid (2 ml, 26 mmol) at RT), 1-(2-bromoethyl)-4-nitrobenzene (47 mg, 0.21 mmol), and Hunig's Base (0.054 ml, 0.31 mmol in 1 ml DMF was stirred at 60° C. for 21 hours. The reaction was shaken with 1 ml 1 N NaOH and 1 mL DCM. The organic layer was separated and evaporated to dryness. The residue was purified by mass directed HPLC to yield 6-{4-[2-(4-nitrophenyl)ethyl]piperazin-1yl}-5,6,7,8-tetrahydronaphthalene-2-carbonitrile. LC-MS (IE, m/z): 391 [M+1]+. (0.050 μM)

Example 4

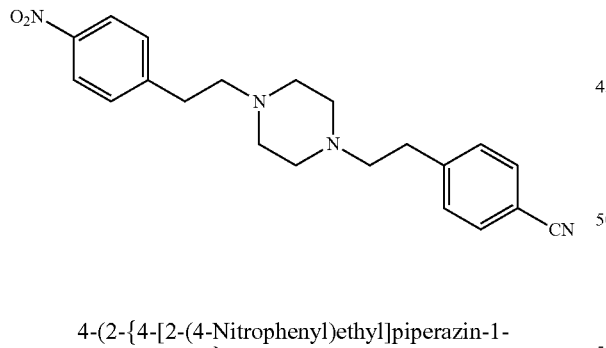

4-(2-{4-[2-(4-Nitrophenyl)ethyl]piperazin-1-yl}ethyl)benzonitrile

Step A: 1-[2-(4-bromophenyl)ethyl]-4-[2-(4-nitrophenyl)ethyl]piperazine

A solution of 1-[2-(4-nitrophenyl)ethyl]piperazine (300 mg, 1.3 mmol), 1-bromo-4-(2-bromoethyl)benzene (400 mg, 1.5 mmol), and triethylamine (0.89 mL, 6.4 mmol) in DMF (5 mL) was heated to 60° C. for 16 hours. LC showed formation of the desired product. The desired product was purified by silica gel chromatography (10% MeOH in EtOAc). LC-MS (IE, m/z): 420 (M+1)+.

Step B: 4-(2-{4-[2-(4-nitrophenyl)ethyl]piperazin-1-yl}ethyl)benzonitrile

A solution of 1-[2-(4-bromophenyl)ethyl]-4-[2-(4-nitrophenyl)ethyl]piperazine (100 mg, 0.24 mmol), Zinc cyanide (84 mg, 0.72 mmol), and tetrakis(triphenylphosphine)palladium in DMF (1 mL) was heated to 85° C. for 1 hour. LC showed formation of the desired product, which was separated by mass-directed HPLC. LC-MS (IE, m/z): 365 (M+1)+. (0.079 μM)

Example 5

2 Diasteroemers

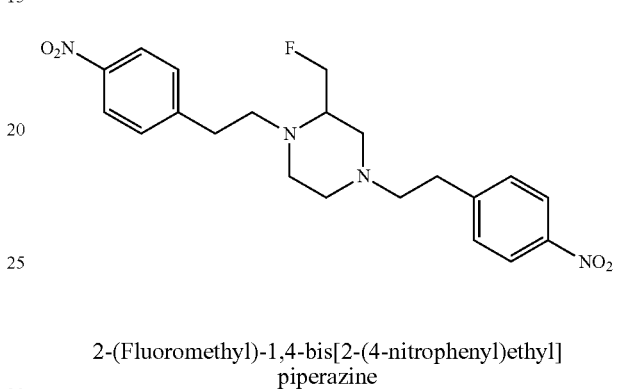

2-(Fluoromethyl)-1,4-bis[2-(4-nitrophenyl)ethyl] piperazine

A mixture of 2-(fluoromethyl)piperazine diacetate (30 mg, 0.17 mmol), 1-(2-bromoethyl)-4-nitrobenzene (150 mg, 0.67 mmol), tetrabutylammonium iodide (6.2 mg, 0.017 mmol), and $K_2CO_3$ (58 mg, 0.42 mmol) in DMF (2 mL) was heated to 60° C. for 16 hours. LC showed formation of the desired product, which was separated by mass-directed HPLC. LC-MS (IE, m/z): 417 (M+1)+. (0.18 μM)

Example 6

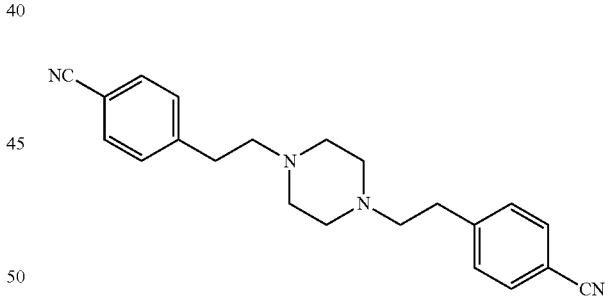

4,4'-(Piperazine-1,4-diyldiethane-2,1-diyl)dibenzonitrile

Step A: 1,4-Bis[2-(4-bromophenyl)ethyl]piperazine

Hunig's Base (3.0 ml, 17 mmol) was added to a stirred solution of piperazine (250 mg, 2.9 mmol) and 1-bromo-4-(2-bromoethyl)benzene (0.89 ml, 5.8 mmol) at 50° C. for 16 hours. The reaction was then poured into water and extracted with ethyl acetate. The ethyl acetate layer was separated and dried over $Na_2SO_4$ and evaporated to dryness. The residue was purified thru 40 gram ISCO Redi-sep column and eluted with 0-5% MeOH in DCM to give yellow solids of 1,4-bis[2-(4-bromophenyl)ethyl]piperazine (0.88 g, 1.95 mmol). LC-MS (IE, m/z): 453 [M+1]+.

Step B: 4,4'-(Piperazine-1,4-diyldiethane-2,1-diyl)dibenzonitrile

Tetrakis(triphenylphosphine)palladium (15 mg, 0.013 mmol), zinc cyanide (52 mg, 0.44 mmol), and 1,4-bis[2-(4-bromophenyl)ethyl]piperazine (100 mg, 0.22 mmol) were stirred in microwave tube containing 2 ml DMF then microwaved at 80° C. for 1 hour. LC-MS showed product peak at 2.1 (M+1=345) and also the mono cyano at 2.5 (M+1=400). Added more $Zn(CN)_2$ (52 mg, 0.44 mmol) and microwaved for another 1 hour. The reaction mixture was cooled and filtered. To the filtrate was added 1 N NaOH then extracted with ethyl acetate. The organic layer was then washed with brine then dried over $MgSO_4$ and evaporated to dryness. The residue was purified by prep TLC plate using 2.5% (NH4OH:MeOH 1:9) in DCM. The major spot isolated was 4,4'-(piperazine-1,4-diyldiethane-2,1-diyl)dibenzonitrile. LC-MS (IE, m/z): 345 [M+1]$^+$. (0.79 μm)

Example 7

2 Diastereomers

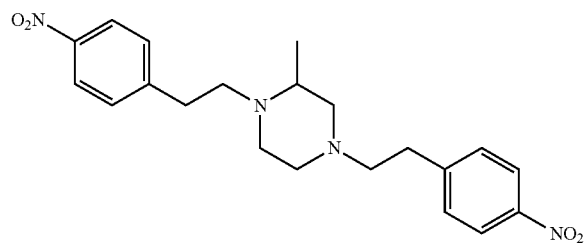 [SMILES: CC1CN(CCc2ccc([N+](=O)[O-])cc2)CCN1CCc1ccc([N+](=O)[O-])cc1]

2-Methyl-1,4-bis[2-(4-nitrophenyl)ethyl]piperazine

To a flask charged with 2-methyl-[2-(4-nitrophenyl)ethyl]piperazine hydrochloride (40 mg, 0.14 mmol) and a stir bar was added 1-(2-bromoethyl)-4-nitrobenzene (65 mg, 0.28 mmol), tetrabutylammonium iodide (5.2 mg, 0.014 mmol), $K_2CO_3$ (48 mg, 0.35 mmol), and DMF (2 mL). The mixture was heated to 80° C. for 16 hours. LC showed formation of the desired product, which was separated by mass-directed HPLC. LC-MS (IE, m/z): 399 [M+1]$^+$. (0.14 μM)

Example 8

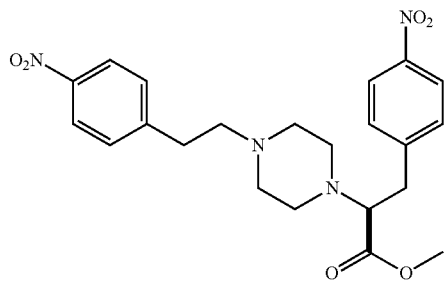 [SMILES: COC(=O)[C@H](Cc1ccc([N+](=O)[O-])cc1)N1CCN(CCc2ccc([N+](=O)[O-])cc2)CC1]

Methyl(2S)-3-(4-nitrophenyl)-2-{4-[2-(4-nitrophenyl)ethyl]piperazin-1-yl}propanoate

Step A: Methyl(2S)-3-(4-nitrophenyl)-2-piperazin-1-ylpropanoate hydrochloride To a cooled solution of tert-butyl diallylcarbamate (145 mg, 0.74 mmol) in DCM (15 mL) at −78° C. was bubbled ozone for about 5 minutes. The solution was light blue at that point. Excess ozone was removed by flushing nitrogen through the reaction. To the reaction was added methyl(2S)-2-amino-3-(4-nitrophenyl)propanoate hydrochloride and triethylamine (74 mg, 0.74 mmol), followed by $NaB(OAc)_3H$ (940 mg, 4.4 mmol). The reaction was allowed to warm to RT, and stir for an additional 4 hours. The mixture was poured into water, extracted with DCM. The organic layer was washed with brine, dried with $MgSO_4$, and purified by prep-TLC (50% EtOAc and Hexanes) to afford 93 mg of the desired tert-butyl 4-[(1S)-2-methoxy-1-(4-nitrobenzyl)-2-oxoethyl]piperazine-1-carboxylate. LC-MS (IE, m/z): 394 [M+1]$^+$.

The above material was further treated with 4N HCl in dioxane to remove the Boc group. The crude methyl(2S)-3-(4-nitrophenyl)-2-piperazin-1-ylpropanoate hydrochloride was used directly in the next step.

Step B: Methyl(2S)-3-(4-nitrophenyl)-2-{4-[2-(4-nitrophenyl)ethyl]piperazin-1-yl}propanoate A mixture of methyl(2S)-3-(4-nitrophenyl)-2-piperazin-1-ylpropanoate hydrochloride (100 mg, 0.30 mmol), 1-(2-bromoethyl)-4-nitrobenzene (77 mg, 0.33 mmol), and triethylamine (92 mg, 0.91 mmol) in DMF was heated to 60° C. for 16 hours. LC showed some product. More 1-(2-bromoethyl)-4-nitrobenzene (77 mg, 0.33 mmol) and triethylamine (92 mg, 0.91 mmol) were added to the reaction, and the mixture was allowed to heat for another 24 hours. LC showed complete reaction at that point. The reaction was diluted with EtOAc, washed with water, and purified by HPLC to deliver the desired product. LC-MS (IE, m/z): 443 [M+1]$^+$. (0.51 μM)

Example 9

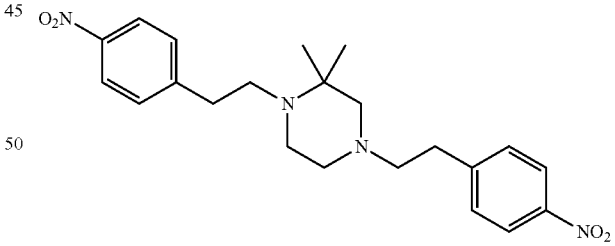

2,2-Dimethyl-1,4-bis[2-(4-nitrophenyl)ethyl]piperazine

A mixture of 2,2-dimethylpiperazine (35 mg, 0.31 mmol), 1-(2-bromoethyl)-4-nitrobenzene (280 mg, 1.2 mmol), tetrabutylammonium iodide (11 mg, 0.031 mmol), and $K_2CO_3$ (169 mg, 1.2 mmol) in DMF (2 mL) was heated to 60° C. for 16 hours. LC showed formation of the desired product, which was separated by mass-directed HPLC. LC-MS (IE, m/z): 413 [M+1]$^+$. (0.21 μm)

Example 10

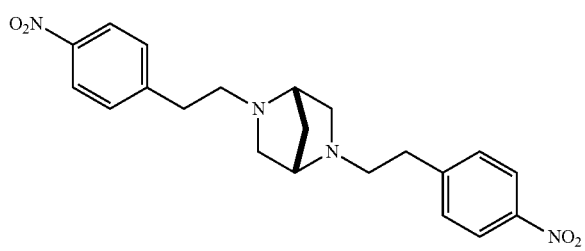

(1S,4S)-2,5-Bis[2-(4-nitrophenyl)ethyl]-2,5-diazabicyclo[2.2.1]heptane

A mixture of (1S,4S)-2,5-diazabicyclo[2.2.1]heptane dihydrobromide (60 mg, 0.23 mmol), 1-(2-bromoethyl)-4-nitrobenzene (210 mg, 0.92 mmol), tetrabutylammonium iodide (8.5 mg, 0.023 mmol), and $K_2CO_3$ (128 mg, 0.92 mmol) in DMF (2 mL) was heated to 60° C. for 16 hours. LC showed formation of the desired product, which was separated by mass-directed HPLC. LC-MS (IE, m/z): 397 $[M+1]^+$. (0.11 µM)

Example 11

2 Diastereomers

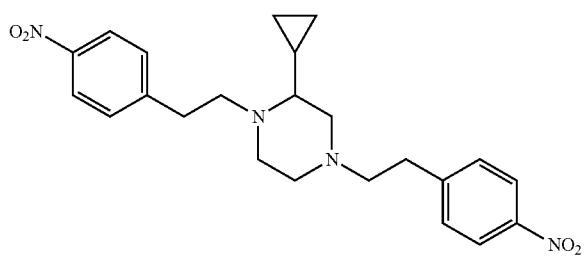 [SMILES: O=[N+]([O-])c1ccc(CCN2CCN(CCc3ccc([N+](=O)[O-])cc3)C(C3CC3)C2)cc1]

2-Cyclopropyl-1,4-bis[2-(4-nitrophenyl)ethyl]piperazine

A mixture of 2-cyclopropyl piperazine (50 mg, 0.40 mmol), 1-(2-bromoethyl)-4-nitrobenzene (360 mg, 1.6 mmol), tetrabutylammonium iodide (15 mg, 0.16 mmol), and $K_2CO_3$ (220 mg, 1.6 mmol) in DMF (2 mL) was heated to 60° C. for 16 hours. LC showed formation of the desired product, which was separated by mass-directed HPLC. LC-MS (IE, m/z): 425 $[M+1]^+$. (0.86 µm)

Example 12

2 Diastereomers

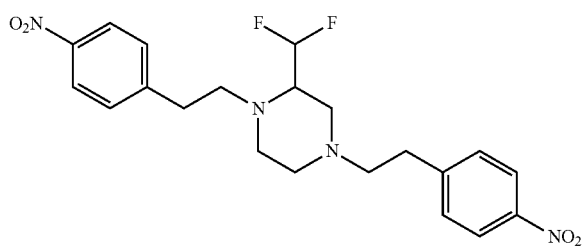 [SMILES: O=[N+]([O-])c1ccc(CCN2CCN(CCc3ccc([N+](=O)[O-])cc3)C(C(F)F)C2)cc1]

2-(Difluoromethyl)-1,4-bis[2-(4-nitrophenyl)ethyl]piperazine

A mixture of 2-Difluoromethyl Piperazine (80 mg, 0.41 mmol), 1-(2-bromoethyl)-4-nitrobenzene (373 mg, 1.6 mmol), tetrabutylammonium iodide (15 mg, 0.16 mmol), and $K_2CO_3$ (220 mg, 1.6 mmol) in DMF (2 mL) was heated to 80° C. for 2 days. LC showed formation of the desired product, which was separated by mass-directed HPLC. LC-MS (IE, m/z): 435 $[M+1]^+$. (0.44 µM)

Example 13

2 Diastereomers

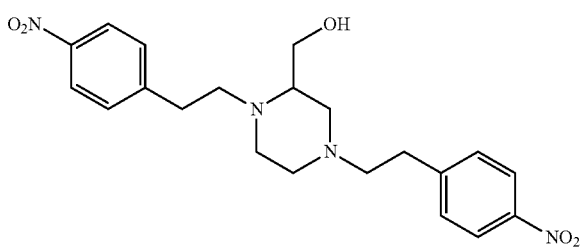 [SMILES: O=[N+]([O-])c1ccc(CCN2CCN(CCc3ccc([N+](=O)[O-])cc3)C(CO)C2)cc1]

{1,4-Bis[2-(4-nitrophenyl)ethyl]piperazin-2-yl}methanol

Step A: 2-(tert-Butoxymethyl)-1,4-bis[2-(4-nitrophenyl)ethyl]piperazine

A mixture of 2-(tert-butoxymethyl)piperazinediium diacetate (60 mg, 0.26 mmol), 1-(2-bromoethyl)-4-nitrobenzene (240 mg, 1.0 mmol), tetrabutylammonium iodide (10 mg, 0.026 mmol), and $K_2CO_3$ (140 mg, 1.0 mmol) in DMF (2 mL) was heated to 80° C. for 16 hours. LC showed formation of the desired product, which was separated by mass-directed HPLC. LC-MS (IE, m/z): 471 $[M+1]^+$.

Step B: {1,4-Bis[2-(4-nitrophenyl)ethyl]piperazin-2-yl}methanol

To a solution of 2-(tert-butoxymethyl)-1,4-bis[2-(4-nitrophenyl)ethyl]piperazine (30 mg) in DCM (2 mL) was added TFA (2 mL). The reaction was allowed to stir at 25° C. for 2 hours. LC showed complete removal of the tert-butyl group. The solvents were removed under reduced pressure, and the residue was collected without further purification. LC-MS (IE, m/z): 415 $[M+1]^+$. (0.26 µM)

Example 14

2 Diastereomers

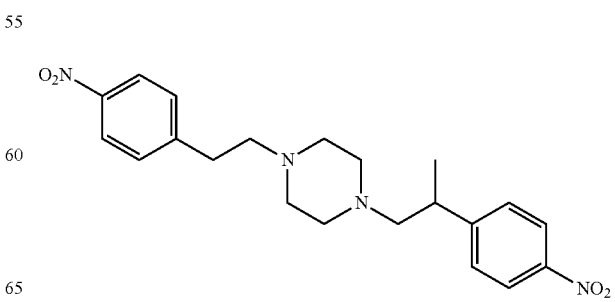

1-[2-(4-Nitrophenyl)ethyl]-4-[2-(4-nitrophenyl)propyl]piperazine

Step A: 1-[2-(4-Nitrophenyl)ethyl]-4-[2-(4-nitrophenyl)propanoyl]piperazine

EDC (113 mg, 0.591 mmol) was added to a solution of 2-(4-nitrophenyl) propionic acid (92 mg, 0.473 mmol), Hunig's Base (0.083 ml, 0.473 mmol) and 1-[2-(4-Nitrophenyl)ethyl]piperazine hydrochloride (107 mg, 0.394 mmol) in 5 ml DCM and stirred at room temperature for 3 hours. The crude mixture was diluted with ethyl acetate and washed with saturated solution of $NH_4Cl$, brine, dried over sodium sulfate, filtered and concentrated. Residue was purified by prep-TLC plate with 5% ($NH_4OH$:MeOH 9:1) in DCM to yield 1-[2-(4-nitrophenyl)ethyl]-4-[2-(4-nitrophenyl)propanoyl]piperazine (100 mg, 0.24 mmol). $^1$H-NMR (500 MHz, DMSO) δ ppm 8.19 (d, J=9 Hz, 2H), 8.11 (d, J=9 Hz, 2H), 7.54 (d, J=9.Hz, 2H), 7.48 (d, J=9.Hz, 2H), 4.33 (q, 1H), 3.39-3.48 (m, 3H), 3.26-3.42 9 m, 2H), 2.82 (t, J=7.0 Hz, 2H), 2.5 (b, 1H), 2.35-2.40 (m, 2H), 2.26 (b, 1H), 2.0 (b, 1H), 1.30 (d, J=7 Hz, 3H).

Step B: 1-[2-(4-Nitrophenyl)ethyl]-4-[2-(4-nitrophenyl)propyl]piperazine

Borane tetrahydrofuran complex 1M (0.714 ml, 0.714 mmol) was added to a stirred solution of 1-[2-(4-nitrophenyl)ethyl]-4-[2-(4-nitrophenyl)propanoyl]piperazine (92 mg, 0.22 mmol) in THF then refluxed for 1 hr. LC-MS and TLC showed starting material left. More borane-THF complex 1M (0.71 ml, 0.71 mmol) was added to the reaction and refluxed for 5 hrs. The reaction was cooled and added 6N HCl and then warmed to 65° C. for 0.5 hour. The reaction was poured into 1N NaOH and extracted with ethyl acetate. The ethyl acetate layer was washed with water and brine then dried and concentrated. The residue was purified by mass directed HPLC. LC-MS (IE, m/z): 399 [M+1]$^+$. (0.34 μM)

Example 15

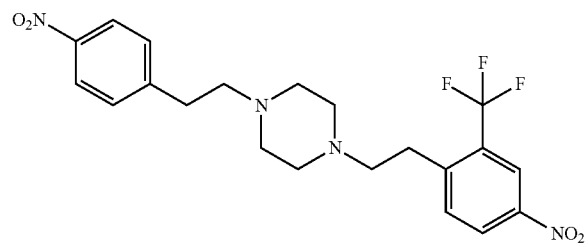 [SMILES: O=[N+]([O-])c1ccc(CCN2CCN(CCc3ccc([N+](=O)[O-])cc3C(F)(F)F)CC2)cc1]

1-[2-(4-Nitrophenyl)ethyl]-4-{2-[4-nitro-2-(trifluoromethyl)phenyl]ethyl}piperazine

Step A: 1-Allyl-4-nitro-2-(trifluoromethyl)benzene

To a flask charged with 1-allyl-4-nitro-2-(trifluoromethyl)benzene (1.0 g, 3.7 mmol) and a stir bar was added tetrakis(triphenylphosphine)palladium (214 mg, 0.18 mmol), Allyl Tri-n-butyltin (1.5 mL, 4.4 mmol), LiCl (470 mg, 11 mmol), and toluene (30 mL). The reaction was heated to 125° C. for 16 hours under an atmosphere of nitrogen. TLC showed complete reaction at that point. The product was purified by MPLC (Hexane:EtOAc) to furnish a light yellow oil. $^1$H-NMR (500 MHz, CDCl$_3$) δ ppm 8.53 (m, 1H), 8.35 (m, 1H), 7.60 (d, J=8.5 Hz, 1H), 5.95 (m, 1H), 5.23 (d, J=10 Hz, 1H), 5.17 (d, J=17 Hz, 1H), 3.69 (m, 2H).

Step B: 1-[2-(4-Nitrophenyl)ethyl]-4-{2-[4-nitro-2-(trifluoromethyl)phenyl]ethyl}piperazine A solution of 1-Allyl-4-nitro-2-(trifluoromethyl)benzene (300 mg, 1.3 mmol) in DCM (10 mL) and MeOH (30 mL) was treated with ozone at −78° C. When the solution turned blue, triphenylphosphine (680 mg, 2.6 mmol) was added to the reaction, and it was allowed to warm up slowly. The desired aldehyde was purified by silica gel chromatography (Hexane:EtOAc). To the aldehyde (17 mg, 0.074 mmol) obtained above was added 1-[2-(4-nitrophenyl)ethyl]piperazine hydrochloride (20 mg, 0.074 mmol), Titanium (IV) isopropoxide (0.22 mL, 0.74 mmol), and sodium cyanoborohydride (46 mg, 0.74 mmol). The mixture was allowed to stir at RT for 10 minutes before ethanol (2 mL) was added to the reaction. LC showed formation of the desired product within 2 hours. The reaction was diluted with EtOAc, washed with brine, dried over sodium sulfate, concentrated and purified by mass-directed HPLC (0.1% TFA in water and acetonitrile). LC-MS (IE, m/z): 453 [M+1]$^+$. (0.44 μM)

Example 16

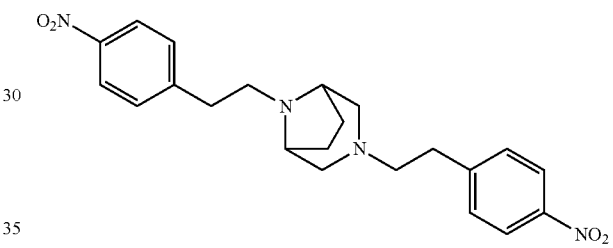

3,8-Bis-[2-(4-nitrophenyl)ethyl]-3,8-diazabicyclo[3.2.1]octane

A mixture of 3,8-diazabicyclo[3.2.1]octane (55 mg, 0.49 mmol), 1-(2-bromoethyl)-4-nitrobenzene (340 mg, 1.5 mmol), tetrabutylammonium iodide (18 mg, 0.049 mmol), and $K_2CO_3$ (270 mg, 2.0 mmol) in DMF (2 mL) was heated to 80° C. for 16 hours. LC showed formation of the desired product, which was separated by mass-directed HPLC. LC-MS (IE, m/z): 411 [M+1]$^+$. (0.19 μM)

Example 17

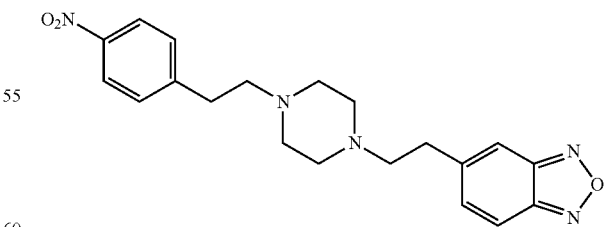

5-(2-{4-[2-(4-Nitrophenyl)ethyl]piperazin-1-yl}ethyl)-2,1,3-benzoxadiazole

Titanium(IV) isopropoxide (1.8 ml, 6.0 mmol) was added to a mixture of 1-[2-(4-nitrophenyl)ethyl]piperazine hydrochloride (0.82 g, 3.0 mmol) and 2,1,3-benzodiazole-5-yl acetaldehyde (0.49 g, 3 mmol) in ethanol (5 ml) then added sodium cyanoborohydride (0.75 g, 12.0 mmol) and 2 drops of acetic acid. The reaction was stirred at room temperature for 16 hours. The reaction mixture was filtered and poured into 1N NaOH then extracted with ethyl acetate. The organic layer was separated, washed with brine, dried over $MgSO_4$, filtered and concentrated. The residue was first purified by prep-TLC plate using 5% (1:9 $NH_4OH$: MeOH) in DCM then repurified with mass-directed HPLC to yield 5-(2-{4-[2-(4-nitrophenyl)ethyl]piperazin-1-yl}ethyl)-2,1,3-benzoxadiazole. LC-MS (IE, m/z): 382 [M+1]$^+$. $^1$H-NMR (500 MHz, DMSO) δ ppm 8.19 (d, J=8.7 Hz, 2H), 8.03 (d, J=9.2 Hz, 1H), 7.90 (2, 1H), 7.56 (d, J=2.2 Hz, 2H), 7.54 (d, J=1.0 Hz, 1H), 3.04-3.65 (b, 16H). (0.17 μM)

Example 18

2 Diastereomers

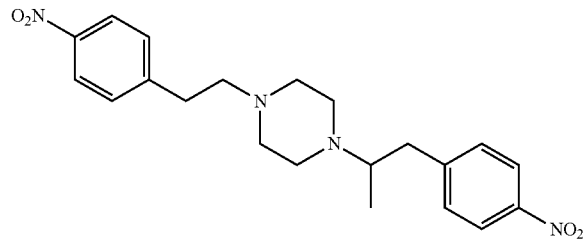 [SMILES: CC(Cc1ccc([N+](=O)[O-])cc1)N1CCN(CCc2ccc([N+](=O)[O-])cc2)CC1]

1-[1-Methyl-2-(4-nitrophenyl)ethyl]-4-[2-(4-nitrophenyl)ethyl]piperazine

4-Nitrophenylacetone (33 mg, 0.18 mmol) and 1-[2-(4-nitrophenyl)ethyl]piperazine hydrochloride (50 mg, 0.18 mmol) were added to Titanium(IV) Isopropoxide (110 μl, 0.37 mmol) and stirred for 1 hour. Ethanol was added followed by sodium cyanoborohydride (23 mg, 0.37 mmol) and stirred at room temperature overnight. Poured into 1N NaOH and extracted with ethyl acetate then washed with brine, dried and evaporated to dryness. The residue was purified by mass directed HPLC to yield 1-[2-(4-nitrophenyl)ethyl]-4-[1-(4-nitrophenyl)propan-2-yl]piperazine. LC-MS (IE, m/z): 399 [M+1]$^+$. $^1$H-NMR (500 MHz, DMSO) δ ppm 8.19 (t, J=8.5 Hz, 4H), 7.56 (d, J=9.7 Hz, 2H), 7.54 (d, J=9.7 Hz, 2H), 2.76-4.4 (m, 15H), 1.02 (d, J=6.1 Hz, 3H). (0.24 μM)

Example 19

4 Diastereomers

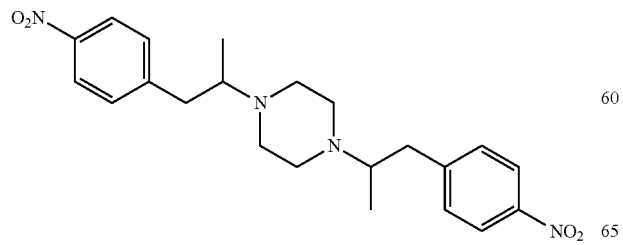

1,4-Bis[1-methyl-2-(4-nitrophenyl)ethyl]piperazine

4-Nitrophenylacetone (208 mg, 1.161 mmol) was added to piperazine (50 mg, 0.58 mmol) and titanium(iv) isopropoxide (0.68 ml, 2.3 mmol) then stirred for 1 hour. Added ethanol (2 ml) and sodium cyanoborohydride (146 mg, 2.3 mmol) then stirred overnight. Poured into 1N NaOH and extracted with ethyl acetate then washed with brine, dried and evaporated to dryness. The residue was purified by mass directed HPLC to yield 1,4-bis[1-(4-nitrophenyl)propan-2-yl]piperazine.
LC-MS (IE, m/z): 413 [M+1]$^+$. $^1$H-NMR (500 MHz, DMSO) δ ppm 8.199 (d, J=8.5 Hz, 4H), 7.55 (d, J=8.9 Hz, 4H), 3.41 (b, 6H), 3.20 (b, 2H), 3.01 (b, 4H), 2.82 (t, J=10.72 Hz, 2H), 1.043 (d, J=6.11, 6 H). (0.33 μM)

Example 20

2 Diastereomers

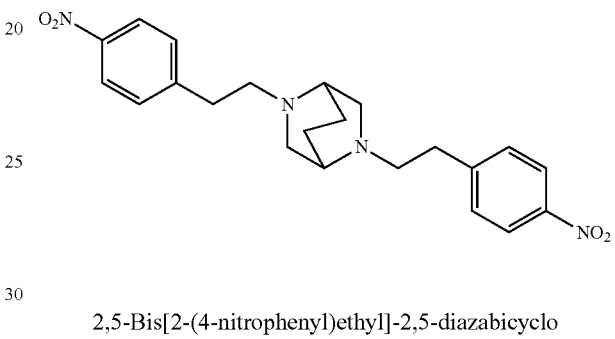

2,5-Bis[2-(4-nitrophenyl)ethyl]-2,5-diazabicyclo[2.2.2]octane

To a flask charged with tert-butyl 2,5-diazabicyclo[2.2.2]octane-2-carboxylate (200 mg, 0.94 mmol) and a stir bar was added TFA (5 mL). The mixture was allowed to stir at RT for 2 hours. The volatiles were removed under reduced pressure. To the residue was added 1-(2-bromoethyl)-4-nitrobenzene (650 mg, 2.8 mmol), tetrabutylammonium iodide (35 mg, 0.094 mmol), $K_2CO_3$ (521 mg, 3.8 mmol), and DMF (5 mL). The mixture was heated to 80° C. for 16 hours. LC showed formation of the desired product, which was separated by mass-directed HPLC. LC-MS (IE, m/z): 411 [M+1]$^+$. (0.21 μM)

Example 21

2 Diastereomers

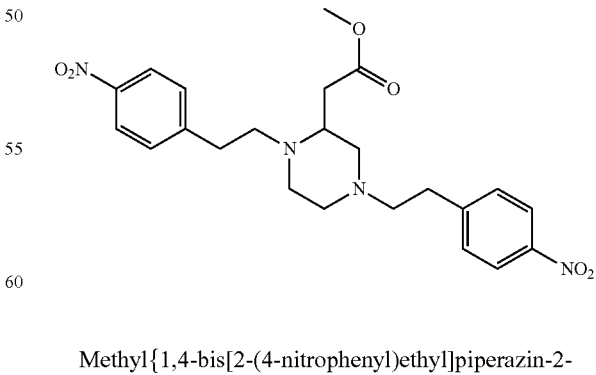

Methyl{1,4-bis[2-(4-nitrophenyl)ethyl]piperazin-2-yl}acetate

To a suspension of methyl piperazin-2-ylacetate (0.40 g, 1.73 mmol) in DMF (2.5 mL) was added 1-(2-bromoethyl)-

4-nitrobenzene (1.0 g, 4.3 mmol), tetrabutyl ammonium iodide (cat.) and potassium carbonate (1.20 g, 8.7 mmol). The mixture was stirred at room temperature for 12 hours. The reaction mixture was diluted with water and extracted with ethyl acetate (3×). The combined organics were washed with water (2×) and brine, then dried ($Na_2SO_4$), filtered and concentrated. The desired methyl {1,4-bis[2-(4-nitrophenyl)ethyl]piperazin-2-yl}acetate was purified by mass-directed HPLC. LC-MS (IE, m/z): 456.2 [M+1]$^+$. (0.39 μM)

Example 22

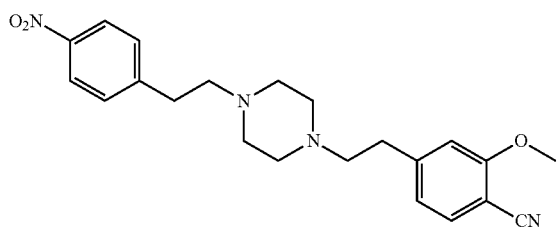 [SMILES: COc1cc(CCN2CCN(CCc3ccc([N+](=O)[O-])cc3)CC2)ccc1C#N]

2-Methoxy-4-(2-{4-[2-(4-nitrophenyl)ethyl]piperazin-1-yl}ethyl)benzonitrile

Step A: 4-Formyl-2-methoxybenzonitrile

To a stirred solution of 4-bromo-2-methoxybenzonitrile (1.0 g, 4.7 mmol) in 30 mL of anhydrous THF was added BuLi (1.6 M, 3.3 mL, 5.2 mmol) dropwise at −78° C. under nitrogen atmosphere. After the addition, the pale red solution was stirred for 5 min at −78° C. and dry DMF (0.6 mL) then added dropwise. After 20 min, the reaction mixture was poured onto a saturated solution of sodium chloride (50 mL). The organic phase was separated, extracted with diethyl ether (100 mL), dried over $Na_2SO_4$ and distilled off the solvent to afford 4-formyl-2-methoxybenzonitrile. MS m/z: 162 (M+1)$^+$.

Step B: Ethyl 3-(4-cyano-3-methoxyphenyl)oxirane-2-carboxylate

A mixture of 4-formyl-2-methoxybenzonitrile (383 mg, 2.38 mmol) and chloroacetic acid ethyl ester (291 mg, 2.38 mmol) were dissolved in 10 mL of dry benzene. Freshly prepared EtONa (3.09 mmol) in 2.5 mL of ethanol was added, and the mixture were stirred at room temperature for 2 hours. The mixture was added water, then extracted with EtOAc. The organic layers were dried over $Na_2SO_4$ and concentrated to afford ethyl 3-(4-cyano-3-methoxyphenyl)oxirane-2-carboxylate. MS m/z: 248 (M+1)$^+$.

Step C: 2-Methoxy-4-(2-oxoethyl)benzonitrile

A solution of ethyl 3-(4-cyano-3-methoxyphenyl)oxirane-2-carboxylate (400 mg, 1.6 mmol) in 5 mL of dry ethanol was cooled to 0° C. Freshly prepared EtONa (2.1 mmol) in 4 mL of ethanol was added and stirred at 0° C. for 10 min. Then dropwise addition of 0.1 g of water, stirred at 0° C. for 2 hours, and the sodium salt of the epoxy compound was filtered. The sodium salt of the epoxy compound was then dissolved in 10 mL of water and added 10 mL of 1 N of HCl and 20 mL of toluene. The mixture was heated to reflux for 2 hours. The organic phase was separated, washed by saturated sodium chloride, dried over $Na_2SO_4$ and distilled off solvent to afford crude 2-methoxy-4-(2-oxoethyl)benzonitrile. MS m/z: 176 (M+1)$^+$.

Step D: 2-Methoxy-4-(2-{4-[2-(4-nitrophenyl)ethyl]piperazin-1-yl}ethyl)benzonitrile A solution of 2-methoxy-4-(2-oxoethyl)benzonitrile (100 mg, 0.57 mmol), 1-[2-(4-Nitrophenyl)ethyl]piperazine (134 mg, 0.51 mmol) in 60 mL of dry methanol were added 2 drop of HOAc and then stirred at room temperature for 1 hr. Then NaBH(OAc)$_3$ (362 mg, 1.71 mmol) was added an the then the mixture was stirred overnight. Concentrated and the residue was purified via prep-TLC to give 2-methoxy-4-(2-{4-[2-(4-nitrophenyl)ethyl]piperazin-1-yl}ethyl)benzonitrile.
$^1$H-NMR (300 MHz, CDCl$_3$) δ ppm 8.14 (d, J=8.6 Hz, 2H), 7.35~7.47 (m, 3H), 6.79~6.85 (m, 2H), 3.12 (s, 3H), 2.48~2.96 (m, 16H). MS m/z: 395 (M+1)$^+$. (0.052 μM)

Example 23

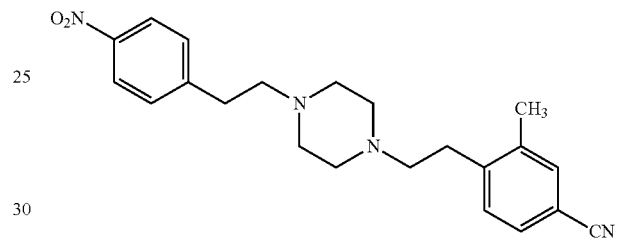

3-Methyl-4-(2-{4-[2-(4-nitrophenyl)ethyl]piperazin-1-yl}ethyl)benzonitrile

Step A: 4-Formyl-3-methylbenzonitrile

To a stirred solution of 4-bromo-3-methylbenzonitrile (4.0 g, 20 mmol) in 100 mL of anhydrous THF was added BuLi (1.6 M, 12.8 mL) dropwise at −78° C. under nitrogen atmosphere. After the addition, the pale red solution was stirred for 5 min at −78° C. and dry DMF (2.2 mL) then added drop wise. After 20 min, the reaction mixture was poured onto a saturated solution of sodium chloride (100 mL). The organic phase was separated, extracted with diethyl ether (100 mL), dried over $Na_2SO_4$ and distilled off the solvent to afford 3.5 g of crude 4-formyl-3-methylbenzonitrile. MS m/z: 146 (M+1)$^+$.

Step B: Ethyl 3-(4-cyano-2-methylphenyl)oxirane-2-carboxylate

A mixture of 4-formyl-3-methylbenzonitrile (1.5 g, 10.3 mmol) and chloroacetic acid ethyl ester (1.2 g, 10 mmol) were dissolved in 60 mL of dry benzene. Freshly prepared EtONa (12.4 mmol) in 8 mL of ethanol was added, and the mixture were stirred at room temperature for 2 hours. The mixture was added water, then extracted with EA, dried over $Na_2SO_4$ and distilled off solvent to afford 1.7 g of crude ethyl 3-(4-cyano-2-methylphenyl)oxirane-2-carboxylate. MS m/z: 232 (M+1)$^+$.

Step C: 3-Methyl-4-(2-oxoethyl)benzonitrile

A solution of ethyl 3-(4-cyano-2-methylphenyl)oxirane-2-carboxylate (927 mg, 4.0 mmol) in 10 mL of dry ethanol was cooled to 0° C. Freshly prepared EtONa (12.4 mmol) in 8 mL of ethanol was added and stirred at 0 for 10 min. Then dropwise addition of 0.1 g of water, stirred at 0° C. for 2 hours, and the sodium salt of the epoxy compound was filtered. The sodium salt of the epoxy compound was then dissolved in 5 mL of water and added 5 mL of 1 N of HCl and 20 mL of toluene. The mixture was heated to reflux for 2 hours. The organic phase was separated, washed by saturated sodium chloride, dried over $Na_2SO_4$ and distilled off solvent to afford 130 mg of crude 3-methyl-4-(2-oxoethyl)benzonitrile. MS m/z: 160 (M+1)$^+$.

Step D: 3-Methyl-4-((E)-2-{4-[2-(4-nitrophenyl)ethyl]piperazin-1-yl}vinyl)benzonitrile A mixture of 3-methyl-4-(2-oxoethyl)benzonitrile (130 mg, 0.8 mmol), 1-[2-(4-nitrophenyl)ethyl]piperazine (188 mg, 0.8 mmol) and NaBH(OAc)$_3$ in 25 mL of dry methanol were stirred at room temperature over night. The solid was filtered to get 160 mg of 3-methyl-4-((E)-2-{4-[2-(4-nitrophenyl)ethyl]piperazin-1-yl}vinyl)benzonitrile. $^1$H-NMR (300 MHz, CDCl$_3$) δ ppm 8.15 (d, J=8.6 Hz, 2H), 7.31~7.40 (m, 5H), 6.72 (d, J=13.5 Hz, 1H), 5.35 (d, J=13.9 Hz, 1H), 3.20 (s, 4H), 2.95 (s, 2H), 2.57~2.75 (m, 6H), 2.26 (s, 3H). MS m/z: 377 (M+1)$^+$.

Step E: 3-Methyl-4-(2-{4-[2-(4-nitrophenyl)ethyl]piperazin-1-yl}ethyl)benzonitrile A solution of 3-methyl-4-((E)-2-{4-[2-(4-nitrophenyl)ethyl]piperazin-1-yl}vinyl)benzonitrile (100 mg, 0.24 mmol) in 15 mL of methanol and 10 mL of DCM was added NaBH$_4$ (508 mg, 2.4 mmol), then stirred at room temperature overnight. The crude product was purified via prepare TLC (methanol/DCM 1:10) to give 3-methyl-4-(2-{4-[2-(4-nitrophenyl)ethyl]piperazin-1-yl}ethyl)benzonitrile. $^1$H-NMR (300 MHz, CDCl$_3$) δ ppm 8.12 (d, J=8.6 Hz, 2H), 7.23~7.40 (m, 5H), 3.01~3.21 (m, 2H), 2.80~2.92 (m, 4H), 2.50~2.65 (m, 10H), 2.33 (s, 3H). MS m/z: 379 (M+1)$^+$. (0.062 μM)

Example 24

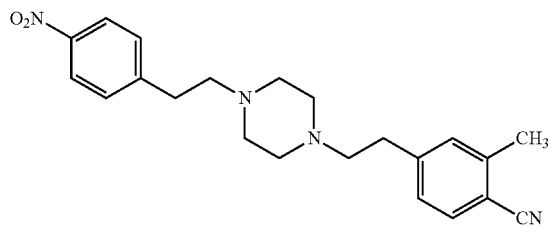 [SMILES: Cc1cc(CCN2CCN(CCc3ccc([N+](=O)[O-])cc3)CC2)ccc1C#N]

2-Methyl-4-(2-{4-[2-(4-nitrophenyl)ethyl]piperazin-1-yl}ethyl)benzonitrile

Step A: 4-Formyl-2-methylbenzonitrile

To a stirred solution of 4-bromo-2-methylbenzonitrile (4.0 g, 20 mmol) in 100 mL of anhydrous THF was added BuLi (1.6 M, 12.8 mL) dropwise at −78° C. under nitrogen atmosphere. After the addition, the pale red solution was stirred for 5 min at −78° C. and dry DMF (2.2 mL) then added dropwise. After 20 min, the reaction mixture was poured onto a saturated solution of sodium chloride (100 mL). The organic phase was separated, extracted with diethyl ether (100 mL), dried over $Na_2SO_4$ and distilled off the solvent to afford 4-formyl-2-methylbenzonitrile. MS m/z: 146 (M+1)$^+$.

Step B: Ethyl 3-(4-cyano-3-methylphenyl)oxirane-2-carboxylate

A mixture of 4-formyl-2-methylbenzonitrile (1.5 g, 10.3 mmol) and chloroacetic acid ethyl ester (1.2 g, 10 mmol) were dissolved in 60 mL of dry benzene. Freshly prepared EtONa (12.4 mmol) in 5 mL of ethanol was added, and the mixture was stirred at room temperature for 2 hours. The mixture was added water, then extracted with EtOAc. The organic layers were dried over $Na_2SO_4$ and concentrated to afford ethyl 3-(4-cyano-3-methylphenyl)oxirane-2-carboxylate. MS m/z: 232 (M+1)$^+$.

Step C: 2-Methyl-4-(2-oxoethyl)benzonitrile

A solution of 3-(4-cyano-3-methylphenyl)oxirane-2-carboxylate (927 mg, 4.0 mmol) in 5 mL of dry ethanol was cooled to 0° C. Freshly prepared EtONa (5 mmol) in 4 mL of ethanol was added and stirred at 0° C. for 10 min. Then dropwise addition of 0.1 g of water, stirred at 0° C. for 2 hours, and the sodium salt of the epoxy compound was filtered. The sodium salt of the epoxy compound was then dissolved in 5 mL of water and added 5 mL of 1 N of HCl and 20 mL of toluene. The mixture was heated to reflux for 2 hours. The organic phase was separated, washed by saturated sodium chloride, dried over $Na_2SO_4$ and distilled off solvent to afford crude 2-methyl-4-(2-oxoethyl)benzonitrile. MS m/z: 160 (M+1)$^+$.

Step D: 2-Methyl-4-(2-{4-[2-(4-nitrophenyl)ethyl]piperazin-1-yl}ethyl)benzonitrile A solution of 2-methyl-4-(2-oxoethyl)benzonitrile (130 mg, 0.8 mmol), 1-[2-(4-nitrophenyl)ethyl]piperazine (190 mg, 0.8 mmol) in 25 mL of dry methanol were added 2 drop of HOAc and then stirred at room temperature for 1 hr. Then NaBH(OAc)$_3$ (380 mg, 1.8 mmol) was added an the then the mixture was stirred overnight. Concentrated and the residue was purified via prep-TLC to give 2-Methyl-4-(2-{4-[2-(4-nitrophenyl)ethyl]piperazin-1-yl}ethyl)benzonitrile. $^1$H-NMR (300 MHz, CDCl$_3$) δ ppm 8.15 (d, J=8.6 Hz, 2H), 7.36~7.53 (m, 3H), 7.12 (t, J=9.4 Hz, 2H), 2.65~2.97 (m, 16H), 2.52 (s, 3H). MS m/e: 379 (M+1)$^+$. (0.19 μM)

Example 25

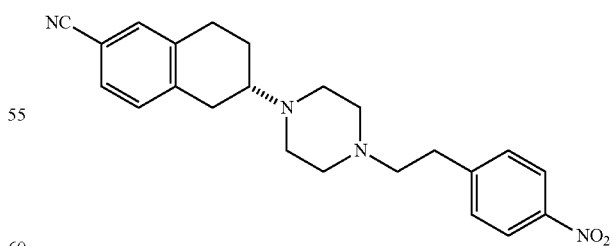

(6S)-6-{4-[2-(4-Nitrophenyl)ethyl]piperazin-1-yl}-5,6,7,8-tetrahydronaphthalene-2-carbonitrile A mixture (6S)-6-piperazin-1-yl-5,6,7,8-tetrahydronaphthalene-2-carbonitrile (0.31 mg, 0.13 mmol), 1-(2-bromoethyl)-4-nitrobenzene (80 mg, 0.35 mmol), and triethylamine (0.15 mL, 1.1 mmol) in DMF was heated to 60° C. for 30 hours. LC showed formation of the desired product. The reaction was diluted with EtOAc, washed with water and brine, dried over MgSO₄, and purified by MPLC to deliver 13 mg of (6S)-6-{4-[2-(4-nitrophenyl)ethyl]piperazin-1-yl}-5, 6,7,8-tetrahydronaphthalene-2-carbonitrile. LC-MS (IE, m/z): 391 [M+1]⁺. (0.083 μM)

Example 26

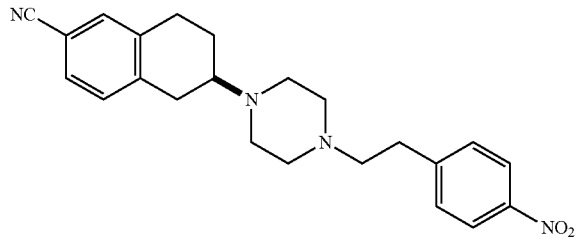 [SMILES: N#Cc1ccc2c(c1)CC[C@@H](N1CCN(CCc3ccc([N+](=O)[O-])cc3)CC1)C2]

(6R)-6-{4-[2-(4-Nitrophenyl)ethyl]piperazin-1-yl}-5,6,7,8-tetrahydronaphthalene-2-carbonitrile (6R)-6-{4-[2-(4-nitrophenyl)ethyl]piperazin-1-yl}-5,6,7, 8-tetrahydronaphthalene-2-carbonitrile Was prepared following the same procedure of EXAMPLE 25 from (6R)-6-piperazin-1-yl-5,6,7,8-tetrahydronaphthalene-2-carbonitrile. LC-MS (IE, m/z): 391 [M+1]⁺. (0.066 μM)

Example 27

2 Diastereomers

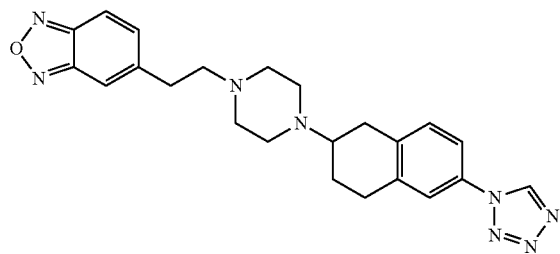 [SMILES: c1cc2nonc2cc1CCN1CCN(C2CCc3cc(-n4cnnn4)ccc3C2)CC1]

5-(2-{4-[6-(1H-Tetrazol-1-yl)-1,2,3,4-tetrahydronaphthalen-2-yl]piperazin-1-yl}ethyl)-2,1,3-benzoxadiazole To a flask charged with 5-(2-piperazin-1-ylethyl)-2,1,3-benzoxadiazole hydrochloride (25 mg, 0.093 mmol) and a stir bar was added 6-(1H-tetrazol-1-yl)-3,4-dihydronaphthalen-2 (1H)-one (30 mg, 0.14 mmol), Titanium (IV) isopropoxide (0.27 mL, 0.93 mmol), and sodium cyanoborohydride (29 mg, 0.46 mmol). The mixture was allowed to stir for 3 hours. LC showed formation of the desired product. The reaction was diluted with EtOAc, washed with brine, dried over sodium sulfate, filtered, concentrated and purified by mass-directed HPLC (0.1% TFA in water and acetonitrile). LC-MS (IE, m/z): 431 [M+1]⁺. (0.98 μM)

Example 28

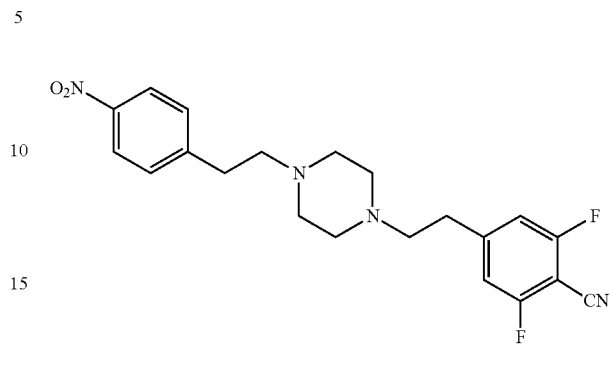

2,6-Difluoro-4-(2-{4-[2-(4-nitrophenyl)ethyl]piperazin-1-yl}ethyl)benzonitrile

Step A: 4-Allyl-2,6-difluorobenzonitrile

A mixture of 4-bromo-2,6-difluorobenzonitrile (2.0 g, 9.2 mmol), allyl-tributyl-stannane (3.65 g, 11.0 mmol), LiCl (1.17 mg, 28 mmol) and Pd(PPh)₄ (0.2 g) in 70 mL of anhydrous toluene was refluxed under N₂ overnight. Checked the reaction with TLC and concentrated under reduced pressure. The residue was purified by silica gel column chromatography to give the product 4-allyl-2,6-difluorobenzonitrile. MS m/z: 180 (M+1)⁺.

Step B: 4-(2,3-Dihydroxypropyl)-2,6-difluorobenzonitrile

To a solution of 4-allyl-2,6-difluorobenzonitrile (1.7 g, 9.2 mmol) in 30 mL of methanol and 10 mL of water was added OsO₄ (210 mg) and NMO (3.11 g, 23 mmol), and the mixture was stirred at ambient temperature overnight. Remove the methanol under reduced pressure, the residue was dissolved in EtOAc, washed with brine, dried over anhydrous sodium sulfate and concentrated. The residue was purified by fast column chromatograph to give 4-(2,3-dihydroxypropyl)-2,6-difluorobenzonitrile. MS m/z: 214 (M+1)⁺.

Step C: 2,6-Difluoro-4-(2-oxoethyl)benzonitrile

A solution of 4-(2,3-dihydroxypropyl)-2,6-difluorobenzonitrile (500 mg, 2.4 mmol) in 10 mL of methanol and 3 mL of water was cooled to 0° C. by ice bath, then NaIO₄ (754 mg, 3.5 mmol) was added and the mixture was stirred at 0° C. for two hours. The reaction was monitored according to TLC. The mixture was filtered and concentrated. The residue was dissolved in DCM, dried over anhydrous sodium sulfate, and then purified by flash column chromatography to give 2,6-difluoro-4-(2-oxoethyl)benzonitrile. MS m/z: 182 (M+1)⁺.

Step D: 2,6-Difluoro-4-(2-{4-[2-(4-nitrophenyl) ethyl]piperazin-1-yl}ethyl)benzonitrile A solution of 2,6-difluoro-4-(2-oxoethyl)benzonitrile (185 mg, 1.0 mmol), 1-[2-(4-nitrophenyl)ethyl]piperazine (200 mg, 0.85 mmol) and NaBH(OAc)₃ (720 mg, 3.4 mmol) in anhydrous DCM (10 mL) was stirred at ambient temperature overnight. The reaction was completed according to TLC. The reaction mixture was added 20 mL of DCM, washed with brine, separated the organic layer, dried over anhydrous sodium sulfate and concentrated. The residue was purified by preparative TLC to give the product. $^1$H-NMR (400 MHz, CDCl$_3$) δ ppm 8.15~8.17 (d, J=8.6 Hz, 2H), 7.37~7.39 (d, J=8.6 Hz, 2H), 6.92~6.94 (d, J=8.6 Hz, 2H), 2.50~3.11 (m, 16H). MS m/z: 401 (M+1)$^+$. (0.16 μM)

Example 29

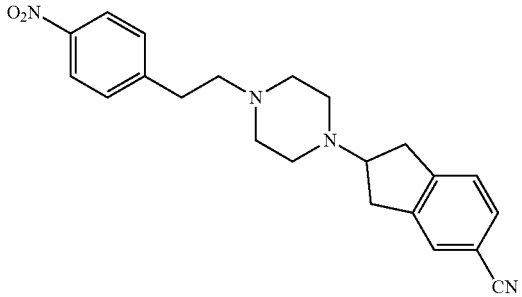 [SMILES: N#Cc1ccc2c(c1)CC(N1CCN(CCc3ccc([N+](=O)[O-])cc3)CC1)C2]

2-{4-[2-(4-Nitrophenyl)ethyl]piperazin-1-yl}-2,3-dihydro-1H-indene-5-carbonitrile To a 12 mL reaction vial was added 1-(2-bromoethyl)-4-nitrobenzene (42 mg, 0.18 mmol), 4-(5-cyano-2,3-dihydro-1H-inden-2-yl)piperazin-1-ium chloride (33 mg, 0.12 mmol) and acetonitrile (2 mL). To a stirred solution of above mixture was added N-ethyl-N-(propan-2-yl)propan-2-amine (32 mg, 0.24 mmol). The reaction was stirred at 60° C. for 5 hr, then concentrated and purified by preparative TLC to give the desired product. LC-MS (IE, m/z): 377 [M+1]$^+$. (0.73 μm)

Example 30

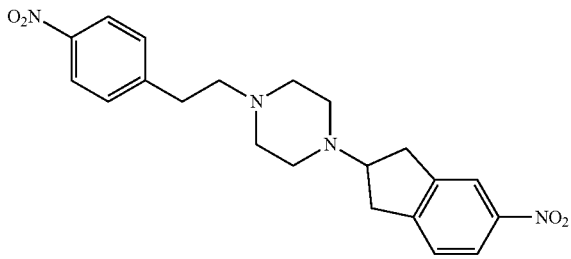 [SMILES: O=[N+]([O-])c1ccc(CCN2CCN(C3Cc4ccc([N+](=O)[O-])cc4C3)CC2)cc1]

1-(5-Nitro-2,3-dihydro-1H-inden-2-yl)-4-[2-(4-nitrophenyl)ethyl]piperazine

A mixture of 1-[2-(4-Nitrophenyl)ethyl]piperazine hydrochloride (50 mg, 0.18 mmol), 5-nitro-1,3-dihydro-2H-inden-2-one (39 mg, 0.22 mmol), sodium cyanoborohydride (58 mg, 0.92 mmol, and Titanium (IV) Isopropoxide (0.54 mL, 1.8 mmol) was allowed to stir at RT for 3 hours. LC showed formation of the desired product. The reaction was diluted with EtOAc, washed with brine, dried over sodium sulfate, filtered, concentrated and purified by mass-directed HPLC (0.1% TFA in water and acetonitrile). LC-MS (IE, m/z): 397 (M+1)$^+$. (0.31 μM)

Example 31

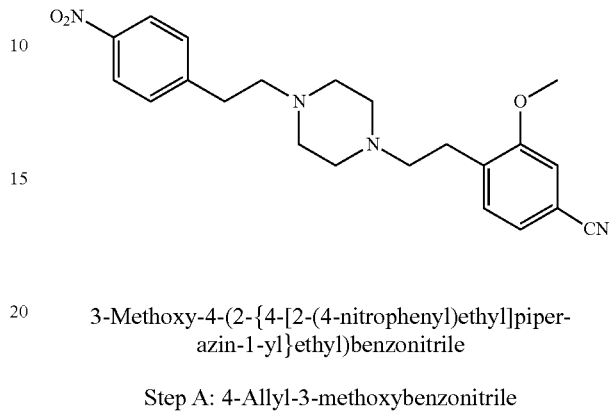

3-Methoxy-4-(2-{4-[2-(4-nitrophenyl)ethyl]piperazin-1-yl}ethyl)benzonitrile

Step A: 4-Allyl-3-methoxybenzonitrile

A mixture of 4-bromo-3-methoxybenzonitrile (1.4 g, 6.7 mmol), allyl-tributyl-stannane (2.7 g, 8.1 mmol), LiCl (0.86 mg, 20 mmol) and Pd(PPh)$_4$ (0.2 g) in 25 mL of anhydrous toluene was refluxed under N$_2$ overnight. Checked the reaction with TLC and concentrated under reduced pressure. The residue was purified by silica gel column chromatography to give the product 4-allyl-3-methoxybenzonitrile. MS m/z: 174 (M+1)$^+$.

Step B: 4-(2,3-Dihydroxypropyl)-3-methoxybenzonitrile

To a solution of 4-allyl-3-methoxybenzonitrile (1.1 g, 6.4 mmol) in 30 mL of methanol and 10 mL of water was added OsO$_4$ (140 mg) and NMO (2.2 g, 16 mmol), and the mixture was stirred at ambient temperature overnight. Remove the methanol under reduced pressure, the residue was dissolved in EtOAc, washed with brine, dried over anhydrous sodium sulfate and concentrated. The residue was purified by fast column chromatograph to give 4-(2,3-dihydroxypropyl)-3-methoxybenzonitrile. MS m/z: 208 (M+1)$^+$.

Step C: 3-Methoxy-4-(2-oxoethyl)benzonitrile

A solution of 4-(2,3-dihydroxypropyl)-3-methoxybenzonitrile (500 mg, 2.6 mmol) in 10 mL of methanol and 3 mL of water was cooled to 0° C. by ice bath, then NaIO$_4$ (830 mg, 3.9 mmol) was added and the mixture was stirred at 0° C. for two hours. The reaction was monitored according to TLC. The mixture was filtered and concentrated. The residue was dissolved in DCM, dried over anhydrous sodium sulfate, and then purified by flash column chromatography to give 3-methoxy-4-(2-oxoethyl)benzonitrile. MS m/z 176 (M+1)$^+$.

Step D: 3-Methoxy-4-(2-{4-[2-(4-nitrophenyl)ethyl]piperazin-1-yl}ethyl)benzonitrile A solution of 3-methoxy-4-(2-oxoethyl)benzonitrile (91 mg, 0.56 mmol), 1-[2-(4-nitrophenyl)ethyl]piperazine (110 mg, 0.56 mmol) and NaBH(OAc)$_3$ (393 mg, 1.87 mmol) in anhydrous DCM (15 mL) was stirred at ambient temperature overnight. The reaction was completed according to TLC. The reaction mixture was added 15 mL of DCM, washed with brine, separated the organic layer, dried over anhydrous sodium sulfate and concentrated. The residue was purified by preparative TLC to give the product. ¹H-NMR (400 MHz, CDCl₃) δ 8.15 (d, J=8.5 Hz, 3H), 7.37 (d, J=8.5 Hz, 3H), 7.05 (s, 1H), 3.85 (s, 3H), 2.85~2.96 (m, 5H), 2.49~2.75 (m, 11H). MS m/z: 395 (M+1)⁺. (0.30 μM)

Example 32

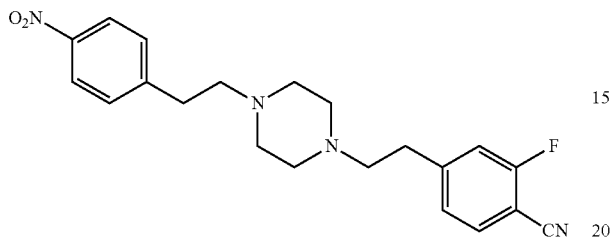

2-Fluoro-4-(2-{4-[2-(4-nitrophenyl)ethyl]piperazin-1-yl}ethyl)benzonitrile

Step A: 4-Allyl-2-fluorobenzonitrile

A mixture of 4-bromo-2-fluorobenzonitrile (250 mg, 1.3 mmol), allyl-tributyl-stannane (500 mg, 1.5 mmol), LiCl (160 mg, 3.8 mmol) and Pd(PPh)₄ (15 mg) in 5 mL of anhydrous toluene was refluxed under N₂ overnight. Checked the reaction with TLC and concentrated under reduced pressure. The residue was purified by silica gel column chromatography to give the product 4-allyl-2-fluorobenzonitrile. MS m/z: 162 (M+1)⁺.

Step B: 4-(2,3-Dihydroxypropyl)-2-fluorobenzonitrile

To a solution of 4-allyl-2-fluorobenzonitrile (1.3 g, 8.1 mmol) in 30 mL of methanol and 10 mL of water was added OsO₄ (200 mg) and NMO (2.7 g, 20 mmol), and the mixture was stirred at ambient temperature overnight. Remove the methanol under reduced pressure, the residue was dissolved in EtOAc, washed with brine, dried over anhydrous sodium sulfate and concentrated. The residue was purified by fast column chromatograph to give 4-(2,3-dihydroxypropyl)-2-fluorobenzonitrile. MS m/z: 196 (M+1)⁺.

Step C: 2-Fluoro-4-(2-oxoethyl)benzonitrile

A solution of 4-(2,3-dihydroxypropyl)-2-fluorobenzonitrile (500 mg, 2.6 mmol) in 10 mL of methanol and 3 mL of water was cooled to 0° C. by ice bath, then NaIO₄ (820 mg, 3.8 mmol) was added and the mixture was stirred at 0° C. for two hours. The reaction was monitored according to TLC. The mixture was filtered and concentrated. The residue was dissolved in DCM, dried over anhydrous sodium sulfate, and then purified by flash column chromatography to give 2-fluoro-4-(2-oxoethyl)benzonitrile. MS m/z: 164 (M+1)⁺.

Step D: 2-Fluoro-4-(2-{4-[2-(4-nitrophenyl)ethyl]piperazin-1-yl}ethyl)benzonitrile A solution of 2-fluoro-4-(2-oxoethyl)benzonitrile (140 mg, 0.88 mmol), 1-[2-(4-nitrophenyl)ethyl]piperazine (170 mg, 0.73 mmol) and NaBH(OAc)₃ (620 mg, 2.9 mmol) in anhydrous DCM (10 mL) was stirred at ambient temperature overnight. The reaction was completed according to TLC. The reaction mixture was added 20 mL of DCM, washed with brine, separated the organic layer, dried over anhydrous sodium sulfate and concentrated. The residue was purified by preparative TLC to give the product. ¹H-NMR (400 MHz, CDCl₃) δ ppm 8.13~8.16 (d, J=8.6 Hz, 2H), 7.52~7.55 (t, J=6.6 Hz, 1H), 7.36~7.38 (d, J=8.6 Hz, 2H), 7.08~7.12 (m, 2H), 2.89~3.00 (m, 4H), 2.56~2.78 (m, 12H). MS m/z: 383 (M+1)⁺. (0.24 μM)

Example 33

2 Diastereomers

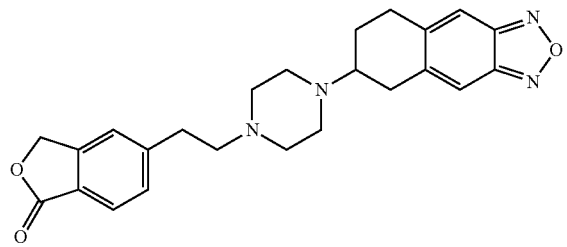 [SMILES: O=C1OCc2cc(CCN3CCN(C4CCc5cc6nonc6cc5C4)CC3)ccc21]

5-{2-[4-(5,6,7,8-Tetrahydronaphtho[2,3-c][1,2,5]oxadiazol-6-yl)piperazin-1-yl]ethyl}-2-benzofuran-1(3H)-one To a solution of 6-Piperazin-1-yl-5,6,7,8-tetrahydronaphtho[2,3-c][1,2,5]oxadiazole hydrochloride (20 mg, 0.068 mmol), 5-(2-bromoethyl)-2-benzofuran-1(3H)-one (33 mg, 0.14 mmol), and tetrabutylammonium iodide (2.5 mg, 6.8 umol) in DMF (2 mL) was added triethylamine (0.028 mL, 0.20 mmol). The mixture was heated to 55° C. for 6 hours. LC showed formation of the desired product, which was separated by mass-directed HPLC. LC-MS (IE, m/z): 419 [M+1]⁺. (0.21 μM)

Example 34

2 Diastereomers

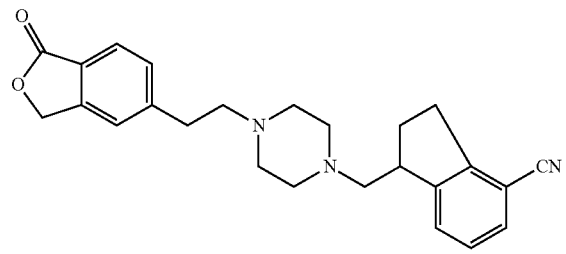 [SMILES: N#Cc1cccc2c1CCC2CN1CCN(CCc2ccc3c(c2)COC3=O)CC1]

1-((4-(2-(1-Oxo-1,3-dihydroisobenzofuran-5-yl)ethyl)piperazin-1-yl)methyl)-2,3-dihydro-1H-indene-4-carbonitrile To a flask containing 1-(piperazin-1-ylmethyl)-2,3-dihydro-1H-indene-4-carbonitrile (0.04 g, 0.17 mmol) was added 5-(2-bromoethyl)-2-benzofuran-1-(3H)-one (0.02 g, 0.06 mmol), tetrabutyl ammonium iodide (0.02 g, 0.06 mmol) and morpholine (0.08 mL, 0.99 mmol); the resulting mixture was dissolved in DMF (3 mL) and stirred at 60° C. Analysis of the reaction mixture indicated that reaction had gone to completion. The solution was concentrated in vacuo and shot into Mass-directed HPLC for separation to give the desired 1-({4-[2-(3-oxo-1,3-dihydro-2-benzofuran-5-yl)ethyl]piperazin-1-yl}methyl)indane-4-carbonitrile. LC-MS (IE, m/z): 402 [M+1]$^+$. (0.27 μM)

Example 35

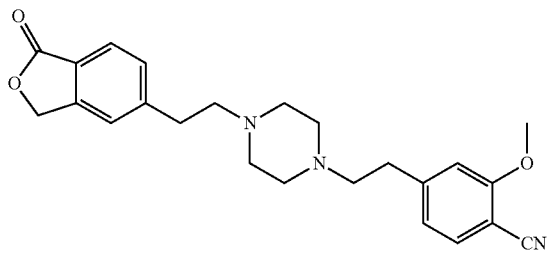 [SMILES: COc1cc(CCN2CCN(CCc3ccc4c(c3)COC4=O)CC2)ccc1C#N]

2-Methoxy-4-(2-{4-[2-(1-oxo-1,3-dihydro-2-benzofuran-5-yl)ethyl]piperazin-1-yl}ethyl)benzonitrile To a mixture of 5-[2-(piperazin-1-yl)ethyl]-2-benzofuran-1(3H)-one methyl (29 mg, 0.10 mmol) and 2-methoxy-4-(2-oxoethyl)benzonitrile (15 mg, 0.085 mmol) in methanol (1.0 mL) at 0° C. was added sodium cyanoborohydride (7.5 mg, 0.12 mmol) and the mixture was stirred at room temperature for 12 hours. The reaction mixture was concentrated and purified by mass-directed HPLC to provide 2-methoxy-4-(2-{4-[2-(1-oxo-1,3-dihydro-2-benzofuran-5-yl)ethyl]piperazin-1-yl}ethyl)benzonitrile. LC-MS (IE, m/z): 405.2 [M+1]$^+$. $^1$H-NMR (500 MHz, CD$_3$OD) δ ppm 7.86 (m, 1H), 7.58 (overlapping m's, 3H), 7.13 (s, 1H), 7.02 (m, 1H), 5.38 (s, 2H), 3.98 (s, 3H), 3.37-3.21 (overlapping m's, 12H) 3.18 (m, 2H), 3.08 (m, 2H). (0.089 μM)

Example 36

2 Diastereomers

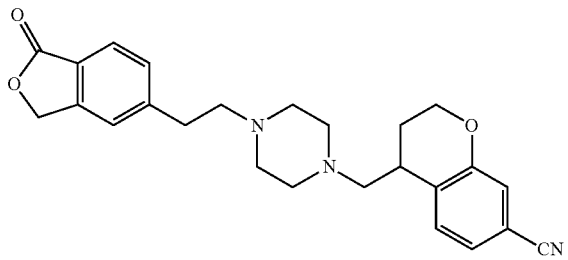 [SMILES: N#Cc1ccc2c(c1)CCCC2CN1CCN(CCc2ccc3c(c2)COC3=O)CC1]

4-({4-[2-(1-Oxo-1,3-dihydro-2-benzofuran-5-yl)ethyl]piperazin-1-yl}methyl)-3,4-dihydro-2H-chromene-7-carbonitrile To a 12 mL reaction vial was added 4-formyl-3,4-dihydro-2H-chromene-7-carbonitrile (50 mg, 0.27 mmol), 5-[2-(piperazin-1-yl)ethyl]-2-benzofuran-1(3H)-one (66 mg, 0.27 mmol) and dichloromethane (3 mL). The solution was stirred at RT under N$_2$ for 10 min. To above solution was added sodium tris(acetoxy) borohydride (224 mg, 1.1 mmol). The reaction was stirred at RT for 18 hours under N$_2$, extracted with DCM, washed with brine and water. The organic phase was dried over MgSO$_4$, filtered and purified by flash column chromatography. LC-MS (IE, m/z): 418.1 [M+1]$^+$. $^1$H NMR (500 MHz, CDCl$_3$, δ in ppm): 7.84 (1H, d, J=7.8 Hz), 7.38 (1H, d, J=7.8 Hz), 7.32 (2H, m), 7.11 (1H, dxd, J=8.0 Hz, J=1.6 Hz), 7.08 (1H, d, J=1.6 Hz), 5.60 (2H, s), 4.4 (2H, m), 3.0 (4H, m), 2.4-2.8 (10H, m), 2.0 (2H, m). (0.092 μM)

Example 37

2 Diastereomers

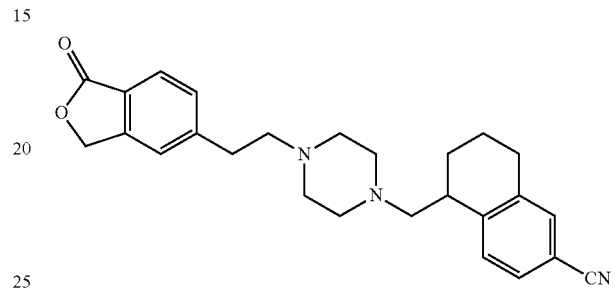

5-({4-[2-(1-Oxo-1,3-dihydro-2-benzofuran-5-yl)ethyl]piperazin-1-yl}methyl)-5,6,7,8-tetrahydronaphalene-2-carbonitrile To a 12 mL reaction vial was added 5-formyl-5,6,7,8-tetrahydronaphthalene-2-carbonitrile (50 mg, 0.27 mmol), 5-[2-(piperazin-1-yl)ethyl]-2-benzofuran-1(3H)-one (66 mg, 0.27 mmol) and dichloromethane (3 mL). The solution was stirred at RT under N$_2$ for 10 min. To above solution was added sodium tris(acetoxy) borohydride (172 mg, 0.81 mmol). The reaction was stirred at RT for 18 hours under N$_2$, extracted with DCM, washed with brine and water. The organic phase was dried over MgSO$_4$, filtered and purified by flash column chromatography. LC-MS (IE, m/z): 416.2 [M+1]$^+$. (0.46 μM)

Example 38

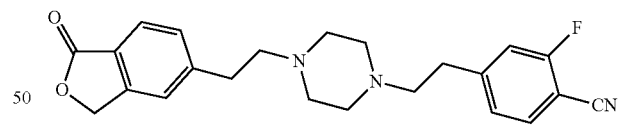

2-Fluoro-4-[2-[4-[2-(1-oxo-3H-isobenzofuran-5-yl)ethyl]piperazin-1-yl]ethyl]benzonitrile To the 2-fluoro-4-(2-oxoethyl)benzonitrile (0.39 g, 2.4 mmol) were added dichloromethane (40 mL) and 5-[2-(piperazin-1-yl)ethyl]-2-benzofuran-1(3H)-one hydrochloride [(0.68 g, 2.4 mmol), in dichloromethane (3 mL), and triethylamine (0.67 mL, 4.8 mmol)], and the mixture was stirred at room temperature for 0.5 h. Sodium triacetoxyborohydride (2.53 g, 12 mmol) was added, and the reaction mixture was stirred at room temperature for 24 h. The reaction was quenched with water (5 mL), and the organics were extracted with EtOAc (2×50 mL). The combined organic layers were washed with water (20 mL) and brine (20 mL) and dried (MgSO$_4$). Filtration followed by concentration afforded an oily residue, which was purified via mass-directed reverse-phase HPLC followed by evaporation and drying of the pure fraction obtained off white TFA salt foam which then converted to HCl salt by triturating in 1M HCl in diethyl ether (1 mL, 1 h). Evaporation and dried under vacuum provided the final product as an off white solid. LC-MS (IE, m/z): 394.24 [M+1]$^+$. (0.049 μM)

Example 39

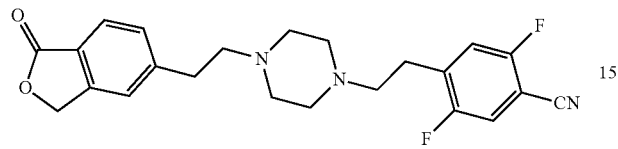

2,5-Difluoro-4-[2-[4-[2-(1-oxo-3H-isobenzofuran-5-yl)ethyl]piperazin-1-yl]ethyl]benzonitrile 2,5-Difluoro-4-[2-[4-[2-(1-oxo-3H-isobenzofuran-5-yl) ethyl]piperazin-1-yl]ethyl]benzonitrile was prepared in a similar fashion to that described for the synthesis of Example 38 starting from 5-[2-(piperazin-1-yl)ethyl]-2-benzofuran-1 (3H)-one hydrochloride and 2,5-difluoro-4-(2-oxoethyl)benzonitrile. LC-MS (IE, m/z): 412.1 [M+1]$^+$. (0.23 μM)

Example 40

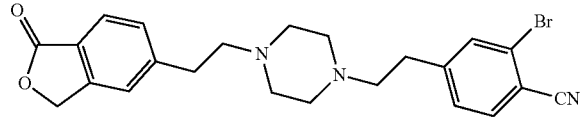 [SMILES: N#Cc1ccc(CCN2CCN(CCc3ccc4c(c3)COC4=O)CC2)cc1Br]

2-Bromo-4-[2-[4-[2-(1-oxo-3H-isobenzofuran-5-yl) ethyl]piperazin-1-yl]ethyl]benzonitrile 2-Bromo-4-[2-[4-[2-(1-oxo-3H-isobenzofuran-5-yl) ethyl]piperazin-1-yl]ethyl]benzonitrile was prepared in a similar fashion to that described for the synthesis of Example 38 starting from 5-[2-(piperazin-1-yl)ethyl]-2-benzofuran-1 (3H)-one hydrochloride and 2-bromo-4-(2-oxoethyl)benzonitrile. LC-MS (IE, m/z): 456.0 [M+1]$^+$. (0.099 μM)

Example 41

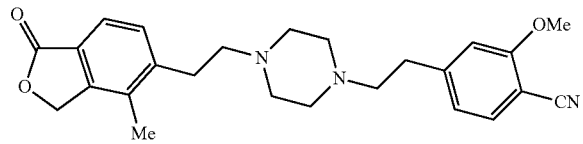 [SMILES: COc1cc(CCN2CCN(CCc3ccc4c(c3C)COC4=O)CC2)ccc1C#N]

2-Methoxy-4-[2-[4-[2-(4-methyl-1-oxo-3H-isobenzofuran-5-yl)ethyl]piperazin-1-yl]ethyl]benzonitrile 2-Methoxy-4-[2-[4-[2-(4-methyl-1-oxo-3H-isobenzofuran-5-yl)ethyl]piperazin-1-yl]ethyl]benzonitrile was prepared in a similar fashion to that described for the synthesis of Example 38 starting from 4-methyl-5-[2-(piperazin-1-yl) ethyl]-2-benzofuran-1(3H)-one hydrochloride and 2-methoxy-4-(2-oxoethyl)benzonitrile. LC-MS (IE, m/z): 420.2 [M+1]$^+$. (0.035 μM)

Example 42

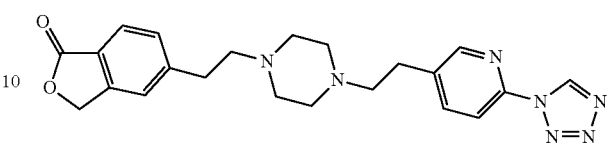

5-[2-[4-[2-[6-(Tetrazol-1-yl)-3-pyridyl]ethyl]piperazin-1-yl]ethyl]-3H-isobenzofuran-1-one 5-[2-[4-[2-[6-(Tetrazol-1-yl)-3-pyridyl]ethyl]piperazin-1-yl]ethyl]-3H-isobenzofuran-1-one was prepared in a similar fashion to that described for the synthesis of Example 38 starting from 5-[2-(piperazin-1-yl)ethyl]-2-benzofuran-1 (3H)-one hydrochloride and [6-(1H-tetrazol-1-yl)pyridin-3-yl]acetaldehyde. LC-MS (IE, m/z): 392.0 [(M+1)$^+$–28]. (0.91 μM)

Example 43

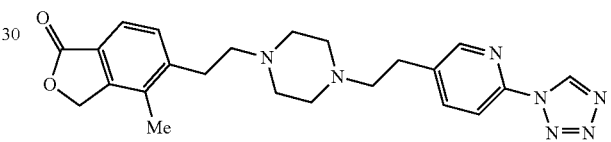

4-Methyl-5-[2-[4-[2-[6-(tetrazol-1-yl)-3-pyridyl] ethyl]piperazin-1-yl]ethyl]-3H-isobenzofuran-1-one 4-Methyl-5-[2-[4-[2-[6-(tetrazol-1-yl)-3-pyridyl]ethyl] piperazin-1-yl]ethyl]-3H-isobenzofuran-1-one was prepared in a similar fashion to that described for the synthesis of Example 38 starting from 4-methyl-5-[2-(piperazin-1-yl) ethyl]-2-benzofuran-1(3H)-one hydrochloride and [6-(1H-tetrazol-1-yl)pyridin-3-yl]acetaldehyde. LC-MS (IE, m/z): 406.1 [(M+1)$^+$–28]. (0.61 μm)

Example 44

2 Diastereomers

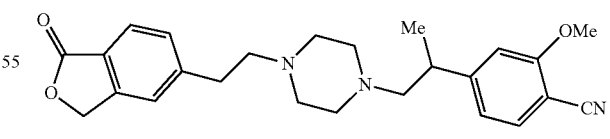

2-Methoxy-4-[1-methyl-2-[4-[2-(1-oxo-3H-isobenzofuran-5-yl)ethyl]piperazin-1-yl]ethyl]benzonitrile 2-Methoxy-4-[1-methyl-2-[4-[2-(1-oxo-3H-isobenzofuran-5-yl)ethyl]piperazin-1-yl]ethyl]benzonitrile was prepared in a similar fashion to that described for the synthesis of Example 38 starting from 5-[2-(piperazin-1-yl)ethyl]-2-benzofuran-1(3H)-one hydrochloride and 2-methoxy-4-(1-oxo-propan-2-yl)benzonitrile. LC-MS (IE, m/z): 420.5 [M+1]⁺. (0.28 μM)

Example 45

2 Diastereomers

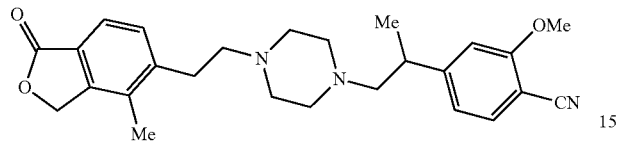

2-Methoxy-4-[1-methyl-2-[4-[2-(4-methyl-1-oxo-3H-isobenzofuran-5-yl)ethyl]piperazin-1-yl]ethyl]benzonitrile 2-Methoxy-4-[1-methyl-2-[4-[2-(4-methyl-1-oxo-3H-isobenzofuran-5-yl)ethyl]piperazin-1-yl]ethyl]benzonitrile was prepared in a similar fashion to that described for the synthesis of Example 38 starting from 4-methyl-5-[2-(piperazin-1-yl)ethyl]-2-benzofuran-1(3H)-one hydrochloride and 2-methoxy-4-(1-oxopropan-2-yl)benzonitrile. LC-MS (IE, m/z): 434.5 [M+1]⁺. (0.15 μM)

Example 46

2 Diastereomers

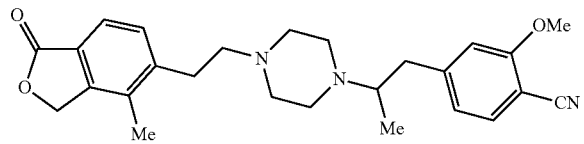 [SMILES: COc1cc(CC(C)N2CCN(CCc3ccc4c(c3C)COC4=O)CC2)ccc1C#N]

2-Methoxy-4-[2-[4-[2-(4-methyl-1-oxo-3H-isobenzofuran-5-yl)ethyl]piperazin-1-yl]propyl]benzonitrile 2-Methoxy-4-[2-[4-[2-(4-methyl-1-oxo-3H-isobenzofuran-5-yl)ethyl]piperazin-1-yl]propyl]benzonitrile was prepared in a similar fashion to that described for the synthesis of Example 38 starting from 4-methyl-5-[2-(piperazin-1-yl)ethyl]-2-benzofuran-1(3H)-one hydrochloride and 2-methoxy-4-(2-oxopropyl)benzonitrile. LC-MS (IE, m/z): 434.4 [M+1]⁺. (0.19 μM)

Example 47

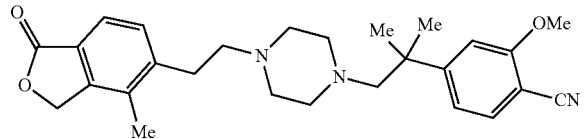 [SMILES: COc1cc(C(C)(C)CN2CCN(CCc3ccc4c(c3C)COC4=O)CC2)ccc1C#N]

4-[1,1-Dimethyl-2-[4-[2-(4-methyl-1-oxo-3H-isobenzofuran-5-yl)ethyl]piperazin-1-yl]ethyl]-2-methoxy-benzonitrile 4-[1,1-Dimethyl-2-[4-[2-(4-methyl-1-oxo-3H-isobenzofuran-5-yl)ethyl]piperazin-1-yl]ethyl]-2-methoxy-benzonitrile was prepared in a similar fashion to that described for the synthesis of Example 38 starting from 4-methyl-5-[2-(piperazin-1-yl)ethyl]-2-benzofuran-1(3H)-one hydrochloride and 2-methoxy-4-(2-methyl-1-oxopropan-2-yl)benzonitrile. LC-MS (IE, m/z): 448.6 [M+1]⁺. (0.30 μM)

Example 48

2-Methoxy-4-[2-[4-[2-(1-oxo-3H-isobenzofuran-5-yl)ethyl]piperazin-1-yl]propyl]benzonitrile 2-Methoxy-4-[2-[4-[2-(1-oxo-3H-isobenzofuran-5-yl)ethyl]piperazin-1-yl]propyl]benzonitrile was prepared in a similar fashion to that described for the synthesis of Example 38 starting from 5-[2-(piperazin-1-yl)ethyl]-2-benzofuran-1(3H)-one hydrochloride and 2-methoxy-4-(2-oxopropyl)benzonitrile. LC-MS (IE, m/z): 420.6 [M+1]⁺. (0.21 μM)

Example 49

2-(Difluoromethoxy)-4-[2-[4-[2-(4-methyl-1-oxo-3H-isobenzofuran-5-yl)ethyl]piperazin-1-yl]ethyl]benzonitrile 2-(Difluoromethoxy)-4-[2-[4-[2-(4-methyl-1-oxo-3H-isobenzofuran-5-yl)ethyl]piperazin-1-yl]ethyl]benzonitrile was prepared in a similar fashion to that described for the synthesis of Example 38 starting from 4-methyl-5-[2-(piperazin-1-yl)ethyl]-2-benzofuran-1(3H)-one hydrochloride and 2-(difluoromethoxy)-4-(2-oxoethyl)benzonitrile. LC-MS (IE, m/z): 456.5 [M+1]⁺. (0.16 µM)

Example 50

2 Diastereomers

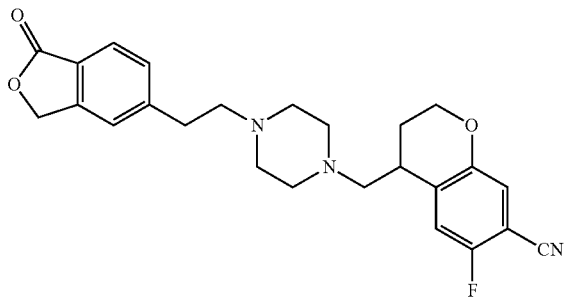 [SMILES: N#Cc1cc2c(cc1F)C(CN1CCN(CCc3ccc4c(c3)COC4=O)CC1)CCO2]

5-Fluoro-3-({4-[2-(1-oxo-1,3-dihydro-2-benzofuran-5-yl)ethyl]piperazin-1-yl}methyl)-3,4-dihydro-2H-chromene-7-carbonitrile To a 12 ml, reaction vial was added 6-fluoro-4-formyl-3,4-dihydro-2H-chromene-7-carbonitrile (12 mg, 0.058 mmol), 5-[2-(piperazin-1-yl)ethyl]-2-benzofuran-1(3H)-one (14.4 mg, 0.058 mmol) and dichloromethane (3 mL). The solution was stirred at r.t. under N₂ for 10 min. To above solution was added sodium triacetoxy borohydride (49.6 mg, 0.23 mmol). The reaction was stirred at RT for 18 hours under N₂, extracted with DCM, washed with brine and water. The organic phase was dried over MgSO₄, filtered and purified by flash column chromatography. LC-MS (IE, m/z): 436.3 [M+1]⁺. (0.44 µM)

Example 51

2 Diastereomers

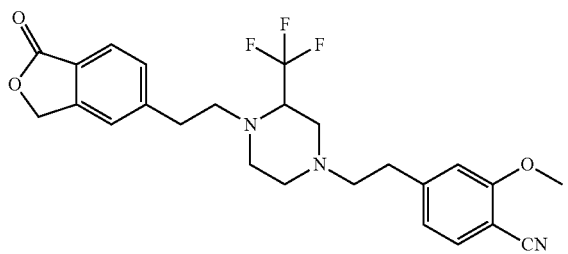 [SMILES: COc1cc(CCN2CCN(CCc3ccc4c(c3)COC4=O)C(C(F)(F)F)C2)ccc1C#N]

2-Methoxy-4-(2-{4-[2-(1-oxo-1,3-dihydro-2-benzofuran-5-yl)ethyl]-3-(trifluoromethyl)piperazin-1-yl}ethyl)benzonitrile Step A: tert-Butyl 4-[2-(1-oxo-1,3-dihydro-2-benzofuran-5-yl)ethyl]-3-(trifluoromethyl)piperazine-1-carboxylate To a solution of (1-oxo-1,3-dihydro-2-benzofuran-5-yl)acetaldehyde (0.495 g, 2.8 mmol) and tert-butyl 3-(trifluoromethyl)piperazine-1-carboxylate (0.65 g, 2.6 mmol) in methanol (5 ml) at 0° C. was added sodium cyanoborohydride (0.21 g, 3.3 mmol) and the reaction stirred 12 hours at RT. The reaction mixture was concentrated and diluted with water. The aqueous was extracted with dichloromethane and the combined organics washed with brine, dried (MgSO₄), filtered and concentrated. MPLC chromatography (2→20% EtOAc:hexane) provided tert-butyl 4-[2-(1-oxo-1,3-dihydro-2-benzofuran-5-yl)ethyl]-3-(trifluoromethyl)piperazine-1-carboxylate. LC-MS (IE, m/z): 415.1 [M+1]⁺.

Step B: 5-{2-[2-(Trifluoromethyl)piperazin-1-yl]ethyl}-2-benzofuran-1(3H)-one

To a solution of tert-butyl 4-[2-(1-oxo-1,3-dihydro-2-benzofuran-5-yl)ethyl]-3-(trifluoromethyl)piperazine-1-carboxylate (183 mg, 0.44 mmol) in 1,4-dioxane (2 ml) was added 4 N HCl in dioxane (1 mL) and the reaction stirred at room temperature for 12 h. LC-MS shows product formation. The reaction mixture was concentrated in vacuo and dried under high vacuum to provide 5-{2-[2-(trifluoromethyl)piperazin-1-yl]ethyl}-2-benzofuran-1(3H)-one which was used directly without further purification. LC-MS (IE, m/z): 194.2 [M+1]⁺.

Step C: 2-Methoxy-4-(2-{4-[2-(1-oxo-1,3-dihydro-2-benzofuran-5-yl)ethyl]-3-(trifluoromethyl)piperazin-1-yl}ethyl)benzonitrile To a mixture of 5-{2-[2-(trifluoromethyl)piperazin-1-yl]ethyl}-2-benzofuran-1(3H)-one (95 mg, 0.27 mmol) and 2-methoxy-4-(2-oxoethyl)benzonitrile (40 mg, 0.23 mmol) in methanol (1.0 mL) at 0° C. was added sodium cyanoborohydride (20 mg, 0.32 mmol) and the mixture was stirred at room temperature for 12 hours. The reaction mixture was concentrated and purified by mass-directed HPLC to provide 2-methoxy-4-(2-{4-[2-(1-oxo-1,3-dihydro-2-benzofuran-5-yl)ethyl]-3-(trifluoromethyl)piperazin-1-yl}ethyl)benzonitrile. LC-MS (IE, m/z): 474.3 [M+1]⁺. ¹H-NMR (500 MHz, CD₃OD) δ ppm 7.82 (m, 1H), 7.60 (overlapping m's, 3H), 7.15 (s, 1H), 7.02 (m, 1H), 5.38 (s, 2H), 3.98 (s, 3H), 3.90 (m, 1H), 3.58 (m, 2H), 3.51 (m, 2H), 3.43 (m, 2H), 3.20 (m, 4H), 3.12 (m, 2H), 3.08 (m, 2H). (0.65 µM)

Example 52

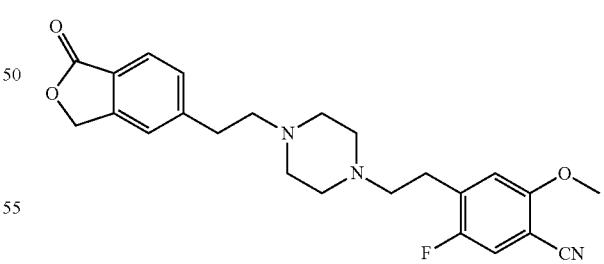

5-Fluoro-2-methoxy-4-(2-{4-[2-(1-oxo-1,3-dihydro-2-benzofuran-5-yl)ethyl]piperazin-1-yl}ethyl)benzonitrile To a mixture of 5-[2-(piperazin-1-yl)ethyl]-2-benzofuran-1(3H)-one (94 mg, 0.33 mmol) and 5-fluoro-2-methoxy-4-(2-oxoethyl)benzonitrile (58 mg, 0.30 mmol) in methanol (3.0 mL) at 0° C. was added sodium cyanoborohydride (29 mg, 0.47 mmol) and the mixture was stirred at room temperature for 12 hours. The reaction mixture was concentrated and purified by mass-directed HPLC to provide 5-fluoro-2-methoxy-4-(2-{4-[2-(1-oxo-1,3-dihydro-2-benzofuran-5-yl)ethyl]piperazin-1-yl}ethyl)benzonitrile. LC-MS (IE, m/z): 424.3 [M+1]$^+$. (0.068 μM)

Example 53

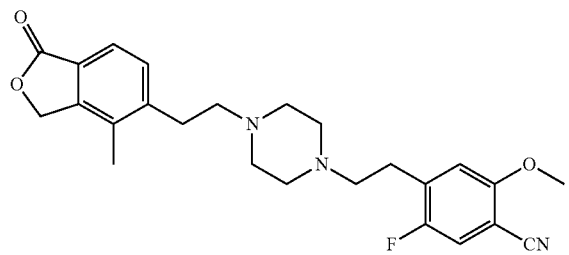 [SMILES: COc1cc(CCN2CCN(CCc3ccc4c(c3C)COC4=O)CC2)c(F)cc1C#N]

5-Fluoro-2-methoxy-4-(2-{4-[2-(4-methyl-1-oxo-1,3-dihydro-2-benzofuran-5-yl)ethyl]piperazin-1-yl}ethyl)benzonitrile To a mixture of 5-[2-(piperazin-1-yl)ethyl]-2-benzofuran-1(3H)-one (95 mg, 0.27 mmol) and 5-fluoro-2-methoxy-4-(2-oxoethyl)benzonitrile (40 mg, 0.23 mmol) in methanol (1.0 mL) at 0° C. was added sodium cyanoborohydride (20 mg, 0.32 mmol) and the mixture was stirred at room temperature for 12 hours. The reaction mixture was concentrated and purified by mass-directed HPLC to provide 5-fluoro-2-methoxy-4-(2-{4-[2-(4-methyl-1-oxo-1,3-dihydro-2-benzofuran-5-yl)ethyl]piperazin-1-yl}ethyl)benzonitrile. LC-MS (IE, m/z): 438.4 [M+1]$^+$. (0.034 μM)

Example 54

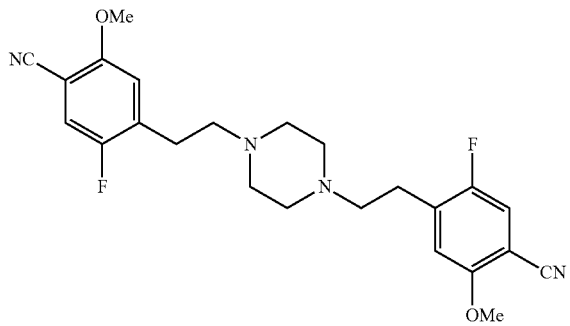 [SMILES: COc1cc(CCN2CCN(CCc3cc(OC)c(C#N)cc3F)CC2)c(F)cc1C#N]

4,4'-(Piperazine-1,4-diyldiethane-2,1-diyl)bis(5-fluoro-2-methoxybenzonitrile)

To a mixture of piperazine (13 mg, 0.15 mmol) and 5-fluoro-2-methoxy-4-(2-oxoethyl)benzonitrile (58 mg, 0.30 mmol) in methanol (3.0 mL) at 0° C. was added sodium cyanoborohydride (24 mg, 0.38 mmol) and the mixture was stirred at room temperature for 12 hours. The reaction mixture was concentrated and purified by mass-directed HPLC to provide 4,4'-(piperazine-1,4-diyldiethane-2,1-diyl)bis(5-fluoro-2-methoxybenzonitrile). LC-MS (IE, m/z): 441.4 [M+1]$^+$. (0.34 μM)

Example 55

2 Diastereomers

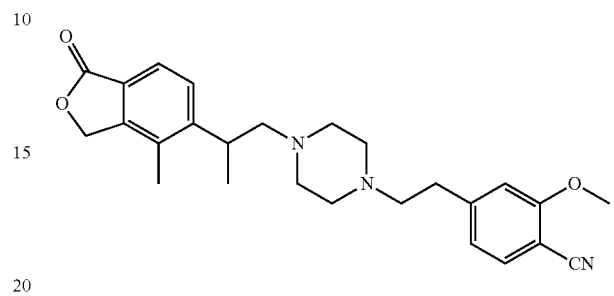

2-Methoxy-4-(2-{4-[2-(4-methyl-1-oxo-1,3-dihydro-2-benzofuran-5-yl)propyl]piperazin-1-yl}ethyl)benzonitrile To a mixture of 4-methyl-5-[1-(piperazin-1-yl)propan-2-yl]-2-benzofuran-1(3H)-one (25 mg, 0.080 mmol) and 2-methoxy-4-(2-oxoethyl)benzonitrile (17 mg, 0.097 mmol) in methanol (1.0 mL) at 0° C. was added sodium cyanoborohydride (7 mg, 0.113 mmol) and the mixture was stirred at room temperature for 12 hours. The reaction mixture was concentrated and purified by mass-directed HPLC to provide 2-methoxy-4-(2-{4-[2-(4-methyl-1-oxo-1,3-dihydro-2-benzofuran-5-yl)propyl]piperazin-1-yl}ethyl)benzonitrile. LC-MS (IE, m/z): 434.3 [M+1]$^+$. (0.17 μM)

Example 56

2 Diastereomers

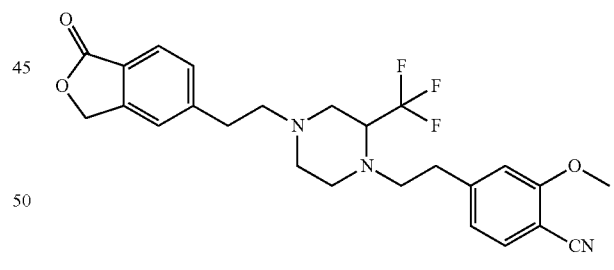

2-Methoxy-4-(2-{4-[2-(1-oxo-1,3-dihydro-2-benzofuran-5-yl)ethyl]-2-(trifluoromethyl)piperazin-1-yl}ethyl)benzonitrile Step A: tert-Butyl 4-[2-(4-cyano-3-methoxyphenyl)ethyl]-3-(trifluoromethyl)piperazine-1-carboxylate To a mixture of tert-butyl 3-(trifluoromethyl)piperazine-1-carboxylate (72 mg, 0.28 mmol) and 2-methoxy-4-(2-oxoethyl)benzonitrile (50 mg, 0.28 mmol) in methanol (2.5 mL) at 0° C. was added sodium cyanoborohydride (25 mg, 0.40 mmol) and the mixture was stirred at room temperature for 12 hours. The reaction mixture was concentrated and purified by column chromatography (4->30% ethyl acetate:hexanes) to provide tert-butyl 4-[2-(4-cyano-3-methoxyphenyl)ethyl]-3-(trifluoromethyl)piperazine-1-carboxylate. LC-MS (IE, m/z): 414.4 [M+1]⁺.

Step B: 2-methoxy-4-{2-[2-(trifluoromethyl)piperazin-1-yl]ethyl}benzonitrile

A solution of tert-butyl 4-[2-(4-cyano-3-methoxyphenyl)ethyl]-3-(trifluoromethyl)piperazine-1-carboxylate (116 mg, 0.282 mmol) in dichloromethane (2 mL) was treated with trifluoroacetic acid (1 mL) and stirred at room temperature for 2 hours. The reaction mixture was concentrated to provide 2-methoxy-4-{2-[2-(trifluoromethyl)piperazin-1-yl]ethyl}benzonitrile. LC-MS (IE, m/z): 314.4 [M+1]⁺.

Step C: 2-Methoxy-4-(2-{4-[2-(1-oxo-1,3-dihydro-2-benzofuran-5-yl)ethyl]-2-(trifluoromethyl)piperazin-1-yl}ethyl)benzonitrile To a mixture of 2-methoxy-4-{2-[2-(trifluoromethyl)piperazin-1-yl]ethyl}benzonitrile (116 mg, 0.28 mmol) and (1-oxo-1,3-dihydro-2-benzofuran-5-yl)acetaldehyde (49 mg, 0.28 mmol) in methanol (1.0 mL) at 0° C. was added sodium cyanoborohydride (18 mg, 0.28 mmol) and the mixture was stirred at room temperature for 12 hours. The reaction mixture was concentrated and purified by mass-directed HPLC to provide 2-methoxy-4-(2-{4-[2-(1-oxo-1,3-dihydro-2-benzofuran-5-yl)ethyl]-2-(trifluoromethyl)piperazin-1-yl}ethyl)benzonitrile. LC-MS (IE, m/z): 474.4 [M+1]⁺. (0.27 μM)

Example 57

2 Diastereomers

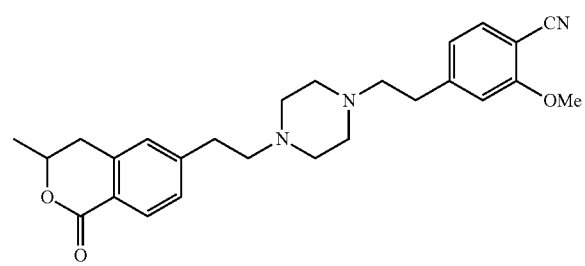 [SMILES: COc1cc(CCN2CCN(CCc3ccc4c(c3)CC(C)OC4=O)CC2)ccc1C#N]

2-Methoxy-4-(2-{4-[2-(3-methyl-1-oxo-3,4-dihydro-1H-isochromen-6-yl)ethyl]piperazin-1-yl}ethyl)benzonitrile To a flask containing 3-methyl-6-[2-(piperazin-1-yl)ethyl]-3,4-dihydro-1H-isochromen-1-one hydrochloride (123 mg, 0.40 mmol) was added in 2 mL of EtOH and NaOH (79 μl, 0.40 mmol). The solvent was removed and the free amine redissolved in DCM and filtered directly into a flask containing 2-methoxy-4-(2-oxoethyl)benzonitrile (58 mg, 0.33 mmol). The mixture was allowed to stir for 20 minutes before sodium triacetoxyborohydride (210 mg, 0.99 mmol) was added. The reaction stirred for 1 hour before being quenched with MeOH. The crude reaction was stirred an additional 30 minutes and the excess solvent was removed. The crude material was redissolved in DCM, filtered, concentrated and purified via MPLC [10-50% (10% MeOH in DCM)/DCM)] to afford 90 mg (63% yield) of 2-methoxy-4-(2-{4-[2-(3-methyl-1-oxo-3,4-dihydro-1H-isochromen-6-yl)ethyl]piperazin-1-yl}ethyl)benzonitrile. ¹H NMR (500 MHz; DMSO): 7.80 (d, J=8.0 Hz, 1H), 7.58 (d, J=8.0 Hz, 1H), 7.27 (d, J=7.8 Hz, 1H), 7.22 (s, 1H), 7.14 (s, 1H), 6.95 (d, J=7.8 Hz, 1H), 4.65 (m, 1H), 3.88 (bs, 4H), 2.94 (m, 4H), 2.78 (m, 4H), 2.43 (m, 4H), 1.38 (d, J=6.8 Hz, 3H). LC-MS (IE, m/z): 375 [M+1]⁺. (0.098 μM)

Example 58

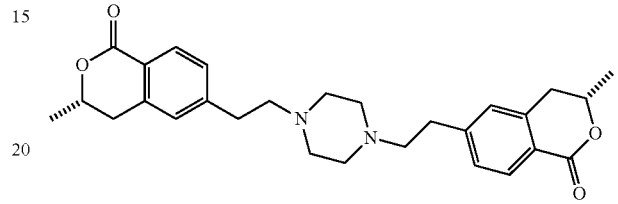

(3S,3'S)-6,6'-(Piperazine-1,4-diyldiethane-2,1-diyl)bis(3-methyl-3,4-dihydro-1H-isochromen-1-one)

The desired product was synthesized according to the procedure described for Example 57, utilizing (3S)-6-(1,3-dioxolan-2-ylmethyl)-3-methyl-3,4-dihydro-1H-isochromen-1-one and (3S)-6-(1,3-dioxolan-2-ylmethyl)-3-methyl-3,4-dihydro-1H-isochromen-1-one as the starting components in the reaction. LC-MS (IE, m/z): 463 [M+1]⁺. (0.65 μM)

Example 59

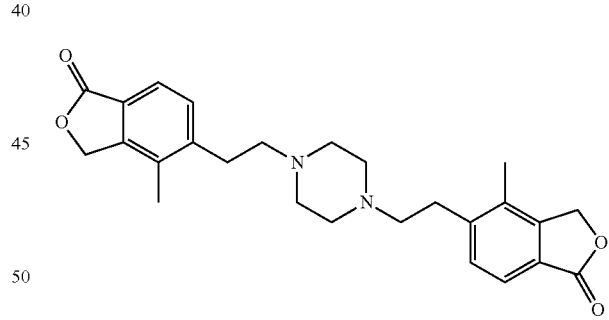

5,5'-(Piperazine-1,4-diyldiethane-2,1-diyl)bis(4-methyl-2-benzofuran-1(3H)-one)

A mixture of 4-methyl-5-(2-piperazin-1-ylethyl)-2-benzofuran-1(3H)-one hydrochloride (62 mg, 0.21 mmol), (1-oxo-1,3-dihydro-2-benzofuran-5-yl)acetaldehyde (40 mg, 0.21 mmol), and sodium triacetoxyborohydride (67 mg, 0.32 mmol) in DCM (5 mL) was stirred overnight with a drop of acetic acid. LC showed formation of the desired product, which was purified by mass-directed HPLC (0.1% TFA in water and acetonitrile). LC-MS (IE, m/z): 435 [M+1]⁺. (0.076 μM)

Example 60

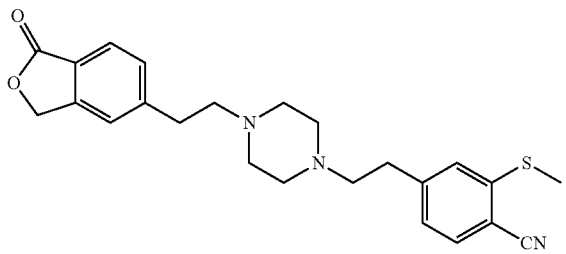 [SMILES: CSc1cc(CCN2CCN(CCc3ccc4c(c3)COC4=O)CC2)ccc1C#N]

2-(Methylthio)-4-(2-{4-[2-(1-oxo-1,3-dihydro-2-benzofuran-5-yl)ethyl]piperazin-1-yl}ethyl)benzonitrile

Step A: 4-Allyl-2-fluorobenzonitrile

To a solution of 4-bromo-2-fluorobenzonitrile (5.0 g, 13 mmol) in 100 ml of toluene was added LiCl (1.7 g, 39 mmol), Pd(PPh$_3$)$_4$ (400 mg), Allyl tributyltin (5.2 g, 16 mmol), and then the mixture was heated to reflux overnight. After the reaction was completed, the reaction solution was diluted with EtOAc and filtered. The filtrate was concentrated and purified with silica gel column chromatograph to give crude 4-allyl-2-fluorobenzonitrile.

Step B: 2-Fluoro-4-(2-oxoethyl)benzonitrile

A solution of 4-allyl-2-fluorobenzonitrile (1 g, 6.2 mmol) in 1:1 CH$_2$Cl$_2$/MeOH (40 mL) containing pyridine (1 mL, 12.4 mmol) was cooled to −78° C., and O$_3$ was passed through until a blue color was present. N$_2$ was then bubbled through to discharge the blue color and Me$_2$S (5 ml) was added. The reaction mixture was allowed to warm and left overnight. The mixture was washed with 1 N HCl and aqueous NaHCO$_3$ and then dried and concentrated to give crude 2-fluoro-4-(2-oxoethyl)benzonitrile. The material was carried on as the crude.

Step C: tert-Butyl 4-[2-(4-cyano-3-fluorophenyl)ethyl]piperazine-1-carboxylate To a solution of crude 2-fluoro-4-(2-oxoethyl)benzonitrile (900 mg, 5.5 mmol) in 20 mL of DCM was added N-Boc Piperazine (1.0 g, 5.5 mmol) and NaBH(OAc)$_3$ (4.7 g, 22 mmol), the mixture was stirred at room temperature overnight. The reaction was diluted with DCM, and washed with brine, the organic layer was dried over anhydrous Na$_2$SO$_4$ and concentrated. The residue was purified by preparative TLC to give tert-butyl 4-[2-(4-cyano-3-fluorophenyl)ethyl]piperazine-1-carboxylate.

Step D: tert-Butyl 4-{2-[4-cyano-3-(methylthio)phenyl]ethyl}piperazine-1-carboxylate To a solution of tert-butyl 4-[2-(4-cyano-3-fluorophenyl)ethyl]piperazine-1-carboxylate (440 mg, 1.32 mmol) in 10 mL of DMF was dropped NaSMe (0.66 mL, 1.8 mmol, 21% in water). The mixture was stirred at 70° C. for 3 hours. The reaction was diluted with 40 mL of EtOAc and 40 mL water. The organic layer was dried over anhydrous sodium sulfate and concentrated. The residue was purified with prep-TLC to give tert-butyl 4-{2-[4-cyano-3-(methylthio)phenyl]ethyl}piperazine-1-carboxylate (250 mg, 52% yield). MS: m/e 362 (M+1)$^+$. To a solution of tert-butyl4-{2-[4-cyano-3-(methylthio)phenyl]ethyl}piperazine-1-carboxylate (250 mg, 0.69 mmol) in 5 mL of DCM was added 5 mL of TFA was stirred at room temperature for 1 hours, and the reaction was concentrated. The residue was diluted with 30 mL of aq. NaHCO$_3$ and 30 mL of DCM: MeOH (v/v=10/1). The organic phase was washed with brine, dried over anhydrous sodium sulfate and concentrated to afford 2-(methylthio)-4-(2-piperazin-1-ylethyl)benzonitrile.

Step E: 2-(Methylthio)-4-(2-{4-[2-(1-oxo-1,3-dihydro-2-benzofuran-5-yl)ethyl]piperazin-1-yl}ethyl)benzonitrile To a solution of 2-(methylthio)-4-(2-piperazin-1-ylethyl)benzonitrile (0.69 mmol) in 20 mL of DCM was added (1-oxo-1,3-dihydro-2-benzofuran-5-yl)acetaldehyde (180 mg, 1.03 mmol) and NaBH(OAc)$_3$ (580 mg, 2.8 mmol), and the mixture was stirred at room temperature overnight. The reaction was diluted with DCM, and washed with brine. The organic layer was dried over anhydrous Na$_2$SO$_4$ and concentrated. The residue was purified by prep-TLC to give 2-(methylthio)-4-(2-{4-[2-(1-oxo-1,3-dihydro-2-benzofuran-5-yl)ethyl]piperazin-1-yl}ethyl)benzonitrile. $^1$H-NMR (400 MHz, CDCl3) δ ppm 7.82 (d, J=8.6 Hz, 1H), 7.49 (d, J=7.8 Hz, 1H), 7.33~7.37 (m, 2H), 7.16 (s, 1H), 7.02~7.05 (m, 1H), 5.27 (s, 2H), 2.49~3.01 (m, 19H). (0.55 μM)

Example 61

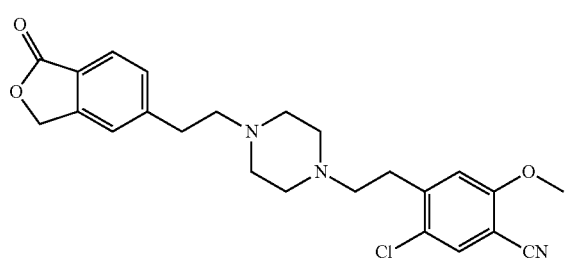 [SMILES: COc1cc(CCN2CCN(CCc3ccc4c(c3)COC4=O)CC2)c(Cl)cc1C#N]

5-Chloro-2-methoxy-4-(2-{4-[2-(1-oxo-1,3-dihydro-2-benzofuran-5-yl)ethyl]piperazin-1-yl}ethyl)benzonitrile To a mixture of 5-(2-piperazin-1-ylethyl)-2-benzofuran-1(3H)-one (90 mg, 0.190 mmol) and NaBH$_3$CN (24 mg, 0.380 mmol) in 20 mL DCM was added 5-chloro-2-methoxy-4-(2-oxoethyl)benzonitrile (40 mg, 0.190 mmol) and the mixture was stirred at RT overnight. Concentrated, and the residue was purified by prep-TLC to give 5-chloro-2-methoxy-4-(2-{4-[2-(1-oxo-1,3-dihydro-2-benzofuran-5-yl)ethyl]piperazin-1-yl}ethyl)benzonitrile. $^1$H-NMR (400 MHz, MeOD) δ ppm 7.82 (d, J=7.8 Hz, 1H), 7.67 (s, 1H), 7.50~7.53 (m, 2H), 7.20 (s, 1H), 5.35 (s, 2H), 3.95 (s, 3H), 3.23~3.26 (m, 6H), 3.10~3.16 (m, 8H), 3.00~3.03 (m, 2H). MS m/e 441 (M+1)+. (0.094 μM)

Example 62

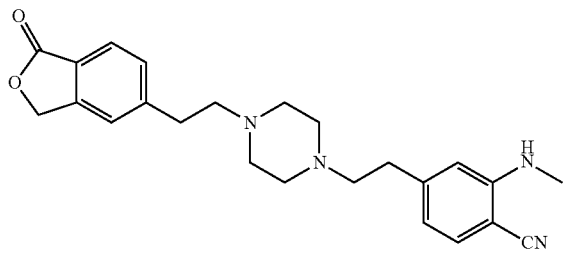 [SMILES: CNc1cc(CCN2CCN(CCc3ccc4c(c3)COC4=O)CC2)ccc1C#N]

2-(Methylamino)-4-(2-{4-[2-(1-oxo-1,3-dihydro-2-benzofuran-5-yl)ethyl]piperazin-1-yl}ethyl)benzonitrile Step A: tert-Butyl 4-{2-[4-cyano-3-(methylamino) phenyl]ethyl}piperazine-1-carboxylate To a solution of tert-butyl 4-[2-(4-cyano-3-fluorophenyl) ethyl]piperazine-1-carboxylate (100 mg, 0.30 mmol) in CH$_3$CN (10 mL) was added aqueous NH$_2$CH$_3$ (10 mL) in a sealed tube, and then heated to 120° C. overnight. The mixture was extracted with EtOAc, washed with brine, dried over anhydrous sodium sulfate and concentrated. The residue was purified via prep-TLC to afford tert-butyl 4-{2-[4-cyano-3-(methylamino)phenyl]ethyl}piperazine-1-carboxylate.

Step B: 2-(Methylamino)-4-(2-piperazin-1-ylethyl) benzonitrile

A solution of tert-butyl 4-{2-[4-cyano-3-(methylamino) phenyl]ethyl}piperazine-1-carboxylate (18 mg, 0.05 mmol) in 5 mL of DCM was added TFA (3 mL), and then stirred at room temperature for 2 hours. The solvents were removed off under vacuum to afford crude 2-(methylamino)-4-(2-piperazin-1-ylethyl)benzonitrile.

Step C: 2-(Methylamino)-4-(2-{4-[2-(1-oxo-1,3-dihydro-2-benzofuran-5-yl)ethyl]piperazin-1-yl}ethyl)benzonitrile A solution of crude 2-(methylamino)-4-(2-piperazin-1-yl-ethyl)benzonitrile (~18 mg, 0.05 mmol), (1-oxo-1,3-dihydro-2-benzofuran-5-yl)acetaldehyde (9 mg, 0.05 mmol) and NaBH(OAc)$_3$ (100 mg, 0.47 mmol) in 10 mL of anhydrous DCM was stirred at ambient temperature overnight. The reaction mixture was added 50 mL of DCM and washed with brine. The organic layer was dried over anhydrous sodium sulfate and concentrated. The residue was purified with prep-TLC to afford 2-(methylamino)-4-(2-{4-[2-(1-oxo-1,3-dihydro-2-benzofuran-5-yl)ethyl]piperazin-1-yl}ethyl)benzonitrile. $^1$H-NMR (400 MHz, CDCl$_3$) δ 7.77 (d, J=7.8, 1H), 7.22~7.32 (m, 3H), 6.42~6.47 (m, 2H), 5.22 (s, 2H), 4.50~4.58 (m, 1H), 2.84~2.91 (m, 7H), 2.72~2.77 (m, 2H), 2.53~2.67 (m, 10H). (0.43 μM)

Example 63

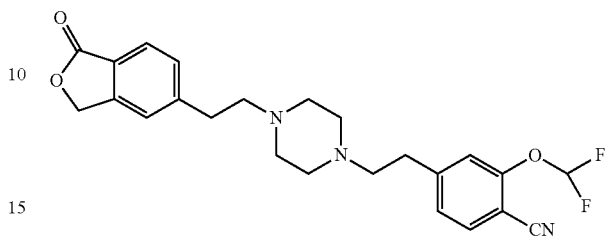

2-(Difluoromethoxy)-4-(2-{4-[2-(1-oxo-1,3-dihydro-2-benzofuran-5-yl)ethyl]piperazin-1-yl}ethyl)benzonitrile Step A: 4-Bromo-2-hydroxybenzonitrile To a stirred solution of 4-bromo-2-fluorobenzonitrile (4.0 g, 20 mmol) in DMF (20 mL) was added 2-(methylsulfonyl) ethanol (3.7 g, 30 mmol) and then NaH (2.4 g, 60% in mineral, 60 mmol) in portions at 0° C. The mixture was then warmed to rt. and quenched with 1N HCl, and extracted by EtOAc. The organic layers were washed with brine and dried over sodium sulfate, concentrated to give 4-bromo-2-hydroxybenzonitrile. $^1$H-NMR (400 MHz, DMSO) δ 7.55-7.57 (d, J=8.61 Hz, 1H), 7.16 (s, 1H), 7.11-7.13 (m, 1H).

Step B: 4-Bromo-2-(difluoromethoxy)benzonitrile

A mixture of 4-bromo-2-hydroxybenzonitrile (2.0 g, 10 mmol), potassium carbonate (1.66 g, 12 mmol), and ClF$_2$CCOONa (3.0 g, 20 mmol) in DMF (18 mL) and H$_2$O (2 mL) was degassed and kept at 100° C. for 2 h. The resulting mixture was cooled to RT and then added concentrated HCl (3 mL) and H$_2$O (4 mL) and then stirred at the temperature overnight. Then the mixture was brought to pH=10.5 by addition of NaOH, and partitioned between water and MTBE. The organic layers were washed by water, saturated K$_3$PO$_4$ solution and brine, dried over sodium sulfate and concentrated to give 4-bromo-2-(difluoromethoxy)benzonitrile. $^1$H-NMR (400 MHz, CDCl3) δ 7.49-7.53 (m, 2H), 7.44-7.47 (m, 1H), 6.47-6.82 (t, J=71.2 Hz, J=71.2 Hz, 1H).

Step C: 4-Allyl-2-(difluoromethoxy)benzonitrile

To a solution of 4-bromo-2-(difluoromethoxy)benzonitrile (620 mg, 2.5 mmol) in 30 ml of toluene was added LiCl (322 mg, 7.5 mmol), Pd(PPh$_3$)$_4$ (60 mg), Allyl tributyltin (990 mg, 3.0 mmol), and then the mixture was heated to reflux overnight. After the reaction was completed, the reaction solution was diluted with EtOAc and filtered. The filtrate was concentrated and purified with silica gel column chromatograph to give crude 4-allyl-2-(difluoromethoxy)benzonitrile.

Step D: 2-(Difluoromethoxy)-4-(2-oxoethyl)benzonitrile

A solution of 4-allyl-2-(difluoromethoxy)benzonitrile (600 mg, 2.9 mmol) in 1:1 CH$_2$Cl$_2$/MeOH (15 mL) containing pyridine (0.5 mL, 6 mmol) was cooled to −78° C., and O$_3$ was passed through until a blue color was present. N₂ was then bubbled through to discharge the blue color and Me₂S (5 ml) was added. The reaction mixture was allowed to warm and left overnight. The mixture was washed with 1 N HCl, aqueous NaHCO₃, dried and concentrated to give crude 2-(difluoromethoxy)-4-(2-oxoethyl)benzonitrile.

Step E: tert-Butyl 4-{2-[4-cyano-3-(difluoromethoxy)phenyl]ethyl}piperazine-1-carboxylate A solution of crude compound 2-(difluoromethoxy)-4-(2-oxoethyl)benzonitrile (100 mg, 0.48 mmol), N-Boc Piperazine (100 mg, 0.54 mmol) and NaBH(OAc)₃ (0.4 g, 2 mmol) in 20 mL of anhydrous DCM was stirred at ambient temperature overnight. The reaction mixture was added 50 mL of DCM, washed with brine. The organic layer was dried over anhydrous sodium sulfate and concentrated. The residue was purified with prep-TLC to afford tert-butyl-4-{2-[4-cyano-3-(difluoromethoxy)phenyl]ethyl}piperazine-1-carboxylate (50 mg, 27% yield). The material was further treated with TFA to remove the Boc group. The crude product was used directly in the next step. MS: m/e 282 (M+1)⁺.

Step F: 2-(Difluoromethoxy)-4-(2-{4-[2-(1-oxo-1,3-dihydro-2-benzofuran-5-yl)ethyl]piperazin-1-yl}ethyl)benzonitrile A solution of crude 2-(difluoromethoxy)-4-(2-piperazin-1-ylethyl)benzonitrile (15 mg, 0.05 mmol), (1-oxo-1,3-dihydro-2-benzofuran-5-yl)acetaldehyde (18 mg, 0.1 mmol) and NaBH(OAc)₃ (100 mg, 0.47 mmol) in 10 mL of anhydrous DCM was stirred at ambient temperature overnight. The reaction mixture was added 50 mL of DCM, washed with brine. The organic layer was dried over anhydrous sodium sulfate and concentrated. The residue was purified with prep-TLC to afford 2-(difluoromethoxy)-4-(2-{4-[2-(1-oxo-1,3-dihydro-2-benzofuran-5-yl)ethyl]piperazin-1-yl}ethyl)benzonitrile.
¹H-NMR (400 MHz, CDCl₃) δ 7.82 (d, J=7.8 Hz, 1H), 7.56 (d, J=8.6 Hz, 1H), 7.33~7.36 (m, 2H), 7.13~7.20 (m, 2H), 6.33 (t, J=71.2 Hz, 1H), 5.26 (s, 2H), 2.99~3.08 (m, 2H), 2.87~2.90 (m, 2H), 2.62~2.84 (m, 12H). (0.15 μm)

Example 64

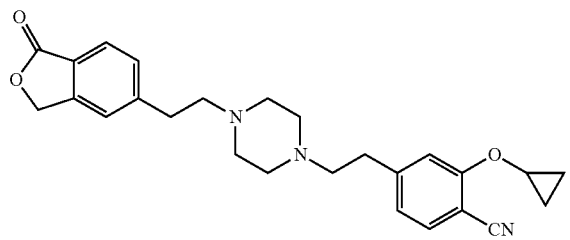 [SMILES: N#Cc1ccc(CCN2CCN(CCc3ccc4c(c3)COC4=O)CC2)cc1OC1CC1]

2-(Cyclopropyloxy)-4-(2-{4-[2-(1-oxo-1,3-dihydro-2-benzofuran-5-yl)ethyl]piperazin-1-yl}ethyl)benzonitrile Step A: 4-Bromo-2-(cyclopropyloxy)benzonitrile A mixture of 4-bromo-2-hydroxybenzonitrile (300 mg, 1.5 mmol), bromo-cyclopropane (480 mg, 4.0 mmol) and Cs₂CO₃ (300 mg, 1.6 mmol) in 2 mL of anhydrous DMF were heated to 170° C. for 2 hours by microwave. The solid was filtered off, and the filtrate was poured to water, and extracted with EtOAc. The organic layer was washed with brine, dried over sodium sulfate and concentrated. The residue was purified with prep-TLC to give 4-bromo-2-(cyclopropyloxy)benzonitrile. ¹H-NMR (400 MHz, CDCl₃) δ ppm 7.46~7.48 (m, 1H), 7.36~7.38 (m, 1H), 7.14~7.16 (m, 1H), 3.79~3.84 (m, 1H), 0.86~0.87 (m, 4H).

Step B: 4-Allyl-2-(cyclopropyloxy)benzonitrile

To a solution of 4-bromo-2-(cyclopropyloxy)benzonitrile (108 mg, 0.45 mmol) in 20 ml of toluene was added LiCl (38 mg, 0.9 mmol), Pd(PPh₃)₄ (15 mg), allyl tributyltin (180 g, 0.55 mmol), then the mixture was heated to reflux overnight. After the reaction was completed, the reaction solution was diluted with EtOAc and filtered, the filtrate was concentrated and purified with silica gel column chromatograph to give crude 4-allyl-2-(cyclopropyloxy)benzonitrile.

Step C: 2-(Cyclopropyloxy)-4-(2-oxoethyl)benzonitrile

A solution of 4-allyl-2-(cyclopropyloxy)benzonitrile (100 mg, 0.5 mmol) in 1:1 CH₂Cl₂/MeOH (15 mL) containing pyridine (0.5 mL, 6 mmol) was cooled to −78° C., and O₃ was passed through until a blue color was present. N₂ was then bubbled through to discharge the blue color and Me₂S (5 ml) was added. The reaction mixture was allowed to warm and left overnight. The mixture was washed with 1 N HCl and aqueous NaHCO₃ and then dried and concentrated to give crude 2-(cyclopropyloxy)-4-(2-oxoethyl)benzonitrile.

Step D: 2-(Cyclopropyloxy)-4-(2-{4-[2-(1-oxo-1,3-dihydro-2-benzofuran-5-yl)ethyl]piperazin-1-yl}ethyl)benzonitrile A solution of crude 2-(cyclopropyloxy)-4-(2-oxoethyl) benzonitrile (80 mg, 0.4 mmol), 5-(2-piperazin-1-ylethyl)-2-benzofuran-1(3H)-one (150 mg, 0.6 mmol) and NaBH(OAc)₃ (400 mg, 2 mmol) in 10 mL of anhydrous DCM was stirred at ambient temperature overnight. The reaction mixture was added 50 mL of DCM and washed with brine. The organic layer was dried over anhydrous sodium sulfate and concentrated. The residue was purified with prep-TLC to afford 2-(cyclopropyloxy)-4-(2-{4-[2-(1-oxo-1,3-dihydro-2-benzofuran-5-yl)ethyl]piperazin-1-yl}ethyl)benzonitrile.
¹H-NMR (400 MHz, CDCl₃) δ ppm 7.77 (d, J=7.8 Hz, 1H), 7.37 (d, J=7.8 Hz, 1H), 7.31 (d, J=7.8 Hz, 1H), 7.27 (s, 1H), 7.11 (s, 1H), 6.78~6.80 (m, 1H), 5.22 (s, 2H), 2.42~2.93 (m, 17H), 0.77~0.80 (m, 4H). (0.28 μM)

Example 65

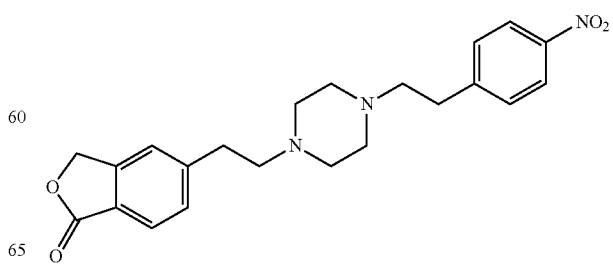

5-(2-{4-[2-(4-Nitrophenyl)ethyl]piperazin-1-yl}ethyl)-2-benzofuran-1(3H)-one Step A: 5-Allyl-2-benzofuran-1(3H)-one A 4-neck, 22-L, round bottom flask equipped with a mechanical stirrer, thermocouple, nitrogen bubbler, and condenser was charged with 5-bromophthalide (650 g, 3.0 mol), allyltri-n-butyltin (1200 g, 3.6 mol), tetrakis(triphenylphosphine)palladium (100 g, 0.089 mol), lithium chloride (250 g, 5.9 mol) and toluene (8.8 L). The mixture was evacuated and flushed with nitrogen 3 times and then was stirred at 100° C. for 4 hours. After slowly cooling to ambient temperature, the mixture was filtered and concentrated. The resulting solid was purified by silica gel column chromatography (heptane:ethyl acetate, 0→40%) to provide 5-allyl-2-benzofuran-1(3H)-one.

$^1$H NMR (500 MHz, CD$_3$OD) δ 7.83 (d, J=8.0 Hz, 1H), 7.38 (d, J=8.0 Hz, 1H), 7.33 (s, 1H), 5.98 (m, 1H), 5.29 (s, 2H), 5.11-5.18 (m, 2H), 3.52 (d, J=8.2 Hz, 2H); LC-MS (IE, m/z): 175.1 [M+1]$^+$.

Step B: 5-(2-{4-[2-(4-Nitrophenyl)ethyl]piperazin-1-yl}ethyl)-2-benzofuran-1(3H)-one Ozone was bubbled through a solution of 5-allyl-2-benzofuran-1(3H)-one (125 mg, 0.72 mmol) in DCM until the color changed to orange. Removed excess ozone by bubbling nitrogen through solution for a minute. Added a solution of 1-[2-(4-nitrophenyl)ethyl]piperazine hydrochloride (65 mg, 0.24 mmol) and triethylamine (0.033 mL, 0.24 mmol) in DCM (2 mL), followed by NaB(OAc)$_3$H (250 mg, 1.2 mmol). The mixture was allowed to stir at RT for 16 hours. HPLC-MS shows product but reaction is not clean. The product was urified by prep-TLC to afford 5-(2-{4-[2-(4-nitrophenyl)ethyl]piperazin-1-yl}ethyl)-2-benzofuran-1(3H)-one as a white solid. LC-MS (IE, m/z): 396 [M+1]$^+$. (0.089 μM)

Example 66

2 Diastereomers

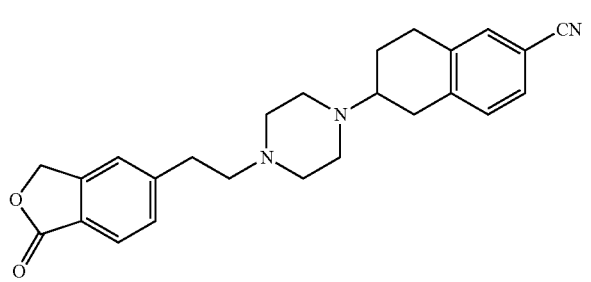 [SMILES: N#Cc1ccc2c(c1)CCC(N1CCN(CCc3ccc4c(c3)COC4=O)CC1)C2]

6-{4-[2-(1-Oxo-1,3-dihydro-2-benzofuran-5-yl)ethyl]piperazin-1-yl}-5,6,7,8-tetrahydronaphthalene-2-carbonitrile The above product was prepared following similar procedure of EXAMPLE 38 from (1-oxo-1,3-dihydro-2-benzofuran-5-yl)acetaldehyde and 6-piperazin-1-yl-5,6,7,8-tetrahydronaphthalene-2-carbonitrile. LC-MS (IE, m/z): 402 [M+1]$^+$. (0.050 μM)

Example 67

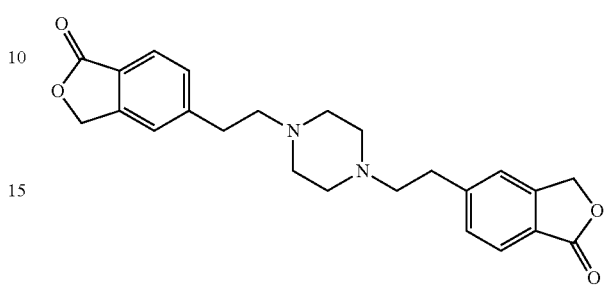

5,5'-(Piperazine-1,4-diyldiethane-2,1-diyl)bis(2-benzofuran-1(3H)-one

A mixture of 5-(2-bromoethyl)-2-benzofuran-1(3H)-one (130 mg, 0.54 mmol) and 5-(2-piperazin-1-ylethyl)-2-benzofuran-1(3H)-one hydrochloride (76 mg, 0.27 mmol) was heated to 60° C. with triethylamine (0.19 mL, 1.3 mmol) and DMF (2 mL) for 24 hours. LC showed formation of the desired product. The crude reaction was diluted with EtOAc, washed with water, dried over magnesium sulfate, and purified by prep-TLC. About 26 mg pure product was collected after removal of solvent. LC-MS (IE, m/z): 407 [M+1]$^+$. (0.089 μM)

Example 68

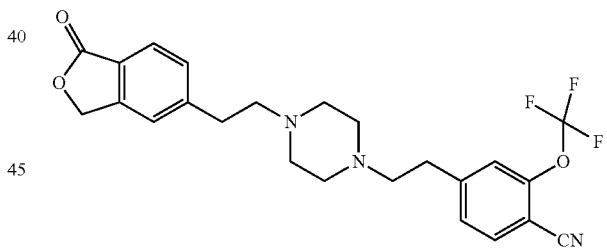

2-Trifluoromethoxy-4-(2-{4-[2-(1-oxo-1,3-dihydro-2-benzofuran-5-yl)ethyl]piperazin-1-yl}ethyl)benzonitrile 2-Trifluoromethoxy-4-(2-oxoethyl)benzonitrile (67 mg, 0.30 mmol) was taken up in 1,2-dichloromethane (DCE) (2 mL) and 5-[2-(piperazin-1-yl)ethyl]-2-benzofuran-1(3H)-one hydrochloride (85 mg, 0.30 mmol) and DIPEA (0.104 mL, 0.60 mmol) were added. After stirring the mixture for 15 minutes at room temperature, sodium triacetoxyborohydride (102 mg, 0.48 mmol) was added. After 16 hours, LC-MS indicated product formation and most of the volatiles were evaporated under a stream of nitrogen. The residue was taken up in acetonitrile/water (total 3 mL) and acidified with TFA. The product was isolated by reverse phase HPLC (eluted with a gradient of 10-50% acetonitrile/water (0.1% TFA) over 24 minutes). The clean main fractions by LC-MS were evaporated to give the TFA salt which was converted to the di-HCl salt of the title compound. LC-MS (IE, m/z): 460 [M+1]+. (0.62 µM)

Example 69

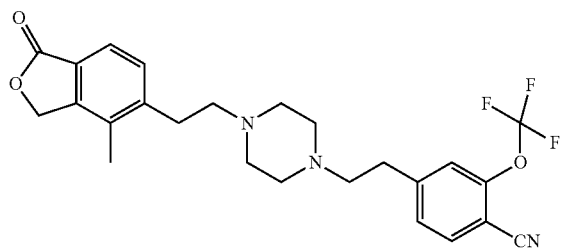 [SMILES: N#Cc1ccc(CCN2CCN(CCc3ccc4c(c3)COC4=O)CC2)cc1OC(F)(F)F]

2-Trifluoromethoxy-4-(2-{4-[2-(4-methyl-1-oxo-1,3-dihydro-2-benzofuran-5-yl)ethyl]piperazin-1-yl}ethyl)benzonitrile 2-Trifluoromethoxy-4-(2-oxoethyl)benzonitrile (67 mg, 0.30 mmol) was taken up in DCE (2 mL) and 4-methyl-5-[2-(piperazin-1-yl)ethyl]-2-benzofuran-1(3H)-one hydrochloride (88 mg, 0.30 mmol) and DIPEA (0.100 mL, 0.60 mmol) were added. After stirring the mixture for 15 minutes at room temperature, sodium triacetoxyborohydride (102 mg, 0.48 mmol) was added. After 16 hours, LC-MS indicated product formation and most of the volatiles were evaporated under a stream of nitrogen. The residue was taken up in acetonitrile/water (total 3 mL) and acidified with TFA. The product was isolated by reverse phase HPLC (eluted with a gradient of 10-50% acetonitrile/water (0.1% TFA) over 24 minutes). The clean main fractions by LC-MS were evaporated to give the TFA salt which was converted to the di-HCl salt of the title compound. LC-MS (IE, m/z): 474 [M+1]+. (0.20 µM)

Example 70

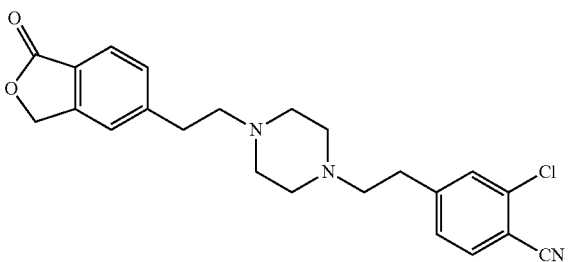 [SMILES: N#Cc1ccc(CCN2CCN(CCc3ccc4c(c3)COC4=O)CC2)cc1Cl]

2-Chloro-4-(2-{4-[2-(1-oxo-1,3-dihydro-2-benzofuran-5-yl)ethyl]piperazin-1-yl}ethyl)benzonitrile 2-Chloro-4-(2-oxoethyl)benzonitrile (79 mg, 0.44 mmol) was taken up in DCE (2 mL) and 5-[2-(piperazin-1-yl)ethyl]-2-benzofuran-1(3H)-one hydrochloride (124 mg, 0.44 mmol) and DIPEA (0.150 mL, 0.88 mmol) were added. After stirring the mixture for 15 minutes at room temperature, sodium triacetoxyborohydride (149 mg, 0.70 mmol) was added. After 16 hours, LC-MS indicated product formation and most of the volatiles were evaporated under a stream of nitrogen. The residue was taken up in acetonitrile/water (total 3 mL) and acidified with TFA. The product was isolated by reverse phase HPLC (eluted with a gradient of 10-50% acetonitrile/water (0.1% TFA) over 24 minutes). The clean main fractions by LC-MS were evaporated to give the TFA salt which was converted to the di-HCl salt of the title compound. LC-MS (IE, m/z): 410/412 [M+1]+. (0.075 µM)

Example 71

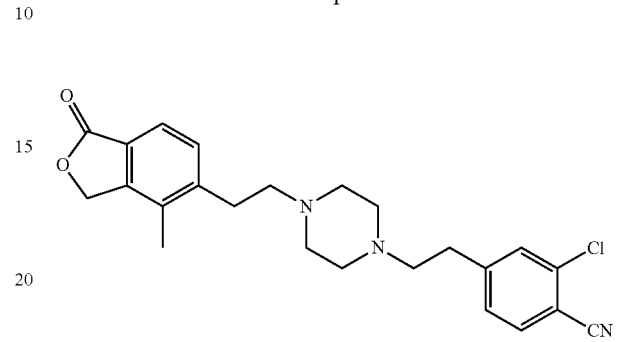

2-Chloro-4-(2-{4-[2-(4-methyl-1-oxo-1,3-dihydro-2-benzofuran-5-yl)ethyl]piperazin-1-yl}ethyl)benzonitrile 2-Chloro-4-(2-oxoethyl)benzonitrile (79 mg, 0.44 mmol) was taken up in DCE (2 mL) and 4-methyl-5-[2-(piperazin-1-yl)ethyl]-2-benzofuran-1(3H)-one hydrochloride (131 mg, 0.44 mmol) and DIPEA (0.150 mL, 0.88 mmol) were added. After stirring the mixture for 5 minutes at room temperature, sodium triacetoxyborohydride (149 mg, 0.70 mmol) was added. After 16 hours, LC-MS indicated product formation and most of the volatiles were evaporated under a stream of nitrogen. The residue was taken up in acetonitrile/water (total 3 mL) and acidified with TFA. The product was isolated by reverse phase HPLC (eluted with a gradient of 10-50% acetonitrile/water (0.1% TFA) over 24 minutes). The main clean fractions by LC-MS were evaporated to give the TFA salt which was converted to the di-HCl salt of the title compound. LC-MS (IE, m/z): 424/426 [M+1]+. (0.035 µM)

Example 72

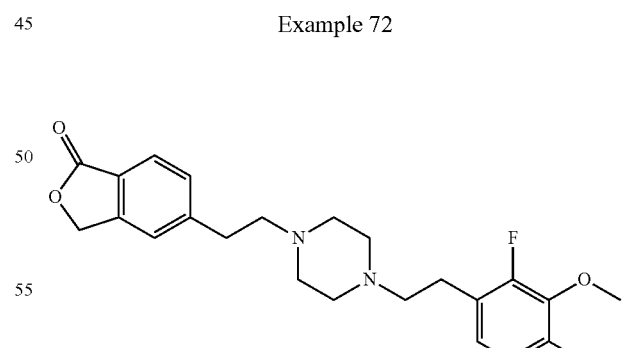

3-Fluoro-2-methoxy-4-(2-{4-[2-(1-oxo-1,3-dihydro-2-benzofuran-5-yl)ethyl]piperazin-1-yl}ethyl)benzonitrile 3-Fluoro-2-methoxy-4-(2-oxoethyl)benzonitrile (15 mg, 0.15 mmol) was taken up in (DCE) (2 mL) and 5-[2-(piperazin-1-yl)ethyl]-2-benzofuran-1(3H)-one hydrochloride (43 mg, 0.15 mmol) and DIPEA (0.55 mL, 0.31 mmol) were added. After stirring the mixture for 15 minutes at room temperature, sodium triacetoxyborohydride (52 mg, 0.25 mmol) was added. After 16 hours, LC-MS indicated product formation and most of the volatiles were evaporated under a stream of nitrogen. The residue was taken up in acetonitrile/water (total 3 mL) and acidified with TFA. The product was isolated by reverse phase HPLC (eluted with a gradient of 10-50% acetonitrile/water (0.1% TFA) over 24 minutes). The clean main fractions by LC-MS were evaporated to give the TFA salt which was converted to the di-HCl salt of the title compound. LC-MS (IE, m/z): 424 [M+1]$^+$. (0.092 µM)

Example 73

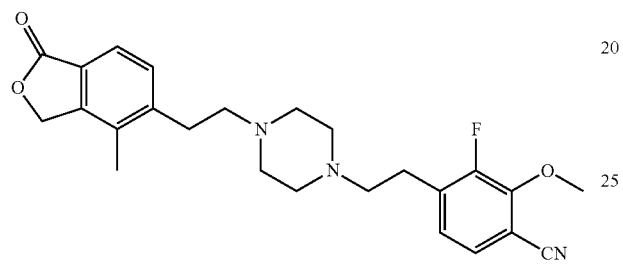

3-Fluoro-2-methoxy-4-(2-{4-[2-(4-methyl-1-oxo-1,3-dihydro-2-benzofuran-5-yl)ethyl]piperazin-1-yl}ethyl)benzonitrile 3-Fluoro-2-methoxy-4-(2-oxoethyl)benzonitrile (30 mg, 0.15 mmol) was taken up in DCE (2 mL) and 4-methyl-5-[2-(piperazin-1-yl)ethyl]-2-benzofuran-1(3H)-one hydrochloride (45 mg, 0.15 mmol) and DIPEA (0.55 mL, 0.31 mmol) were added. After stirring the mixture for 15 minutes at room temperature, sodium triacetoxyborohydride (52 mg, 0.25 mmol) was added. After 16 hours, LC-MS indicated product formation and most of the volatiles were evaporated under a stream of nitrogen. The residue was taken up in acetonitrile/water (total 3 mL) and acidified with TFA. The product was isolated by mass directed LC-MS (eluted with a gradient of 10-50% acetonitrile/water (0.05% TFA)). The main fractions containing M+1=438 were evaporated to give the TFA salt which was converted to the di-HCl salt of the title compound. LC-MS (IE, m/z): 438 [M+1]$^+$. (0.091 µM)

Example 74

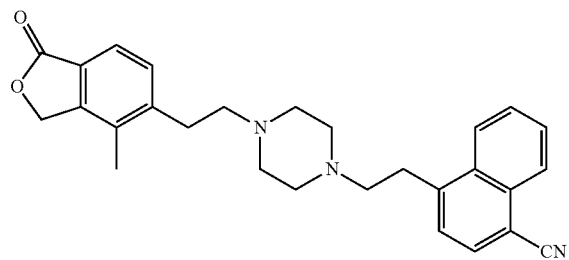 [SMILES: Cc1c(CCN2CCN(CCc3ccc(C#N)c4ccccc34)CC2)ccc2c1COC2=O]

4-(2-{4-[2-(4-Methyl-1-oxo-1,3-dihydro-2-benzofuran-5-yl)ethyl]piperazin-1-yl}ethyl)naphthalene-1-carbonitrile 4-(2-Oxoethyl)naphthalene-1-carbonitrile (21 mg, 0.11 mmol) was taken up in methanol (2 mL) and 4-methyl-5-[2-(piperazin-1-yl)ethyl]-2-benzofuran-1(3H)-one hydrochloride (33 mg, 0.11 mmol) was added (no DIPEA). After stirring the mixture for 15 minutes at room temperature, sodium cyanoborohydride (14 mg, 0.22 mmol) was added. After 16 hours, LC-MS indicated product formation and most of the volatiles were evaporated under a stream of nitrogen. The residue was taken up in acetonitrile/water (total 3 mL) and acidified with TFA. The product was isolated by mass directed LC-MS (eluted with a gradient of 10-50% acetonitrile/water (0.05% TFA)). The main fractions containing M+1=440) were evaporated to give the TFA salt which was converted to the di-HCl salt of the title compound. LC-MS (IE, m/z): 440 [M+1]$^+$. (0.16 µm)

Example 75

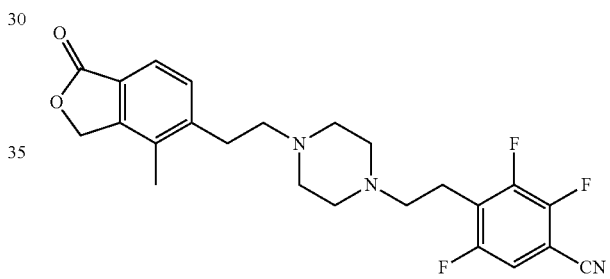

2,3,5-Trifluoro-4-(2-{4-[2-(4-methyl-1-oxo-1,3-dihydro-2-benzofuran-5-yl)ethyl]piperazin-1-yl}ethyl)benzonitrile 4-(2-Oxoethyl)-2,3,5-trifluoro-benzonitrile (22 mg, 0.11 mmol) was taken up in methanol (2 mL) and 4-methyl-5-[2-(piperazin-1-yl)ethyl]-2-benzofuran-1(3H)-one hydrochloride (32 mg, 0.11 mmol) was added (no DIPEA). After stirring the mixture for 10 minutes at room temperature, sodium cyanoborohydride (14 mg, 0.22 mmol) was added. After 16 hours, LC-MS indicated product formation and most of the volatiles were evaporated under a stream of nitrogen. The residue was partitioned with DCM (2×)/aqueous sodium carbonate and the organic layers were washed with brine, dried over sodium sulfate and evaporated. The residue was taken up in acetonitrile/water (total 3 mL) and acidified with TFA. The product was isolated by mass directed LC-MS (eluted with a gradient of 10-50% acetonitrile/water (0.05% TFA)). The main fractions containing M+1=444) were evaporated to give the TFA salt which was converted to the di-HCl salt of the title compound. LC-MS (IE, m/z): 444 [M+1]$^+$. (0.23 µm)

Example 76

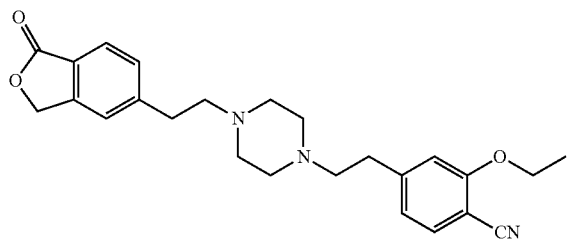 [SMILES: CCOc1cc(CCN2CCN(CCc3ccc4c(c3)COC4=O)CC2)ccc1C#N]

2-Ethoxy-4-(2-{4-[2-(1-oxo-1,3-dihydro-2-benzofuran-5-yl)ethyl]piperazin-1-yl}ethyl)benzonitrile 2-Ethoxy-4-(2-oxoethyl)benzonitrile (26 mg, 0.14 mmol) was taken up in methanol (2 mL) and 5-[2-(piperazin-1-yl)ethyl]-2-benzofuran-1(3H)-one hydrochloride (40 mg, 0.14 mmol) (no DIPEA) was added. After stirring the mixture for 15 minutes at room temperature, sodium cyanoborohydride (18 mg, 0.28 mmol) was added. After 16 hours, LC-MS indicated product formation. Most of the methanol was evaporated under a stream of nitrogen and the residue was diluted with aqueous sodium carbonate and extracted 2× with DCM. The organic layers were washed with brine, dried over sodium sulfate and concentrated in vacuo. The residue was taken up in acetonitrile/water (total 4 mL) and acidified with TFA and the product was isolated by mass directed LC-MS (eluted with a gradient of 10-50% acetonitrile/water (0.05% TFA)). The main fractions containing M+1=420 were evaporated to give the TFA salt which was converted to the di-HCl salt of the title compound. LC-MS (IE, m/z): 420 [M+1]$^+$. $^1$H-NMR (500 MHz, CD$_3$CN) δ ppm 1.335 (t, J=7.0 Hz, 3H), 3.05 (m, 2H), 3.11 (m, 2H), 3.25 (m, 4H), 3.48 (br s, 8H), 4.10 (q, J=7.0 Hz, 2H), 4.0 (v br s, 2 $^+$NH), 5.214 (s, 2H), 6.854 (d, J=7.9 Hz, 1H), 6.947 (s, 1H), 7.375 (d, J=8.1 Hz, 1H), 7.397 (s, 1H), 7.473 (d, J=8.0 Hz, 1H). 7.719 (d, J=7.8 Hz, 1H). (0.053 μM)

Example 77

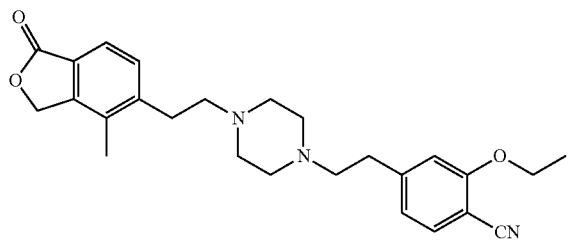 [SMILES: CCOc1cc(CCN2CCN(CCc3ccc4c(c3C)COC4=O)CC2)ccc1C#N]

2-Ethoxy-4-(2-{4-[2-(4-methyl-1-oxo-1,3-dihydro-2-benzofuran-5-yl)ethyl]piperazin-1-yl}ethyl)benzonitrile 2-Ethoxy-4-(2-oxoethyl)benzonitrile (27 mg, 0.14 mmol) was taken up in methanol (2 mL) and 4-methyl-5-[2-(piperazin-1-yl)ethyl]-2-benzofuran-1(3H)-one hydrochloride (42 mg, 0.14 mmol) (no DIPEA) was added. After stirring the mixture for 15 minutes at room temperature, sodium cyanoborohydride (18 mg, 0.28 mmol) was added. After 16 hours, LC-MS indicated product formation and most of the methanol was evaporated under a stream of nitrogen. The residue was diluted with aqueous sodium carbonate and extracted 2× with DCM. The organic layers were washed with brine, dried over sodium sulfate and concentrated in vacuo. The residue was taken up in acetonitrile/water (total 3 mL) and acidified with TFA and the product was isolated by mass directed LC-MS (2 runs, eluted with a gradient of 10-50% acetonitrile/water (0.05% TFA)). The clean main fractions containing M+1=434) were evaporated to give the TFA salt which was converted to the di-HCl salt of the title compound. LC-MS (IE, m/z): 434 [M+1]$^+$. (0.074 μM)

Example 78

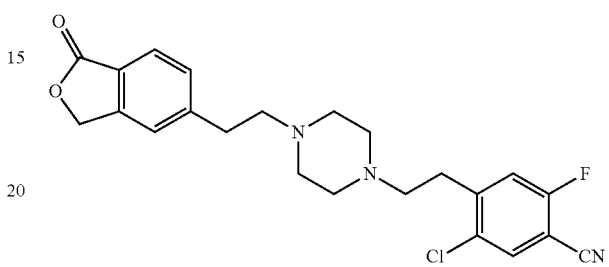

5-Chloro-2-fluoro-4-(2-{4-[2-(1-oxo-1,3-dihydro-2-benzofuran-5-yl)ethyl]piperazin-1-yl}ethyl)benzonitrile 5-Chloro-2-fluoro-4-(2-oxoethyl)benzonitrile (28 mg, 0.14 mmol) was taken up in methanol (2 mL) and 5-[2-(piperazin-1-yl)ethyl]-2-benzofuran-1(3H)-one hydrochloride (40 mg, 0.14 mmol) and DIPEA (0.025 mL, 0.14 mmol) were added. After stirring the mixture for 5 minutes at room temperature, sodium cyanoborohydride (18 mg, 0.28 mmol) was added. After 16 hours, LC-MS indicated product formation. Most of the methanol was evaporated under a stream of nitrogen and the residue was diluted with aqueous sodium carbonate and extracted 2× with DCM. The organic layers were washed with brine, dried over sodium sulfate and concentrated in vacuo. The residue was taken up in acetonitrile/water (total 3 mL) and acidified with TFA and the product was isolated by mass directed LC-MS (eluted with a gradient of 10-50% acetonitrile/water (0.05% TFA)). The main fractions containing M+1=428) were evaporated to give the TFA salt which was converted to the di-HCl salt of the title compound. LC-MS (IE, m/z): 428/430 [M+1]$^+$. (0.076 μM)

Example 79

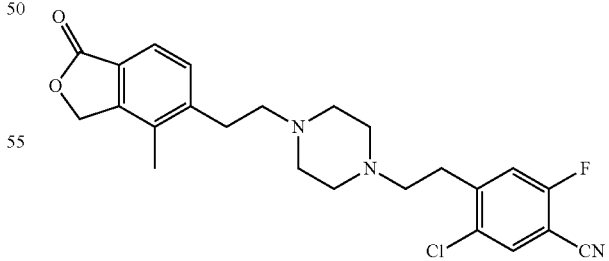

5-Chloro-2-fluoro-4-(2-{4-[2-(4-methyl-1-oxo-1,3-dihydro-2-benzofuran-5-yl)ethyl]piperazin-1-yl}ethyl)benzonitrile 5-Chloro-2-fluoro-4-(2-oxoethyl)benzonitrile (55 mg, 0.28 mmol) was taken up in methanol (2 mL) and 4-methyl- 5-[2-(piperazin-1-yl)ethyl]-2-benzofuran-1(3H)-one hydrochloride (83 mg, 0.28 mmol) and DIPEA (0.050 mL, 0.28 mmol) were added. After stirring the mixture for 5 minutes at room temperature, sodium cyanoborohydride (35 mg, 0.56 mmol) was added. After 16 hours, LC-MS indicated product formation. Most of the methanol was evaporated under a stream of nitrogen. The residue was diluted with aqueous sodium carbonate and extracted 2× with DCM. The organic layers were washed with brine, dried over sodium sulfate and concentrated in vacuo. The residue was taken up in acetonitrile/water (total 4 mL) and acidified with TFA and the product was isolated by mass directed LC-MS (eluted with a gradient of 10-50% acetonitrile/water (0.05% TFA)). The clean main fractions containing M+1=442) were evaporated to give the TFA salt which was converted to the di-HCl salt of the title compound. LC-MS (IE, m/z): 442/444 [M+1]$^+$. $^1$H-NMR (500 MHz, CD$_3$CN) δ ppm 2.210 (s, 3H), 2.7 (v br s, 2 $^+$NH), 2.93 (m, 2H), 3.05 (m, 2H), 3.09 (br s, 8H), 3.12 (br s, 2H), 3.30 br s, 2H) 5.199 (s, 2H), 7.316 (d, J=9.1 Hz, 1H), 7.328 (d, J=7.2 Hz, 1H), 7.563 (d, J=7.8 Hz, 1H). 7.738 (d, J=5.9 Hz, 1H). (0.048 μM)

Example 80

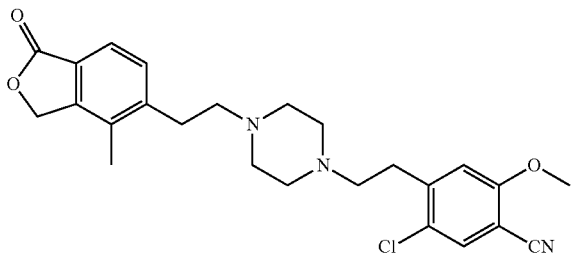 [SMILES: COc1cc(CCN2CCN(CCc3ccc4c(c3C)COC4=O)CC2)c(Cl)cc1C#N]

5-Chloro-2-methoxy-4-(2-{4-[2-(4-methyl-1-oxo-1,3-dihydro-2-benzofuran-5-yl)ethyl]piperazin-1-yl}ethyl)benzonitrile 5-Chloro-2-methoxy-4-(2-oxoethyl)benzonitrile (46 mg, 0.22 mmol) was taken up in methanol (2 mL) and 4-methyl-5-[2-(piperazin-1-yl)ethyl]-2-benzofuran-1(3H)-one hydrochloride (65 mg, 0.22 mmol) and DIPEA (0.040 mL, 0.22 mmol) were added. After stirring the mixture for 5 minutes at room temperature, sodium cyanoborohydride (28 mg, 0.44 mmol) was added. After 16 hours, LC-MS indicated product formation. Most of the methanol was evaporated under a stream of nitrogen. The residue was diluted with aqueous sodium carbonate and extracted 2× with DCM. The organic layers were washed with brine, dried over sodium sulfate and concentrated in vacuo. The residue was taken up in acetonitrile/water (total 3 mL) and acidified with TFA and the product was isolated by mass directed LC-MS (eluted with a gradient of 10-50% acetonitrile/water (0.05% TFA)). The clean main fractions containing M+1=454/456) were evaporated to give the TFA salt which was converted to the di-HCl salt of the title compound. LC-MS (IE, m/z): 454/456 [M+1]$^+$. (0.071 μM)

Example 81

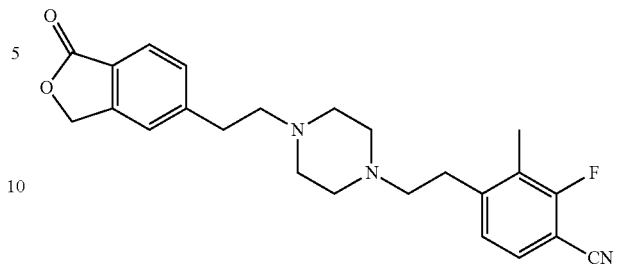

2-Fluoro-3-methyl-4-(2-{4-[2-(1-oxo-1,3-dihydro-2-benzofuran-5-yl)ethyl]piperazin-1-yl}ethyl)benzonitrile 2-Fluoro-3-methyl-4-(2-oxoethyl)benzonitrile (21 mg, 0.12 mmol) was taken up in methanol (2 mL) and 5-[2-(piperazin-1-yl)ethyl]-2-benzofuran-1(3H)-one hydrochloride (34 mg, 0.12 mmol) and DIPEA (0.020 mL, 0.12 mmol) were added. After stirring the mixture for 5 minutes at room temperature, sodium cyanoborohydride (15 mg, 0.24 mmol) was added. After 16 hours, LC-MS indicated product formation. Most of the methanol was evaporated under a stream of nitrogen and the residue was diluted with aqueous sodium carbonate and extracted 2× with DCM. The organic layers were washed with brine, dried over sodium sulfate and concentrated in vacuo. The residue was taken up in acetonitrile/water (total 3 mL) and acidified with TFA and the product was isolated by mass directed LC-MS (eluted with a gradient of 10-50% acetonitrile/water (0.05% TFA)). The main fractions containing M+1=408) were evaporated to give the TFA salt which was converted to the di-HCl salt of the title compound. LC-MS (IE, m/z): 408 [M+1]$^+$. $^1$H-NMR (500 MHz, CD$_3$CN) δ ppm 2.25 (s, 3H), 2.6-3.6 (v br s, 2 $^+$NH), 3.05, 3.15, 3.31 (br s, m, br s, 16H), 5.284 (s, 2H), 7.196 (d, J=8.0 Hz, 1H), 7.460 (d, J=7.8 Hz, 1H), 7.467 (s, 1H), 7.53 (t, J=8.0 Hz, 1H). 7.778 (d, J=7.8 Hz, 1H). (0.080 μm)

Example 82

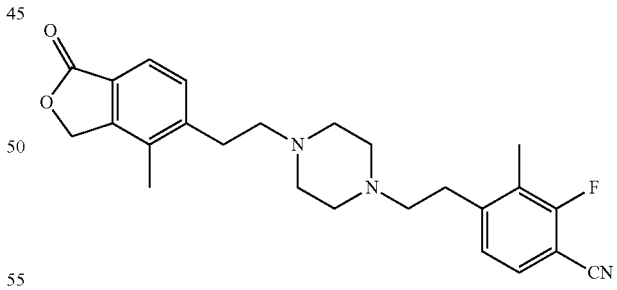

2-Fluoro-3-methyl-4-(2-{4-[2-(4-methyl-1-oxo-1,3-dihydro-2-benzofuran-5-yl)ethyl]piperazin-1-yl}ethyl)benzonitrile 2-Fluoro-3-methyl-4-(2-oxoethyl)benzonitrile (42 mg, 0.24 mmol) was taken up in methanol (4 mL) and 4-methyl-5-[2-(piperazin-1-yl)ethyl]-2-benzofuran-1(3H)-one hydrochloride (71 mg, 0.24 mmol) and DIPEA (0.0420 mL, 0.24 mmol) were added. After stirring the mixture for 5 minutes at room temperature, sodium cyanoborohydride (30 mg, 0.48 mmol) was added. After 16 hours, LC-MS indicated product formation. Most of the methanol was evaporated under a stream of nitrogen. The residue was diluted with aqueous sodium carbonate and extracted 2× with DCM. The organic layers were washed with brine, dried over sodium sulfate and concentrated in vacuo. The residue was taken up in acetonitrile/water (total 3 mL) and acidified with TFA and the product was isolated by mass directed LC-MS (eluted with a gradient of 10-50% acetonitrile/water (0.05% TFA)). The clean main fractions containing M+1=422) were evaporated to give the TFA salt which was converted to the di-HCl salt of the title compound. LC-MS (IE, m/z): 422 [M+1]$^+$. (0.063 μM)

Example 83

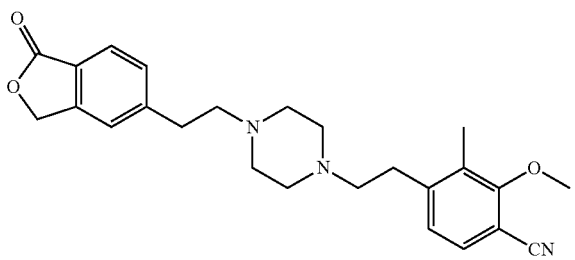 [SMILES: COc1c(C#N)ccc(CCN2CCN(CCc3ccc4c(c3)COC4=O)CC2)c1C]

2-Methoxy-3-methyl-4-(2-{4-[2-(1-oxo-1,3-dihydro-2-benzofuran-5-yl)ethyl]piperazin-1-yl}ethyl)benzonitrile 2-Methoxy-3-methyl-4-(2-oxoethyl)benzonitrile (20 mg, 0.106 mmol) was taken up in methanol (2 mL) and 5-[2-(piperazin-1-yl)ethyl]-2-benzofuran-1(3H)-one hydrochloride (32.5 mg, 0.13 mmol) and DIPEA (0.032 mL, 0.18 mmol) were added. After stirring the mixture for 5 minutes at room temperature, sodium cyanoborohydride (13.2 mg, 0.21 mmol) was added. After 1 hour, LC-MS indicated product formation. Most of the methanol was evaporated under a stream of nitrogen and the residue was diluted with aqueous sodium carbonate and extracted 3× with DCM. The organic layers were washed with brine, dried over sodium sulfate and concentrated in vacuo. The residue was taken up in acetonitrile/water (total 4 mL) and acidified with TFA and the product was isolated by mass directed LC-MS (eluted with a gradient of 10-50% acetonitrile/water (0.05% TFA)). The main fractions containing M+1=420) were evaporated to give the TFA salt which was converted to the di-HCl salt of the title compound. LC-MS (IE, m/z): 420 [M+1]$^+$. (0.18 μM)

Example 84

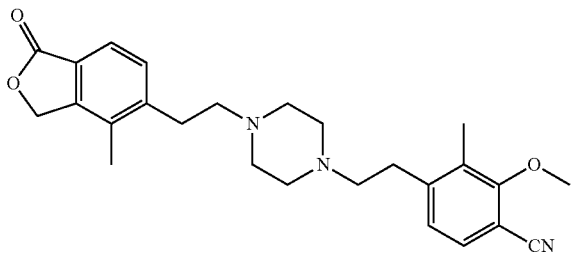 [SMILES: COc1c(C#N)ccc(CCN2CCN(CCc3ccc4c(c3C)COC4=O)CC2)c1C]

2-Methoxy-3-methyl-4-(2-{4-[2-(4-methyl-1-oxo-1,3-dihydro-2-benzofuran-5-yl)ethyl]piperazin-1-yl}ethyl)benzonitrile 2-Methoxy-3-methyl-4-(2-oxoethyl)benzonitrile (40 mg, 0.21 mmol) was taken up in methanol (4 mL) and 4-methyl-5-[2-(piperazin-1-yl)ethyl]-2-benzofuran-1(3H)-one hydrochloride (32.5 mg, 0.132 mmol) and DIPEA (0.065 mL, 0.37 mmol) were added. After stirring the mixture for 5 minutes at room temperature, sodium cyanoborohydride (26.4 mg, 0.42 mmol) was added. After 1 hour, LC-MS indicated product formation. Most of the methanol was evaporated under a stream of nitrogen. The residue was diluted with aqueous sodium carbonate and extracted 3× with DCM. The organic layers were washed with brine, dried over sodium sulfate and concentrated in vacuo. The residue was taken up in acetonitrile/water (total 7 mL) and acidified with TFA and the product was isolated by mass directed LC-MS (2 runs, eluted with a gradient of 10-50% acetonitrile/water (0.05% TFA)). The main fractions containing M+1=434) were evaporated to give the TFA salt which was converted to the di-HCl salt of the title compound. LC-MS (IE, m/z): 434 [M+1]$^+$. (0.078 μM)

Example 85

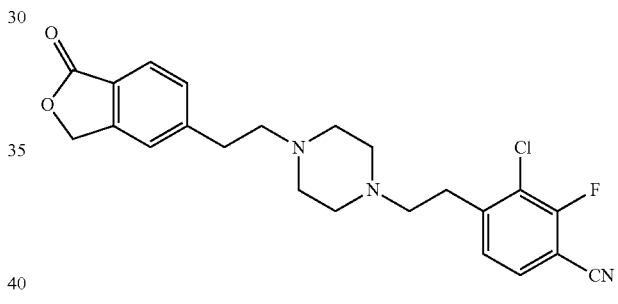

3-Chloro-2-fluoro-4-(2-{4-[2-(1-oxo-1,3-dihydro-2-benzofuran-5-yl)ethyl]piperazin-1-yl}ethyl)benzonitrile 3-Chloro-2-fluoro-4-(2-oxoethyl)benzonitrile (20 mg, 0.10 mmol) was taken up in methanol (3 mL) and 5-[2-(piperazin-1-yl)ethyl]-2-benzofuran-1(3H)-one (20 mg free base, 0.080 mmol) was added (no DIPEA since piperidine free amine was used). After stirring the mixture for 15 minutes at room temperature, sodium cyanoborohydride (10 mg, 0.15 mmol) was added. After 16 hours, LC-MS indicated product formation. Most of the methanol was evaporated under a stream of nitrogen and the residue was diluted with aqueous sodium carbonate and extracted 2× with DCM. The organic layers were washed with brine, dried over sodium sulfate and concentrated in vacuo. The residue was taken up in acetonitrile/water (total 4 mL) and acidified with TFA and the product was isolated by mass directed LC-MS (eluted with a gradient of 10-50% acetonitrile/water (0.05% TFA)). The main fractions containing M+1=428) were evaporated to give the TFA salt which was converted to the di-HCl salt of the title compound. LC-MS (IE, m/z): 428/430 [M+1]$^+$. (0.13 μM)

Example 86

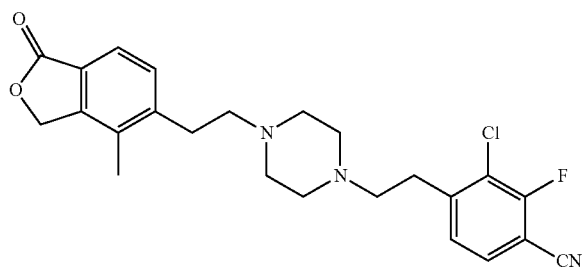 [SMILES: Cc1c(CCN2CCN(CCc3ccc(C#N)c(F)c3Cl)CC2)ccc2c1COC2=O]

3-Chloro-2-fluoro-4-(2-{4-[2-(4-methyl-1-oxo-1,3-dihydro-2-benzofuran-5-yl)ethyl]piperazin-1-yl}ethyl)benzonitrile 3-Chloro-2-fluoro-4-(2-oxoethyl)benzonitrile (42 mg, 0.21 mmol) was taken up in methanol (3 mL) and 4-methyl-5-[2-(piperazin-1-yl)ethyl]-2-benzofuran-1(3H)-one (44 mg, 0.28 mmol free base) was added (no DIPEA since piperidine free amine was used). After stirring the mixture for 5 minutes at room temperature, sodium cyanoborohydride (20 mg, 0.315 mmol) was added. After 16 hours, LC-MS indicated product formation. Most of the methanol was evaporated under a stream of nitrogen. The residue was diluted with aqueous sodium carbonate and extracted 2× with DCM. The organic layers were washed with brine, dried over sodium sulfate and concentrated in vacuo. The residue was taken up in acetonitrile/water (total 3 mL) and acidified with TFA and the product was isolated by mass directed LC-MS (eluted with a gradient of 10-50% acetonitrile/water (0.05% TFA)). The clean main fractions containing M+1=442) were evaporated to give the TFA salt which was converted to the di-HCl salt of the title compound. LC-MS (IE, m/z): 442/444 [M+1]$^+$. (0.078 µM)

Example 87

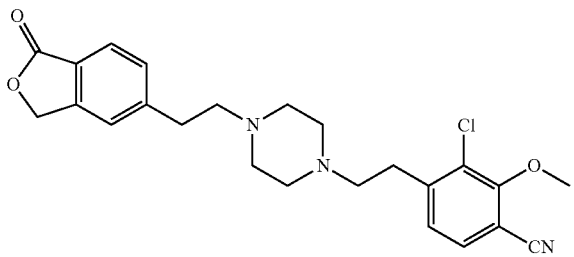

3-Chloro-2-methoxy-4-(2-{4-[2-(1-oxo-1,3-dihydro-2-benzofuran-5-yl)ethyl]piperazin-1-yl}ethyl)benzonitrile 3-Chloro-2-methoxy-4-(2-oxoethyl)benzonitrile (26 mg, 0.125 mmol) was taken up in methanol (2 mL) and 5-[2-(piperazin-1-yl)ethyl]-2-benzofuran-1(3H)-one hydrochloride (28 mg, 0.100 mmol) and DIPEA (0.017 mL, 0.100 mmol) were added. After stirring the mixture for 5 minutes at room temperature, sodium cyanoborohydride (10 mg, 0.150 mmol) was added. After 16 hours, LC-MS indicated product formation. Most of the methanol was evaporated under a stream of nitrogen and the residue was diluted with aqueous sodium carbonate and extracted 2× with DCM. The organic layers were washed with brine, dried over sodium sulfate and concentrated in vacuo. The residue was taken up in acetonitrile/water (total 3 mL) and acidified with TFA and the product was isolated by mass directed LC-MS (eluted with a gradient of 10-50% acetonitrile/water (0.05% TFA)). The main fractions containing M+1=440) were evaporated to give the TFA salt which was converted to the di-HCl salt of the title compound. LC-MS (IE, m/z): 440/442 [M+1]$^+$. (0.16 µM)

Example 88

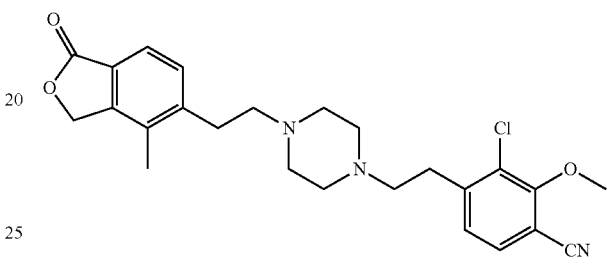

3-Chloro-2-methoxy-4-(2-{4-[2-(4-methyl-1-oxo-1,3-dihydro-2-benzofuran-5-yl)ethyl]piperazin-1-yl}ethyl)benzonitrile 3-Chloro-2-methoxy-4-(2-oxoethyl)benzonitrile (52 mg, 0.25 mmol) was taken up in methanol (2 mL) and 4-methyl-5-[2-(piperazin-1-yl)ethyl]-2-benzofuran-1(3H)-one hydrochloride (67 mg, 0.20 mmol) and DIPEA (0.035 mL, 0.20 mmol) were added. After stirring the mixture for 5 minutes at room temperature, sodium cyanoborohydride (25 mg, 0.40 mmol) was added. After 16 hours, LC-MS indicated product formation. Most of the methanol was evaporated under a stream of nitrogen. The residue was diluted with aqueous sodium carbonate and extracted 2× with DCM. The organic layers were washed with brine, dried over sodium sulfate and concentrated in vacuo. The residue was taken up in acetonitrile/water (total 3 mL) and acidified with TFA and the product was isolated by mass directed LC-MS (eluted with a gradient of 10-50% acetonitrile/water (0.05% TFA)). The clean main fractions containing M+1=454) were evaporated to give the TFA salt which was converted to the di-HCl salt of the title compound. LC-MS (IE, m/z): 454/456 [M+1]$^+$. (0.083 µM)

Example 89

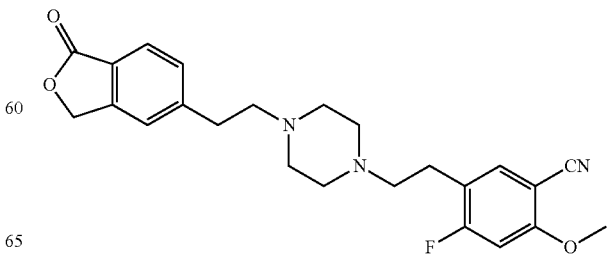

4-Fluoro-2-methoxy-3-(2-{4-[2-(1-oxo-1,3-dihydro-2-benzofuran-5-yl)ethyl]piperazin-1-yl}ethyl)benzonitrile 4-Fluoro-2-methoxy-3-(2-oxoethyl)benzonitrile (35 mg, 0.18 mmol) was taken up in methanol (2 mL) and 5-[2-(piperazin-1-yl)ethyl]-2-benzofuran-1(3H)-one hydrochloride (41 mg, 0.14 mmol) was added (no DIPEA). After stirring the mixture for 5 minutes at room temperature, sodium cyanoborohydride (17 mg, 0.27 mmol) was added. After 16 hours, LC-MS indicated product formation. Most of the methanol was evaporated under a stream of nitrogen and the residue was diluted with aqueous sodium carbonate and extracted 2× with DCM. The organic layers were washed with brine, dried over sodium sulfate and concentrated in vacuo. The residue was taken up in acetonitrile/water (total 3 mL) and acidified with TFA and the product was isolated by mass directed LC-MS (eluted with a gradient of 10-50% acetonitrile/water (0.05% TFA)). The main fractions containing M+1=424) were evaporated to give the TFA salt which was converted to the di-HCl salt of the title compound. LC-MS (IE, m/z): 424 [M+1]$^+$. (0.13 µM)

Example 90

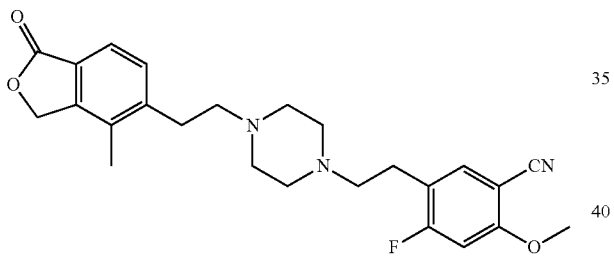

4-Fluoro-2-methoxy-3-(2-{4-[2-(4-methyl-1-oxo-1,3-dihydro-2-benzofuran-5-yl)ethyl]piperazin-1-yl}ethyl)benzonitrile 4-Fluoro-2-methoxy-3-(2-oxoethyl)benzonitrile (35 mg, 0.18 mmol) was taken up in methanol (2 mL) and 4-methyl-5-[2-(piperazin-1-yl)ethyl]-2-benzofuran-1(3H)-one hydrochloride (43 mg, 0.14 mmol) was added (no DIPEA). After stirring the mixture for 5 minutes at room temperature, sodium cyanoborohydride (17 mg, 0.27 mmol) was added. After 16 hours, LC-MS indicated product formation. Most of the methanol was evaporated under a stream of nitrogen. The residue was diluted with aqueous sodium carbonate and extracted 2× with DCM. The organic layers were washed with brine, dried over sodium sulfate and concentrated in vacuo. The residue was taken up in acetonitrile/water (total 3 mL) and acidified with TFA and the product was isolated by mass directed LC-MS (eluted with a gradient of 10-50% acetonitrile/water (0.05% TFA)). The clean main fractions containing M+1=438) were evaporated to give the TFA salt which was converted to the di-HCl salt of the title compound. LC-MS (IE, m/z): 438 [M+1]$^+$. (0.043 µM)

Example 91

2 Diastereomers

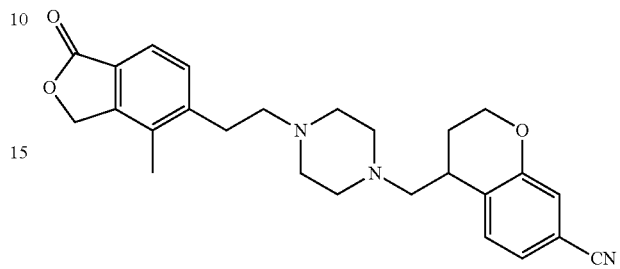

4-({4-[2-(4-Methyl-1-oxo-1,3-dihydro-2-benzofuran-5-yl)ethyl]piperazin-1-yl}methyl)-3,4-dihydro-2H-chromene-7-carbonitrile To a solution of 4-formyl-3,4-dihydro-2H-chromene-7-carbonitrile (50 mg, 0.27 mmol) in DCM (3 mL) was added 4-methyl-5-[2-(piperazine-1-yl)ethyl]-2-benzofuran-1(3H)-one (57 mg, 0.27 mmol), sodium triacetoxyborohydride (27.0 mg, 0.267 mmol) and DIPEA (57 mg, 0.27 mmol). The reaction was stirred under nitrogen at room temperature for 16 hours when LC-MS indicated product formation. The mixture was diluted with DCM and the product was isolated by flash chromatography. LC-MS (IE, m/z): 432 [M+1]$^+$. (0.18 µM)

Example 92

2 Diastereomers

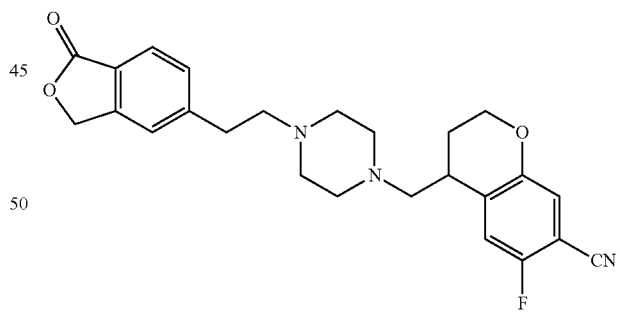

5-Fluoro-3-({4-[2-(1-oxo-1,3-dihydro-2-benzofuran-5-yl)ethyl]piperazin-1-yl}methyl)-3,4-dihydro-2H-chromene-7-carbonitrile To a 12 mL reaction vial was added 6-fluoro-4-formyl-3,4-dihydro-2H-chromene-7-carbonitrile (12 mg, 0.058 mmol), 5-[2-(piperazin-1-yl)ethyl]-2-benzofuran-1(3H)-one (14.4 mg, 0.058 mmol) and dichloromethane (3 mL). The solution was stirred at RT under N$_2$ for 10 min. To above solution was added NaB(OAc)$_3$H (49.6 mg, 0.23 mmol, 4.0 eq). The reaction was stirred at RT for 18 hours under N$_2$, extracted with DCM, washed with brine and water. The organic phase was dried over MgSO$_4$, filtered and purified by flash column chromatography. LC-MS (IE, m/z): 436.3 [M+1]$^+$. (0.44 μM)

Example 93

4 Diastereomers

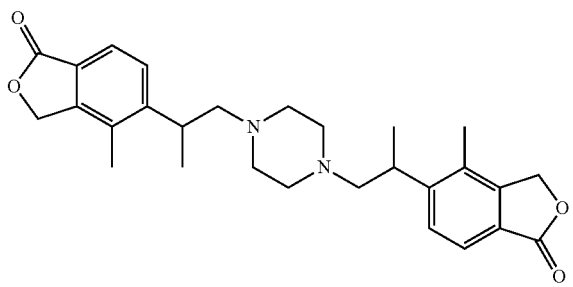 [SMILES: Cc1c(C(C)CN2CCN(CC(C)c3ccc4c(c3C)COC4=O)CC2)ccc2c1COC2=O]

5,5'-(Piperazine-1,4-diyldipropane-1,3-diyl)bis(4-methyl-2-benzofuran-1(3H-one)

To a 12 mL reaction vial was added 2-(4-methyl-1-oxo-1, 3-dihydro-2-benzofuran-5-yl)propanal (60 mg, 0.29 mmol), piperazine (12.7 mg, 0.15 mmol) and dichloromethane (5 mL). The solution was stirred at RT under N$_2$ for 10 min. To above solution was added NaB(OAc)$_3$H (125 mg, 0.59 mmol). The reaction was stirred at RT for 18 hours under N$_2$, extracted with DCM, washed with brine and water. The organic phase was dried over MgSO$_4$, filtered and purified by flash column chromatography to give desired product. LC-MS (IE, m/z): 463.4 [M+1]$^+$. $^1$H NMR (500 MHz, CDCl$_3$, δ in ppm): 7.72 (2H, d, J=8.0 Hz), 7.38 (2H, d, J=8.0 Hz), 5.23 (4H, s), 3.29 (2H, q), 2.3-2.5 (10H, m), 2.27 (6H, s), 1.25 (6H, d, J=6.8 Hz). (0.22 μM)

Example 94

2 Diastereomers

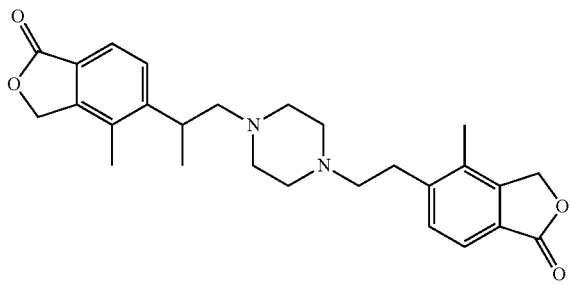 [SMILES: Cc1c(CCN2CCN(CC(C)c3ccc4c(c3C)COC4=O)CC2)ccc2c1COC2=O]

4-Methyl-5-(1-(4-(2-(4-methyl-1-oxo-1,3-dihydroisobenzofuran-5-yl)ethyl)piperazin-1-yl)propan-2-yl)isobenzofuran-1(3H)-one To a 12 mL reaction vial was added 4-methyl-5-[1-(piperazine-1-yl)propan-2-yl]-2-benzofuran-1(3H)-one (57 mg, 0.208 mmol), (4-methyl-1-oxo-1,3-dihydro-2-benzofuran-5-yl)acetaldehyde (47.4 mg, 0.25 mmol) and dichloromethane (5 mL). The solution was stirred at RT under N$_2$ for 10 min. To above solution was added NaB(OAc)$_3$H (88 mg, 0.42 mmol). The reaction was stirred at RT for 18 hours under N$_2$, extracted with DCM, washed with brine and water. The organic phase was dried over MgSO$_4$, filtered and purified by flash column chromatography to give desired product. LC-MS (IE, m/z): 449.4 [M+1]$^+$. $^1$H NMR (500 MHz, CDCl$_3$, δ in ppm): 7.73 (1H, d, J=8.0 Hz), 7.67 (1H, d, J=8.0 Hz), 7.40 (1H, d, J=8.0 Hz), 7.32 (1H, d, J=8.0 Hz), 5.25 (2H, s), 5.23 (2H, s), 3.33 (1H, q), 2.90 (2H, m), 2.4-2.6 (12H, m), 2.30 (3H, s), 2.27 (3H, s), 1.28 (3H, d, J=6.6 Hz). (0.034 μM)

Example 95

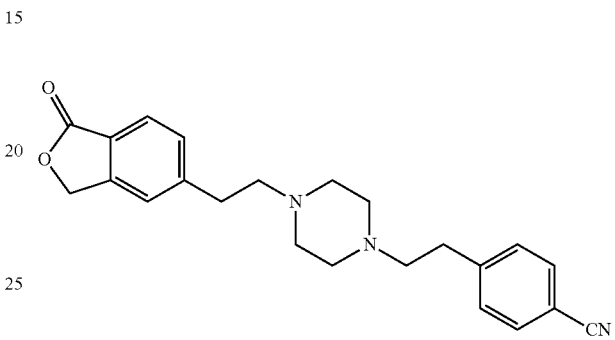

4-(2-{4-[2-(1-Oxo-1,3-dihydro-2-benzofuran-5-yl)ethyl]piperazin-1-yl}ethyl)benzonitrile A mixture of 5-[2-(piperazin-1-yl)ethyl]-2-benzofuran-1 (3H)-one (50 mg, 0.20 mmol), 4-(2-Oxoethyl)benzonitrile (30 mg, 0.20 mmol), Sodium Cyanoborohydride (13 mg, 0.20 mmol), and a drop of HOAc was stirred together in Methanol for 2 hours. LC showed formation of the desired product. The crude was diluted with EtOAc, washed with water, adsorbed onto silica gel, and purified by silica gel chromatography. LC-MS (IE, m/z): 376 [M+1]$^+$. (0.30 μM)

Several assays may be used to measure functional inhibition of the ROMK channel by compounds of the instant invention. One primary assay that can be used is a functional $^{86}$Rb$^+$ efflux assay that measures the ability of ROMK to permeate $^{86}$Rb$^+$, in the absence or presence of test compound. Under control conditions, cells loaded with $^{86}$Rb$^+$ and incubated in Rb$^+$-free medium display a time-dependent efflux of the isotope, the rate of which depends on number of functional channels. When cells are incubated in the presence of a channel inhibitor, efflux of $^{86}$Rb$^+$ is prevented in a concentration-dependent manner, and IC$_{50}$ values of inhibition by compounds can be accurately determined. This assay has been established with cell lines expressing either human, rat or dog ROMK channels, and can operate in 96- or 384-well format. Importantly, the human, rat, and dog $^{86}$Rb$^+$ efflux assays can be carried out in the presence of up to 100% serum allowing, therefore, an accurate estimation of the effect of protein binding on the inhibitory activity of compounds of interest. Another ROMK functional assay makes use of the ability of thallium to permeate through open ROMK channels and increase the fluorescence of a dye previously loaded into the cells. Under control conditions, cells loaded with dye and exposed to thallium-containing medium display a time-dependent increase in fluorescence, the rate of which depends on number of functional channels. When cells are incubated in the presence of a channel inhibitor, the increase in fluorescence is attenuated in a concentration-dependent manner, and IC$_{50}$ values of inhibition by compounds can be accurately determined. This assay has been established with cell lines expressing either human, or rat ROMK channels, and operates in 384-well format.

$^{86}$Rb$^+$ Efflux Assay

Cell Culture Conditions—

CHO-DHFR—cells stably expressing hROMK1 (K$_{ir}$1.1) are grown at 37° C. in a 10% CO$_2$ humidified incubator in Iscove's Modified Dulbecco's Medium (Gibco 12440) supplemented with HT Supplement, Penicillin/Streptomycin/Glutamine, G418 (500 μg/ml) and 10% FBS. Cells are seeded in Sterile and Tissue Culture Treated Packard CulturPlate White Opaque Microplates at a concentration of 5.0E5-7.0E5 cells/ml-PerkinElmer 6005680 (96-well); Corning 3707 (384 well) in complete media containing 1.5 μCi/ml Rubidium-86. Cells are incubated in 37° C.-10% CO$_2$ incubator overnight. On the day of the experiment, the media is removed and cells are washed with low K assay buffer. $^{86}$Rb$^+$ efflux is initiated after addition of assay buffer±test compound followed by 35 min incubation at room temperature. ROMK-sensitive component of efflux is defined in the presence of 10 mM BaCl$_2$. Assay buffer is removed and transferred to a plate and cells are solubilized in the presence of SDS. Radioactivity associated with assay and cell plate is determined.

Step Protocol
1. Remove cell media and wash cells with low K assay buffer (126.9 mM NaCl, 4.6 mM KCl, 2 mM CaCl$_2$, 1 mM MgCl$_2$, 10 mM Hepes/NaOH; pH 7.4)
   200 μl for 96-well plate; 70 μl for 384-well plate
2. Add assay buffer (121.5 mM NaCl, 10 mM KCl, 2 mM CaCl$_2$, 1 mM MgCl$_2$, 10 mM Hepes/NaOH; pH 7.4) ±test compound to cells
   100 μl for 96-well plate; 50 μl for 384-well plate
3. Incubate at ambient temperature (22-24° C.) for 35 min
4. Remove assay buffer add it to a 96- or 384-well plate containing Microscint-20
   96-well Plate: 100 μl buffer, 170 μl MicroScint 20 (for TopCount)
   384-well plate: 20 μl buffer, 50 μl Optiphiase (for MicroLux)
5. Completely remove remaining assay buffer from cell plate
6. Solubilize cells with 1% SDS; than add MicroScint or Optiphase
   96-well Plate: 30 μl SDS, 170 μl MicroScint 20 (for TopCount)
   384-well plate: 20 μl SDS, 50 μl Optiphiase (for MicroLux)
7. Seal both cell and supernatant plates and count Data Calculation—

Radioactivity associated with the assay plate is normalized to the total radioactivity (assay+cell plates) to provide % efflux, under each condition. % efflux in the presence of 10 mM BaCl$_2$ is subtracted from each experimental point to provide the ROMK-sensitive component of $^{86}$Rb$^+$ efflux. In the absence of test compound, this number corresponds to 100% control efflux. IC$_{50}$ values represent the concentration of compound that inhibits 50% of ROMK efflux. Normally, a control compound is included to support that the assay is giving consistent results compared to previous measurements, although the control is not required to obtain the results for the test compounds. The control can be any compound of Formula I of the present invention, preferably with an IC$_{50}$ potency of less than 1 μM in this assay. Alternatively, the control could be another compound (outside the scope of Formula I) that has an IC$_{50}$ potency in this assay of less than 1 μM.

All the Examples of compounds of the present invention described above were tested in the $^{86}$Rb$^+$ Efflux Assay described herein and all had potencies of at least 1 μM or lower. Representative examples of data collected for compounds of the present invention using the $^{86}$Rb$^+$ Efflux Assay are shown in Table 1 below.

TABLE 1

| EXAMPLE | NAME | $^{86}$Rb$^+$ Efflux Assay IC$_{50}$ (μM) |
|---|---|---|
| 1 | 1,4-Bis[2-(4-nitrophenyl)ethyl]piperazine | 0.052 |
| 35 | 2-Methoxy-4-(2-{4-[2-(1-oxo-1,3-dihydro-2-benzofuran-5-yl)ethyl]piperazin-1-yl}ethyl)benzonitrile trifluoroacetic acid salt | 0.089 |
| 41 | 2-Methoxy-4-[2-[4-[2-(4-methyl-1-oxo-3H-isobenzofuran-5-yl)ethyl]piperazin-1-yl]ethyl]benzonitrile HCl salt | 0.035 |
| 59 | 5,5'-(Piperazine-1,4-diyldiethane-2,1-diyl)bis(4-methyl-2-benzofuran-1(3H)-one) trifluoroacetic acid salt | 0.076 |
| 67 | 5,5'-(Piperazine-1,4-diyldiethane-2,1-diyl)bis(2-benzofuran-1(3H)-one | 0.089 |
| 76 | 2-Ethoxy-4-(2-{4-[2-(1-oxo-1,3-dihydro-2-benzofuran-5-yl)ethyl]piperazin-1-yl}ethyl)benzonitrile bis-HCl salt | 0.053 |
| 90 | 4-Fluoro-2-methoxy-3-(2-{4-[2-(4-methyl-1-oxo-1,3-dihydro-2-benzofuran-5-yl)ethyl]piperazin-1-yl}ethyl)benzonitrile bis-HCl salt | 0.043 |
| 94 | 4-Methyl-5-(1-{4-[2-(4-methyl-1-oxo-1,3-dihydro-2-benzofuran-5-yl)ethyl]piperazin-1-yl}-2-benzofuran-1(3H)-one | 0.034 |
| 57 | 2-Methoxy-4-(2-{4-[2-(3-methyl-1-oxo-3,4-dihydro-1H-isochromen-6-yl)ethyl]piperazin-1-yl}ethyl)benzonitrile | 0.098 |
| 9 | 2,2-Dimethyl-1,4-bis[2-(4-nitrophenyl)ethyl]piperazine | 0.21 |
| 10 | (1S,4S)-2,5-Bis[2-(4-nitrophenyl)ethyl]-2,5-diazabicyclo[2.2.1]heptane | 0.11 |
| 26 | (6R)-6-{4-[2-(4-Nitrophenyl)ethyl]piperazin-1-yl}-5,6,7,8-tetrahydronaphthalene-2-carbonitrile HCl salt | 0.066 |
| 43 | 4-Methyl-5-[2-[4-[2-[6-(tetrazol-1-yl)-3-pyridyl]ethyl]piperazin-1-yl]ethyl]-3H-isobenzofuran-1-one | 0.62 |
| 56 | 2-Methoxy-4-(2-{4-[2-(1-oxo-1,3-dihydro-2-benzofuran-5-yl)ethyl]-2-(trifluoromethyl)piperazin-1-yl}ethyl)benzonitrile trifluoroacetic acid salt | 0.27 |
| 74 | 4-(2-{4-[2-(4-Methyl-1-oxo-1,3-dihydro-2-benzofuran-5-yl)ethyl]piperazin-1-yl}ethyl)naphthalene-1-carbonitrile bis-HCl salt | 0.16 |

Thallium Flux Assay

Cell Culture Conditions—

HEK293 cells stably expressing hROMK (hK$_{ir}$1.1) are grown at 37° C. in a 10% CO$_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 ml Calcium/Magnesium-free PBS. Add 5 ml of 1× trypsin (prepared in Ca/Mg Free PBS) to T-225 flask and return flask to 37° C./CO$_2$ incubator for 2-3 minutes. To dislodge the cell, gently bang the side of the flask with your hand. Triturate the cells completely and then transfer the cells to 25 ml complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample is kept at −20° C. Water soluble, 100× after solubilization in 1 ml water. Store at 4° C.
  FluxOR™ Chloride-free Buffer (Component E)—5× Concentrate
  Potassium sulfate ($K_2SO_4$) Concentrate (Component F)—125 mM in water. Store at 4° C.
  Thallium sulfate ($Tl_2SO_4$) Concentrate (Component G)—50 mM in water. Store at 4° C.
  DMSO (dimethyl sulfoxide, Component H)—1 ml (100%)

Reagent Preparation—
FluxOR Working Solutions
  1000× FluxOR™ Reagent: Reconstitute a vial of component A in 100 µl DMSO; Mix well; Store 10 µl aliquots at −20° C.
  1× FluxOR™ Assay Buffer: Dilute Component B 10-fold with water; Adjust pH to 7.4 with Hepes/NaOH; Filter and store at 4° C.
  Probenecid/Assay Buffer: 100 ml of 1× FluxOR™ Assay Buffer; 1 ml of reconstituted component D; Store at 4° C.
  Loading Buffer (per microplate): 10 µl 1000× FluxOR™ Reagent; 100 µl component C; 10 ml Probenecid/Assay Buffer
  Compound Buffer (per microplate): 20 ml Probenecid/Assay Buffer; 0.3 mM ouabain (10 mM ouabain in water can be stored in amber bottle/aluminum foil at room temperature); Test compound
  1× FluxOR™Chloride-Free Buffer: Prepare 1× working solution in water. Can be stored at room temperature
  Stimulant Buffer (prepared at 5× final concentration in 1× FluxOR™Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol—

The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 µl at 20,000 cells/well) in 384-well PDL coated Microplates
2. Allow cells to adhere overnight in humidified 37° C./10% $CO_2$ incubator
3. Completely remove cell growth media from microplate and replace with 25 µl loading buffer
4. Incubate Microplate at room temperature, protected form light, for 90 min
5. Remove loading buffer and replace with 25 µl 1× Assay Buffer±test compound.
6. Incubate microplate at room temperature, protected form light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—

The fluorescence intensity of wells containing 3 µM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—

Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

Representative examples of data collected for compounds of the present invention, including Example 95, using the Thallium Flux Assay are shown in Table 2 below.

TABLE 2

| EXAMPLE | NAME | Thallium Flux Assay $IC_{50}$ (µM) |
|---|---|---|
| 1 | 1,4-Bis[2-(4-nitrophenyl)ethyl]piperazine | 0.066 |
| 95 | 4-(2-{4-[2-(1-oxo-1,3-dihydro-2-benzofuran-5-yl)ethyl]piperazin-1-yl}ethyl)benzonitrile HCl salt | 0.3 |
| 58 | (3S,3'S)-6,6'-(Piperazine-1,4-diyldiethane-2,1-diyl)bis(3-methyl-3,4-dihydro-1H-isochromen-1-one) | 0.24 |
| 62 | 2-(Methylamino)-4-(2-{4-[2-(1-oxo-1,3-dihydro-2-benzofuran-5-yl)ethyl]piperazin-1-yl}ethyl)benzonitrile | 0.41 |
| 38 | 2-Fluoro-4-[2-[4-[2-(1-oxo-3H-isobenzofuran-5-yl)ethyl]piperazin-1-yl]ethyl]benzonitrile | 0.11 |
| 94 | 4-Methyl-5-(1-{4-[2-(4-methyl-1-oxo-1,3-dihydro-2-benzofuran-5-yl)ethyl]piperazin-1-yl}-2-benzofuran-1(3H)-one | 0.012 |
| 64 | 2-(Cyclopropyloxy)-4-(2-{4-[2-(1-oxo-1,3-dihydro-2-benzofuran-5-yl)ethyl]piperazin-1-yl}ethyl)benzonitrile | 0.081 |
| 86 | 3-Chloro-2-fluoro-4-(2-{4-[2-(4-methyl-1-oxo-1,3-dihydro-2-benzofuran-5-yl)ethyl]piperazin-1-yl}ethyl)benzonitrile bis-HCl salt | 0.017 |
| 89 | 4-Fluoro-2-methoxy-3-(2-{4-[2-(1-oxo-1,3-dihydro-2-benzofuran-5-yl)ethyl]piperazin-1-yl}ethyl)benzonitrile bis-HCl salt | 0.05 |

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I:

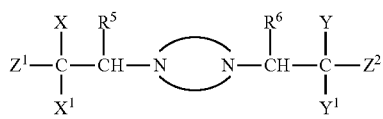

I or a pharmaceutically acceptable salt thereof wherein:

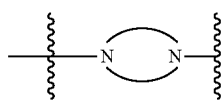

represents:

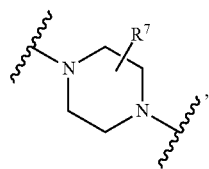

$R^7$ is selected from —H, —F, —CH$_3$, —CF$_3$, —CHF$_2$, —CH$_2$F, —CH$_2$OH, cyclopropyl or —CH$_2$C(=O)O—CH$_3$, or $R^7$ represents di-substitution on a single carbon with two of —F or two of —CH$_3$;

$Z^1$ is selected from:

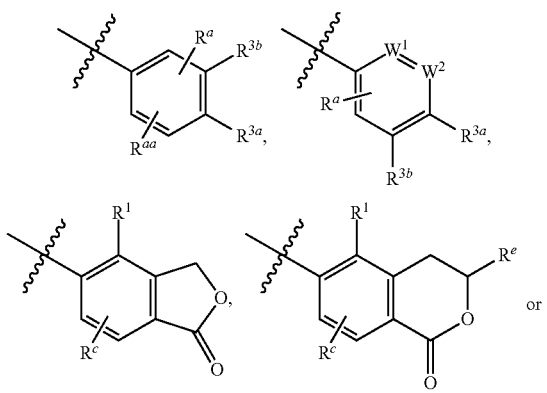

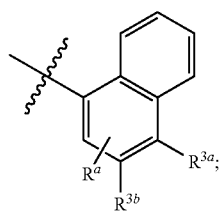

$Z^2$ is selected from:

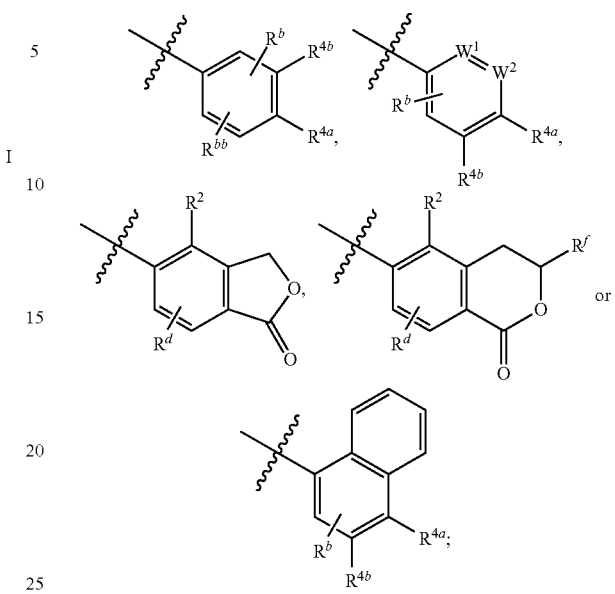

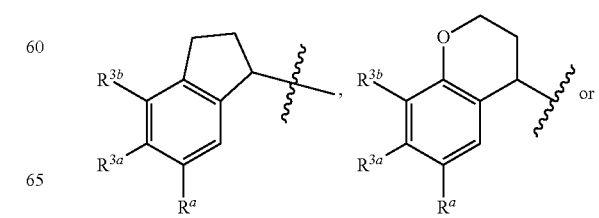

one of $W^1$ and $W^2$ is N and the other is CH;

$R^1$ and $R^2$ are each independently selected from —H, —F, —Cl, —Br, —C$_3$—C$_6$cycloalkyl, —OR$^8$, —SR$^8$, —SOR$^8$, —SO$_2$R$^8$, —(CH$_2$)$_n$OR$^8$ or —C$_{1-6}$alkyl optionally substituted with 1-3 of —F;

one of $R^{3a}$ and $R^{3b}$ is selected from —CN, —NO$_2$ or tetrazoly, and the other is $R^{3c}$ wherein $R^{3c}$ selected from —H, —F, —Cl, —Br, —CH$_3$, —S—CH$_3$, —NH—CH$_3$, —O-cyclopropyl or —OC$_{1-3}$alkyl optionally substituted with 1-3 of —F;

one of $R^{4a}$ and $R^{4b}$ is selected from CN, —NO$_2$ or tetrazolyl, and the other is $R^{4c}$ wherein $R^{4c}$ is selected from —H, —F, —Cl, —Br, —CH$_3$, —S—CH$_3$, —NH—CH$_3$, —O-cyclopropyl or —OC$_{1-3}$alkyl optionally substituted with 1-3 of —F;

$R^a$, $R^{aa}$, $R^b$ and $R^{bb}$ are each independently selected from —H, —F, —Cl, —CH$_3$ optionally substituted with 1 to 3 of —F, or —OCH$_3$ optionally substituted with 1 to 3 of —F;

$R^c$ and $R^d$ are each independently selected from —H, —F, —Cl, —C$_{1-6}$alkyl optionally substituted with 1 to 3 of —F, —C$_{3-6}$cycloalkyl or —OC$_{1-6}$alkyl optionally substituted with 1 to 3 of —F;

$R^e$ and $R^f$ are each independently selected from —H or —CH$_3$;

X and $X^1$ are each independently selected from —H or —C$_{1-6}$alkyl, or $X^1$ is joined together with $Z^1$ and the carbon to which both are attached to form a fused ring system selected from:

-continued

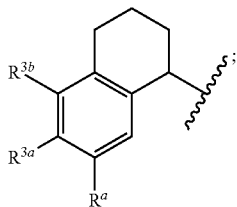

Y and $Y^1$ are each independently selected from —H or —$C_{1-6}$alkyl, or $Y^1$ is joined together with $Z^2$ and the carbon to which both are attached to form a fused ring system selected from

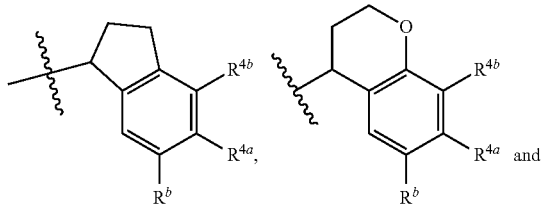

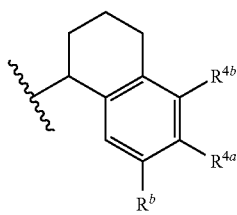

$R^5$ and $R^6$ are each independently selected from —H, —$C_{1-6}$ alkyl or —C(O)O$C_{1-3}$alkyl;

and $R^8$ is selected from —$C_{1-6}$alkyl or —$C_{3-6}$cycloalkyl.

2. The compound of claim 1 wherein:

$Z^1$ is selected from:

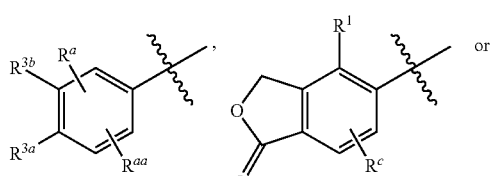

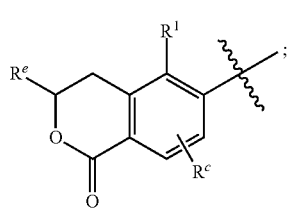

$Z^2$ is selected from:

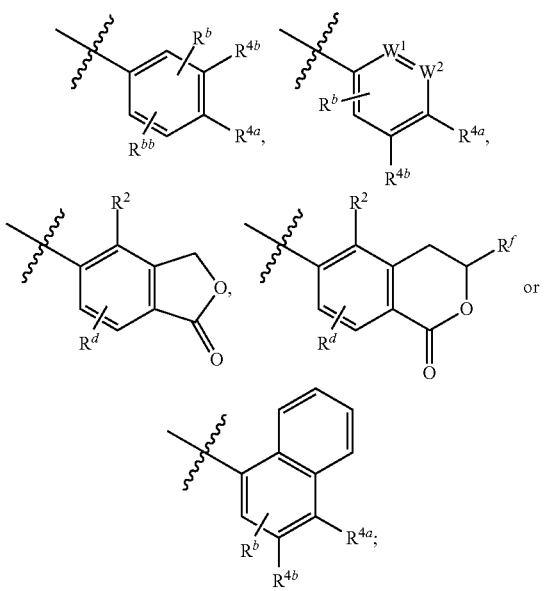

X and $X^1$ are each independently selected from —H or —$C_{1-6}$alkyl;

Y and $Y^1$ are each independently selected from —H or —$C_{1-6}$alkyl, or $Y^1$ is joined together with $Z^2$ and the carbon to which both are attached to form a fused ring system selected from:

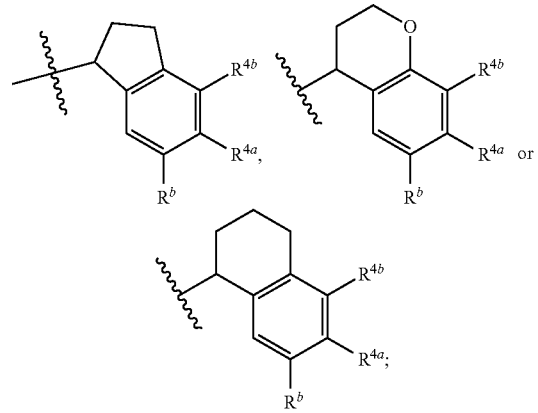

$R^5$ is selected from —H, —$CH_3$, —$C_{1-6}$ alkyl or —C(O)O$C_{1-3}$alkyl; and $R^6$ is selected from —H, —$CH_3$, —$C_{1-6}$ alkyl or —C(O)O$C_{1-3}$alkyl, or a pharmaceutically acceptable salt thereof.

3. The compound of claim 1 wherein $R^7$ is —H;

$R^1$ and $R^2$ are independently selected from —H or —$CH_3$;

$R^a$ and $R^b$ are each independently selected from —H, —F, —Cl, —$CH_3$ optionally substituted with 1 to 3 of —F, or —$OCH_3$ optionally substituted with 1 to 3 of —F;

$R^{aa}$ and $R^{bb}$ are each independently selected from —H or —F $R^c$ and $R^d$ are each independently selected from —H, —F, —Cl, —$CH_3$ optionally substituted with 1 to 3 of —F, or —$OCH_3$ optionally substituted with 1 to 3 of —F;

$R^5$ is selected from —H or —CH$_3$;
$R^6$ is selected from —H or —CH$_3$;
X, X$^1$ and Y are each —H; and
Y$^1$ is —H, or Y$^1$ is joined together with Z$^2$ and the carbon to which both are attached to form a fused ring system as defined in claim 1;
or a pharmaceutically acceptable salt thereof.

4. The compound of claim 1 selected from:
1,4-Bis[2-(4-nitrophenyl)ethyl]piperazine;
2-Methoxy-4-(2-{4-[2-(1-oxo-1,3-dihydro-2-benzofuran-5-yl)ethyl]piperazin-1-yl}ethyl)benzonitrile;
2-Methoxy-4-[2-[4-[2-(4-methyl-1-oxo-3H-isobenzofuran-5-yl)ethyl]piperazin-1-yl]ethyl]benzonitrile;
5,5'-(Piperazine-1,4-diyldiethane-2,1-diyl)bis(4-methyl-2-benzofuran-1(3H)-one);
5,5'-(Piperazine-1,4-diyldiethane-2,1-diyl)bis(2-benzofuran-1(3H)-one
2-Ethoxy-4-(2-{4-[2-(1-oxo-1,3-dihydro-2-benzofuran-5-yl)ethyl]piperazin-1-yl}ethyl)benzonitrile;
4-Fluoro-2-methoxy-3-(2-{4-[2-(4-methyl-1-oxo-1,3-dihydro-2-benzofuran-5-yl)ethyl]piperazin-1-yl}ethyl)benzonitrile;
4-Methyl-5-(1-(4-(2-(4-methyl-1-oxo-1,3-dihydroisobenzofuran-5-yl)ethyl)piperazin-1-yl)propan-2-yl)isobenzofuran-1(3H)-one;
2-Methoxy-4-(2-{4-[2-(3-methyl-1-oxo-3,4-dihydro-1H-isochromen-6-yl)ethyl]piperazin-1-yl}ethyl)benzonitrile;
2,2-Dimethyl-1,4-bis[2-(4-nitrophenyl)ethyl]piperazine;
4-Methyl-5-[2-[4-[2-[6-(tetrazol-1-yl)-3-pyridyl]ethyl]piperazin-1-yl]ethyl]-3H-isobenzofuran-1-one;
2-Methoxy-4-(2-{4-[2-(1-oxo-1,3-dihydro-2-benzofuran-5-yl)ethyl]-2-(trifluoromethyl)piperazin-1-yl}ethyl)benzonitrile;
4-(2-{4-[2-(4-Methyl-1-oxo-1,3-dihydro-2-benzofuran-5-yl)ethyl]piperazin-1-yl}ethyl)naphthalene-1-carbonitrile;
4-(2-{4-[2-(1-oxo-1,3-dihydro-2-benzofuran-5-yl)ethyl]piperazin-1-yl}ethyl)benzonitrile;
(3S,3'S)-6,6'-(Piperazine-1,4-diyldiethane-2,1-diyl)bis(3-methyl-3,4-dihydro-1H-isochromen-1-one);
2-(Methylamino)-4-(2-{4-[2-(1-oxo-1,3-dihydro-2-benzofuran-5-yl)ethyl]piperazin-1-yl}ethyl)benzonitrile;
2-Fluoro-4-[2-[4-[2-(1-oxo-3H-isobenzofuran-5-yl)ethyl]piperazin-1-yl]ethyl]benzonitrile;
2-(Cyclopropyloxy)-4-(2-{4-[2-(1-oxo-1,3-dihydro-2-benzofuran-5-yl)ethyl]piperazin-1-yl}ethyl)benzonitrile;
3-Chloro-2-fluoro-4-(2-{4-[2-(4-methyl-1-oxo-1,3-dihydro-2-benzofuran-5-yl)ethyl]piperazin-1-yl}ethyl)benzonitrile; or
4-Fluoro-2-methoxy-3-(2-{4-[2-(1-oxo-1,3-dihydro-2-benzofuran-5-yl)ethyl]piperazin-1-yl}ethyl)benzonitrile;
or a pharmaceutically acceptable salt thereof.

5. The compound of claim 1 selected from:
1,4-Bis[2-(4-nitrophenyl)ethyl]piperazine;
4,4'-(Piperazine-1,4-diyldiethane-2,1-diyl)dibenzonitrile;
2-Methoxy-4-(2-{4-[2-(1-oxo-1,3-dihydro-2-benzofuran-5-yl)ethyl]piperazin-1-yl}ethyl)benzonitrile;
2-Methoxy-4-[2-[4-[2-(4-methyl-1-oxo-3H-isobenzofuran-5-yl)ethyl]piperazin-1-yl]ethyl]benzonitrile;
5,5'-(Piperazine-1,4-diyldiethane-2,1-diyl)bis(4-methyl-2-benzofuran-1(3H)-one);
5,5'-(Piperazine-1,4-diyldiethane-2,1-diyl)bis(2-benzofuran-1(3H)-one;
2-Ethoxy-4-(2-{4-[2-(1-oxo-1,3-dihydro-2-benzofuran-5-yl)ethyl]piperazin-1-yl}ethyl)benzonitrile;
4-Fluoro-2-methoxy-3-(2-{4-[2-(4-methyl-1-oxo-1,3-dihydro-2-benzofuran-5-yl)ethyl]piperazin-1-yl}ethyl)benzonitrile;
4-Methyl-5-(1-(4-(2-(4-methyl-1-oxo-1,3-dihydroisobenzofuran-5-yl)ethyl)piperazin-1-yl)propan-2-yl)isobenzofuran-1(3H)-one; or
4-(2-{4-[2-(1-oxo-1,3-dihydro-2-benzofuran-5-yl)ethyl]piperazin-1-yl}ethyl)benzonitrile;
or a pharmaceutically acceptable salt thereof.

6. A pharmaceutical composition comprised of a compound of claim 1 and a pharmaceutically acceptable carrier.

7. A compound selected from:
1,4-Bis[2-(4-nitrophenyl)ethyl]piperazine;
1-[2-(4-Nitrophenyl)ethyl]-4-[2-(5-nitropyridin-2-yl)ethyl]piperazine;
4-(2-{4-[2-(4-Nitrophenyl)ethyl]piperazin-1-yl}ethyl)benzonitrile;
2-(Fluoromethyl)-1,4-bis[2-(4-nitrophenyl)ethyl]piperazine;
4,4'-(Piperazine-1,4-diyldiethane-2,1-diyl)dibenzonitrile;
2-Methyl-1,4-bis[2-(4-nitrophenyl)ethyl]piperazine;
Methyl(2S)-3-(4-nitrophenyl)-2-{4-[2-(4-nitrophenyl)ethyl]piperazin-1-yl}propanoate;
2,2-Dimethyl-1,4-bis[2-(4-nitrophenyl)ethyl]piperazine;
2-Cyclopropyl-1,4-bis[2-(4-nitrophenyl)ethyl]piperazine;
2-(Difluoromethyl)-1,4-bis[2-(4-nitrophenyl)ethyl]piperazine;
{1,4-Bis[2-(4-nitrophenyl)ethyl]piperazin-2-yl}methanol;
1-[2-(4-Nitrophenyl)ethyl]-4-[2-(4-nitrophenyl)propyl]piperazine;
1-[2-(4-Nitrophenyl)ethyl]-4-{2-[4-nitro-2-(trifluoromethyl)phenyl]ethyl}piperazine;
1-[1-Methyl-2-(4-nitrophenyl)ethyl]-4-[2-(4-nitrophenyl)ethyl]piperazine;
1,4-Bis[1-methyl-2-(4-nitrophenyl)ethyl]piperazine;
Methyl {1,4-bis[2-(4-nitrophenyl)ethyl]piperazin-2-yl}acetate;
2-Methoxy-4-(2-{4-[2-(4-nitrophenyl)ethyl]piperazin-1-yl}ethyl)benzonitrile;
3-Methyl-4-(2-{4-[2-(4-nitrophenyl)ethyl]piperazin-1-yl}ethyl)benzonitrile;
2-Methyl-4-(2-{4-[2-(4-nitrophenyl)ethyl]piperazin-1-yl}ethyl)benzonitrile;
2,6-Difluoro-4-(2-{4-[2-(4-nitrophenyl)ethyl]piperazin-1-yl}ethyl)benzonitrile;
3-Methoxy-4-(2-{4-[2-(4-nitrophenyl)ethyl]piperazin-1-yl}ethyl)benzonitrile;
2-Fluoro-4-(2-{4-[2-(4-nitrophenyl)ethyl]piperazin-1-yl}ethyl)benzonitrile;
1-((4-(2-(1-Oxo-1,3-dihydroisobenzofuran-5-yl)ethyl)piperazin-1-yl)methyl)-2,3-dihydro-1H-indene-4-carbonitrile;
2-Methoxy-4-(2-{4-[2-(1-oxo-1,3-dihydro-2-benzofuran-5-yl)ethyl]piperazin-1-yl}ethyl)benzonitrile;
4-({4-[2-(1-Oxo-1,3-dihydro-2-benzofuran-5-yl)ethyl]piperazin-1-yl}methyl)-3,4-dihydro-2H-chromene-7-carbonitrile;
5-({4-[2-(1-Oxo-1,3-dihydro-2-benzofuran-5-yl)ethyl]piperazin-1-yl}methyl)-5,6,7,8-tetrahydronaphalene-2-carbonitrile;
2-Fluoro-4-[2-[4-[2-(1-oxo-3H-isobenzofuran-5-yl)ethyl]piperazin-1-yl]ethyl]benzonitrile;
2,5-Difluoro-4-[2-[4-[2-(1-oxo-3H-isobenzofuran-5-yl)ethyl]piperazin-1-yl]ethyl]benzonitrile;

2-Bromo-4-[2-[4-[2-(1-oxo-3H-isobenzofuran-5-yl)ethyl]piperazin-1-yl]ethyl]benzonitrile;
2-Methoxy-4-[2-[4-[2-(4-methyl-1-oxo-3H-isobenzofuran-5-yl)ethyl]piperazin-1-yl]ethyl]benzonitrile;
5-[2-[4-[2-[6-(Tetrazol-1-yl)-3-pyridyl]ethyl]piperazin-1-yl]ethyl]-3H-isobenzofuran-1-one;
4-Methyl-5-[2-[4-[2-[6-(tetrazol-1-yl)-3-pyridyl]ethyl]piperazin-1-yl]ethyl]-3H-isobenzofuran-1-one;
2-Methoxy-4-[1-methyl-2-[4-[2-(1-oxo-3H-isobenzofuran-5-yl)ethyl]piperazin-1-yl]ethyl]benzonitrile;
2-Methoxy-4-[1-methyl-2-[4-[2-(4-methyl-1-oxo-3H-isobenzofuran-5-yl)ethyl]piperazin-1-yl]ethyl]benzonitrile;
2-Methoxy-4-[2-[4-[2-(4-methyl-1-oxo-3H-isobenzofuran-5-yl)ethyl]piperazin-1-yl]propyl]benzonitrile;
4-[1,1-Dimethyl-2-[4-[2-(4-methyl-1-oxo-3H-isobenzofuran-5-yl)ethyl]piperazin-1-yl]ethyl]-2-methoxy-benzonitrile;
2-Methoxy-4-[2-[4-[2-(1-oxo-3H-isobenzofuran-5-yl)ethyl]piperazin-1-yl]propyl]benzonitrile;
2-(Difluoromethoxy)-4-[2-[4-[2-(4-methyl-1-oxo-3H-isobenzofuran-5-yl)ethyl]piperazin-1-yl]ethyl]benzonitrile;
5-Fluoro-3-({4-[2-(1-oxo-1,3-dihydro-2-benzofuran-5-yl)ethyl]piperazin-1-yl}methyl)-3,4-dihydro-2H-chromene-7-carbonitrile;
2-Methoxy-4-(2-{4-[2-(1-oxo-1,3-dihydro-2-benzofuran-5-yl)ethyl]-3-(trifluoromethyl)piperazin-1-yl}ethyl)benzonitrile;
5-Fluoro-2-methoxy-4-(2-{4-[2-(1-oxo-1,3-dihydro-2-benzofuran-5-yl)ethyl]piperazin-1-yl}ethyl)benzonitrile;
5-Fluoro-2-methoxy-4-(2-{4-[2-(4-methyl-1-oxo-1,3-dihydro-2-benzofuran-5-yl)ethyl]piperazin-1-yl}ethyl)benzonitrile;
4,4'-(Piperazine-1,4-diyldiethane-2,1-diyl)bis(5-fluoro-2-methoxybenzonitrile);
2-Methoxy-4-(2-{4-[2-(4-methyl-1-oxo-1,3-dihydro-2-benzofuran-5-yl)propyl]piperazin-1-yl}ethyl)benzonitrile;
2-Methoxy-4-(2-{4-[2-(1-oxo-1,3-dihydro-2-benzofuran-5-yl)ethyl]-2-(trifluoromethyl)piperazin-1-yl}ethyl)benzonitrile;
2-Methoxy-4-(2-{4-[2-(3-methyl-1-oxo-3,4-dihydro-1H-isochromen-6-yl)ethyl]piperazin-1-yl}ethyl)benzonitrile;
(3S,3'S)-6,6'-(Piperazine-1,4-diyldiethane-2,1-diyl)bis(3-methyl-3,4-dihydro-1H-isochromen-1-one);
5,5'-(Piperazine-1,4-diyldiethane-2,1-diyl)bis(4-methyl-2-benzofuran-1(3H)-one);
2-(Methylthio)-4-(2-{4-[2-(1-oxo-1,3-dihydro-2-benzofuran-5-yl)ethyl]piperazin-1-yl}ethyl)benzonitrile:
5-Chloro-2-methoxy-4-(2-{4-[2-(1-oxo-1,3-dihydro-2-benzofuran-5-yl)ethyl]piperazin-1-yl}ethyl)benzonitrile;
2-(Methylamino)-4-(2-{4-[2-(1-oxo-1,3-dihydro-2-benzofuran-5-yl)ethyl]piperazin-1-yl}ethyl)benzonitrile;
2-(Difluoromethoxy)-4-(2-{4-[2-(1-oxo-1,3-dihydro-2-benzofuran-5-yl)ethyl]piperazin-1-yl}ethyl)benzonitrile;
2-(Cyclopropyloxy)-4-(2-{4-[2-(1-oxo-1,3-dihydro-2-benzofuran-5-yl)ethyl]piperazin-1-yl}ethyl)benzonitrile;
5-(2-{4-[2-(4-Nitrophenyl)ethyl]piperazin-1-yl}ethyl)-2-benzofuran-1(3H)-one;
5,5'-(Piperazine-1,4-diyldiethane-2,1-diyl)bis(2-benzofuran-1(3H)-one;
2-Trifluoromethoxy-4-(2-{4-[2-(1-oxo-1,3-dihydro-2-benzofuran-5-yl)ethyl]piperazin-1-yl}ethyl)benzonitrile;
2-Trifluoromethoxy-4-(2-{4-[2-(4-methyl-1-oxo-1,3-dihydro-2-benzofuran-5-yl)ethyl]piperazin-1-yl}ethyl)benzonitrile;
2-Chloro-4-(2-{4-[2-(1-oxo-1,3-dihydro-2-benzofuran-5-yl)ethyl]piperazin-1-yl}ethyl)benzonitrile;
2-Chloro-4-(2-{4-[2-(4-methyl-1-oxo-1,3-dihydro-2-benzofuran-5-yl)ethyl]piperazin-1-yl}ethyl)benzonitrile;
3-Fluoro-2-methoxy-4-(2-{4-[2-(1-oxo-1,3-dihydro-2-benzofuran-5-yl)ethyl]piperazin-1-yl}ethyl)benzonitrile;
3-Fluoro-2-methoxy-4-(2-{4-[2-(4-methyl-1-oxo-1,3-dihydro-2-benzofuran-5-yl)ethyl]piperazin-1-yl}ethyl)benzonitrile;
4-(2-{4-[2-(4-Methyl-1-oxo-1,3-dihydro-2-benzofuran-5-yl)ethyl]piperazin-1-yl}ethyl)naphthalene-1-carbonitrile;
2,3,5-Trifluoro-4-(2-{4-[2-(4-methyl-1-oxo-1,3-dihydro-2-benzofuran-5-yl)ethyl]piperazin-1-yl}ethyl)benzonitrile;
2-Ethoxy-4-(2-{4-[2-(1-oxo-1,3-dihydro-2-benzofuran-5-yl)ethyl]piperazin-1-yl}ethyl)benzonitrile;
2-Ethoxy-4-(2-{4-[2-(4-methyl-1-oxo-1,3-dihydro-2-benzofuran-5-yl)ethyl]piperazin-1-yl}ethyl)benzonitrile;
5-Chloro-2-fluoro-4-(2-{4-[2-(1-oxo-1,3-dihydro-2-benzofuran-5-yl)ethyl]piperazin-1-yl}ethyl)benzonitrile;
5-Chloro-2-fluoro-4-(2-{4-[2-(4-methyl-1-oxo-1,3-dihydro-2-benzofuran-5-yl)ethyl]piperazin-1-yl}ethyl)benzonitrile;
5-Chloro-2-methoxy-4-(2-{4-[2-(4-methyl-1-oxo-1,3-dihydro-2-benzofuran-5-yl)ethyl]piperazin-1-yl}ethyl)benzonitrile;
2-Fluoro-3-methyl-4-(2-{4-[2-(1-oxo-1,3-dihydro-2-benzofuran-5-yl)ethyl]piperazin-1-yl}ethyl)benzonitrile;
2-Fluoro-3-methyl-4-(2-{4-[2-(4-methyl-1-oxo-1,3-dihydro-2-benzofuran-5-yl)ethyl]piperazin-1-yl}ethyl)benzonitrile;
2-Methoxy-3-methyl-4-(2-{4-[2-(1-oxo-1,3-dihydro-2-benzofuran-5-yl)ethyl]piperazin-1-yl}ethyl)benzonitrile;
2-Methoxy-3-methyl-4-(2-{4-[2-(4-methyl-1-oxo-1,3-dihydro-2-benzofuran-5-yl)ethyl]piperazin-1-yl}ethyl)benzonitrile;
3-Chloro-2-fluoro-4-(2-{4-[2-(1-oxo-1,3-dihydro-2-benzofuran-5-yl)ethyl]piperazin-1-yl}ethyl)benzonitrile;
3-Chloro-2-fluoro-4-(2-{4-[2-(4-methyl-1-oxo-1,3-dihydro-2-benzofuran-5-yl)ethyl]piperazin-1-yl}ethyl)benzonitrile;
3-Chloro-2-methoxy-4-(2-{4-[2-(1-oxo-1,3-dihydro-2-benzofuran-5-yl)ethyl]piperazin-1-yl}ethyl)benzonitrile;
3-Chloro-2-methoxy-4-(2-{4-[2-(4-methyl-1-oxo-1,3-dihydro-2-benzofuran-5-yl)ethyl]piperazin-1-yl}ethyl)benzonitrile;
4-Fluoro-2-methoxy-3-(2-{4-[2-(1-oxo-1,3-dihydro-2-benzofuran-5-yl)ethyl]piperazin-1-yl}ethyl)benzonitrile;
4-Fluoro-2-methoxy-3-(2-{4-[2-(4-methyl-1-oxo-1,3-dihydro-2-benzofuran-5-yl)ethyl]piperazin-1-yl}ethyl)benzonitrile;
4-({4-[2-(4-Methyl-1-oxo-1,3-dihydro-2-benzofuran-5-yl)ethyl]piperazin-1-yl}methyl)-3,4-dihydro-2H-chromene-7-carbonitrile;

5-Fluoro-3-({4-[2-(1-oxo-1,3-dihydro-2-benzofuran-5-yl)ethyl]piperazin-1-yl}methyl)-3,4-dihydro-2H-chromene-7-carbonitrile;
5,5'-(Piperazine-1,4-diyldipropane-1,3-diyl)bis(4-methyl-2-benzofuran-1(3H-one);
4-Methyl-5-(1-(4-(2-(4-methyl-1-oxo-1,3-dihydroisobenzofuran-5-yl)ethyl)piperazin-1-yl)propan-2-yl)isobenzofuran-1(3H)-one;
4-(2-{4-[2-(1-Oxo-1,3-dihydro-2-benzofuran-5-yl)ethyl]piperazin-1-yl}ethyl)benzonitrile;
or a pharmaceutically acceptable salt thereof.

* * * * *